US010669268B2

(12) United States Patent
Hert et al.

(10) Patent No.: US 10,669,268 B2
(45) Date of Patent: Jun. 2, 2020

(54) BICYCLIC DERIVATIVES

(71) Applicant: Hoffmann-La Roche Inc., Little Falls, NJ (US)

(72) Inventors: Jerome Hert, Basel (CH); Daniel Hunziker, Moehlin (CH); Patrizio Mattei, Riehen (CH); Harald Mauser, Riehen (CH); Guozhi Tang, Riehen (CH); Lisha Wang, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/583,679

(22) Filed: May 1, 2017

(65) Prior Publication Data

US 2018/0118741 A1  May 3, 2018

Related U.S. Application Data

(63) Continuation of application No. 14/719,063, filed on May 21, 2015, now abandoned, which is a continuation of application No. PCT/EP2013/069679, filed on Sep. 23, 2013.

(30) Foreign Application Priority Data

Sep. 25, 2012 (EP) .................................... 12185941

(51) Int. Cl.
| C07D 231/56 | (2006.01) |
| C07D 235/04 | (2006.01) |
| C07D 471/04 | (2006.01) |
| C07D 519/00 | (2006.01) |
| C07D 413/12 | (2006.01) |
| C07D 403/12 | (2006.01) |
| C07D 487/04 | (2006.01) |

(52) U.S. Cl.
CPC ......... *C07D 471/04* (2013.01); *C07D 403/12* (2013.01); *C07D 413/12* (2013.01); *C07D 487/04* (2013.01); *C07D 519/00* (2013.01)

(58) Field of Classification Search
CPC ............................ C07D 231/56; C07D 235/04
USPC ............... 546/143, 148; 514/319; 548/304.4, 548/361.1
See application file for complete search history.

(56) References Cited

U.S. PATENT DOCUMENTS

| 3,392,149 A | 7/1968 | von der Emden et al. |
| 5,202,322 A | 4/1993 | Allen et al. |
| 5,238,942 A | 8/1993 | Chakravarty et al. |
| 5,240,928 A | 8/1993 | Allen et al. |
| 5,290,780 A | 3/1994 | Venkatesan et al. |
| 5,304,565 A | 4/1994 | Morimoto et al. |
| 5,358,951 A | 10/1994 | Levin et al. |
| 5,472,961 A | 5/1995 | Gottschlich et al. |
| 5,470,975 A | 11/1995 | Atwal et al. |
| 5,532,243 A | 2/1996 | Gilligan |
| 6,821,964 B2 | 11/2004 | Colon-Cruz et al. |
| 6,841,560 B2 * | 1/2005 | Thompson ........... C07D 217/02 514/310 |
| 8,329,907 B2 | 12/2012 | Schultz et al. |
| 8,697,883 B2 | 4/2014 | Abouabdellah et al. |
| 8,841,324 B2 | 9/2014 | Staehle et al. |
| 9,029,387 B2 | 5/2015 | Staehle et al. |
| 9,493,486 B2 | 11/2016 | Hunziker et al. |
| 9,802,944 B2 | 10/2017 | Di Giorgio et al. |
| 10,208,052 B1 | 2/2019 | Zheng et al. |
| 2005/0203112 A1 | 9/2005 | Castonguay et al. |
| 2008/0090802 A1 | 4/2008 | Letourneau et al. |
| 2010/0222341 A1 | 9/2010 | Schiemann et al. |
| 2010/0298290 A1 | 11/2010 | Anand et al. |
| 2011/0230471 A1 | 9/2011 | Staehle et al. |
| 2012/0015959 A1 | 1/2012 | Staehle et al. |
| 2012/0095040 A1 | 4/2012 | Abouabdellah et al. |
| 2012/0115852 A1 | 5/2012 | Schultz et al. |
| 2012/0115858 A1 | 10/2012 | Tesconi et al. |
| 2015/0353559 A1 | 12/2015 | Hert et al. |
| 2015/0376194 A1 | 12/2015 | Hert et al. |
| 2016/0264586 A1 | 9/2016 | Mattei et al. |
| 2017/0008900 A1 | 1/2017 | Di Giorgio et al. |
| 2017/0008913 A1 | 1/2017 | Hunziker et al. |

(Continued)

FOREIGN PATENT DOCUMENTS

| CA | 2 768 095 | 1/2011 |
| CA | 2878442 A1 | 4/2014 |

(Continued)

OTHER PUBLICATIONS 1206969-43-8,Database Registry [retrieved online May 25, 2016] Chemical Abstracts Service, Feb. 22, 2010 (Feb. 22, 2010), BroadPharm: XP002707619, retrieved from STN Database accession No. 1206969-43-8 the whole document.
959567-58-9,Database Registry [retrieved online May 25, 2016] Chemical Abstracts Service Dec. 26, 2007 (Dec. 26, 2007), NIH Chemical Genomics Center: XP002707620, retrieved from STN Database accession No. 959567-58-9.
Albers et al., "Chemical Evolution of Autotaxin Inhibitors" Chemical Reviews (XP055073234), 112(5):2593-2603 (May 9, 2012).
Barbayianni et al., "Autotaxin inhibitors: a patent review" Expert Opin Ther Patents 23(9):1123-1132 ( 2013).
Benesh et al., Febs Lett 588:2712-2727 ( 2014).

(Continued)

*Primary Examiner* — Niloofar Rahmani
(74) *Attorney, Agent, or Firm* — Katherine J. Mackenzie

(57) ABSTRACT

The invention provides novel compounds having the general formula (I)

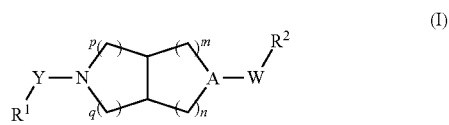

wherein $R^1$, Y, A, W, $R^2$, m, n, p and q are as described herein, compositions including the compounds and methods of using the compounds.

55 Claims, No Drawings

(56) References Cited

U.S. PATENT DOCUMENTS

| | | |
|---|---|---|
| 2017/0029425 A1 | 2/2017 | Hunziker et al. |
| 2017/0050960 A1 | 2/2017 | Hert et al. |

FOREIGN PATENT DOCUMENTS

| | | |
|---|---|---|
| CN | 1751047 A1 | 3/2006 |
| CN | 102459207 A | 5/2012 |
| EP | 0 417 631 A2 | 3/1991 |
| EP | 2 301 936 A1 | 3/2011 |
| EP | 3385261 A1 | 10/2018 |
| JP | 2001039950 | 2/2001 |
| JP | 2008-501743 | 1/2008 |
| JP | 2008-31064 | 2/2008 |
| JP | 2008-31064 A | 2/2008 |
| JP | 2008-540547 | 11/2008 |
| JP | 2009-161449 | 7/2009 |
| JP | 2011-502150 | 1/2011 |
| RU | 2 375 352 C2 | 12/2009 |
| WO | 99/40070 | 8/1999 |
| WO | 01/30780 | 5/2001 |
| WO | 02/070523 | 9/2002 |
| WO | 2004/074291 | 9/2004 |
| WO | 2005/023762 A1 | 3/2005 |
| WO | 2005/040167 A1 | 5/2005 |
| WO | 2005/058798 A2 | 6/2005 |
| WO | 2005/084667 | 9/2005 |
| WO | 2005/121145 | 12/2005 |
| WO | 2006/015985 A1 | 2/2006 |
| WO | 2006/077035 A1 | 7/2006 |
| WO | 2006/122137 | 11/2006 |
| WO | 2007/030061 A1 | 3/2007 |
| WO | 2007/049771 | 5/2007 |
| WO | 2007/058322 | 5/2007 |
| WO | 2007/103719 | 9/2007 |
| WO | 2008/033456 A1 | 3/2008 |
| WO | 2008/033764 A2 | 3/2008 |
| WO | 2008/059026 A1 | 5/2008 |
| WO | 2008/060767 A2 | 5/2008 |
| WO | 2008/076223 A1 | 6/2008 |
| WO | 2008/116881 A1 | 10/2008 |
| WO | 2008/119662 A1 | 10/2008 |
| WO | 2008/126034 | 10/2008 |
| WO | 2008135141 A1 | 11/2008 |
| WO | 2009/046841 A2 | 4/2009 |
| WO | 2009/054914 A1 | 4/2009 |
| WO | 2009/058347 | 5/2009 |
| WO | 2011/017561 | 2/2010 |
| WO | 2010/028761 | 3/2010 |
| WO | 2010/051977 | 5/2010 |
| WO | 2010/055006 A1 | 5/2010 |
| WO | 2010/060532 A1 | 6/2010 |
| WO | 2010/063352 A1 | 6/2010 |
| WO | 2010/099938 | 9/2010 |
| WO | 2010/108651 | 9/2010 |
| WO | 2010/112116 A1 | 10/2010 |
| WO | 2010/112124 A1 | 10/2010 |
| WO | 2010/115491 A2 | 10/2010 |
| WO | 2010/130944 A1 | 11/2010 |
| WO | 2010/135524 | 11/2010 |
| WO | 2010/141817 A1 | 12/2010 |
| WO | 2011/006569 A1 | 1/2011 |
| WO | 2011/017350 | 2/2011 |
| WO | 2011/053948 | 5/2011 |
| WO | 2011/085170 | 7/2011 |
| WO | 2011/114271 A1 | 9/2011 |
| WO | 2011/115813 A1 | 9/2011 |
| WO | 2011/116867 | 9/2011 |
| WO | 2011/141716 A2 | 11/2011 |
| WO | 2009/154132 | 12/2011 |
| WO | 2011/151461 A2 | 12/2011 |
| WO | 2012/020008 | 2/2012 |
| WO | 2012/024620 | 2/2012 |
| WO | 2012/028243 | 3/2012 |
| WO | 2012/080727 | 6/2012 |
| WO | 2012/166415 | 12/2012 |
| WO | 2013/186159 | 12/2012 |
| WO | 2013/033059 A1 | 3/2013 |
| WO | 2013/054185 A1 | 4/2013 |
| WO | 2013/064467 A1 | 5/2013 |
| WO | 2013/065712 A1 | 5/2013 |
| WO | 2013/079223 A1 | 6/2013 |
| WO | 2013/175053 | 11/2013 |
| WO | 2014/007951 | 1/2014 |
| WO | 2014/018881 | 1/2014 |
| WO | 2014/018891 | 1/2014 |
| WO | 2014/048865 A1 | 4/2014 |
| WO | 2014/048881 | 4/2014 |
| WO | 2014/055548 | 4/2014 |
| WO | 2014/066659 | 5/2014 |
| WO | 2014/133112 | 9/2014 |
| WO | 2014/139324 | 9/2014 |
| WO | 2014/139978 | 9/2014 |
| WO | 2014/143579 | 9/2014 |
| WO | 2014/152725 A1 | 9/2014 |
| WO | 2014/164905 | 10/2014 |
| WO | 2015/008230 A1 | 1/2015 |
| WO | 2015/058031 | 4/2015 |
| WO | 2015/077503 | 5/2015 |
| WO | 2015/078800 A1 | 6/2015 |
| WO | 2015/078803 | 6/2015 |
| WO | 2015/144480 | 10/2015 |
| WO | 2015/144605 A1 | 10/2015 |
| WO | 2015/144609 | 10/2015 |
| WO | 2015/144803 | 10/2015 |
| WO | 2015/154023 A1 | 10/2015 |
| WO | 2016/061160 | 4/2016 |
| WO | 2016/128529 A1 | 8/2016 |
| WO | 2016/162390 | 10/2016 |
| WO | 2017/005073 | 1/2017 |
| WO | 2017005073 | 1/2017 |
| WO | 2017/037146 | 3/2017 |
| WO | 2017/037670 | 3/2017 |
| WO | 2017/050732 | 3/2017 |
| WO | 2017/050747 | 3/2017 |
| WO | 2017/050791 | 3/2017 |
| WO | 2017/050792 | 3/2017 |
| WO | 2017/053722 | 3/2017 |
| WO | 2017/091673 | 6/2017 |
| WO | 2017/139978 | 8/2017 |
| WO | 2018/167001 A1 | 9/2018 |
| WO | 2018/167113 | 9/2018 |

OTHER PUBLICATIONS

CAS Registry Database, 1300725-30-7,Database Registry [retrieved online May 25, 2016] Chemical Abstracts Service May 25, 2011 (May 25, 2011), Focus Synthesis LLC: XP002707618, retrieved from STN Database accession No. 1300725-30-7 the whole document.

CAS Registry Database, 1352926-14-7,Database Registry [retrieved online May 25, 2016] Chemical Abstracts Service Jan. 12, 2012 (Jan. 12, 2012), All i chem LLC: XP002707617, retrieved from STN Database accession No. 1352926-14-7 see also RN: 1135295-74-6; the whole document.

Database Capulus (online) Chemical Abstracts Service Columbus Ohio, 1993, Database accession No. 1994:483155 RN156411-73-3, 156411-74-4 (1993).

Garcia-Gutierrez et al., "Novel inhibitors to Taenia solium Cu/Zn superoxide dismutase identifed by virtual screening" J. Computer. Aided Molecular Design 25:1135-1145 ( 2011).

Gierse et al., Pharmacol Exp Ther 334:310-317 ( 2010).

Harald M.H.G. Albers et al., "Discovery and Optimization of Boronic Acid Based Inhibitors of Autotaxin" Journal of Medicinal Chemistry 53(13):4958-4967 (Jul. 8, 2010).

Hoeglund et al., "Optimization of a pidemidic acid autotaxin inhibitor" Journal of Medicinal Chemistry 53:1056-1066 (Dec. 30, 2009).

International Search Report for International Patent Application No. PCT/EP2014/075360.

ISR for PCT/EP2013/061890.

ISR for PCT/EP2013/069679.

Jones et al., ACS Med Chem Lett 7:857-861 ( 2016).

(56) References Cited

OTHER PUBLICATIONS

Kung et al., "Identification of spirocyclic piperidine-azetidine inverse agonists of the ghrelin receptor" Bioorganic & Medicinal Chemistry Letters (XP028490993), 22(13):4281-4287 (May 8, 2012).
Litherland et al., "The Amino-derivatives of Pentuerythritol. Part I. Preparation." (Published on Jan. 1, 1938. Downloaded by Roche Group on May 24, 2016 17:23:15.),:1588-1595.
Mayo Clinic Staff, (Lupus[online], retrieved from the internet on Jan. 24, 2017; http://www.mayoclinic.org/diseases-conditions/lupus basics/definition/CON-20019676) 2017.
Orr et al., "One-pot synthesis of chiral azetidines from chloroaldehyde and chiral amines" Tetrahedron Letters (XP055073241), 52:3618-3620 (2011).
Overberger et al., "Absolute Configuration of 2,7-Diazaspiro[4.4.1nonane. A Reassignment" J. Org. Chem. (XP055072840), 46:2757-2764 (1981).
Sippy et al., "Preparation and characterization of N-(3-pyridinyl) spirocyclic diamines as ligands for nicotinic acetylcholine receptors" Bioorganic & Medicinal Chemistry Letters 19:1682-1685 (2009).
Stocks et al., "A Practical Method for Targeted Library Design Balancing Lead-like Properties with Diversity" Chem Med Chem (XP002707616), 4:800-808 (2009).
Written Opinion for PCT/EP2013/061890.
Written Opinion for PCT/EP2013/069679.
pp. 1-13 (STN Columbus (STN International) Oct. 9, 2015).
Sheridan et al., "The Most Common Chemical Replacements in Drug-Like Compounds" J. Chem. Inf. Comput. Sci. 42(1):103-108 (2002).
Albers et al., "Structure-Based Design of Novel Boronic Acid-Based Inhibitors of Autotaxin" Journal of Medicinal Chemistry 54(13):4619-4626 (2011).
CAS Registry Database, 959567-58-9, pp. 1-38 Dec. 26, 2007.
ISR for PCT/EP2016/072277, 3 pages.
Patani et al., "Bioisosterism: A Rational Approach in Drug Design," Chem.Ref. (1996), vol. 96, pp. 3147-3176.
Sheridan et al., "Cautious optimism surrounds early clinical data for PD-1 blocker" Nature Biotechnology 30:729-730 (2012).
Albers, H., et al., "Discovery and Optimization of Boronic Acid Based Inhibitors of Autotaxin" J Med Chem 53:4958-4967 (Jun. 10, 2010).
Anderson, "The Process of Structure-Based Drug Design" Chemistry & Biology 10:787-797 (Sep 2003).
Angeli et al., "Synthesis and carbonic anhydrase inhibition of polycyclic imides moieties" Bioorganic & Medicinal Chemistry 25(20):5373-5379 (Oct. 20, 2017).
Armstrong, J., et al., "Purification and Properties of Human Erythrocyte Carbonic Anhydrases" The Journal of Biological Chemistry 241(21):5137-5149 (Nov. 10, 1966).
Bora, Rajesh O., et al., "[1, 2, 4]-Oxadiazoles: Synthesis and Biological Applications" Mini-Reviews in Med. Chem 14(4):355-369 (Mar. 13, 2014).
Erdik, Ender, "Transition Metal Catalyzed Reactions of Organozinc Reagents" Tetrahedron Report No. 23 48(44):9577-9648 (Jan. 1, 1992).
Farina, V. et al. Organic Reactions "The Stille Reaction" Paquette, Leo A., New York -US:Wiley and Sons, vol. 50:1-704 (Apr. 1, 1997).
Green et al. Protective Groups in Organic Synthesis (Table of Contents only, in 4 pages), Second edition, New York:John Wiley & Sons, Inc., (1991).
Hall, Dennis.. ed. et al. Boronic Acids: Preparation, Applications in Organic Synthesis and Medicine (Description and table of contents only, 2 pages), Hall, Dennis, Wiley,:1-571 (Jan. 1, 2006).
Hemming, K. Science of Synthesis, Product 13: 1, 2, 3-Triazoles "Product Class 6: 1,2,4-Oxadiazoles" Storr, R.C. & Gilchrist, T.L., eds., Stuttgart-DE:Thieme Verlagsgruppe, vol. 13:127-184 (Jan. 1, 2004).

Henke, Brad R., et al., "Optimization of 3-(1H-Indazol-3-ylmethyl)-1,5-benzodiazepines as Potent, Orally Active CCK-A Agonists" J Med Chem 40:2706-2725 (Apr. 22, 1997).
"International Preliminary Report on Patentability—PCT/EP2018/056140":pp. 1-8 (Sep. 26, 2019).
"International Search Report—PCT/EP2014/054631":pp. 1-4 (Apr. 15, 2014).
"International Search Report—PCT/EP2015/056041":pp. 1-5 (May 6, 2015).
"International Search Report—PCT/EP2016/072349":pp. 1-5 (Nov. 29, 2016).
"International Search Report—PCT/EP2018/056140":pp. 1-9 (May 4, 2018).
"International Search Report—PCT/EP2018/056324" (x-cite P33952),:pp. 1-7 (May 8, 2018).
"International Search Report—PCT/EP2015/056032" (x-cite; P32055),:pp. 1-5 (Apr. 23, 2015).
"International Search Report—PCT/EP2016/057549":pp. 1-5 (Jun. 22, 2016).
"International Search Report—PCT/EP2016/072243":pp. 1-5 (Dec. 6, 2016).
"International Search Report—PCT/EP2016/072347":pp. 1-5 (Jan. 17, 2017).
"International Search Report—PCT/EP2016/070561":pp. 1-6 (Oct. 28, 2016).
Li, Jie Jack et al. Name Reactions for Homologation, Part 1 "Name Reactions for Homologation, Part 1" (Abstract of text, author information, and table of contents only, 2 pages), Wiley and Sons,:1-685 (May 1, 2009).
Matralis et al., "Development and therapeutic potential of autotaxin small molecule inhibitors: From bench to advanced clinical trials" Med. Res. Rev.:1-38 (2018).
Mitchell, Terence N., "Palladium-Catalysed Reactions of Organotin Compounds" Synthesis 9:803-815 (Aug. 16, 1991).
Negishi, et al. Metal-Catalyzed Cross-Coupling Reactions "Chapter 1: Palladium or NickelCatalyzed Cross Coupling with Organometals Containg Zinc, Magnesium, Aluminum, and Zirconium" (Preface, table of contents, list of contributors only, 22 pages), Diederich, Francois, Stang, Peter J., eds., Weinheim, DE:Wiley-VCH Verlag GmbH,:1-47 (Jan. 1, 2004).
Polshetti, V., et al., "Suzuki-Miyaura Cross-Coupling Reactions in Aqueous Media: Green and Sustainable Syntheses of Biaryls"Chem SUS Chem 3:502-522 (Jan. 1, 2010).
Pouliot, Marie-France et al., "Synthesis of 1,3,4-oxadiazoles from 1,2-diacylhydrazines using [Et2NSF2]BF4 as a practical cyclodehyration agent" Org. Biomol. Chem 10:988-993 (Oct. 27, 2012).
Schlaeger, E. et al., "The protein hydrolysate, primatone RL, is a cost-effective multiple growth promoter of mammalian cel culture in serum-containing and serum-free medi and displays anti-apoptosis properties" J Immunol Methods 164:191-199 (Apr. 12, 1996).
Stille, John K., "Palladium-Catalyzed Cross-Coupling Reactions of Organotin Reagents with Organic Electrophiles" Angew Chem. Int. Ed. Engl. 25:508-524 (Jan. 1, 1986).
Suzuki, A., et al., "Palladium-Catalyzed Cross-Coupling Reactions of Organoboron Compounds" Chem Rev. 95:2457-2483 (Jan. 31, 1995).
Suzuki, A., et al., "Recent advances in the cross-coupling reactions of organoboron derivatives with organic electrophiles, 1995-1998" J Organomet Chem 576:147-168 (Jan. 1, 1999).
Suzuki, A., et al., "Synthetic Studies via the cross-coupling reaction of organoboron derivatives with organic halides" Pure Appl Chem 63(3):419-422 (Jan. 1, 1991).
Thiel,, "Structure-aided drug design's next generation" Nat Biotechnol 22(5):513-519 (May 1, 2004).
Tucker, T., et al., "Discovery of 3-{5-[(6-Amino-1H-pyrazolo[3,4-b]pyridine-3-yl)methoxy]-2-chlorophenoxy}-5-chlorobenzonitrile (MK-4965): A Potent, Orally Bioavailable HIV-1 non-Nucleoside Reverse Transcriptase Inhibitor with Improved Potency against Key Mutant Viruses" J Med Chem 51:6503-6511 (Jul. 11, 2008).

* cited by examiner

BICYCLIC DERIVATIVES

RELATED APPLICATIONS

This application is a continuation of U.S. application Ser. No. 14/719,063, filed May 21, 2015, which is a continuation of International Application No. PCT/EP2013/069679, filed Sep. 23, 2013, claiming priority to Application No. EP12185941.7, filed, Sep. 25, 2012, the contents of which are incorporated herein by reference.

The present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I)

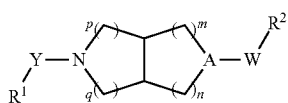

wherein $R^1$ is alkyl, haloalkyl, substituted cycloalkyl, substituted cycloalkylalkyl, substituted piperazinyl, substituted piperidinyl, substituted indanyloxyalkyl, substituted phenyl, substituted phenylalkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, naphtyl, substituted naphthyl, quinolyl, substituted quinolinyl, isoquinolyl, substituted isoquinolinyl, substituted 2,3-dihydro-1H-isoindol-2-yl, substituted 1H-indol-2-yl or substituted benzofuran-2-yl wherein substituted cycloalkyl, substituted cycloalkylalkyl, substituted piperazinyl, substituted piperidinyl, substituted indanyloxyalkyl, substituted phenyl, substituted phenylalkyl, substituted phenylalkynyl, substituted phenoxyalkyl, substituted phenylcycloalkyl, substituted phenylalkenyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted naphthyl, substituted quinolinyl, substituted isoquinolinyl, substituted 2,3-dihydro-1H-isoindol-2-yl, substituted 1H-indol-2-yl and substituted benzofuran-2-yl are substituted with $R^8$, $R^9$ and $R^{10}$;

Y is —OC(O)—, —NR C(O)—, —C(O)—, —S(O)$_2$—,

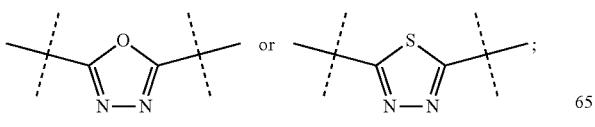

A is —N— or $CR^5$—;

W is —O—, —S—, —NR$^6$—, —C(O)—, —S(O)$_2$—, —C(O)—NR$^6$— or —CR$^3$R$^4$—;

$R^3$ and $R^4$ are independently selected from H, halogen, alkyl and cycloalkyl;

$R^5$, $R^6$ and $R^7$ are independently selected from H, alkyl and cycloalkyl;

$R^8$, $R^9$ and $R^{10}$ are independently selected from H, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, phenyl, substituted phenyl, pyridinyl, substituted pyridinyl, pyrrolyl, substituted pyrrolyl, pyrrolydinyl, substituted pyrrolydinyl, tetrahydrofuranyl, substituted tetrahydrofuranyl, halogen, hydroxy, cyano, alkylsulfanyl, haloalkylsulfanyl, cycloalkylsulfanyl, alkylsulfinyl, haloalkylsulfinyl, cycloalkylsulfinyl, alkylcarbonyl, haloalkylcarbonyl, cycloalkylcarbonyl, alkylsulfonyl, haloalkylsulfonyl, cycloalkylsulfonyl, substituted aminosulfonyl, substituted amino and substituted aminoalkyl, wherein substituted aminosulfonyl, substituted amino and substituted aminoalkyl are substituted on the nitrogen atom with one to two substituents independently selected from H, alkyl, cycloalkyl, cycloalkylalkyl, hydroxyalkyl, alkoxyalkyl, alkylcarbonyl and cycloalkylcarbonyl, and wherein substituted phenyl, substituted pyrrolyl, substituted pyrrolydinyl, substituted tetrahydrofuranyl, and substituted pyridinyl are substituted with one to three substituents independently selected from alkyl, halogen, haloalkyl, alkoxy and haloalkoxy;

m, n, p and q are independently selected from 1 or 2;

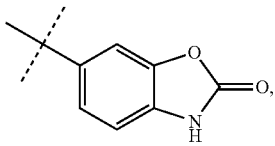

B

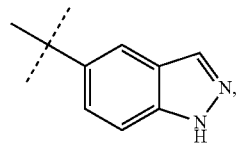

C

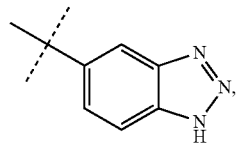

D

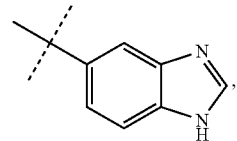

E

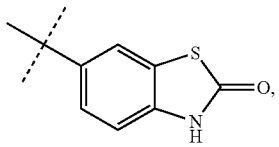

F

-continued

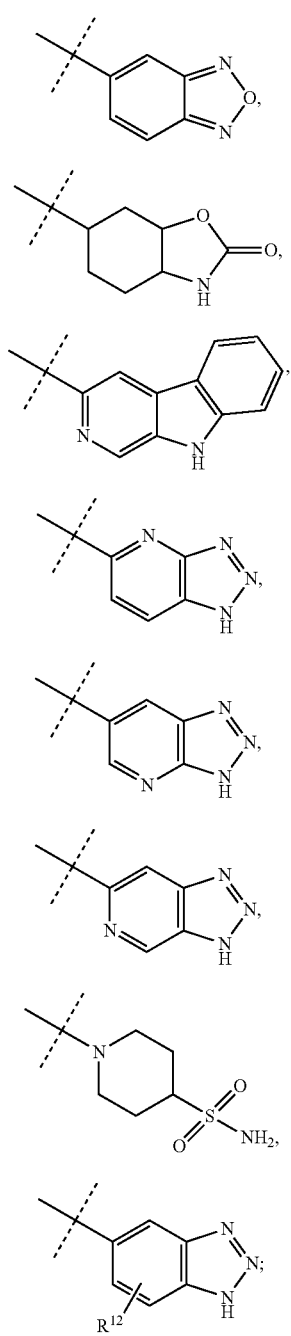

$R^{11}$ is H, alkyl, haloalkyl or cycloalkyl;
$R^{12}$ is alkyl, halogen, haloalkyl and alkoxy;
$R^2$ is selected from the ring systems B, C, D, E, F, G, H, I, J, K, L, M, N, O, P, Q, R, S, T, U, V, X, Z, AA, AB, AC, AD, AE, AF, AG, AH, AI and AJ;
and pharmaceutically acceptable salts.

Autotaxin (ATX) is a secreted enzyme also called ecto-nucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1 (vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and—chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl and iso-butenyl. Particular alkenyl group is ethenyl.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl group include include methoxymethyl, methoxyethyl and isopropoxymethyl.

The term "alkoxyhaloalkyl" denotes a haloalkyl group wherein at least one of the hydrogen atoms of the haloalkyl group has been replaced by an alkoxy group. Exemplary alkoxyhaloalkyl groups include methoxytrifluoroethyl, ethoxytrifluoroethyl, methoxytrifluoropropyl, ethoxytrifluoropropyl and isopropoxytrifluoroethyl. Particular alkoxyhaloalkyl group include include methoxytrifluoroethyl.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl and sec-butyl, pentyl. Particular alkyl groups include methyl, ethyl, propyl and isopropyl. More particular alkyl groups are methyl and isoropyl.

The term "alkylcarbonyl" denotes a group of the formula —C(O)—R', wherein R' is an alkyl group. Examples of alkylcarbonyl groups include groups of the formula —C(O)—R', wherein R' is methyl or ethyl. Particular alkylcarbonyl groups include groups of the formula —C(O)—R', wherein R' is methyl.

The term "alkylsulfanyl" denotes a group of the formula —S—R', wherein R' is an alkyl group. Examples of alkylsulfanyl groups include groups of the formula —S—R', wherein R' is methyl, ethyl, n-propyl, isopropyl, n-butyl, isobutyl or tert-butyl. Particular alkylsulfanyl groups include group of the formula —S—R', wherein R' is methyl.

The term "alkylsulfinyl" denotes a group of the formula —S(O)—R', wherein R' is an alkyl group. Examples of alkylsulfinyl groups include groups of the formula —S(O)—R', wherein R' is methyl, ethyl, n-propyl, isopropyl, n-butyl, isobutyl or tert-butyl. Particular alkylsulfinyl groups include group of the formula —S(O)—R', wherein R' is methyl.

The term "alkylsulfonyl" denotes a group of the formula —S(O)$_2$—R', wherein R' is an alkyl group. Examples of alkylsulfonyl groups include groups of the formula —S(O)$_2$—R', wherein R' is methyl, ethyl, n-propyl, isopropyl, n-butyl, isobutyl or tert-butyl. Particular alkylsulfonyl groups include group of the formula —S(O)$_2$—R', wherein R' is methyl.

The term "alkynyl" denotes a monovalent linear or branched saturated hydrocarbon group of 2 to 7 carbon atoms comprising one, two or three triple bonds. In particular embodiments alkynyl has from 2 to 4 carbon atoms comprising one or two triple bonds. Examples of alkynyl include ethynyl, propynyl, prop-2-ynyl, isopropynyl and n-butynyl.

The term "amino" denotes a —NH$_2$ group.

The term "aminoalkyl" denotes an alkyl group wherein at least one of the hydrogen atoms of the alkyl group has been replaced by an aminogroup. Examples of aminoalkyl include aminomethyl, aminoethyl, amino-1-methyl-ethyl, aminopropyl, aminomethylpropyl and aminopropyl. Particular examples are aminomethyl and haminoethyl.

The term "aminosulfonyl" denotes a —S(O)$_2$—NH$_2$ group.

The term "carbonyl" denotes a —C(O)— group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl groups include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamentanylmethyl and adamantanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl, bicyclo[2.2.2]octanylethyl, adamentanylmethyl and adamantanylethyl.

Further particular examples cycloalkylalkyl are cyclohexylmethyl, cyclohexylethyl, bicyclo[4.1.0]heptanylmethyl, bicyclo[2.2.2]octanylmethyl, adamentanylmethyl and adamantanyl ethyl.

The term "cycloalkylcarbonyl" of the formula —C(O)—R', wherein R' is a cycloalkyl group. Examples of cycloalkylcarbonyl groups include groups of the formula —C(O)—R', wherein R' is cyclopropyl.

The term "cycloalkylsulfanyl" denotes a group of the formula —S—R', wherein R' is a cycloalkyl group. Examples of cycloalkylsulfanyl groups include groups of the formula —S—R', wherein R' is cyclopropyl.

The term "cycloalkylsulfinyl" denotes a group of the formula —S(O)—R', wherein R' is a cycloalkyl group. Examples of cycloalkylsulfinyl groups include groups of the formula —S(O)—R', wherein R' is cyclopropyl.

The term "cycloalkylsulfonyl" denotes a group of the formula —S(O)$_2$—R', wherein R' is a cycloalkyl group. Examples of cycloalkylsulfonyl groups include groups of the formula —S(O)$_2$—R', wherein R' is cyclopropyl.

The term "haloalkoxy" denotes an alkoxy group wherein at least one of the hydrogen atoms of the alkoxy group has been replaced by the same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy group is trifluoromethoxy.

The term "haloalkyl" denotes an alkyl group wherein at least one of the hydrogen atoms of the alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "haloalkylsulfanyl" denotes a group of the formula —S—R', wherein R' is a haloalkyl group. Examples of haloalkylsulfanyl groups include groups of the formula —S—R', wherein R' is trifluoromethyl.

The term "haloalkylsulfinyl" denotes a group of the formula —S(O)—R', wherein R' is a haloalkyl group. Examples of haloalkylsulfinyl groups include groups of the formula —S(O)—R', wherein R' is trifluoromethyl.

The term "haloalkylsulfonyl" denotes a group of the formula —S(O)$_2$—R', wherein R' is a haloalkyl group. Examples of haloalkylsulfonyl groups include groups of the formula —S(O)$_2$—R', wherein R' is trifluoromethyl.

The term "halogen" and "halo" are used interchangeably herein and denote fluoro, chloro, bromo, or iodo. Particular halogens are chloro, fluoro and bromo. More particular halogens are chloro and fluoro.

The term "hydroxy" denotes an —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxy-1-methyl-ethyl, hydroxypropyl, hydroxymethylpropyl and dihydroxypropyl. Particular examples are hydroxymethyl and hydroxyethyl.

The term "hydroxyhaloalkyl" denotes a haloalkyl group wherein at least one of the hydrogen atoms of the haloalkyl group has been replaced by an hydroxy group. Exemplary hydroxyhaloalkyl groups include hydroxytrifluoroethyl and hydroxytrifluoropropyl. Particular hydroxyhaloalkyl groups include hydroxytrifluoroethyl.

The term "indanyloxy" denotes a group of the formula —O—R', wherein R' is an indanyl.

The term "indanyloxyalkyl" denotes an alkyl group wherein at least one of the hydrogen atoms of the alkyl group has been replaced by a indanyloxy group. Exemplary indanyloxyalkyl groups include indanyloxymethyl, indanyloxyethyl and indanyloxypropyl. Particular indanyloxyalkyl group is indanyloxymethyl.

The term "phenoxy" denotes a group of the formula —O—R', wherein R' is a phenyl.

The term "phenoxyalkyl" denotes an alkyl group wherein at least one of the hydrogen atoms of the alkyl group has been replaced by a phenoxy group. Exemplary phenoxyalkyl groups include phenoxymethyl, phenoxyethyl and phenoxypropyl. Particular phenoxyalkyl group is phenoxymethyl.

The term "phenylalkenyl" denotes an alkenyl group wherein at least one of the hydrogen atoms of the alkenyl group has been replaced a phenyl. Particular phenylalkenyl group is phenylethenyl.

The term "phenylalkyl" denotes an alkyl group wherein at least one of the hydrogen atoms of the alkyl group has been replaced a phenyl. Particular phenylalkyl groups are benzyl, phenethyl and phenylpropyl. More particular phenylalkyl groups are benzyl and phenethyl. Further particular phenylalkyl group is benzyl.

The term "phenylalkynyl" denotes an alkynyl group wherein at least one of the hydrogen atoms of the alkynyl group has been replaced a phenyl. Particular phenylalkynyl group is phenylethynyl.

The term "phenylcyloalkyl" denotes a cycloalkyl group wherein at least one of the hydrogen atoms of the cycloalkyl group has been replaced a phenyl. Particular phenylcycloalkyl group is phenylcyclopropyl.

The term "pyridinylalkenyl" denotes an alkenyl group wherein at least one of the hydrogen atoms of the alkenyl group has been replaced a pyridinyl. Particular pyridinylalkenyl group is pyridinylethenyl.

The term "pyridinylalkyl" denotes an alkyl group wherein at least one of the hydrogen atoms of the alkyl group has been replaced a pyridinyl. Particular pyridinylalkyl groups are pyridinylmethyl, pyridinylethyl and pyridinylpropyl. More particular pyridinylalkyl group is pyridinylethyl.

The term "pyridinylalkynyl" denotes an alkynyl group wherein at least one of the hydrogen atoms of the alkynyl group has been replaced a pyridinyl. Particular pyridinylalkynyl group is pyridinylethynyl. The term "thiophenylalkenyl" denotes an alkenyl group wherein at least one of the hydrogen atoms of the alkenyl group has been replaced a thiophenyl. Particular thiophenylalkenyl group is thiophenylethenyl.

The term "thiophenylalkyl" denotes an alkyl group wherein at least one of the hydrogen atoms of the alkyl group has been replaced a thiophenyl. Particular thiophenylalkyl groups are thiophenylmethyl, thiophenylethyl and thiophenylpropyl. More particular thiophenylalkyl group is thiophenylmethyl.

The term "thiophenylalkynyl" denotes an alkynyl group wherein at least one of the hydrogen atoms of the alkynyl group has been replaced a thiophenyl. Particular thiophenylalkynyl group is thiophenylethynyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol µM.

The abbreviation uL means microliter and is equivalent to the symbol µL.

The abbreviation ug means microgram and is equivalent to the symbol µg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein $R^1$ is alkyl, haloalkyl, substituted cycloalkyl, substituted cycloalkylalkyl, substituted phenyl, substituted phenylalkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl or substituted benzofuran-2-yl wherein substituted cycloalkyl, substituted cycloalkylalkyl, substituted phenyl, substituted phenylalkyl, substituted phenylalkynyl, substituted phenoxyalkyl, substituted phenylcycloalkyl, substituted phenylalkenyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl and substituted benzofuran-2-yl are substituted with $R^8$, $R^9$ and $R^{10}$;

Y is —OC(O)—, —NR C(O)—, —C(O)—, —S(O)$_2$—,

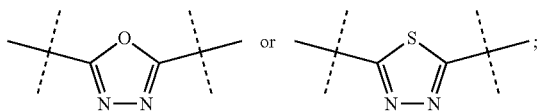

A is —N— or CR$^5$—;
W is —O—, —S—, —NR$^6$—, —C(O)—, —S(O)$_2$—, —C(O)—NR$^6$— or —CR$^3$R$^4$—;
$R^3$ and $R^4$ are independently selected from H, halogen, alkyl and cycloalkyl;

$R^5$, $R^6$ and $R^7$ are independently selected from H, alkyl and cycloalkyl;

$R^8$, $R^9$ and $R^{10}$ are independently selected from H, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, phenyl, substituted phenyl, pyridinyl, substituted pyridinyl, halogen, hydroxy, cyano, alkylsulfanyl, haloalkylsulfanyl, cycloalkylsulfanyl, alkylsulfinyl, haloalkylsulfinyl, cycloalkylsulfinyl, alkylsulfonyl, haloalkylsulfonyl, cycloalkylsulfonyl, substituted aminosulfonyl, substituted amino and substituted aminoalkyl, wherein substituted aminosulfonyl, substituted amino and substituted aminoalkyl are substituted on the nitrogen atom with one to two substituents independently selected from H, alkyl, cycloalkyl, cycloalkylalkyl, hydroxyalkyl, alkoxyalkyl, alkylcarbonyl and cycloalkylcarbonyl, and wherein substituted phenyl and substituted pyridinyl are optionally substituted with one to three substituents independently selected from alkyl, halogen, haloalkyl, alkoxy and haloalkoxy;

m, n, p and q are independently selected from 1 or 2;

B
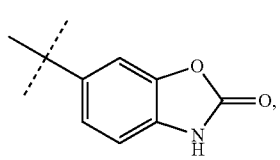

C
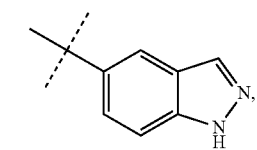

D
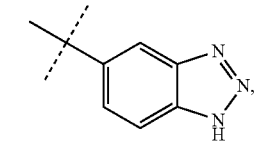

E
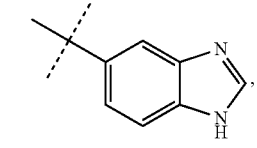

F
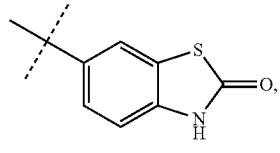

G
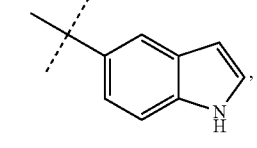

H
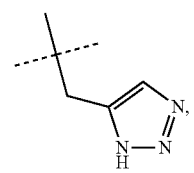

I
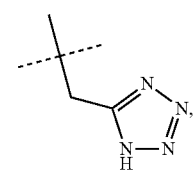

J
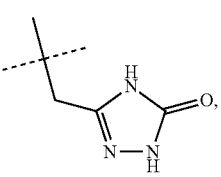

K
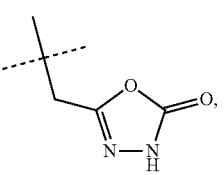

L
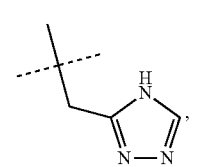

M
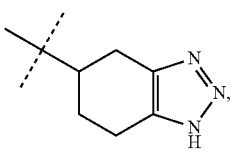

N
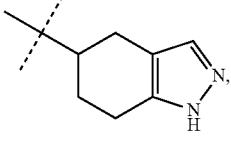

O
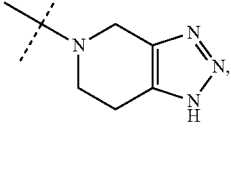

P
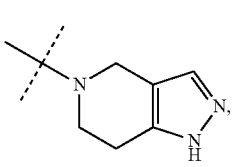

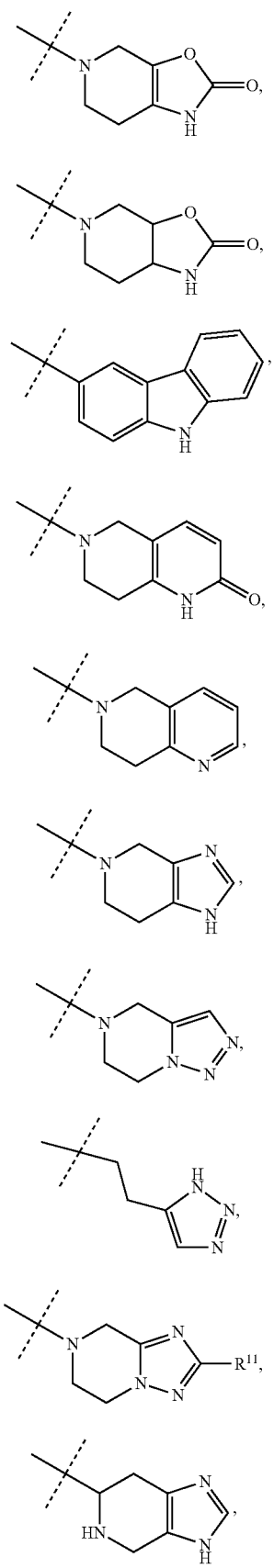
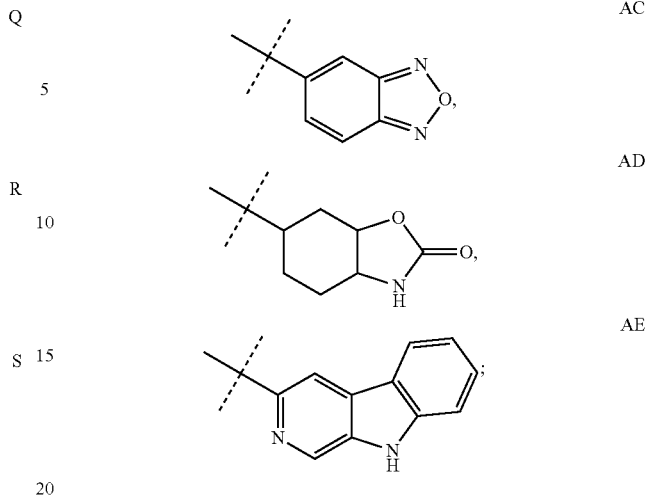

$R^{11}$ is H, alkyl, haloalkyl or cycloalkyl;

$R^2$ is selected from the ring systems B, C, D, E, F, G, H, I, J, K, L, M, N, O, P, Q, R, S, T, U, V, X, Z, AA, AB, AC, AD and AE;

and pharmaceutically acceptable salts.

A further embodiment of the present invention are compounds according to formula (I) as described herein, wherein $R^1$ is substituted cycloalkylalkyl, substituted piperazinyl, substituted piperidinyl, substituted indanyloxyalkyl, substituted phenyl, substituted phenylalkyl, substituted phenoxyalkyl, substituted phenylcycloalkyl, substituted phenylalkenyl, substituted pyridinylalkyl, substituted pyridinylalkenyl, naphtyl, substituted naphthyl, substituted quinolinyl, substituted isoquinolinyl, or substituted 1H-indol-2-yl, wherein substituted cycloalkylalkyl, substituted piperazinyl, substituted piperidinyl, substituted indanyloxyalkyl, substituted phenyl, substituted phenylalkyl, substituted phenoxyalkyl, substituted phenylcycloalkyl, substituted phenylalkenyl, substituted pyridinylalkyl, substituted pyridinylalkenyl, substituted naphthyl, substituted quinolinyl, substituted isoquinolinyl and substituted 1H-indol-2-yl are substituted with $R^8$, $R^9$ and $R^{10}$.

Another further embodiment of the present invention are compounds according to formula (I) as described herein, wherein $R^1$ is substituted cycloalkylalkyl, substituted phenyl, substituted phenylalkyl, substituted phenoxyalkyl, substituted phenylcycloalkyl, substituted phenylalkenyl, substituted pyridinylalkyl, substituted pyridinylalkenyl or substituted 1H-indol-2-yl, wherein substituted cycloalkylalkyl, substituted phenyl, substituted phenylalkyl, substituted phenoxyalkyl, substituted phenylcycloalkyl, substituted phenylalkenyl, substituted pyridinylalkyl, substituted pyridinylalkenyl, and substituted 1H-indol-2-yl are substituted with $R^8$, $R^9$ and $R^{10}$.

A particular embodiment of the present invention are compounds according to formula (I) as described herein, wherein $R^1$ is substituted phenylalkyl or substituted phenylalkenyl, wherein substituted phenylalkyl and substituted phenylalkenyl are substituted with $R^8$, $R^9$ and $R^{10}$.

In a further embodiment of the present invention are compounds according to formula (I) as described herein, wherein $R^1$ is phenylalkyl substituted with $R^8$, $R^9$ and $R^{10}$.

The present invention also relates to compounds according to formula (I) as described herein, wherein Y is —OC(O)—, —C(O)—, —S(O)$_2$— or

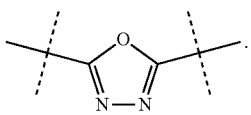

A further particular embodiment of the present invention are compounds according to formula (I) as described herein, wherein Y is —OC(O)— or —C(O)—.

Another further embodiment of the present invention are compounds according to formula (I) as described herein, wherein Y is —OC(O)— and of formula (In).

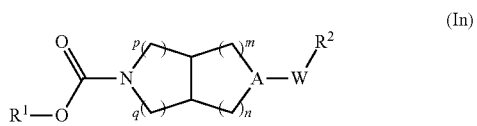

(In)

Another embodiment of the present invention are compounds according to formula (I) as described herein, wherein Y is —C(O)—.

A more particular embodiment of the present invention are compounds according to formula (I) as described herein, wherein A is —N—.

Also an embodiment of the present invention are compounds according to formula (I) as described herein, wherein W is —O—, —$NR^6$—, —C(O)—, —$S(O)_2$—, —C(O)—$NR^6$— or —$CR^3R^4$—.

Another embodiment of the present invention are compounds according to formula (I) as described herein, wherein W is —C(O)—, —C(O)—$NR^6$— or —$CR^3R^4$—.

Another embodiment of the present invention are compounds according to formula (I) as described herein, wherein W is —C(O)—.

A further particular embodiment of the present invention are compounds according to formula (I) as described herein, wherein $R^2$ is selected from the ring systems B, C, D, E, G, H, M, O, P, R, S, T, U, V, X, Z, AA, AB, AC, AD, AE, AF, AG, AH and AI.

Another further particular embodiment of the present invention are compounds according to formula (I) as described herein, wherein $R^2$ is selected from the ring systems B, C, D, E, G, H, M, O, P, R, S, T, U, V, X, Z, AA, AB, AC, AD and AE.

Also a further particular embodiment of the present invention are compounds according to formula (I) as described herein, wherein $R^2$ is selected from the ring systems B, D, H, M, O, R and AJ.

A further particular embodiment of the present invention are compounds according to formula (I) as described herein, wherein $R^2$ is selected from the ring systems B, D, H, O and R.

A further particular embodiment of the present invention are compounds according to formula (I) as described herein, wherein $R^2$ is selected from the ring systems B and D.

A further particular embodiment of the present invention are compounds according to formula (I) as described herein, wherein $R^2$ is the ring system D.

A further particular embodiment of the present invention are compounds according to formula (I) as described herein, wherein $R^3$ and $R^4$ are H.

A further particular embodiment of the present invention are compounds according to formula (I) as described herein, wherein $R^5$ is H.

A further particular embodiment of the present invention are compounds according to formula (I) as described herein, wherein $R^6$ is H or alkyl.

A further particular embodiment of the present invention are compounds according to formula (I) as described herein, wherein $R^8$, $R^9$ and $R^{10}$ are independently selected from H, alkyl, haloalkyl, hydroxyhaloalkyl, alkoxy, haloalkoxy, alkoxyhaloalkyl, phenyl, pyridinyl, halogen, cyano, haloalkylsulfanyl, haloalkylsulfinyl, alkylsulfonyl, haloalkylsulfonyl, pyrrolyl substituted with one alkyl, pyrrolydinyl, tetrahydrofuranyl, alkylcarbonyl, and aminosulfonyl substituted on the nitrogen atom with one to two substituents independently selected from H, alkyl, cycloalkyl, cycloalkylalkyl, hydroxyalkyl, alkoxyalkyl, alkylcarbonyl and cycloalkylcarbonyl.

Also a further particular embodiment of the present invention are compounds according to formula (I) as described herein, wherein $R^8$, $R^9$ and $R^{10}$ are independently selected from H, alkyl, haloalkyl, hydroxyhaloalkyl, alkoxy, haloalkoxy, alkoxyhaloalkyl, phenyl, pyridinyl, halogen, cyano, haloalkylsulfanyl, haloalkylsulfinyl, alkylsulfonyl, haloalkylsulfonyl and aminosulfonyl substituted on the nitrogen atom with one to two substituents independently selected from H, alkyl, cycloalkyl, cycloalkylalkyl, hydroxyalkyl, alkoxyalkyl, alkylcarbonyl and cycloalkylcarbonyl.

A further particular embodiment of the present invention are compounds according to formula (I) as described herein, wherein $R^8$, $R^9$ and $R^{10}$ are independently selected from H, alkyl, haloalkyl, hydroxyhaloalkyl, alkoxy, haloalkoxy, alkoxyhaloalkyl, phenyl, pyridinyl, halogen, cyano, haloalkylsulfanyl, haloalkylsulfinyl, alkylsulfonyl, haloalkylsulfonyl and aminosulfonyl substituted on the nitrogen atom with two alkyl.

A further particular embodiment of the present invention are compounds according to formula (I) as described herein, wherein $R^8$, $R^9$ and $R^{10}$ are independently selected from H, alkyl, haloalkyl, haloalkoxy, halogen and alkylsulfonyl.

A further particular embodiment of the present invention are compounds according to formula (I) as described herein, wherein $R^8$ is H, alkyl, haloalkyl, hydroxyhaloalkyl, alkoxy, haloalkoxy, alkoxyhaloalkyl, phenyl, pyridinyl, halogen, cyano, haloalkylsulfanyl, haloalkylsulfinyl, alkylsulfonyl, haloalkylsulfonyl, pyrrolyl substituted with one alkyl, pyrrolydinyl, tetrahydrofuranyl, alkylcarbonyl, or aminosulfonyl substituted on the nitrogen atom with two alkyl.

A further particular embodiment of the present invention are compounds according to formula (I) as described herein, wherein $R^8$ is H, alkyl, haloalkyl, hydroxyhaloalkyl, alkoxy, haloalkoxy, alkoxyhaloalkyl, phenyl, pyridinyl, halogen, cyano, haloalkylsulfanyl, haloalkylsulfinyl, alkylsulfonyl, haloalkylsulfonyl or aminosulfonyl substituted on the nitrogen atom with two alkyl.

A further particular embodiment of the present invention are compounds according to formula (I) as described herein, wherein $R^8$ is haloalkyl, haloalkoxy, halogen or alkylsulfonyl.

A particular embodiment of the present invention are compounds according to formula (I) as described herein, wherein $R^8$ is haloalkoxy or halogen.

Also an embodiment of the present invention are compounds according to formula (I) as described herein, wherein $R^8$ is halogen.

The present invention also relates to compounds according to formula (I) as described herein, wherein $R^9$ is H, alkyl, haloalkyl, cycloalkyl, cycloalkoxy, alkoxy, haloalkoxy, alkoxyalkoxy, cyano or halogen.

The present invention also relates to compounds according to formula (I) as described herein, wherein $R^9$ is H, alkyl, haloalkyl, alkoxy or halogen.

Another embodiment of the present invention are compounds according to formula (I) as described herein, wherein $R^9$ is H, alkyl or halogen.

The present invention also relates to compounds according to formula (I) as described herein, wherein $R^8$ and $R^9$ are halogen.

Also an embodiment of the present invention are compounds according to formula (I) as described herein, wherein $R^9$ is H, alkyl, haloalkyl, cycloalkyl, cycloalkoxy, alkoxy, haloalkoxy, alkoxyalkoxy, cyano or halogen.

Also an embodiment of the present invention are compounds according to formula (I) as described herein, wherein $R^{10}$ is H or alkyl.

Another embodiment of the present invention are compounds according to formula (I) as described herein, wherein $R^{10}$ is H.

Also an embodiment of the present invention are compounds according to formula (I) as described herein, wherein $R^{11}$ is haloalkyl.

A particular embodiment of the present invention are compounds according to formula (I) as described herein, wherein m is 1.

A further particular embodiment of the present invention are compounds according to formula (I) as described herein, wherein n is 1.

A more particular embodiment of the present invention are compounds according to formula (I) as described herein, wherein m and n are 1.

Also a particular embodiment of the present invention are compounds according to formula (I) as described herein, wherein p and q are 1.

The present invention also relates to compounds according to formula (I) as described herein, wherein m, n, p and q are 1.

A furthermore particular embodiment of the present invention are compounds according to formula (I) as described herein, wherein $R^1$ is substituted phenylalkyl or substituted phenylalkenyl, wherein substituted phenylalkyl and substituted phenylalkenyl are substituted with $R^8$, $R^9$ and $R^{10}$;
Y is —OC(O)— or —C(O)—;
A is —N—;
W is —C(O)—;
$R^8$ is haloalkyl, haloalkoxy, halogen or alkylsulfonyl;
$R^9$ is H, alkyl or halogen;
$R^{10}$ is H or alkyl;
m and n are 1;
p and q are independently selected from 1 or 2;
$R^2$ is selected from the ring systems B, D, H, M, O, R and AJ;
$R^{12}$ is halogen
and pharmaceutically acceptable salts.

Also a furthermore particular embodiment of the present invention are compounds according to formula (I) as described herein, wherein $R^1$ is substituted phenylalkyl or substituted phenylalkenyl, wherein substituted phenylalkyl and substituted phenylalkenyl are substituted with $R^8$, $R^9$ and $R^{10}$;
Y is —OC(O)— or —C(O)—;
A is —N—;
W is —C(O)—;
$R^8$ is haloalkyl, haloalkoxy, halogen or alkylsulfonyl;
$R^9$ is H, alkyl or halogen;
$R^{10}$ is H or alkyl;
m and n are 1;
p and q are independently selected from 1 or 2;
$R^2$ is selected from the ring systems B and D;
and pharmaceutically acceptable salts.

Particular examples of compounds of formula (I) as described herein are selected from (E)-1-[(3aS,8aR)-2-(4,5,6,7-tetrahydro-1H-benzotriazole-5-carbonyl)-octahydro-pyrrolo[3,4-d]azepin-6-yl]-3-(4-trifluoromethoxy-phenyl)-prop-2-ene-1-one;

1-((3aR,6aS)-5-(1H-benzo[d][1,2,3]triazole-5-carbonyl) hexahydropyrrolo[3,4-c]pyrrol-2(1H)-yl)-3-(3,5-dichlorophenyl)propan-1-one;

6-((3aR,6aS)-5-(3-(3,5-dichlorophenyl)propanoyl)octahydropyrrolo[3,4-c]pyrrole-2-carbonyl)benzo[d]oxazol-2 (3H)-one;

(3aR,6aS)-3,5-dichlorobenzyl 5-(1H-benzo[d][1,2,3]triazole-5-carbonyl)hexahydropyrrolo[3,4-c]pyrrole-2(1H)-carboxylate;

(3aR,6aS)-3,5-dichlorobenzyl 5-(9H-pyrido[3,4-b]indole-3-carbonyl)hexahydropyrrolo[3,4-c]pyrrole-2(1H)-carboxylate;

(3aR,6aS)-3,5-dichlorobenzyl 5-(1H-indole-5-carbonyl) hexahydropyrrolo[3,4-c]pyrrole-2(1H)-carboxylate;

(3aR,6aS)-3,5-dichlorobenzyl 5-(9H-carbazole-3-carbonyl) hexahydropyrrolo[3,4-c]pyrrole-2(1H)-carboxylate;

(3aR,6aS)-3,5-dichlorobenzyl 5-(1H-indazole-5-carbonyl) hexahydropyrrolo[3,4-c]pyrrole-2(1H)-carboxylate;

(3aR,6aS)-3,5-dichlorobenzyl 5-(1H-benzo[d]imidazole-5-carbonyl)hexahydropyrrolo[3,4-c]pyrrole-2(1H)-carboxylate;

trans-3,5-dichlorobenzyl 2-(1H-benzo[d][1,2,3]triazole-5-carbonyl)hexahydro-1H-pyrrolo[3,4-c]pyridine-5 (6H)-carboxylate;

cis-3,5-dichlorobenzyl 2-(1H-benzo[d][1,2,3]triazole-5-carbonyl)hexahydro-1H-pyrrolo[3,4-c]pyridine-5 (6H)-carboxylate;

(3aR,8aS)-3,5-dichlorobenzyl 2-(1H-benzo[d][1,2,3]triazole-5-carbonyl)octahydropyrrolo[3,4-d]azepine-6(7H)-carboxylate;

(1H-benzotriazol-5-yl)-{(3aS,6aR)-5-[2-(3-chloro-phenyl)-ethanesulfonyl]-hexahydro-pyrrolo[3,4-c]pyrrol-2-yl}-methanone;

(3aR,6aS)-3,5-dichlorobenzyl 5-(4,5,6,7-tetrahydro-1H-benzo[d][1,2,3]triazole-5-carbonyl)hexahydropyrrolo[3,4-c]pyrrole-2(1H)-carboxylate;

1-((3aR,8aS)-2-(1H-benzo[d][1,2,3]triazole-5-carbonyl)octahydropyrrolo[3,4-d]azepin-6(7H)-yl)-3-(3-chlorophenyl)-2,2-dimethylpropan-1-one;

(E)-1-((3aR,8aS)-2-(1H-benzo[d][1,2,3]triazole-5-carbonyl)octahydropyrrolo[3,4-d]azepin-6(7H)-yl)-3-(3-fluoro-4-(trifluoromethoxy)phenyl)prop-2-en-1-one;

(3aSR,6SR,7aSR)-6-{(3aS,8aR)-6-[(E)-3-(4-trifluoromethoxy-phenyl)-acryloyl]-octahydro-pyrrolo[3,4-d]azepine-2-carbonyl}-hexahydro-benzooxazol-2-one;

(E)-1-[(3aS,8aR)-2-(benzo[c][1,2,5]oxadiazole-5-carbonyl)-octahydro-pyrrolo[3,4-d]azepin-6-yl]-3-(4-trifluoromethoxy-phenyl)-prop-2-ene-1-one;

(E)-1-((3aR,8aS)-2-(1H-benzo[d][1,2,3]triazole-5-carbonyl)octahydropyrrolo[3,4-d]azepin-6(7H)-yl)-3-(2-methyl-4-(trifluoromethoxy)phenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(3-fluoro-4-methoxyphenyl)prop-2-en-1-one;

(E)-1-[(3aS,8aR)-2-((S)-4,5,6,7-tetrahydro-1H-benzotriazole-5-carbonyl)-octahydro-pyrrolo[3,4-d]azepin-6-yl]-3-(4-trifluoromethoxy-phenyl)-prop-2-ene-1-one (E)-1-[(3aS,8aR)-2-((R)-4,5,6,7-tetrahydro-1H-benzotriaz-ole-5-carbonyl)-octahydro-pyrrolo[3,4-d]azepin-6-yl]-3-(4-trifluoromethoxy-phenyl)-prop-2-ene-1-one (E)-1-[(3aS,8aR)-2-(1H-benzotriazole-5-carbonyl)-octahydro-pyrrolo[3,4-d]azepin-6-yl]-3-(2-isopropyl-phenyl)-prop-2-ene-1-one;
trans-3,5-dichlorobenzyl 2-(2-oxo-2,3-dihydrobenzo[d]oxazole-6-carbonyl)hexahydro-1H-pyrrolo[3,4-c]pyridine-5 (6H)-carboxylate;
(3aR,6aS)-3,5-dichlorobenzyl 5-(2-oxo-2,3-dihydrobenzo[d]oxazole-6-carbonyl)hexahydropyrrolo[3,4-c]pyrrole-2(1H)-carboxylate;
6-{(3aS,8aR)-6-[(E)-3-(4-trifluoromethoxy-phenyl)-acryloyl]-octahydro-pyrrolo[3,4-d]azepine-2-carbonyl}-3H-benzooxazol-2-one;
(3aR,5s,6aS)-3,5-dichlorobenzyl 5-(2-oxo-2,3-dihydrobenzo[d]oxazol-6-yloxy)hexahydrocyclopenta[c]pyrrole-2(1H)-carboxylate;
(3aR,5r,6aS)-3,5-dichlorobenzyl 5-(2-oxo-2,3-dihydrobenzo[d]oxazol-6-yloxy)hexahydrocyclopenta[c]pyrrole-2(1H)-carboxylate;
(3aS,6aS)-3,5-dichlorobenzyl 5-(1H-benzotriazole-5-carbonyl)hexahydropyrrolo[3,4-c]pyrrole-2(1H)-carboxylate;
trans-5-(1H-benzotriazole-5-carbonyl)-octahydro-pyrrolo[3,4-c]pyridine-2-carboxylic acid 3-methanesulfonyl-5-trifluoromethyl-benzyl ester;
(3aR,6aR)-3,5-dichlorobenzyl 5-(1H-benzo[d][1,2,3]triazole-5-carbonyl)hexahydropyrrolo[3,4-c]pyrrole-2(1H)-carboxylate;
(3aS,6aS)-5-(1H-benzotriazole-5-carbonyl)-hexahydro-pyrrolo[3,4-c]pyrrole-2-carboxylic acid 3-chloro-5-methanesulfonyl-benzyl ester;
(3aS,6aR)-5-(1H-benzotriazole-5-carbonyl)-hexahydro-pyrrolo[3,4-c]pyrrole-2-carboxylic acid 3-chloro-5-methanesulfonyl-benzyl ester;
(3aS,8aR)-2-(1H-benzotriazole-5-carbonyl)-octahydro-pyrrolo[3,4-d]azepine-6-carboxylic acid 3-methanesulfonyl-5-trifluoromethyl-benzyl ester;
(3aS,8aR)-2-(1H-benzotriazole-5-carbonyl)-octahydro-pyrrolo[3,4-d]azepine-6-carboxylic acid 3-chloro-5-methanesulfonyl-benzyl ester;
(3aS,6aR)-5-(1H-benzotriazole-5-carbonyl)-hexahydro-pyrrolo[3,4-c]pyrrole-2-carboxylic acid 3-methanesulfonyl-5-trifluoromethyl-benzyl ester;
cis-3,5-dichlorobenzyl 5-(1H-benzo[d][1,2,3]triazole-5-carbonyl)hexahydro-1H-pyrrolo[3,4-c]pyridine-2(3H)-carboxylate;
(3aS,7aR)-5-(1H-benzotriazole-5-carbonyl)-octahydro-pyrrolo[3,4-c]pyridine-2-carboxylic acid 3-chloro-5-methanesulfonyl-benzyl ester;
trans-3,5-dichlorobenzyl 5-(1H-benzo[d][1,2,3]triazole-5-carbonyl)hexahydro-1H-pyrrolo[3,4-c]pyridine-2(3H)-carboxylate;
(3aR,8aS)-3,5-dichlorobenzyl 6-(1H-benzo[d][1,2,3]triazole-5-carbonyl)octahydropyrrolo[3,4-d]azepine-2(1H)-carboxylate;
(3aS,6aR)-5-(1H-benzotriazole-5-carbonyl)-hexahydro-pyrrolo[3,4-c]pyrrole-2-carboxylic acid 1-(3-chloro-phenyl)-cyclopropyl ester;
(3aS,6aR)-5-(1H-benzotriazole-5-carbonyl)-hexahydro-pyrrolo[3,4-c]pyrrole-2-carboxylic acid bicyclo[4.1.0]hept-7-ylmethyl ester;
(3aS,6aR)-5-(1H-benzotriazole-5-carbonyl)-hexahydro-pyrrolo[3,4-c]pyrrole-2-carboxylic acid adamantan-2-ylmethyl ester;
(3aS,6aR)-5-(1H-benzotriazole-5-carbonyl)-hexahydro-pyrrolo[3,4-c]pyrrole-2-carboxylic acid 1-fluoro-cyclohexylmethyl ester;
(3aS,6aR)-5-(1H-benzotriazole-5-carbonyl)-hexahydro-pyrrolo[3,4-c]pyrrole-2-carboxylic acid 2-adamantan-2-yl-ethyl ester;
(3aS,6aR)-5-(1H-benzotriazole-5-carbonyl)-hexahydro-pyrrolo[3,4-c]pyrrole-2-carboxylic acid 2-adamantan-1-yl-ethyl ester;
(3aS,6aR)-5-(1H-benzotriazole-5-carbonyl)-hexahydro-pyrrolo[3,4-c]pyrrole-2-carboxylic acid adamantan-1-ylmethyl ester;
(3aS,6aR)-5-(1H-benzotriazole-5-carbonyl)-hexahydro-pyrrolo[3,4-c]pyrrole-2-carboxylic acid cyclohexylmethyl ester;
cis-5-(1H-benzotriazole-5-carbonyl)-hexahydro-pyrrolo[3,4-c]pyrrole-2-carboxylic acid 3-(2,2,2-trifluoro-1-methoxy-ethyl)-benzyl ester;
cis-5-(1H-benzotriazole-5-carbonyl)-hexahydro-pyrrolo[3,4-c]pyrrole-2-carboxylic acid 3-(2,2,2-trifluoro-1-hydroxy-ethyl)-benzyl ester;
(3aR,6aS)-2-cyclohexylethyl 5-(1H-benzo[d][1,2,3]triazole-5-carbonyl)hexahydropyrrolo[3,4-c]pyrrole-2(1H)-carboxylate;
(3aS,6aR)-5-(1H-benzotriazole-5-carbonyl)-hexahydro-pyrrolo[3,4-c]pyrrole-2-carboxylic acid 3-fluoro-5-trifluoromethoxy-benzyl ester;
(3aR,6aS)-3-chloro-5-cyanobenzyl 5-(1H-benzo[d][1,2,3]triazole-5-carbonyl)hexahydropyrrolo[3,4-c]pyrrole-2(1H)-carboxylate;
(3aS,6aR)-5-(1H-benzotriazole-5-carbonyl)-hexahydro-pyrrolo[3,4-c]pyrrole-2-carboxylic acid 3-trifluoromethoxy-benzyl ester;
(3aS,6aR)-5-(1H-benzotriazole-5-carbonyl)-hexahydro-pyrrolo[3,4-c]pyrrole-2-carboxylic acid 3-fluoro-5-trifluoromethyl-benzyl ester;
(3aS,6aR)-5-(1H-benzotriazole-5-carbonyl)-hexahydro-pyrrolo[3,4-c]pyrrole-2-carboxylic acid 3-chloro-5-trifluoromethoxy-benzyl ester;
(3aS,6aR)-5-(1H-benzotriazole-5-carbonyl)-hexahydro-pyrrolo[3,4-c]pyrrole-2-carboxylic acid 4-fluoro-3-trifluoromethoxy-benzyl ester;
(3aR,6aS)-3-cyano-5-fluorobenzyl 5-(1H-benzo[d][1,2,3]triazole-5-carbonyl)hexahydropyrrolo[3,4-c]pyrrole-2(1H)-carboxylate;
(3aR,6aS)-3-chloro-5-methoxybenzyl 5-(1H-benzo[d][1,2,3]triazole-5-carbonyl)hexahydropyrrolo[3,4-c]pyrrole-2(1H)-carboxylate;
(3aS,6aR)-5-(1H-benzotriazole-5-carbonyl)-hexahydro-pyrrolo[3,4-c]pyrrole-2-carboxylic acid (1S,4R)-3-methyl-bicyclo[2.2.1]hept-2-ylmethyl ester;
(3aS,6aR)-5-(1H-benzotriazole-5-carbonyl)-hexahydro-pyrrolo[3,4-c]pyrrole-2-carboxylic acid (1R,4S)-1-bicyclo[2.2.1]hept-2-ylmethyl ester;
(3aR,5S,6aS)-5-[(3H-[1,2,3]triazol-4-ylmethyl)-carbamoyl]-hexahydro-cyclopenta[c]pyrrole-2-carboxylic acid 3,5-dichloro-benzyl ester;
(3aS,6aS)-5-(1,4,6,7-tetrahydro-[1,2,3]triazolo[4,5-c]pyridine-5-carbonyl)-hexahydro-pyrrolo[3,4-c]pyrrole-2-carboxylic acid 3-chloro-5-methanesulfonyl-benzyl ester;
(3aS,6aR)-5-[(1H-[1,2,3]triazol-4-ylmethyl)-carbamoyl]-hexahydro-pyrrolo[3,4-c]pyrrole-2-carboxylic acid 3,5-dichloro-benzyl ester;
(3aS,6aS)-5-(1H-benzotriazole-5-carbonyl)-hexahydro-pyrrolo[3,4-c]pyrrole-2-carboxylic acid 4-trifluoromethoxy-benzyl ester;

(3aR,5r,6aS)-3,5-dichlorobenzyl 5-(2-oxo-2,3-dihydrobenzo[d]oxazol-6-ylamino)hexahydrocyclopenta[c]pyrrole-2(1H)-carboxylate;

(3aR,6aS)-3,5-dichlorobenzyl 5-((1H-benzo[d]imidazol-5-yl)methyl)hexahydropyrrolo[3,4-c]pyrrole-2(1H)-carboxylate;

1-((3aR,6aS)-5-((1H-benzo[d][1,2,3]triazol-5-yl)methyl)hexahydropyrrolo[3,4-c]pyrrol-2(1H)-yl)-3-(3,5-dichlorophenyl)propan-1-one;

(3aR,6aS)-3,5-dichlorobenzyl 5-((1H-indazol-5-yl)methyl)hexahydropyrrolo[3,4-c]pyrrole-2(1H)-carboxylate;

(3aR,6aS)-3,5-dichlorobenzyl 5-((2-oxo-2,3-dihydrobenzo[d]oxazol-6-yl)methyl)hexahydropyrrolo[3,4-c]pyrrole-2(1H)-carboxylate;

6-(((3aR,6aS)-5-(3-(3,5-dichlorophenyl)propanoyl)hexahydropyrrolo[3,4-c]pyrrol-2(1H)-yl)methyl)benzo[d]oxazol-2(3H)-one;

4-{(E)-3-[(3aS,8aR)-2-(1H-benzotriazol-5-ylmethyl)-octahydro-pyrrolo[3,4-d]azepin-6-yl]-3-oxo-propenyl}-benzonitrile;

(E)-1-[(3aS,8aR)-2-(1H-benzotriazol-5-ylmethyl)-octahydro-pyrrolo[3,4-d]azepin-6-yl]-3-(4 trifluoromethoxy-phenyl)-prop-2-ene-1-one;

(3aR,6aS)-3,5-dichlorobenzyl 5-(2-oxo-2,3-dihydrobenzo[d]oxazol-6-ylsulfonyl)hexahydropyrrolo[3,4-c]pyrrole-2(1H)-carboxylate;

(3aR,6aS)-3,5-dichlorobenzyl 5-(4,5,6,7-tetrahydro-1H-[1,2,3]triazolo[4,5-c]pyridine-5-carbonyl)hexahydropyrrolo[3,4-c]pyrrole-2(1H)-carboxylate;

(E)-1-[(3aS,8aR)-2-(1,4,6,7-tetrahydro-[1,2,3]triazolo[4,5-c]pyridine-5-carbonyl)-octahydro-pyrrolo[3,4-d]azepin-6-yl]-3-(4-trifluoromethoxy-phenyl)-prop-2-ene-1-one;

(E)-1-[(3aS,8aR)-2-(1,4,6,7-tetrahydro-pyrazolo[4,3-c]pyridine-5-carbonyl)-octahydro-pyrrolo[3,4-d]azepin-6-yl]-3-(4-trifluoromethoxy-phenyl)-prop-2-ene-1-one;

cis-5-((3aR,8aS)-6-((E)-3-(4-(trifluoromethoxy)phenyl)acryloyl)decahydropyrrolo[3,4-d]azepine-2-carbonyl)hexahydrooxazolo[5,4-c]pyridin-2(1H)-one;

6-{(3aS,8aR)-6-[(E)-3-(4-trifluoromethoxy-phenyl)-acryloyl]-octahydro-pyrrolo[3,4-d]azepine-2-carbonyl}-5,6,7,8-tetrahydro-1H-[1,6]naphthyridin-2-one;

(3aR,7aR)-5-{(3aS,8aR)-6-[(E)-3-(4-trifluoromethoxy-phenyl)-acryloyl]-octahydro-pyrrolo[3,4-d]azepine-2-carbonyl}-hexahydro-oxazolo[5,4-c]pyridin-2-one;

(E)-1-[(3aS,8aR)-2-(7,8-Dihydro-5H-[1,6]naphthyridine-6-carbonyl)-octahydro-pyrrolo[3,4-d]azepin-6-yl]-3-(4-trifluoromethoxy-phenyl)-prop-2-ene-1-one;

(E)-3-(4-trifluoromethoxy-phenyl)-1-[(3aS,8aR)-2-(2-trifluoromethyl-5,6-dihydro-8H-[1,2,4]triazolo[1,5-a]pyrazine-7-carbonyl)-octahydro-pyrrolo[3,4-d]azepin-6-yl]-prop-2-ene-1-one;

(3aS,8aR)-6-[(E)-3-(3-trifluoromethoxy-phenyl)-acryloyl]-octahydro-pyrrolo[3,4-d]azepine-2-carboxylic acid (1H-[1,2,3]triazol-4-ylmethyl)-amide;

(3aR,8aS)—N-((1H-1,2,3-triazol-5-yl)methyl)-6-((E)-3-(4-(trifluoromethoxy)phenyl)acryloyl)octahydropyrrolo[3,4-d]azepine-2(1H)-carboxamide;

(3aS,6aR)-5-[(E)-3-(4-trifluoromethoxy-phenyl)-acryloyl]-hexahydro-pyrrolo[3,4-c]pyrrole-2-carboxylic acid (1H-[1,2,3]triazol-4-ylmethyl)-amide;

(3aR,8aS)—N-((1H-1,2,3-triazol-5-yl)methyl)-6-((E)-3-(3-fluoro-4-(trifluoromethoxy)phenyl)acryloyl)octahydropyrrolo[3,4-d]azepine-2(1H)-carboxamide;

(3aS,8aR)-6-[(E)-3-(4-trifluoromethoxy-phenyl)-acryloyl]-octahydro-pyrrolo[3,4-d]azepine-2-carboxylic acid (4H-[1,2,4]triazol-3-ylmethyl)-amide;

(E)-1-[(3aS,8aR)-2-(6,7-dihydro-4H-[1,2,3]triazolo[1,5-a]pyrazine-5-carbonyl)-octahydro-pyrrolo[3,4-d]azepin-6-yl]-3-(4-trifluoromethoxy-phenyl)-prop-2-ene-1-one;

(E)-1-[(3aS,8aR)-2-(1,4,6,7-tetrahydro-imidazo[4,5-c]pyridine-5-carbonyl)-octahydro-pyrrolo[3,4-d]azepin-6-yl]-3-(4-trifluoromethoxy-phenyl)-prop-2-ene-1-one;

(3aR,8aS)—N-((1H-1,2,3-triazol-5-yl)methyl)-N-methyl-6-((E)-3-(4-(trifluoromethoxy)phenyl)acryloyl)octahydropyrrolo[3,4-d]azepine-2(1H)-carboxamide;

(3aS,8aR)-6-[3-(3-chloro-phenyl)-2,2-dimethyl-propionyl]-octahydro-pyrrolo[3,4-d]azepine-2-carboxylic acid (3H-[1,2,3]triazol-4-ylmethyl)-amide;

(3aR,8aS)—N-(2-(1H-1,2,3-triazol-5-yl)ethyl)-6-((E)-3-(4-(trifluoromethoxy)phenyl)acryloyl)octahydropyrrolo[3,4-d]azepine-2(1H)-carboxamide;

(3aR,7aS)-2-(1H-benzotriazole-5-carbonyl)-octahydro-pyrrolo[3,4-c]pyridine-5-carboxylic acid 3,5-dichloro-benzyl ester;

(3aS,7aR)-2-(1H-benzotriazole-5-carbonyl)-octahydro-pyrrolo[3,4-c]pyridine-5-carboxylic acid 3,5-dichloro-benzyl ester;

(+)-trans-3,5-dichlorobenzyl 2-(1H-benzo[d][1,2,3]triazole-5-carbonyl)hexahydro-1H-pyrrolo[3,4-c]pyridine-5 (6H)-carboxylate;

(−)-trans-3,5-dichlorobenzyl 2-(1H-benzo[d][1,2,3]triazole-5-carbonyl)hexahydro-1H-pyrrolo[3,4-c]pyridine-5 (6H)-carboxylate;

(−)-trans-3,5-dichlorobenzyl 5-(1H-benzo[d][1,2,3]triazole-5-carbonyl)hexahydro-1H-pyrrolo[3,4-c]pyridine-2(3H)-carboxylate;

(+)-trans-3,5-dichlorobenzyl 5-(1H-benzo[d][1,2,3]triazole-5-carbonyl)hexahydro-1H-pyrrolo[3,4-c]pyridine-2(3H)-carboxylate;

(E)-1-[trans-2-(1H-benzotriazole-5-carbonyl)-octahydro-pyrrolo[3,4-c]pyridin-5-yl]-3-(3,5-dichloro-phenyl)-prop-2-en-1-one;

(1H-benzotriazol-5-yl)-{trans-2-[5-(4-chloro-phenyl)-[1,3,4]oxadiazol-2-yl]-octahydro-pyrrolo[3,4-c]pyridin-5-yl}-methanone;

(E)-1-((3aR,6aS)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one;

(1H-benzotriazol-5-yl)-[(3aR,6aS)-5-(5-chloro-1H-indole-2-carbonyl)-hexahydro-pyrrolo[3,4-c]pyrrol-2-yl]-methanone;

(E)-1-[(3aR,6aS)-5-(1H-benzotriazole-5-carbonyl)-hexahydro-pyrrolo[3,4-c]pyrrol-2-yl]-3-(3-fluoro-5-trifluoromethyl-phenyl)-prop-2-en-1-one;

1-[(3aR,6aS)-5-(1H-benzotriazole-5-carbonyl)-hexahydro-pyrrolo[3,4-c]pyrrol-2-yl]-3-(3-fluoro-5-trifluoromethyl-phenyl)-propan-1-one;

(1H-benzotriazol-5-yl)-[(3aR,6aS)-5-(6-chloro-1H-indole-2-carbonyl)-hexahydro-pyrrolo[3,4-c]pyrrol-2-yl]-methanone;

(E)-1-((3aR,8aS)-2-(1H-benzo[d][1,2,3]triazole-5-carbonyl)octahydropyrrolo[3,4-d]azepin-6(7H)-yl)-3-(4-(trifluoromethylsulfonyl)phenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(4-chlorophenyl)prop-2-en-1-one;

(E)-1-((3aR,8aS)-2-(1H-benzo[d][1,2,3]triazole-5-carbonyl)octahydropyrroo[3,4-d]azepin-6(7H)-yl)-3-p-tolyl-prop-2-en-1-one;

4-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)-N,N-dimethylbenzenesulfonamide;

(E)-1-((3aR,8aS)-2-(1H-benzo[d][1,2,3]triazole-5-carbonyl)octahydropyrroo[3,4-d]azepin-6(7H)-yl)-3-(4-methoxyphenyl)prop-2-en-1-one;
(E)-1-((3aR,8aS)-6-(1H-benzo[d][1,2,3]triazole-5-carbonyl)octahydropyrrolo[3,4-d]azepin-2(1H)-yl)-3-(4-(trifluoromethoxy)phenyl)prop-2-en-1-one;
4-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)benzonitrile;
(E)-1-((3aR,6aR)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one;
1-((3aR,6aS)-5-(1H-benzo[d][1,2,3]triazole-5-carbonyl)hexahydropyrrolo[3,4-c]pyrrol-2(1H)-yl)-3-(4-(trifluoromethoxy)phenyl)propan-1-one;
(E)-1-((3aR,8aS)-2-(1H-benzo[d][1,2,3]triazole-5-carbonyl)octahydropyrrolo[3,4-d]azepin-6(7H)-yl)-3-(4-fluorophenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-phenylprop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(pyridin-2-yl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(pyridin-3-yl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(3-chlorophenyl)prop-2-en-1-one;
(E)-1-((3aR,8aS)-6-(1H-benzo[d][1,2,3]triazole-5-carbonyl)octahydropyrrolo[3,4-d]azepin-2(1H)-yl)-3-(4-chlorophenyl)prop-2-en-1-one;
(E)-1-((3aR,8aS)-6-(1H-benzo[d][1,2,3]triazole-5-carbonyl)octahydropyrrolo[3,4-d]azepin-2(1H)-yl)-3-(3-(trifluoromethoxy)phenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(4-(difluoromethoxy)phenyl)prop-2-en-1-one;
(E)-1-((3aR,6aR)-5-(1H-benzo[d][1,2,3]triazole-5-carbonyl)hexahydropyrrolo[3,4-c]pyrrol-2(1H)-yl)-3-(3-(trifluoromethoxy)phenyl)prop-2-en-1-one;
4-((E)-3-((3aR,6aR)-5-(1H-benzo[d][1,2,3]triazole-5-carbonyl)hexahydropyrrolo[3,4-c]pyrrol-2(1H)-yl)-3-oxoprop-1-enyl)benzonitrile;
(E)-1-((3aS,6aS)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one;
(−)-(E)-1-[trans-5-(1H-benzotriazole-5-carbonyl)-octahydro-pyrrolo[3,4-c]pyridin-2-yl]-3-(4-trifluoromethoxyphenyl)-prop-2-ene-1-one;
(+)-(E)-1-[trans-5-(1H-benzotriazole-5-carbonyl)-octahydro-pyrrolo[3,4-c]pyridin-2-yl]-3-(4-trifluoromethoxyphenyl)-prop-2-ene-1-one;
(E)-1-((3aR,8aS)-2-(1H-benzo[d][1,2,3]triazole-5-carbonyl)octahydropyrrolo[3,4-d]azepin-6(7H)-yl)-3-(3,5-dichlorophenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(pyridin-4-yl)prop-2-en-1-one;
(E)-1-((3aR,8aS)-2-(1H-benzo[d][1,2,3]triazole-5-carbonyl)octahydropyrroo[3,4-d]azepin-6(7H)-yl)-3-(2,4-difluorophenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(2,4-dichlorophenyl)prop-2-en-1-one;
(E)-1-((3aR,8aS)-2-(1H-benzo[d][1,2,3]triazole-5-carbonyl)octahydropyrroo[3,4-d]azepin-6(7H)-yl)-3-(3,4-dichlorophenyl)prop-2-en-1-one;
(E)-1-[(3aS,7aS)-5-(1H-benzotriazole-5-carbonyl)-octahydro-pyrrolo[3,4-c]pyridin-2-yl]-3-(4-difluoromethoxy-phenyl)-prop-2-ene-1-one;
4-{(E)-3-[(3aS,7aS)-5-(1H-benzotriazole-5-carbonyl)-octahydro-pyridin-2-yl]-3-oxo-propenyl}-benzonitrile;
4-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)-3-fluorobenzonitrile;
4-((E)-3-((3aR,6aR)-5-(1H-benzo[d][1,2,3]triazole-5-carbonyl)hexahydropyrrolo[3,4-c]pyrrol-2(1H)-yl)-3-oxoprop-1-enyl)-3-fluorobenzonitrile;
(E)-1-((3aR,6aR)-5-(1H-benzo[d][1,2,3]triazole-5-carbonyl)hexahydropyrrolo[3,4-c]pyrrol-2(1H)-yl)-3-(4-(difluoromethoxy)phenyl)prop-2-en-1-one;
(E)-1-[cis-2-(1H-benzotriazole-5-carbonyl)-octahydro-pyrrolo[3,4-c]pyridin-5-yl]-3-(4-trifluoromethoxy-phenyl)-prop-2-ene-1-one;
3-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)benzonitrile;
(E)-1-((3aR,8aS)-2-(1H-benzo[d][1,2,3]triazole-5-carbonyl)octahydropyrrolo[3,4-d]azepin-6(7H)-yl)-3-(2-fluoro-4-(trifluoromethoxy)phenyl)prop-2-en-1-one;
(E)-1-((3aR,6aR)-5-(1H-benzo[d][1,2,3]triazole-5-carbonyl)hexahydropyrrolo[3,4-c]pyrrol-2(1H)-yl)-3-(2-fluoro-4-(trifluoromethoxy)phenyl)prop-2-en-1-one;
(E)-1-((3aR,6aR)-5-(1H-benzo[d][1,2,3]triazole-5-carbonyl)hexahydropyrrolo[3,4-c]pyrrol-2(1H)-yl)-3-(4-chloro-2-fluorophenyl)prop-2-en-1-one;
(E)-1-((3aR,6aR)-5-(1H-benzo[d][1,2,3]triazole-5-carbonyl)hexahydropyrrolo[3,4-c]pyrrol-2(1H)-yl)-3-(3,5-dichlorophenyl)prop-2-en-1-one;
(E)-1-((3aR,6aS)-5-(4,5,6,7-tetrahydro-1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one;
1-[(3aR,6aR)-5-(1H-benzotriazole-5-carbonyl)-hexahydro-pyrrolo[3,4-c]pyrrol-2-yl]-3-(4-trifluoromethoxy-phenyl)-propan-1-one;
(E)-1-[(3aS,6aR)-5-(1,4,6,7-tetrahydro-[1,2,3]triazolo[4,5-c]pyridine-5-carbonyl)-hexahydro-pyrrolo[3,4-c]pyrrol-2-yl]-3-(4-trifluoromethoxy-phenyl)-prop-2-ene-1-one;
(E)-1-[(3aR,6aR)-5-(1H-benzotriazole-5-carbonyl)-hexahydro-pyrrolo[3,4-c]pyrrol-2-yl]-3-(3-chloro-5-methanesulfonyl-phenyl)-prop-2-ene-1-one;
(E)-1-[(3aR,6R)-5-(1H-benztriazole-5-carbonyl)-hexahydro-pyrrolo[3,4-c]pyrrol-2-yl]-3-(3,5-dimethoxy-phenyl)-prop-2-ene-1-one;
(E)-1-[(3aR,6aR)-5-(1H-benzotriazole-5-carbonyl)-hexahydro-pyrrolo[3,4-c]pyrrol-2-yl]-3-(3-chloro-5-trifluoromethoxy-phenyl)-prop-2-ene-1-one;
(E)-1-[(3aR,6aR)-5-(1H-benzotriazole-5-carbonyl)-hexahydro-pyrrolo[3,4-c]pyrrol-2-yl]-3-(3-chloro-5-methoxy-phenyl)-prop-2-ene-1-one;
3-{(E)-3-[(3aR,6aR)-5-(1H-benzotriazole-5-carbonyl)-hexahydro-pyrrolo[3,4-c]pyrrol-2-yl]-3-oxo-propenyl}-5-chloro-benzonitrile;
(E)-1-[(3aR,6aR)-5-(1H-benzotriazole-5-carbonyl)-hexahydro-pyrrolo[3,4-c]pyrrol-2-yl]-3-(3-methoxy-5-trifluoromethoxy-phenyl)-prop-2-ene-1-one;
(E)-1-[(3aR,6aR)-5-(1,4,6,7-tetrahydro-[1,2,3]triazolo[4,5-c]pyridine-5-carbonyl)-hexahydro-pyrrolo[3,4-c]pyrrol-2-yl]-3-(4-trifluoromethoxy-phenyl)-prop-2-ene-1-one;

1-[(3aR,6aR)-5-(1,4,6,7-tetrahydro-[1,2,3]triazolo[4,5-c]
pyridine-5-carbonyl)-hexahydro-pyrrolo[3,4-c]pyrrol-2-
yl]-3-(4-trifluoromethoxy-phenyl)-propan-1-one;
(3aR,7aR)-5-{(3aR,6aR)-5-[(E)-3-(4-trifluoromethoxy-phenyl)-acryloyl]-hexahydro-pyrrolo[3,4-c]pyrrole-2-carbonyl}-hexahydro-oxazolo[5,4-c]pyridin-2-one;
(3aR,7aR)-5-{(3aR,6aR)-5-[3-(4-trifluoromethoxy-phenyl)-propionyl]-hexahydro-pyrrolo[3,4-c]pyrrole-2-carbonyl}-hexahydro-oxazolo[5,4-c]pyridin-2-one;
(E)-1-[(3aR,6aR)-5-(1H-benzotriazole-5-carbonyl)-hexahydro-pyrrolo[3,4-c]pyrrol-2-yl]-3-phenyl-prop-2-ene-1-one;
1-[(3aR,6aR)-5-(1H-benzotriazole-5-carbonyl)-hexahydropyrrolo[3,4-c]pyrrol-2-yl]-3-phenyl-propan-1-one;
(E)-1-[(3aR,6aR)-5-(1H-benzotriazole-5-carbonyl)-hexahydro-pyrrolo[3,4-c]pyrrol-2-yl]-3-(4 trifluoromethyl-phenyl)-prop-2-ene-1-one;
1-[(3aR,6aR)-5-(1H-benzotriazole-5-carbonyl)-hexahydropyrrolo[3,4-c]pyrrol-2-yl]-3-(4-trifluoromethyl-phenyl)-propan-1-one;
(3aR,6aS)—N-((1H-1,2,3-triazol-5-yl)methyl)-N-methyl-5-(3-(4-(trifluoromethoxy)phenyl)propanoyl)hexahydropyrrolo[3,4-c]pyrrole-2(1H)-carboxamide;
(3aR,8aS)—N-((1H-1,2,3-triazol-5-yl)methyl)-6-((E)-3-(3-fluoro-4-(trifluoromethoxy)phenyl)acryloyl)-N-methyl-octahydropyrrolo[3,4-d]azepine-2(1H)-carboxamide;
1-[(3aR,6aR)-5-(1H-benzotriazole-5-carbonyl)-hexahydropyrrolo[3,4-c]pyrrol-2-yl]-3-(6-trifluoromethyl-pyridin-3-yl)-propan-1-one;
1-[(3aS,6aS)-5-(1H-benzotriazole-5-carbonyl)-hexahydropyrrolo[3,4-c]pyrrol-2-yl]-2-(4-trifluoromethoxy-phenoxy)-ethanone;
1-[(3aS,6aS)-5-(1H-benzotriazole-5-carbonyl)-hexahydropyrrolo[3,4-c]pyrrol-2-yl]-2-(4-chloro-2-isopropyl-5-methyl-phenoxy)-ethanone;
1-[(3aR,6aR)-5-(1H-benzotriazole-5-carbonyl)-hexahydropyrrolo[3,4-c]pyrrol-2-yl]-3-biphenyl-4-yl-propan-1-one;
(E)-1-((3aR,8aS)-2-(1H-benzo[d][1,2,3]triazole-5-carbonyl)octahydropyrrolo[3,4-d]azepin-6(7H)-yl)-3-(4-fluoro-2-(trifluoromethyl)phenyl)prop-2-en-1-one;
1-[(3aS,6aR)-5-(1H-Benzotriazole-5-carbonyl)-hexahydropyrrolo[3,4-c]pyrrol-2-yl]-2-(4-chloro-2-isopropyl-5-methyl-phenoxy)-ethanone;
(E)-1-((3aR,8aS)-2-(1H-benzo[d][1,2,3]triazole-5-carbonyl)octahydropyrrolo[3,4-d]azepin-6(7H)-yl)-3-(4-(methylsulfonyl)phenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(4-(trifluoromethylthio)phenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(4-(trifluoromethoxy)phenyl)prop-2-en-1-one;
1-((3aR,6aS)-5-(1H-benzo[d][1,2,3]triazole-5-carbonyl)hexahydropyrrolo[3,4-c]pyrrol-2(1H)-yl)-2-(3-(trifluoromethoxy)phenoxy)ethanone;
(E)-1-((3aR,8aS)-2-(1H-benzo[d][1,2,3]triazole-5-carbonyl)octahydropyrrolo[3,4-d]azepin-6(7H)-yl)-3-(3-(trifluoromethoxy)phenyl)prop-2-en-1-one;
(E)-1-[trans-5-(1H-benzotriazole-5-carbonyl)-octahydropyrrolo[3,4-c]pyridin-2-yl]-3-(3-trifluoromethoxy-phenyl)-prop-2-en-1-one;
(E)-1-[trans-5-(1H-benzotriazole-5-carbonyl)-octahydropyrrolo[3,4-c]pyridin-2-yl]-3-(4-trifluoromethoxy-phenyl)-prop-2-en-1-one;
(E)-1-[trans-5-(1H-benzotriazole-5-carbonyl)-octahydropyrrolo[3,4-c]pyridin-2-yl]-3-(3-chloro-5-trifluoromethoxy-phenyl)-prop-2-en-1-one;
(E)-1-[trans-5-(1H-benzotriazole-5-carbonyl)-octahydropyrrolo[3,4-c]pyridin-2-yl]-3-(3,5-dichloro-phenyl)-prop-2-en-1-one;
(E)-1-[(3aR,6aR)-5-(1H-benzotriazole-5-carbonyl)-hexahydro-pyrrolo[3,4-c]pyrrol-2-yl]-3-(6-phenyl-pyridin-3-yl)-prop-2-ene-1-one;
(E)-1-[(3aR,6aR)-5-(1H-benzotriazole-5-carbonyl)-hexahydro-pyrrolo[3,4-c]pyrrol-2-yl]-3-(5-trifluoromethyl-pyridin-2-yl)-prop-2-ene-1-one;
(E)-1-[(3aR,6aR)-5-(1H-benzotriazole-5-carbonyl)-hexahydro-pyrrolo[3,4-c]pyrrol-2-yl]-3-(4-pyridin-4-yl-phenyl)-prop-2-ene-1-one;
(E)-1-[(3aR,6aR)-5-(1H-benzotriazole-5-carbonyl)-hexahydro-pyrrolo[3,4-c]pyrrol-2-yl]-3-(4-pyridin-3-yl-phenyl)-prop-2-ene-1-one;
(E)-1-[(3aR,6aR)-5-(1H-benzotriazole-5-carbonyl)-hexahydro-pyrrolo[3,4-c]pyrrol-2-yl]-3-(4-pyridin-2-yl-phenyl)-prop-2-ene-1-one;
1-[(3aS,6aR)-5-(1H-benzotriazole-5-carbonyl)-hexahydropyrrolo[3,4-c]pyrrol-2-yl]-2-(4-chloro-3-methyl-phenoxy)-ethanone;
1-[(3aS,6aR)-5-(1H-benzotriazole-5-carbonyl)-hexahydropyrrolo[3,4-c]pyrrol-2-yl]-2-(4-chloro-2-methyl-phenoxy)-ethanone;
(E)-1-[(3aR,6aR)-5-(1H-benzotriazole-5-carbonyl)-hexahydro-pyrrolo[3,4-c]pyrrol-2-yl]-3-(5-phenyl-pyridin-2-yl)-prop-2-ene-1-one;
(E)-1-((3aR,8aS)-2-(1H-benzo[d][1,2,3]triazole-5-carbonyl)octahydropyrrolo[3,4-d]azepin-6(7H)-yl)-3-(4-(trifluoromethylsulfinyl)phenyl)prop-2-en-1-one;
1-((3aR,8aS)-2-(1H-benzo[d][1,2,3]triazole-5-carbonyl)octahydropyrrolo[3,4-d]azepin-6(7H)-yl)-3-(3-fluoro-4-(trifluoromethoxy)phenyl)propan-1-one;
(3aR,8aS)—N-((1H-1,2,3-triazol-5-yl)methyl)-N-methyl-6-(3-(4-(trifluoromethoxy)phenyl)propanoyl)octahydropyrrolo[3,4-d]azepine-2(1H)-carboxamide;
(3aR,8aS)—N-((1H-1,2,3-triazol-5-yl)methyl)-6-(3-(3-fluoro-4-(trifluoromethoxy)phenyl)propanoyl)-N-methyloctahydropyrrolo[3,4-d]azepine-2(1H)-carboxamide;
1-[(3aR,6aR)-5-(1H-benzotriazole-5-carbonyl)-hexahydropyrrolo[3,4-c]pyrrol-2-yl]-3-(4-difluoromethoxy-phenyl)-propan-1-one;
1-[(3aR,6aR)-5-(1H-benzotriazole-5-carbonyl)-hexahydropyrrolo[3,4-c]pyrrolo-2-yl]-3-(2-fluoro-4-trifluoromethoxy-phenyl)-propan-1-one;
1-((3aR,8aS)-2-(1H-benzo[d][1,2,3]triazole-5-carbonyl)octahydropyrrolo[3,4-d]azepin-6(7H)-yl)-3-(4-fluoro-2-(trifluoromethyl)phenyl)propan-1-one;
1-((3aR,8aS)-2-(1H-benzo[d][1,2,3]triazole-5-carbonyl)octahydropyrrolo[3,4-d]azepin-6(7H)-yl)-3-(2-methyl-4-(trifluoromethoxy)phenyl)propan-1-one;
1-((3aR,8aS)-2-(1H-benzo[d][1,2,3]triazole-5-carbonyl)octahydropyrrolo[3,4-d]azepin-6(7H)-yl)-3-(3-fluoro-4-methoxyphenyl)propan-1-one;
1-[(3aS,8aR)-2-(1H-benzotriazole-5-carbonyl)-octahydropyrrolo[3,4-d]azepin-6-yl]-3-(2-isopropyl-phenyl)-propan-1-one;
1-[(3aR,6aR)-5-(1H-benzotriazole-5-carbonyl)-hexahydropyrrolo[3,4-c]pyrrol-2-yl]-3-(5-trifluoromethyl-pyridin-2-yl)-propan-1-one;
1-[(3aR,6aR)-5-(1H-benzotriazole-5-carbonyl)-hexahydropyrrolo[3,4-c]pyrrol-2-yl]-3-(5-phenyl-pyridin-2-yl)-propan-1-one;
1-[(3aR,6aR)-5-(1H-benzotriazole-5-carbonyl)-hexahydropyrrolo[3,4-c]pyrrol-2-yl]-3-(4-pyridin-4-yl-phenyl)-propan-1-one;

1-[(3aR,6aR)-5-(1H-benzotriazole-5-carbonyl)-hexahydro-pyrrolo[3,4-c]pyrrol-2-yl]-3-(4-pyridin-3-yl-phenyl)-propan-1-one;

1-[(3aR,6aR)-5-(1H-benzotriazole-5-carbonyl)-hexahydro-pyrrolo[3,4-c]pyrrol-2-yl]-3-(4-pyridin-2-yl-phenyl)-propan-1-one;

(3aS,8aR)-6-[3-(4-trifluoromethoxy-phenyl)-propionyl]-octahydro-pyrrolo[3,4-d]azepine-2-carboxylic acid [2-(3H-[1,2,3]triazol-4-yl)-ethyl]-amide;

(E)-3-[4-(trifluoro-methoxy)-phenyl]-1-[(3aS,8aR)-2-((S)-4,5,6,7-tetrahydro-1H-imidazo[4,5-c]pyridine-6-carbonyl)-octahydro-pyrrolo[3,4-d]azepin-6-yl]-prop-2-ene-1-one hydrochloride;

and pharmaceutically acceptable salts thereof.

Also particular examples of compounds of formula (I) as described herein are selected from trans-2-(1H-benzotriazole-5-carbonyl)-octahydro-pyrrolo[3,4-c]pyridine-5-carboxylic acid 3-chloro-5-methanesulfonyl-benzyl ester;

trans-2-(1H-benzotriazole-5-carbonyl)-octahydro-pyrrolo[3,4-c]pyridine-5-carboxylic acid 4-trifluoromethoxy-benzyl ester;

1-[trans-2-(1H-benzotriazole-5-carbonyl)-octahydro-pyrrolo[3,4-c]pyridin-5-yl]-2-(4-trifluoromethoxy-phenoxy)-ethanone;

(E)-1-[trans-2-(1H-benzotriazole-5-carbonyl)-octahydro-pyrrolo[3,4-c]pyridin-5-yl]-3-(4-trifluoromethoxy-phenyl)-propenone;

(E)-1-((3aR,8aS)-2-(1H-benzo[d][1,2,3]triazole-5-carbonyl)octahydropyrrolo[3,4-d]azepin-6(7H)-yl)-3-(3-chloro-5-(trifluoromethyl)phenyl)prop-2-en-1-one;

(E)-1-((3aR,8aS)-2-(1H-benzo[d][1,2,3]triazole-5-carbonyl)octahydropyrroo[3,4-d]azepin-6(7H)-yl)-3-(4-methoxy-2-(trifluoromethyl)phenyl)prop-2-en-1-one;

(E)-1-((3aR,8aS)-2-(1H-benzo[d][1,2,3]triazole-5-carbonyl)octahydropyrroo[3,4-d]azepin-6(7H)-yl)-3-(2-cyclopropylphenyl)prop-2-en-1-one;

trans-2-(1H-benzotriazole-5-carbonyl)-octahydro-pyrrolo[3,4-c]pyridine-5-carboxylic acid 4-fluoro-2-trifluoromethyl-benzyl ester;

trans-2-(1H-benzotriazole-5-carbonyl)-octahydro-pyrrolo[3,4-c]pyridine-5-carboxylic acid 2-cyclopropyl-4-trifluoromethyl-benzyl ester;

1-[(3aS,8aR)-2-(1H-benzotriazole-5-carbonyl)-octahydro-pyrrolo[3,4-d]azepin-6-yl]-2-(2-trifluoromethoxy-phenoxy)-ethanone;

trans-2-(1H-benzotriazole-5-carbonyl)-octahydro-pyrrolo[3,4-c]pyridine-5-carboxylic acid 2-methoxy-4-trifluoromethoxy-benzyl ester;

4-{2-[(3aS,8aR)-2-(1H-benzotriazole-5-carbonyl)-octahydro-pyrrolo[3,4-d]azepin-6-yl]-2-oxo-ethoxy}-3-trifluoromethyl-benzonitrile;

1-[(3aS,8aR)-2-(1H-benzotriazole-5-carbonyl)-octahydro-pyrrolo[3,4-d]azepin-6-yl]-2-(4-chloro-2-isopropyl-5-methyl-phenoxy)-ethanone;

1-[(3aS,8aR)-2-(1H-benzotriazole-5-carbonyl)-octahydro-pyrrolo[3,4-d]azepin-6-yl]-2-[4-methyl-2-(1-methyl-pyrrolidin-3-yl)-phenoxy]-ethanone;

1-[(3aS,8aR)-2-(1H-benzotriazole-5-carbonyl)-octahydro-pyrrolo[3,4-d]azepin-6-yl]-2-(2-chloro-4-fluoro-phenoxy)-ethanone;

1-((3aR,8aS)-2-(1H-benzo[d][1,2,3]triazole-5-carbonyl)octahydropyrrolo[3,4-d]azepin-6(7H)-yl)-2-(2-chloro-4-(trifluoromethyl)phenoxy)ethanone;

1-((3aR,8aS)-2-(1H-benzo[d][1,2,3]triazole-5-carbonyl)octahydropyrrolo[3,4-d]azepin-6(7H)-yl)-2-(6-isopropyl-3,3-dimethyl-2,3-dihydro-1H-inden-5-yloxy)ethanone;

(3aS,8aR)-2-(1H-benzotriazole-5-carbonyl)-octahydro-pyrrolo[3,4-d]azepine-6-carboxylic acid 2-fluoro-4-trifluoromethoxy-benzyl ester;

1-((3aR,8aS)-2-(1H-benzo[d][1,2,3]triazole-5-carbonyl)octahydropyrrolo[3,4-d]azepin-6(7H)-yl)-2-(5-chloro-2-(trifluoromethyl)phenoxy)ethanone;

1-[(3aS,8aR)-2-(1H-benzotriazole-5-carbonyl)-1,3,3a,4,5,7,8,8a-octahydropyrrolo[3,4-d]azepin-6-yl]-2-(2-tert-butyl-4-methoxyphenoxy)ethanone;

4-[2-[(3aS,8aR)-2-(1H-benzotriazole-5-carbonyl)-1,3,3a,4,5,7,8,8a-octahydropyrrolo[3,4-d]azepin-6-yl]-2-oxoethoxy]-3-propan-2-ylbenzonitrile;

1-[(3aS,8aR)-2-(1H-benzotriazole-5-carbonyl)-1,3,3a,4,5,7,8,8a-octahydropyrrolo[3,4-d]azepin-6-yl]-3-[3-fluoro-4-(2,2,2-trifluoroethoxy)phenyl]propan-1-one;

1-[(3aS,8aR)-2-(1H-benzotriazole-5-carbonyl)-1,3,3a,4,5,7,8,8a-octahydropyrrolo[3,4-d]azepin-6-yl]-3-[2-fluoro-4-(2,2,2-trifluoroethoxy)phenyl]propan-1-one;

(3aS,8aR)-2-(1H-benzotriazole-5-carbonyl)-octahydro-pyrrolo[3,4-d]azepine-6-carboxylic acid 3-fluoro-4-(2,2,2-trifluoro-ethoxy)-benzyl ester;

(3aS,8aR)-2-(1H-benzotriazole-5-carbonyl)-octahydro-pyrrolo[3,4-d]azepine-6-carboxylic acid 2-fluoro-4-(2,2,2-trifluoro-ethoxy)-benzyl ester;

(3aS,8aR)-2-(1H-benzotriazole-5-carbonyl)-octahydro-pyrrolo[3,4-d]azepine-6-carboxylic acid 4-(2,2,2-trifluoro-ethoxy)-benzyl ester;

(3aS,6aS)-5-(3H-[1,2,3]triazolo[4,5-b]pyridine-6-carbonyl)-hexahydro-pyrrolo[3,4-c]pyrrole-2-carboxylic acid 4-trifluoromethoxy-benzyl ester;

1-[(3aR,6aR)-5-(1H-triazolo[4,5-b]pyridine-5-carbonyl)-1,3,3a,4,6,6a-hexahydropyrrolo[3,4-c]pyrrol-2-yl]-3-[4-(trifluoromethoxy)phenyl]propan-1-one;

(3aS,6aS)-5-(3H-[1,2,3]triazolo[4,5-c]pyridine-6-carbonyl)-hexahydro-pyrrolo[3,4-c]pyrrole-2-carboxylic acid 4-trifluoromethoxy-benzyl ester;

(3aS,6aS)-5-(4-fluoro-1H-benzotriazole-5-carbonyl)-hexahydro-pyrrolo[3,4-c]pyrrole-2-carboxylic acid 4-trifluoromethoxy-benzyl ester;

(3aS,6aS)-5-(7-fluoro-1H-benzotriazole-5-carbonyl)-hexahydro-pyrrolo[3,4-c]pyrrole-2-carboxylic acid 4-trifluoromethoxy-benzyl ester;

(3aS,6aS)-5-(6-fluoro-1H-benzotriazole-5-carbonyl)-hexahydro-pyrrolo[3,4-c]pyrrole-2-carboxylic acid 4-trifluoromethoxy-benzyl ester;

(3aS,6aS)-5-(4-chloro-1H-benzotriazole-5-carbonyl)-hexahydro-pyrrolo[3,4-c]pyrrole-2-carboxylic acid 4-trifluoromethoxy-benzyl ester;

(3aS,6aS)-5-(6-trifluoromethyl-1H-benzotriazole-5-carbonyl)-hexahydro-pyrrolo[3,4-c]pyrrole-2-carboxylic acid 4-trifluoromethoxy-benzyl ester;

(3aS,6aS)-5-(4-methyl-1H-benzotriazole-5-carbonyl)-hexahydro-pyrrolo[3,4-c]pyrrole-2-carboxylic acid 4-trifluoromethoxy-benzyl ester;

(3aS,6aS)-5-(6-methyl-1H-benzotriazole-5-carbonyl)-hexahydro-pyrrolo[3,4-c]pyrrole-2-carboxylic acid 4-trifluoromethoxy-benzyl ester;

1-[(3aR,6aR)-5-(4-fluoro-1H-benzotriazole-5-carbonyl)-hexahydro-pyrrolo[3,4-c]pyrrol-2-yl]-3-(4-trifluoromethoxy-phenyl)-propan-1-one;

(4-ethoxyquinolin-2-yl)((3aS,6aS)-5-((R)-4,5,6,7-tetrahydro-1H-benzo[d][1,2,3]triazole-5-carbonyl)hexahydropyrrolo[3,4-c]pyrrol-2(1H)-yl)methanone;

(4-ethoxyquinolin-2-yl)((3aS,6aS)-5-(4-fluoro-1H-benzo[d][1,2,3]triazole-5-carbonyl)hexahydropyrrolo[3,4-c]pyrrol-2(1H)-yl)methanone;

6-[(3aR,6aR)-2-[3-[4-(trifluoromethoxy)phenyl]propanoyl]-1,3,3a,4,6,6a-hexahydropyrrolo[3,4-c]pyrrole-5-carbonyl]-3H-1,3-benzoxazol-2-one;

(3aS,6aS)-5-(2-oxo-2,3-dihydro-benzooxazole-6-carbonyl)-hexahydro-pyrrolo[3,4-c]pyrrole-2-carboxylic acid 4-trifluoromethoxy-benzyl ester;

(3aS,6aS)-5-(1H-benzotriazole-5-carbonyl)-hexahydro-pyrrolo[3,4-c]pyrrole-2-carboxylic acid 4-cyano-benzyl ester;

(3aS,6aS)-5-(1H-benzotriazole-5-carbonyl)-hexahydro-pyrrolo[3,4-c]pyrrole-2-carboxylic acid 4-(1,1,2,2-tetrafluoro-ethoxy)-benzyl ester;

(3aS,6aS)-5-(1H-benzotriazole-5-carbonyl)-hexahydro-pyrrolo[3,4-c]pyrrole-2-carboxylic acid 4-difluoromethoxy-3-fluoro-benzyl ester;

(3aS,6aS)-5-(1H-[1,2,3]triazolo[4,5-b]pyridine-5-carbonyl)-hexahydro-pyrrolo[3,4-c]pyrrole-2-carboxylic acid 3-fluoro-4-trifluoromethoxy-benzyl ester;

(3aS,6aS)-5-(1H-benzotriazole-5-carbonyl)-hexahydro-pyrrolo[3,4-c]pyrrole-2-carboxylic acid 4-difluoromethoxy-benzyl ester;

(3aS,6aS)-5-(1H-[1,2,3]triazolo[4,5-b]pyridine-5-carbonyl)-hexahydro-pyrrolo[3,4-c]pyrrole-2-carboxylic acid 4-trifluoromethoxy-benzyl ester;

(3aS,6aS)-5-(1H-benzotriazole-5-carbonyl)-hexahydro-pyrrolo[3,4-c]pyrrole-2-carboxylic acid 3-fluoro-4-trifluoromethoxy-benzyl ester;

(3aS,6aS)-5-(1H-benzotriazole-5-carbonyl)-hexahydro-pyrrolo[3,4-c]pyrrole-2-carboxylic acid 4-(2,2,2-trifluoro-ethoxy)-benzyl ester;

(3aS,6aS)-5-(1H-benzotriazole-5-carbonyl)-hexahydro-pyrrolo[3,4-c]pyrrole-2-carboxylic acid 5-trifluoromethoxy-pyridin-2-ylmethyl ester;

(3aS,6aS)-5-((R)-4,5,6,7-tetrahydro-1H-benzotriazole-5-carbonyl)-hexahydro-pyrrolo[3,4-c]pyrrole-2-carboxylic acid 4-cyano-2-isopropyl-benzyl ester;

(3aS,6aS)-5-((R)-4,5,6,7-tetrahydro-1H-benzotriazole-5-carbonyl)-hexahydro-pyrrolo[3,4-c]pyrrole-2-carboxylic acid 4-cyano-2-isopropyl-5-methyl-benzyl ester;

(3aS,6aS)-5-((R)-4,5,6,7-tetrahydro-1H-benzotriazole-5-carbonyl)-hexahydro-pyrrolo[3,4-c]pyrrole-2-carboxylic acid 2-fluoro-4-trifluoromethoxy-benzyl ester;

(3aS,6aS)-5-(1H-benzotriazole-5-carbonyl)-hexahydro-pyrrolo[3,4-c]pyrrole-2-carboxylic acid 2-fluoro-4-trifluoromethoxy-benzyl ester;

(3aS,6aS)-5-(1H-benzotriazole-5-carbonyl)-hexahydro-pyrrolo[3,4-c]pyrrole-2-carboxylic acid 4-cyano-2-ethoxy-benzyl ester;

(3aS,6aS)-5-((R)-4,5,6,7-tetrahydro-1H-benzotriazole-5-carbonyl)-hexahydro-pyrrolo[3,4-c]pyrrole-2-carboxylic acid 3-fluoro-4-trifluoromethoxy-benzyl ester;

(3aS,6aS)-5-(1H-benzotriazole-5-carbonyl)-hexahydro-pyrrolo[3,4-c]pyrrole-2-carboxylic acid 4-cyano-2-isopropyl-benzyl ester;

(3aS,6aS)-5-(1H-benzotriazole-5-carbonyl)-hexahydro-pyrrolo[3,4-c]pyrrole-2-carboxylic acid 4-cyano-2-isopropyl-5-methyl-benzyl ester;

(3aS,6aS)-5-(1,4,6,7-tetrahydro-[1,2,3]triazolo[4,5-c]pyridine-5-carbonyl)-hexahydro-pyrrolo[3,4-c]pyrrole-2-carboxylic acid 4-trifluoromethoxy-benzyl ester;

(3aR,6aR)-5-(1H-benzotriazole-5-carbonyl)-hexahydro-pyrrolo[3,4-c]pyrrole-2-carboxylic acid 4-trifluoromethoxy-benzyl ester;

(3aS,6aS)-5-(1H-benzotriazole-5-carbonyl)-hexahydro-pyrrolo[3,4-c]pyrrole-2-carboxylic acid 2-fluoro-4-trifluoromethyl-benzyl ester;

(3aS,6aS)-5-(1H-benzotriazole-5-carbonyl)-hexahydro-pyrrolo[3,4-c]pyrrole-2-carboxylic acid 4-trifluoromethyl-benzyl ester;

(3aS,6aS)-5-((R)-4,5,6,7-Tetrahydro-1H-benzotriazole-5-carbonyl)-hexahydro-pyrrolo[3,4-c]pyrrole-2-carboxylic acid 4-trifluoromethoxy-benzyl ester;

(3aS,6aS)-5-((R)-4,5,6,7-Tetrahydro-1H-benzotriazole-5-carbonyl)-hexahydro-pyrrolo[3,4-c]pyrrole-2-carboxylic acid 4-trifluoromethyl-benzyl ester;

(3aS,6aS)-5-((R)-4,5,6,7-Tetrahydro-1H-benzotriazole-5-carbonyl)-hexahydro-pyrrolo[3,4-c]pyrrole-2-carboxylic acid 3-chloro-5-methanesulfonyl-benzyl ester;

(3aS,6aS)-5-(1H-benzotriazole-5-carbonyl)-hexahydro-pyrrolo[3,4-c]pyrrole-2-carboxylic acid 4-cyano-2-methanesulfonyl-benzyl ester;

(3aS,6aS)-5-(1H-benzotriazole-5-carbonyl)-hexahydro-pyrrolo[3,4-c]pyrrole-2-carboxylic acid 4-cyano-2-ethoxy-5-fluoro-benzyl ester;

(3aS,6aS)-5-(4-methoxy-1H-benzotriazole-5-carbonyl)-hexahydro-pyrrolo[3,4-c]pyrrole-carboxylic acid 4-trifluoromethoxy-benzyl ester;

(3aS,6aS)-5-(1H-benzotriazole-5-carbonyl)-hexahydro-pyrrolo[3,4-c]pyrrole-2-carboxylic acid 4-cyano-2-cyclobutoxy-benzyl ester;

(3aS,6aS)-5-(1H-benzotriazole-5-carbonyl)-hexahydro-pyrrolo[3,4-c]pyrrole-2-carboxylic acid 4-cyano-2-isopropoxy-benzyl ester;

(3aS,6aS)-5-(1H-benzotriazole-5-carbonyl)-hexahydro-pyrrolo[3,4-c]pyrrole-2-carboxylic acid 4-cyano-2-(2,2,2-trifluoro-ethoxy)-benzyl ester;

(3aS,6aS)-5-(1H-benzotriazole-5-carbonyl)-hexahydro-pyrrolo[3,4-c]pyrrole-2-carboxylic acid 4-chloro-2-ethoxy-5-fluoro-benzyl ester;

(E)-1-[trans-2-(1H-benzotriazol-5-ylmethyl)-octahydro-pyrrolo[3,4-c]pyridin-5-yl]-3-(4-trifluoromethoxy-phenyl)-propenone;

(3aS,6aS)-5-(4-sulfamoyl-piperidine-1-carbonyl)-hexahydro-pyrrolo[3,4-c]pyrrole-2-carboxylic acid 4-trifluoromethoxy-benzyl ester;

1-[(3aR,6aR)-5-(1H-benzotriazole-5-carbonyl)-hexahydro-pyrrolo[3,4-c]pyrrol-2-yl]-3-(6-phenyl-pyridin-3-yl)-propan-1-one;

1-[(3aS,6aS)-5-(1H-benzotriazole-5-carbonyl)-hexahydro-pyrrolo[3,4-c]pyrrol-2-yl]-2-(2-isopropyl-phenoxy)-ethanone;

1-[(3aS,6aS)-5-(1H-benzotriazole-5-carbonyl)-hexahydro-pyrrolo[3,4-c]pyrrol-2-yl]-2-(2-trifluoromethyl-phenoxy)-ethanone;

1-[(3aS,6aS)-5-(1H-benzotriazole-5-carbonyl)-hexahydro-pyrrolo[3,4-c]pyrrol-2-yl]-2-(biphenyl-2-yloxy)-ethanone;

(E)-1-[(3aS,6aS)-5-((R)-4,5,6,7-Tetrahydro-1H-benzotriazole-5-carbonyl)-hexahydro-pyrrolo[3,4-c]pyrrol-2-yl]-3-(4-trifluoromethoxy-phenyl)-propenone;

1-((3aR,6aR)-5-((R)-4,5,6,7-tetrahydro-1H-benzo[d][1,2,3]triazole-5-carbonyl)hexahydropyrrolo[3,4-c]pyrrol-2(1H)-yl)-3-(4-(trifluoromethoxy)phenyl)propan-1-one;

1-[(3aS,6aS)-5-(1H-benzotriazole-5-carbonyl)-hexahydro-pyrrolo[3,4-c]pyrrol-2-yl]-2-(2-chloro-4-trifluoromethoxy-phenoxy)-ethanone;

1-[(3aS,6aS)-5-(1H-benzotriazole-5-carbonyl)-hexahydro-pyrrolo[3,4-c]pyrrol-2-yl]-2-(2-pyrrol-1-yl-phenoxy)-ethanone;

4-{2-[(3aS,6aS)-5-(1H-benzotriazole-5-carbonyl)-hexahydro-pyrrolo[3,4-c]pyrrol-2-yl]-2-oxo-ethoxy}-3-methoxy-benzonitrile;

4-{2-[(3aS,6aS)-5-(1H-benzotriazole-5-carbonyl)-hexahydro-pyrrolo[3,4-c]pyrrol-2-yl]-2-oxo-ethoxy}-benzonitrile;
1-[(3aS,6aS)-5-(1H-benzotriazole-5-carbonyl)-hexahydro-pyrrolo[3,4-c]pyrrol-2-yl]-2-phenoxy-ethanone;
2-{2-[(3aS,6aS)-5-(1H-benzotriazole-5-carbonyl)-hexahydro-pyrrolo[3,4-c]pyrrol-2-yl]-2-oxo-ethoxy}-5-trifluoromethoxy-benzonitrile;
1-((3aR,8aS)-2-(1H-benzo[d][1,2,3]triazole-5-carbonyl)octahydropyrrolo[3,4-d]azepin-6(7H)-yl)-2-(2-isopropyl-5-methylphenoxy)ethanone;
(1H-benzotriazol-5-yl)-[(3aS,6aS)-5-(6-trifluoromethoxy-1H-indole-2-carbonyl)-hexahydro-pyrrolo[3,4-c]pyrrol-2-yl]-methanone;
(1H-benzotriazol-5-yl)-[(3aS,6aS)-5-(5-trifluoromethoxy-1H-indole-2-carbonyl)-hexahydro-pyrrolo[3,4-c]pyrrol-2-yl]-methanone;
1-[trans-2-(1H-benzotriazole-5-carbonyl)-octahydro-pyrrolo[3,4-c]pyridin-5-yl]-3-(4-trifluoromethoxy-phenyl)-propan-1-one;
1-[trans-2-(1H-benzotriazol-5-ylmethyl)-octahydro-pyrrolo[3,4-c]pyridin-5-yl]-3-(4-trifluoromethoxy-phenyl)-propan-1-one;
1-((3aR,8aS)-2-(1H-benzo[d][1,2,3]triazole-5-carbonyl)octahydropyrrolo[3,4-d]azepin-6(7H)-yl)-3-(3-chloro-5-(trifluoromethyl)phenyl)propan-1-one;
1-((3aR,8aS)-2-(1H-benzo[d][1,2,3]triazole-5-carbonyl)octahydropyrrolo[3,4-d]azepin-6(7H)-yl)-3-(4-methoxy-2-(trifluoromethyl)phenyl)propan-1-one;
1-((3aR,8aS)-2-(1H-benzo[d][1,2,3]triazole-5-carbonyl)octahydropyrrolo[3,4-d]azepin-6(7H)-yl)-3-(2-cyclopropyl-phenyl)propan-1-one;
1-[(3aR,6aR)-5-(1H-benzotriazole-5-carbonyl)-1,3,3a,4,6,6a-hexahydropyrrolo[3,4-c]pyrrol-2-yl]-3-[3-methoxy-5-(trifluoromethoxy)phenyl]propan-1-one;
1-[(3aS,6aS)-5-(1H-benzotriazole-5-carbonyl)-hexahydro-pyrrolo[3,4-c]pyrrol-2-yl]-2-(2-isopropyl-5-methyl-phenoxy)-ethanone;
1-[(3aS,6aS)-5-(1H-benzotriazole-5-carbonyl)-hexahydro-pyrrolo[3,4-c]pyrrol-2-yl]-2-(2-bromo-4-trifluoromethoxy-phenoxy)-ethanone;
(1H-benzotriazol-5-yl)-[(3aR,6aR)-5-(4'-chloro-biphenyl-4-carbonyl)-hexahydro-pyrrolo[3,4-c]pyrrol-2-yl]-methanone;
4-{2-[(3aS,6aS)-5-(1H-benzotriazole-5-carbonyl)-hexahydro-pyrrolo[3,4-c]pyrrol-2-yl]-2-oxo-ethoxy}-3-isopropyl-benzonitrile;
2-(2-Acetyl-phenoxy)-1-[(3aS,6aS)-5-(1H-benzotriazole-5-carbonyl)-hexahydro-pyrrolo[3,4-c]pyrrol-2-yl]-ethanone;
4-{2-[(3aS,6aS)-5-(1H-benzotriazole-5-carbonyl)-hexahydro-pyrrolo[3,4-c]pyrrol-2-yl]-2-oxo-ethoxy}-5-isopropyl-2-methyl-benzonitrile;
(1H-benzotriazol-5-yl)-[(3aR,6aR)-5-(naphthalene-2-carbonyl)-hexahydro-pyrrolo[3,4-c]pyrrol-2-yl]-methanone;
(1H-benzotriazol-5-yl)-[(3aS,6aS)-5-(4-methoxy-naphthalene-2-carbonyl)-hexahydro-pyrrolo[3,4-c]pyrrol-2-yl]-methanone;
4-{2-[(3aS,6aS)-5-(1H-benzotriazole-5-carbonyl)-hexahydro-pyrrolo[3,4-c]pyrrol-2-yl]-2-oxo-ethoxy}-3-ethoxy-benzonitrile;
1-[(3aR,6aR)-5-(1H-benzotriazole-5-carbonyl)-hexahydro-pyrrolo[3,4-c]pyrrol-2-yl]-3-(3-fluoro-4-trifluoromethoxy-phenyl)-propan-1-one;
1-[(3aS,6aS)-5-(1H-benzotriazole-5-carbonyl)-hexahydro-pyrrolo[3,4-c]pyrrol-2-yl]-2-(4-chloro-2-isopropyl-phenoxy)-ethanone;
[(3aS,6aS)-5-(4'-Chloro-biphenyl-4-carbonyl)-hexahydro-pyrrolo[3,4-c]pyrrol-2-yl]-(R)-4,5,6,7-tetrahydro-1H-benzotriazol-5-yl-methanone;
1-[(3aS,6aS)-5-(1H-benzotriazole-5-carbonyl)-hexahydro-pyrrolo[3,4-c]pyrrol-2-yl]-3-(4-trifluoromethoxy-phenyl)-propan-1-one;
(1H-benzotriazol-5-yl)-[(3aS,6aS)-5-(4'-chloro-biphenyl-4-carbonyl)-hexahydro-pyrrolo[3,4-c]pyrrol-2-yl]-methanone;
1-[(3aS,6aS)-5-(1H-benzotriazole-5-carbonyl)-hexahydro-pyrrolo[3,4-c]pyrrol-2-yl]-2-[2-(tetrahydro-furan-2-yl)-phenoxy]-ethanone;
(1H-benzotriazol-5-yl)-[(3aR,6aR)-5-(4-methoxy-naphthalene-2-carbonyl)-hexahydro-pyrrolo[3,4-c]pyrrol-2-yl]-methanone;
1-[(3aS,6aS)-5-(1H-benzotriazole-5-carbonyl)-hexahydro-pyrrolo[3,4-c]pyrrol-2-yl]-2-(2-tert-butyl-phenoxy)-ethanone;
[(3aR,6aR)-5-(1H-benzotriazole-5-carbonyl)-hexahydro-pyrrolo[3,4-c]pyrrol-2-yl]-[trans-4-(4-chloro-phenyl)-cyclohexyl]-methanone;
1-[(3aR,6aR)-5-(1H-benzotriazole-5-carbonyl)-hexahydro-pyrrolo[3,4-c]pyrrol-2-yl]-3-(3-fluoro-4-trifluoromethyl-phenyl)-propan-1-one;
1-[(3aR,6aR)-5-(1H-benzotriazole-5-carbonyl)-hexahydro-pyrrolo[3,4-c]pyrrol-2-yl]-3-(2-fluoro-4-trifluoromethyl-phenyl)-propan-1-one;
1-[(3aS,6aS)-5-(1H-benzotriazole-5-carbonyl)-1,3,3a,4,6,6a-hexahydropyrrolo[3,4-c]pyrrol-2-yl]-2-(2-pyridin-3-ylphenoxy)ethanone;
4-[3-[(3aR,6aR)-5-(1H-benzotriazole-5-carbonyl)-1,3,3a,4,6,6a-hexahydropyrrolo[3,4-c]pyrrol-2-yl]-3-oxopropyl]-2-methyl-5-propan-2-ylbenzonitrile;
4-[3-[(3aR,6aR)-5-(1H-benzotriazole-5-carbonyl)-1,3,3a,4,6,6a-hexahydropyrrolo[3,4-c]pyrrol-2-yl]-3-oxopropyl]-3-propan-2-ylbenzonitrile;
[(3aR,6aR)-5-[1-(4-chlorophenyl)piperidine-4-carbonyl]-1,3,3a,4,6,6a-hexahydropyrrolo[3,4-c]pyrrol-2-yl]-(1H-benzotriazol-5-yl)methanone;
[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-(4-propan-2-yloxynaphthalen-2-yl)methanone;
[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-(4-propan-2-yloxyquinolin-2-yl)methanone;
1-[(3aR,6aR)-5-[(5R)-4,5,6,7-tetrahydro-1H-benzotriazole-5-carbonyl]-1,3,3a,4,6,6a-hexahydropyrrolo[3,4-c]pyrrol-2-yl]-3-[2-fluoro-4-(trifluoromethoxy)phenyl]propan-1-one;
4-[2-[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-2-oxoethoxy]-2-methyl-5-propan-2-ylbenzonitrile;
[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-[1-(2,2,2-trifluoroethoxy)isoquinolin-3-yl]methanone;
1-[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-2-(4-bromo-2-tert-butylphenoxy)ethanone;
1-[(3aS,6aS)-5-(1H-benzotriazole-5-carbonyl)-1,3,3a,4,6,6a-hexahydropyrrolo[3,4-c]pyrrol-2-yl]-2-(4-bromo-2-tert-butylphenoxy)ethanone;
4-[2-[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-2-oxoethoxy]-3-tert-butylbenzonitrile;

4-[2-[(3aS,6aS)-5-(1H-benzotriazole-5-carbonyl)-1,3,3a,4,6,6a-hexahydropyrrolo[3,4-c]pyrrol-2-yl]-2-oxoethoxy]-3-tert-butylbenzonitrile;
[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-[1-methyl-5-(trifluoromethoxy)indol-2-yl]methanone;
1-[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-2-[4-(trifluoromethoxy)phenoxy]ethanone;
[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-(1-ethoxyisoquinolin-3-yl)methanone;
1-[(3aS,6aS)-5-(1H-benzotriazole-5-carbonyl)-1,3,3a,4,6,6a-hexahydropyrrolo[3,4-c]pyrrol-2-yl]-2-(2-tert-butyl-4-methoxyphenoxy)ethanone;
((3aS,6aS)-5-(1H-benzo[d][1,2,3]triazole-5-carbonyl)hexahydropyrrolo[3,4-c]pyrrol-2(1H)-yl)(4-ethoxyquinolin-2-yl)methanone;
((3aS,6aS)-5-(1H-benzo[d][1,2,3]triazole-5-carbonyl)hexahydropyrrolo[3,4-c]pyrrol-2(1H)-yl)(4-(2,2,2-trifluoroethoxy)quinolin-2-yl)methanone;
((3aS,6aS)-5-(1H-benzo[d][1,2,3]triazole-5-carbonyl)hexahydropyrrolo[3,4-c]pyrrol-2(1H)-yl)(6-cyclobutoxy-5-(trifluoromethyl)pyridin-3-yl)methanone;
((3aS,6aS)-5-(1H-benzo[d][1,2,3]triazole-5-carbonyl)hexahydropyrrolo[3,4-c]pyrrol-2(1H)-yl)(5-bromo-6-(2-methoxyethoxy)pyridin-3-yl)methanone;
((3aS,6aS)-5-(1H-benzo[d][1,2,3]triazole-5-carbonyl)hexahydropyrrolo[3,4-c]pyrrol-2(1H)-yl)(5-bromo-6-(cyclopropylmethoxy)pyridin-3-yl)methanone;
((3aS,6aS)-5-(1H-benzo[d][1,2,3]triazole-5-carbonyl)hexahydropyrrolo[3,4-c]pyrrol-2(1H)-yl)(5-cyclopropyl-6-(2,2,2-trifluoroethoxy)pyridin-3-yl)methanone;
((3aS,6aS)-5-(1H-benzo[d][1,2,3]triazole-5-carbonyl)hexahydropyrrolo[3,4-c]pyrrol-2(1H)-yl)(6-(2,2,2-trifluoroethoxy)-5-(trifluoromethyl)pyridin-3-yl)methanone;
(1H-benzotriazol-5-yl)-{(3aS,6aS)-5-[4-(4-chloro-phenyl)-piperidine-1-carbonyl]-hexahydro-pyrrolo[3,4-c]pyrrol-2-yl}-methanone;
(1H-benzotriazol-5-yl)-{(3aS,6aS)-5-[4-(4-chloro-phenyl)-piperazine-1-carbonyl]-hexahydro-pyrrolo[3,4-c]pyrrol-2-yl}-methanone;
and pharmaceutically acceptable salts thereof.

Further particular examples of compounds of formula (I) as described herein are selected from
trans-3,5-dichlorobenzyl 2-(1H-benzo[d][1,2,3]triazole-5-carbonyl)hexahydro-1H-pyrrolo[3,4-c]pyridine-5 (6H)-carboxylate;
trans-3,5-dichlorobenzyl 2-(2-oxo-2,3-dihydrobenzo[d]oxazole-6-carbonyl)hexahydro-1H-pyrrolo[3,4-c]pyridine-5 (6H)-carboxylate;
(3aS,6aS)-5-(1H-benzotriazole-5-carbonyl)-hexahydro-pyrrolo[3,4-c]pyrrole-2-carboxylic acid 3-chloro-5-methanesulfonyl-benzyl ester;
(3aS,6aS)-5-(1H-benzotriazole-5-carbonyl)-hexahydro-pyrrolo[3,4-c]pyrrole-2-carboxylic acid 4-trifluoromethoxy-benzyl ester;
(E)-1-((3aR,6aR)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one;
1-((3aR,6aS)-5-(1H-benzo[d][1,2,3]triazole-5-carbonyl)hexahydropyrrolo[3,4-c]pyrrol-2(1H)-yl)-3-(4-(trifluoromethoxy)phenyl)propan-1-one;
1-[(3aR,6aR)-5-(1H-benzotriazole-5-carbonyl)-hexahydropyrrolo[3,4-c]pyrrol-2-yl]-3-(4-trifluoromethoxy-phenyl)-propan-1-one;
1-[(3aR,6aR)-5-(1H-benzotriazole-5-carbonyl)-hexahydropyrrolo[3,4-c]pyrrol-2-yl]-3-(4-trifluoromethyl-phenyl)-propan-1-one;
1-[(3aS,6aS)-5-(1H-benzotriazole-5-carbonyl)-hexahydropyrrolo[3,4-c]pyrrol-2-yl]-2-(4-chloro-2-isopropyl-5-methyl-phenoxy)-ethanone;
and pharmaceutically acceptable salts thereof.

Also further particular examples of compounds of formula (I) as described herein are selected from
trans-3,5-dichlorobenzyl 2-(1H-benzo[d][1,2,3]triazole-5-carbonyl)hexahydro-1H-pyrrolo[3,4-c]pyridine-5 (6H)-carboxylate;
trans-3,5-dichlorobenzyl 2-(2-oxo-2,3-dihydrobenzo[d]oxazole-6-carbonyl)hexahydro-1H-pyrrolo[3,4-c]pyridine-5 (6H)-carboxylate;
(3aS,6aS)-5-(1H-benzotriazole-5-carbonyl)-hexahydro-pyrrolo[3,4-c]pyrrole-2-carboxylic acid 3-chloro-5-methanesulfonyl-benzyl ester;
(3aS,6aS)-5-(1H-benzotriazole-5-carbonyl)-hexahydro-pyrrolo[3,4-c]pyrrole-2-carboxylic acid 4-trifluoromethoxy-benzyl ester;
(E)-1-((3aR,6aR)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one;
1-((3aR,6aS)-5-(1H-benzo[d][1,2,3]triazole-5-carbonyl) hexahydropyrrolo[3,4-c]pyrrol-2(1H)-yl)-3-(4-(trifluoromethoxy)phenyl)propan-1-one;
1-[(3aR,6aR)-5-(1H-benzotriazole-5-carbonyl)-hexahydropyrrolo[3,4-c]pyrrol-2-yl]-3-(4-trifluoromethoxy-phenyl)-propan-1-one;
1-[(3aR,6aR)-5-(1H-benzotriazole-5-carbonyl)-hexahydropyrrolo[3,4-c]pyrrol-2-yl]-3-(4-trifluoromethyl-phenyl)-propan-1-one;
1-[(3aS,6aS)-5-(1H-benzotriazole-5-carbonyl)-hexahydropyrrolo[3,4-c]pyrrol-2-yl]-2-(4-chloro-2-isopropyl-5-methyl-phenoxy)-ethanone;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

Compounds of general formula (I) can be synthesised from amine precursor 1 and appropriate reagents, using methods well known in the art.

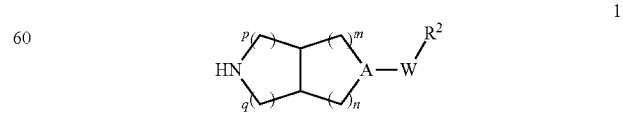

1

For instance, amine 1 is reacted with a suitable chloroformate ester of formula $R^1$—O—C(O)—Cl (2), or with an imidazole-1-carboxylate ester of formula (3A), or with a succinimidyl carbonate derivative of formula (3B), leading to a compound of formula (I) wherein Y is —OC(O)—.

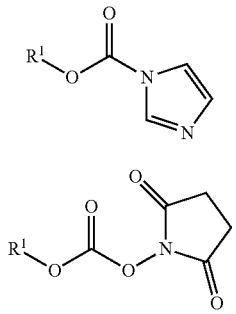

The reaction is performed in a suitable solvent such as dichloromethane, tetrahydrofuran, N,N-dimethylformamide, acetonitrile, acetone, water, or mixtures thereof, in the presence or not of a base, e. g., triethylamine, diisopropylethylamine, pyridine, potassium hydrogencarbonate, potassium carbonate, at temperatures between 0° C. and the boiling point of the solvent or solvent mixture.

Chloroformate esters 2 are commercially available or can be synthesised from the corresponding alcohol of formula $R^1$—OH, by reaction with phosgene or a phosgene equivalent (e. g., diphosgene, triphosgene), as described in the literature.

Imidazole-1-carboxylate esters 3A are synthesised from the corresponding alcohols of formula $R^1$—OH, by reaction with 1,1'-carbonyldiimidazole. The reaction is performed at room temperature, in a solvent such as dichloromethane, tetrahydrofuran or acetonitrile. The imidazole-1-carboxylate esters 3A are typically not isolated but directly reacted with amines 1 as described above.

Succinimidyl carbonate derivatives 3B are synthesised from the corresponding alcohols of formula $R^1$—OH, by reaction with N,N'-disuccinimidyl carbonate. The reaction is performed at room temperature, in a solvent such as dichloromethane, tetrahydrofuran, or acetonitrile, optionally in the presence of a base, e. g., triethylamine. The succinimidyl carbonate derivatives 3B are typically not isolated but directly reacted with amines 1 as described above.

Alcohols of formula $R^1$—OH are commercially available or can be produced by methods described herein or known in the art.

Alternatively, amine 1 is reacted with a suitable N-(chlorocarbonyl)amine of formula $R^1$—N($R^7$)—C(O)—Cl (4), or, in the case where $R^7$ is H, with an isocyanate of formula $R^1$—NCO (5), leading to compounds of formula (I) wherein Y is —N$R^7$C(O)—.

N-(Chlorocarbonyl)amines (4) are synthesised from the corresponding amines of formula $R^1$—N($R^7$)H by reaction with phosgene or a phosgene equivalent, as described in the literature.

Isocyanates 5 are commercially available or can be prepared from the corresponding amines of formula $R^1$—NH$_2$, by reaction with phosgene or a phosgene equivalent (e. g., diphosgene, triphosgene, 1,1'-carbonyldiimidazole), as described in the literature.

Alternatively, amine 1 is reacted with a suitable carboxylic acid of formula $R^1$—COOH (6) leading to a compound of formula (I), wherein Y is —C(O)—. The reaction is performed in the presence of a coupling agent such as 1,1'-carbonyldiimidazole, N,N'-dicyclohexylcarbodiimide, 1-(3-dimethyl aminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 1 can also be reacted with suitable acylating reagents such as acyl chlorides of formula $R^1$—COCl (7) to lead to compounds of formula (I) wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Carboxylic acids (6) and acyl halides (7) are commercially available or can be prepared as described herein or in the literature.

Alternatively, amine 1 is reacted with a suitable sulfonyl chloride of formula $R^1$—SO$_2$Cl (8), leading to compounds of formula (I) wherein Y is —S(O$_2$)—. The reaction is performed in a suitable solvent such as dichloromethane, tetrahydrofuran, N,N-dimethylformamide, acetonitrile, acetone, water, or mixtures thereof, in the presence of a base, e. g., triethylamine, diisopropylethylamine, pyridine, potassium hydrogencarbonate, potassium carbonate, at temperatures between 0° C. and the boiling point of the solvent or solvent mixture.

Sulfonyl chlorides (8) are commercially available or can be synthesised as described herein or in the literature.

Alternatively, amine 1 is reacted with a suitable chlorooxadiazole reagent of general formula 9, or with oxadiazolone reagent 10, leading to a compound of formula (I), wherein Y is

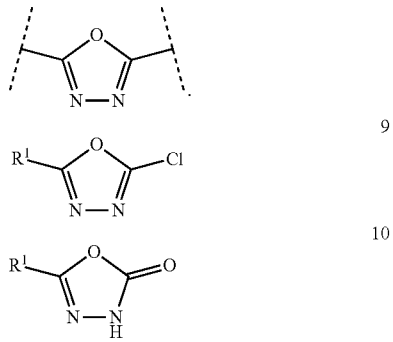

In the case where compounds of formula (I) are produced from amine 1 and chloro-oxadiazole 9, the reaction is performed in the presence of a base, e. g., potassium carbonate, triethylamine, or 1,8-diazabicyclo[5.4.0]undec-7-ene, in a solvent such as toluene, ethanol, N,N-dimethylformamide, or 1,4-dioxane at temperatures between 20° C. and 150° C.

In the case where compounds of formula (I) are produced from amine 1 and oxadiazolone 10, the reaction is performed in the presence of a coupling agent, e. g. benzotriazol-1-yloxy-tris-(dimethylamino)-phosphonium hexafluorophosphate and a base, e. g., diisopropylethylamine or 4-methylmorpholine, in a solvent such as N,N-dimethylformamide, at temperatures between 20° C. and 100° C. as described in the literature.

Oxadiazolones 10 are commercially available or can be produced as described in the literature.

Chloro-oxadiazoles 9 are commercially available or can be produced from the corresponding oxadiazolones, by reaction with a suitable halogenating reagent, e. g. phosphorus oxychloride and/or phosphorus pentachloride, at temperatures between 60° C. and 120° C.

Alternatively, amine 1 is reacted with a suitable halothiadiazole reagent of general formula 11 (X=Cl or Br), or with thiadiazolethione reagent 12, leading to compounds of (I) wherein Y is

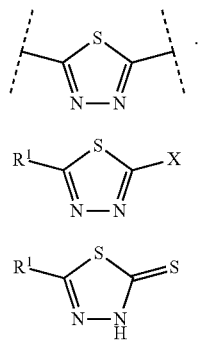

In the case where compounds of formula (I) are produced from amine 1 and halo-thiadiazole 11, the reaction is performed in the presence of a base, e. g. potassium carbonate, triethylamine or 1,8-diazabicyclo[5.4.0]undec-7-ene, in a solvent such as toluene, ethanol, N,N-dimethylformamide or 1,4-dioxane, at temperatures between 20° C. and 150° C.

In the case where compounds of formula (I) are produced from amine 1 and thiadiazolethione 12, the reaction is performed in a solvent such as ethanol or N,N-dimethylformamide at temperatures between 20° C. and 100° C. as described in the literature.

Thiadiazolethiones 12 are commercially available or can be produced as described in the literature.

Halo-thiadiazoles 11 are commercially available or can be produced as described in the literature.

Amines of general formula 1 are synthesised from suitably protected precursors 13.

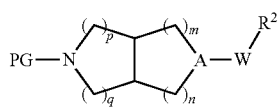

Suitable protective groups (PG) are tert-butoxycarbonyl, benzyloxycarbonyl and substituted benzyloxycarbonyl such as 3,5-dichloro benzyloxycarbonyl. The deprotection of intermediates 13 can be performed using methods and reagents known in the art.

For instance, in the case where PG is optionally substituted benzyloxycarbonyl, the deprotection may be performed by hydrogenation at pressures between 1 bar and 100 bar, in the presence of a suitable catalyst such as palladium on activated charcoal, at temperatures between 20° C. and 150° C. in solvents such as methanol or ethanol.

Alternatively, in the case where PG is tert-butoxycarbonyl, the deprotection may be performed in the presence of a suitable acid, e. g, hydrochloric acid or trifluoroacetic acid, in a solvent such as water, 2-propanol, dichloromethane, or 1,4-dioxane at temperatures between 0° C. and 30° C.

Carbamates 13, wherein A is N are represented by general structure 13A.

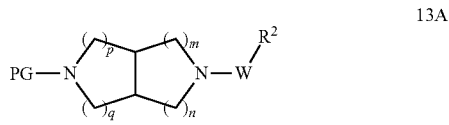

PG is a suitable protective group, e. g., tert-butoxycarbonyl, benzyloxycarbonyl and substituted benzyloxycarbonyl such as 3,5-dichloro benzyloxycarbonyl.

Carbamates 13A can be produced from amine precursors of general formula 14 by reaction with appropriate reagents, using methods known in the art.

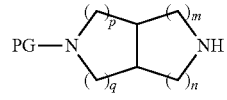

For instance, 14 is reacted with alkylating agents of general formula X—CR$^3$R$^4$—R$^2$ (15) where X is a leaving group such as Cl, Br, I, or OSO$_2$CH$_3$, leading to 13A, wherein W is —CR$^3$R$^4$—. This reaction is performed in a solvent such as tetrahydrofuran or N,N-dimethylformamide, in the presence of a base, e. g. triethylamine or potassium carbonate, at temperatures between 0° C. and 100° C.

Alternatively, for compounds of formula 13A, wherein W is —CR$^3$R$^4$—, R$^4$ is hydrogen, alkyl or cycloalkyl, and R$^3$ is H, amine 14 is reacted with aldehydes or ketones of general formula R$^4$—C(O)—R$^2$ (16) in a reductive amination reaction, leading to 13A. This reaction is performed in the presence of a suitable reducing agent, e. g., sodium borohydride or sodium triacetoxyborohydride, in a solvent such as methanol, acetic acid, tetrahydrofuran, 1,2-dichloroethane or mixtures thereof, at temperatures between 0° C. and 50° C.

Alternatively, amine 14 is reacted with a suitable carboxylic acid of formula R$^2$—COOH (17), leading to compounds of formula 13A, wherein W is —C(O)—. The reaction is performed in the presence of a coupling agent such as 1,1'-carbonyldiimidazole, N,N'-dicyclohexylcarbodiimide, 1-(3-dimethyl aminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Alternatively, amine 14 is reacted with a suitable sulfonyl chloride of formula R$^2$—SO$_2$Cl (18), leading to compounds of formula 13A, wherein W is —S(O$_2$)—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Alternatively, amine 14 is reacted with a suitable N-(chlorocarbonyl)amine of formula $R^2$—N($R^6$)—C(O)—Cl (19) leading to compounds of formula 13A, wherein W is —C(O)—$NR^6$—, or with an isocyanate of formula $R^2$—NCO (20), leading to compounds of formula 13A, wherein W is —C(O)—$NR^6$— and $R^6$ is H.

Alternatively, amine 14 is reacted with phosgene or phosgene equivalent (diphosgene, triphosgene) in the presence of a base (e. g., pyridine, triethylamine) in a solvent such as dichloromethane or tetrahydrofuran, to provide the corresponding N-(chlorocarbonyl)amine of formula 21, which is then reacted with amine of formula HN($R^6$)$R^2$ (22), in the presence of a base such as triethylamine or diisopropylethylamine, in a solvent such as dichloromethane, tetrahydrofuran, or N,N-dimethylformamide, leading to compounds of formula 13A, wherein W is —C(O)—$NR^6$—.

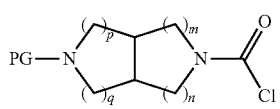

21

Alternatively, amine 14 is reacted with phosgene or a phosgene equivalent (diphosgene, triphosgene) in the presence of a base (e. g., pyridine, triethylamine), in a solvent such as dichloromethane or tetrahydrofuran, to the corresponding N-(chlorocarbonyl)amine of formula 21, which is then reacted with amines of formula H-O, H-P, H-Q, H-R, H-T, H-U, H-V, H-X, H-AA or H-AF, in the presence of a base such as triethylamine or diisopropylethylamine, in a solvent such as dichloromethane, tetrahydrofuran, or N,N-dimethylformamide, leading to compounds of formula 13A, wherein W is —C(O)— and $R^2$ is O, P, Q, R, T, U, V, X, AA or AF.

N-(Chlorocarbonyl)amines 19 are synthesised from the corresponding amines 22 by reaction with phosgene or a phosgene equivalent (diphosgene, triphosgene) as described in the literature.

Isocyanates 20 are commercially available or can be prepared from the corresponding amines of formula $R^2$—NH$_2$, by reaction with phosgene or a phosgene equivalent (e. g., diphosgene, triphosgene, 1,1'-carbonyldiimidazole) as described in the literature.

Amines 14, alkylating agents 15, aldehydes/ketones 16, carboxylic acids 17, sulfonyl chlorides 18, and amines 22 are commercially available or can be synthesised as described in the literature.

Carbamates 13 wherein A is $CR^5$ and $R^5$ is H are represented by general formula 13B, wherein PG is a suitable protective group, e. g tert-butoxycarbonyl, benzyloxycarbonyl and substituted benzyloxycarbonyl such as 3,5-dichloro benzyloxycarbonyl.

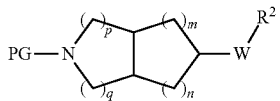

13B

Compound 13B, wherein W is —$NR^6$—, is produced from ketone 23 by reaction with an amine of formula HN($R^6$)$R^2$ (22) in the presence of a suitable reducing agent, e. g. sodium borohydride or sodium triacetoxyborohydride, in a solvent such as methanol, acetic acid, tetrahydrofuran, 1,2-dichloroethane, or mixtures thereof, at temperatures between 0° C. and 50° C.

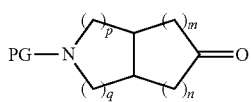

23

Ketones 23 and amines 22 are commercially available or can be prepared as described in the literature.

Compound 13B, wherein W is —O— or —S—, is produced from alcohol 24 using methods and reagents known in the art.

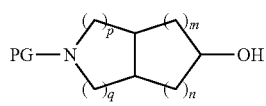

24

For instance, alcohol 24 is reacted at room temperature with phenol HO—$R^2$ or thiophenol HS—$R^2$ in the presence of triphenylphosphine and an dialkylazodicarboxylate, e. g. diisopropylazodicarboxylate or diethylazodicarboxylate, in a solvent such as toluene, dichloromethane, or tetrahydrofuran, leading to 13B, wherein W is —O— or —S—.

In the case wherein W is —O— or and $R^2$ is B, compounds of formula 13B can also be produced from alcohol 24 in a three-step sequence. Therefore, 24 is reacted in step 1 at room temperature with 2,4-dihydroxybenzoic acid alkyl ester in the presence of triphenylphosphine and an dialkylazodicarboxylate, e. g. diisopropylazodicarboxylate or diethylazodicarboxylate, in a solvent such as toluene, dichloromethane or tetrahydrofuran, converting the hydroxy group into a 3-hydroxy-4-(alkoxycarbonyl)-phenyl ether substituent. This is hydrolysed in step 2 to the corresponding 3-hydroxy-4-carboxyphenyl group, using a base such as sodium hydroxide in water and in the presence of co-solvents such as tetrahydrofuran and/or methanol or ethanol. In step 3, the 3-hydroxy-4-carboxyphenyl ether intermediate can be subjected to a Curtius rearrangement as described in the literature, e. g. by using diphenylphorphoryl azide, in a solvent such as toluene, in the presence of a base, e. g., triethylamine, at temperatures between 60° C. and 110° C., leading to the corresponding 2-oxo-2,3-dihydro-benzoox-azol-6-yl ether 13B, wherein W is —O— and $R^2$ is B.

Alternatively, conversion of alcohol 24 to the corresponding methanesulfonate using methanesulfonyl chloride in the presence of a base, e. g. triethylamine, in a solvent such as dichloromethane or tetrahydrofuran, at temperatures between −20° C. and +30° C., and treatment of the methanesulfonate intermediate with phenol HO—$R^2$ or thiophenol HS—$R^2$ in the presence of a base, e. g., potassium carbonate, in a solvent such as N,N-dimethylformamide or acetonitrile, at temperatures between 20° C. and 100° C., leads to 13B, wherein W is —O— or —S—.

Compound 13B, wherein W is —SO$_2$—, is produced from compound 13B, wherein W is —S— by oxidation with a suitable reagent, e. g., hydrogen peroxide or 3-chloroperbenzoic acid, in a solvent such as formic acid, acetic acid, or dichloromethane, at temperatures between 0° C. and 50° C.

Alcohols 24 are produced from ketones 23 using a suitable reducing agent, e. g., sodium borohydride, in a solvent such as methanol, at temperatures between 0° C. and 50° C.

Carbamates 13 wherein A is $CR^5$, $R^5$ is H, and W is $-C(O)-N(R^6)-$ are represented by general formula 13C, wherein $R^{12}$ is $N(R^6)R^2$, O, P, Q, R, T, U, V, X, AA or AF.

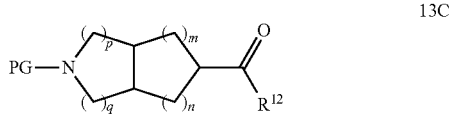

13C

Amide 13C is produced from carboxylic acid 25 by coupling reaction with an amine of formula $HN(R^6)R^2$ (22), H-O, H-P, H-Q, H-R, H-T, H-U, H-V, H-X, H-AA or H-AF.

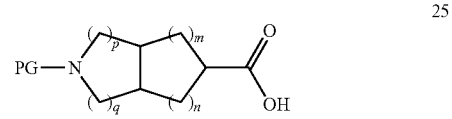

25

The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Carboxylic acids 25 are commercially available or can be produced as described in the literature.

Compounds of formula (I), wherein A is N can be produced from amine precursors of general formula 26 by reaction with appropriate reagents, using methods known in the art.

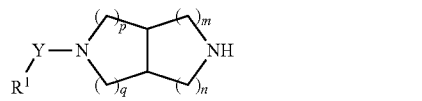

26

For instance, an amine of formula 26 is reacted with alkylating agents of general formula $X-CR^3R^4-R^2$ (15) where X is a leaving group such as Cl, Br, I, or $OSO_2CH_3$, leading to compounds of formula (I), wherein A is N and W is $-CR^3R^4-$. This reaction is performed in a solvent such as tetrahydrofuran or N,N-dimethylformamide, in the presence of a base, e. g., triethylamine or potassium carbonate, at temperatures between 0° C. and 100° C.

Alternatively, an amine of formula 26 is reacted with aldehydes or ketones of general formula $R^4-C(O)-R^2$ (16) in a reductive amination reaction, leading to compounds of formula (I) wherein A is N, W is $-CR^3R^4-$, $R^4$ is hydrogen, alkyl or cycloalkyl, and $R^3$ is H. This reaction is performed in the presence of a suitable reducing agent, e. g. sodium borohydride or sodium triacetoxyborohydride, in a solvent such as methanol, acetic acid, tetrahydrofuran, 1,2-dichloroethane or mixtures thereof, at temperatures between 0° C. and 50° C.

Alternatively, amine 26 is reacted with a suitable carboxylic acid of formula $R^2-COOH$ (17), leading to compounds of formula (I) wherein A is N and W is $-C(O)-$. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Alternatively, amine 26 is reacted with a suitable sulfonyl chloride of formula $R^2-SO_2Cl$ (18), leading to (I) wherein A is N and W is $-S(O_2)-$. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Alternatively, amine of formula 26 is reacted with a suitable N-(chlorocarbonyl)amine of formula $R^2-N(R^6)-C(O)-Cl$ (19) leading to compounds of formula (I), wherein A is N and W is $C(O)-NR^6$, or with isocyanate $R^2-NCO$ (20), leading to compounds of formula (I), wherein A is N, W is $-C(O)-NR^6-$ and $R^6$ is H.

Alternatively, amine 26 is reacted with phosgene or a phosgene equivalent (diphosgene, triphosgene) in the presence of a base (e. g., pyridine, triethylamine), in a solvent such as dichloromethane or tetrahydrofuran, to the corresponding N-(chlorocarbonyl)amine of formula 27, which is then reacted with an amine of formula H-O, H-P, H-Q, H-R, H-T, H-U, H-V, H-X, H-AA or H-AF in the presence of a base such as triethylamine or diisopropylethylamine, in a solvent such as dichloromethane, tetrahydrofuran, or N,N-dimethylformamide, leading to compounds of formula (I), wherein A is N, W is $-C(O)-$ and $R^2$ is O, P, Q, R, T, U, V, X, AA or AF.

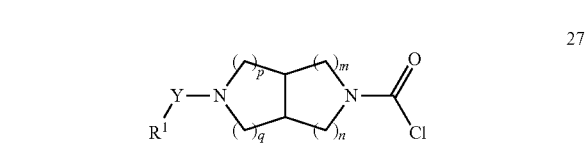

27

Amines 26 can be synthesised from their tert-butyl carbamate derivatives of formula 28 by carbamate deprotection. The deprotection may be performed in the presence of a suitable acid, e. g, hydrochloric acid or trifluoroacetic acid, in a solvent such as water, 2-propanol, dichloromethane, or 1,4-dioxane, at temperatures between 0° C. and 30° C.

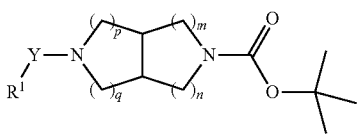

tert-Butyl carbamates 28 can be synthesised from amine precursors of formula 29 and appropriate reagents, using methods well known in the art.

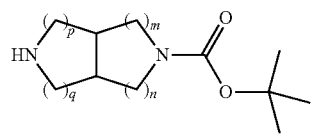

For instance, an amine of formula 29 is reacted with a suitable chloroformate ester of formula $R^1$—O—C(O)—Cl (2), or with an imidazole-1-carboxylate ester of formula (3A) or with a succinimidyl carbonate derivative of formula (3B), leading to compounds of formula 28, wherein Y is —OC(O)—. The reaction is performed in a suitable solvent such as dichloromethane, tetrahydrofuran, N,N-dimethylformamide, acetonitrile, acetone, water, or mixtures thereof, in the presence or not of a base, e. g. triethylamine, diisopropylethylamine, pyridine, potassium hydrogencarbonate, potassium carbonate, at temperatures between 0° C. and the boiling point of the solvent or solvent mixture.

Alternatively, an amine of formula 29 is reacted with a suitable N-(chlorocarbonyl)amine of formula $R^1$—N($R^7$)—C(O)—Cl (4) leading to compounds of formula 28, wherein Y is —$NR^7$C(O)—, or with an isocyanate of formula $R^1$—NCO (5) leading to compounds of formula 28, wherein Y is —$NR^7$C(O)— and $R^7$ is H.

Alternatively, amine 29 is reacted with a suitable carboxylic acid of formula $R^1$—COOH (6) leading to compounds of formula 28, wherein Y is —C(O)—. The reaction is performed in the presence of a coupling agent such as 1,1'-carbonyldiimidazole, N,N'-dicyclohexylcarbodiimide, 1-(3-dimethyl aminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tri s-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 29 can also be reacted with suitable acylating reagents, such as acyl chlorides of formula $R^1$—COCl (7) to provide compounds of formula 28, wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 29 is reacted with a suitable sulfonyl chloride, of formula $R^1$—$SO_2$Cl (8), leading to compounds of formula 28, wherein Y is —S($O_2$)—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Alternatively, amine 29 is reacted with a suitable chlorooxadiazole reagent of general formula 9, or with oxadiazolone reagent 10, leading to compounds of formula 28, wherein Y is

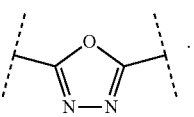

In the case where 28 is produced from amine 29 and chloro-oxadiazole 9, the reaction is performed in the presence of a base, e. g. potassium carbonate, triethylamine, or 1,8-diazabicyclo[5.4.0]undec-7-ene, in a solvent such as toluene, ethanol, N,N-dimethylformamide, or 1,4-dioxane, at temperatures between 20° C. and 150° C.

In the case where 28 is produced from amine 29 and oxadiazolone 10, the reaction is performed in the presence of a coupling agent, e. g., benzotriazol-1-yl-oxy-tris-(dimethylamino)-phosphonium hexafluorophosphate, and a base, e. g. diisopropylethylamine or 4-methylmorpholine, in a solvent such as N,N-dimethylformamide, at temperatures between 20° C. and 100° C., as described in the literature).

Alternatively, amine 29 is reacted with a suitable halothiadiazole reagent of general formula 11 (X is Cl or Br), or with thiadiazolethione reagent 12, leading to compounds of formula 28, wherein Y is

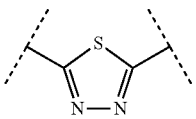

In the case where 28 is produced from amine 29 and halo-thiadiazole 11, the reaction is performed in the presence of a base, e. g. potassium carbonate, triethylamine, or 1,8-diazabicyclo[5.4.0]undec-7-ene, in a solvent such as toluene, ethanol, N,N-dimethylformamide, or 1,4-dioxane, at temperatures between 20° C. and 150° C.

In the case where 28 is produced from amine 29 and thiadiazolethione 12, the reaction is performed in a solvent such as ethanol or N,N-dimethylformamide, at temperatures between 20° C. and 100° C., as described in the literature.

Alternatively, amine 29 is acylated with a haloalkanoyl halide, e. g., bromoacetyl chloride, in the presence of a base, e. g. triethylamine, in a solvent such as dichloromethane or tetrahydrofuran, at temperatures between −78° C. and +20° C., leading to the corresponding haloalkanamide intermediate, which in the presence of a base, e. g. potassium carbonate or caesium carbonate, in a solvent such as N,N-dimethylformamide undergoes a nucleophilic substitution reaction with a substituted phenol, leading to compounds of formula 28, wherein Y is —C(O)— and $R^1$ is substituted phenoxyalkyl.

Amines of formula 29 are commercially available or can be produced as described in the literature.

Compounds of formula (I), wherein A is $CR^5$ and W is -C(O)—N($R^6$)— can be produced from carboxylic acid precursors of general formula 30 by reaction with appropriate amine reagents of general formula $HN(R^6)R^2$, H-O, H-P, H-Q, H-R, H-T, H-U, H-V, H-X, H-AA or H-AF using methods known in the art.

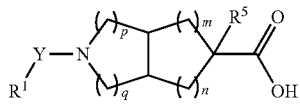

For instance, this reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Carboxylic acids 30 can be produced from the corresponding ester precursors 31, wherein $R^a$ is lower alkyl, e. g. methyl or ethyl, using methods and reagents known in the art. For instance, the reaction is performed in the presence of a base, e. g., potassium hydroxide, sodium hydroxide, or lithium hydroxide, in solvents such as water, methanol, ethanol, tetrahydrofuran, or mixtures thereof, at temperatures between 20° C. and 100° C.

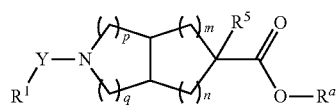

Compounds of formula 31 can be synthesised from amine precursors of formula 32 and appropriate reagents, using methods well known in the art.

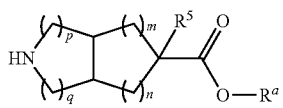

For instance, an amine of formula 32 is reacted with a suitable chloroformate ester of formula R'—O—C(O)—Cl (2), or with an imidazole-1-carboxylate ester of formula 3, leading to compounds of formula 31, wherein Y is —OC(O)—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Alternatively, an amine of formula 32 is reacted with a suitable N-(chlorocarbonyl)amine of formula $R^1$—N($R^7$)—C(O)—Cl (4) leading to compounds of formula 31, wherein Y is —$NR^7C(O)$—, or with an isocyanate of formula $R^1$—NCO (5) leading to leading to compounds of formula 31, wherein Y is —$NR^7C(O)$— and $R^7$ is H.

Alternatively, amine 32 is reacted with a suitable carboxylic acid of formula $R^1$—COOH (6) leading to compounds of formula 31, wherein Y is —C(O)—. The reaction is performed in the presence of a coupling agent such as 1,1'-carbonyldiimidazole, N,N'-dicyclohexylcarbodiimide, 1-(3-dimethyl aminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tri s-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 32 can also be reacted with suitable acylating reagents, such as acyl chlorides of formula $R^1$—COCl (7) to lead to compounds of formula 31, wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 32 is reacted with a suitable sulfonyl chloride of formula $R^1$—$SO_2Cl$ (8), leading to compounds of formula 31, wherein Y is —$S(O_2)$—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Alternatively, amine 32 is reacted with a suitable chlorooxadiazole reagent of general formula 9, or with oxadiazolone reagent 10, leading to compounds of formula 31, wherein Y is

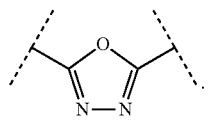

In the case where 31 is produced from amine 32 and chloro-oxadiazole 9, the reaction is performed in the presence of a base, e. g. potassium carbonate, triethylamine, or 1,8-diazabicyclo[5.4.0]undec-7-ene, in a solvent such as toluene, ethanol, N,N-dimethylformamide, or 1,4-dioxane, at temperatures between 20° C. and 150° C.

In the case where 31 is produced from amine 32 and oxadiazolone 10, the reaction is performed in the presence of a coupling agent, e. g. benzotriazol-1-yl-oxy-tris-(dimethylamino)-phosphonium hexafluorophosphate, and a base, e. g. diisopropylethylamine or 4-methylmorpholine, in a solvent such as N,N-dimethylformamide, at temperatures between 20° C. and 100° C., as described in the literature.

Alternatively, amine 32 is reacted with a suitable halothiadiazole reagent of general formula 11 (X is Cl or Br), or with thiadiazolethione reagent 12, leading to compounds of formula 31, wherein Y is

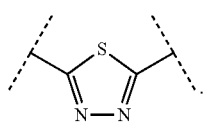

In the case where 31 is produced from amine 32 and halo-thiadiazole 11, the reaction is performed in the presence of a base, e. g. potassium carbonate, triethylamine, or 1,8-diazabicyclo[5.4.0]undec-7-ene, in a solvent such as toluene, ethanol, N,N-dimethylformamide or 1,4-dioxane, at temperatures between 20° C. and 150° C.

In the case where 31 is produced from amine 32 and thiadiazolethione 12, the reaction is performed in a solvent such as ethanol or N,N-dimethylformamide, at temperatures between 20° C. and 100° C., as described in the literature.

Amines of general formula 32 are synthesised from suitably protected precursors 33.

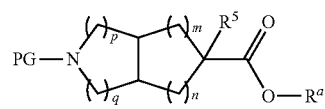

Suitable protective groups (PG) are tert-butoxycarbonyl or benzyloxycarbonyl. The deprotection of intermediates 33 can be performed using methods and reagents known in the art.

For instance, in the case where PG is benzyloxycarbonyl, the deprotection may be performed by hydrogenation at pressures between 1 bar and 100 bar, in the presence of a suitable catalyst such as palladium on activated charcoal, at temperatures between 20° C. and 150° C., in solvents such as methanol or ethanol.

Alternatively, in the case where PG is tert-butoxycarbonyl, the deprotection may be performed in the presence of a suitable acid, e. g, hydrochloric acid or trifluoroacetic acid, in a solvent such as water, 2-propanol, dichloromethane, or 1,4-dioxane, at temperatures between 0° C. and 30° C.

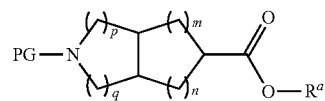

Substituents $R^5$ may be introduced starting from ester precursor 34, using suitable reagents and methods known in the art. For instance, 34 is reacted with alkylating agents of general formula $R^5$—X wherein $R^5$ is alkyl or cycloalkyl and X is a leaving group such as Cl, Br, I, or $OSO_2CH_3$, leading to 33, wherein $R^5$ is alkyl or cycloalkyl. This reaction is performed in the presence of a suitable base, e. g., sodium hydride, lithium diisopropylamide, lithium bis(trimethylsilyl)amide, or lithium pyrrolidide, in a solvent such as tetrahydrofuran or toluene, at temperatures between −78° C. and +50° C.

Esters 34, wherein $R^a$ is methyl or ethyl, are produced from carboxylic acids 25, using methods and reagents known in the art. For instance, 25 alkylated with methyl iodide or ethyl bromide, in the presence of a base, e. g., potassium carbonate, in a solvent such as N,N-dimethylformamide, at −20° C. and +30° C., leading to the methyl or ethyl ester 34, respectively.

Also an embodiment of the present invention is a process to prepare a compound of formula (I) as defined above comprising the reaction of a compound of formula (II) in the presence of a compound of formula (III);

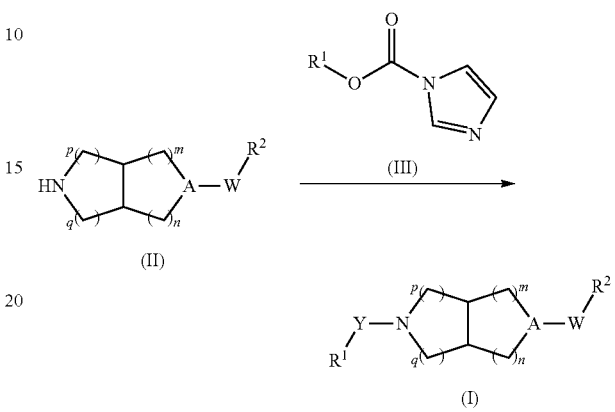

wherein $R^1$, $R^2$, A, W, m, n, p and q are as defined above, Y is —OC(O)—.

In particular, in the presence of a coupling agent such as O-(7-azabenzotriazol-1-yl)-N,N,N',N'-tetramethyluronium hexafluoro-phosphate, in a solvent such as N,N-dimethylformamide, in the presence of a base such as 4-methylmorpholine and at a temperature comprised between −78° C. and reflux, particularly between −10° C. and room temperature.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/ systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

In a particular embodiment, the compounds of formula (I) or their pharmaceutically acceptable salts and esters can be used for the treatment or prophylaxis of organ or skin fibrosis.

In another embodiment, the fibrotic disease is renal tubulo-interstitial fibrosis or glomerulosclerosis.

In another embodiment, the fibrotic disease is non-alcoholic liver steatosis, liver fibrosis or liver cirrhosis.

In another embodiment, the fibrotic disease is idiopathic pulmonary fibrosis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like.

Metabolic conditions include, but are not limited to, obesity and diabetes.

In another embodiment, the compounds of formula (I) or their pharmaceutically acceptable salts and esters can be used for the treatment or prophylaxis of cholestatic or non-cholestatic chronic pruritus.

The present invention also relates to the use of a compound according to formula (I) as described herein for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the treatment or prophylaxis of renal conditions, liver conditions and fibrotic diseases.

A particular embodiment of the present invention is a compound according to formula (I) as described herein for the treatment or prophylaxis of renal conditions, liver conditions, inflammatory conditions, conditions of the nervous system, fibrotic diseases and acute and chronic organ transplant rejection.

A particular embodiment of the present invention is a compound according to formula (I) as described herein for the treatment or prophylaxis of renal conditions, liver conditions and fibrotic diseases.

The present invention also relates to the use of a compound according to formula (I) as described herein for the preparation of a medicament for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the preparation of a medicament for the treatment or prophylaxis of renal conditions, liver conditions and fibrotic diseases.

Also an object of the invention is a method for the treatment or prophylaxis of renal conditions, liver conditions, inflammatory conditions, conditions of the nervous system, fibrotic diseases and acute and chronic organ transplant rejection, which method comprises administering an effective amount of a compound according to formula (I) as described herein.

Also an object of the invention is a method for the treatment or prophylaxis of renal conditions, liver conditions and fibrotic diseases, which method comprises administering an effective amount of a compound according to formula (I) as described herein.

In a particular embodiment, the renal condition is selected from the group consisting of acute kidney injury, chronic kidney disease, diabetic nephropathy, acute kidney transplant rejection and chronic allograft nephropathy.

In another particular embodiment, the renal condition is acute kidney injury.

In another particular embodiment, the renal condition is chronic kidney disease.

In a further particular embodiment, the renal condition is diabetic nephropathy.

In another particular embodiment, the renal condition is acute kidney transplant rejection.

In another particular embodiment, the renal condition is chronic allograft nephropathy.

In a particular embodiment, the liver condition is acute and chronic liver transplant rejection In a particular embodiment, the inflammatory condition is arthritis.

In a particular embodiment, the condition of the nervous system is neuropathic pain.

In another embodiment, the fibrotic disease is encapsulating peritonitis.

In another embodiment, the fibrotic disease is idiopathic pulmonary fibrosis.

In another embodiment, the fibrotic disease is non-alcoholic liver steatosis, liver fibrosis or liver cirrhosis.

Also an embodiment of the present invention are compounds of formula (I) as described herein, when manufactured according to any one of the described processes.

Assay Procedures

Production of Human Full Length ATX, with and without His Tag

Autotaxin (ATX-ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification:

20 liter of culture supernatant were conditioned for ultra-filtration by adding Brij 35 to a final concentration of 0.02% and by adjusting the pH to 7.0 using 1 M HCl. Then the supernatant was first microfiltred through a 0.2 µm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$.

The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane.

The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylamino]-ethoxy}-hydroxy-phosphoryloxy)-2-hydroxy-propyl ester (Ferguson et al., Org Lett 2006, 8 (10), 2023) was labeled with MR121 fluorophore (CAS 185308-24-1, 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:

Assay buffer (50 mM Tris-HCl, 140 mM NaCl, 5 mM KCl, 1 mM $CaCl_2$, 1 mM $MgCl_2$, 0.01% Triton-X-100, pH 8.0;

ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;

MR121 substrate solution: MR121 substrate stock solution (800 µM MR121 substrate in DMSO), diluted to 2-5× final concentration in assay buffer.

Test compounds (10 mM stock in DMSO, 8 µL) were obtained in 384 well sample plates (Corning Costar #3655) and diluted with 8 µL DMSO. Row-wise serial dilutions were made by transferring 8 µL cpd solution to the next row up to row O. The compound and control solutions were mixed five times and 2 µL were transferred to 384 well assay plates (Corning Costar #3702). Then, 15 µL of 41.7 nM ATX solution was added (30 nM final concentration), mixed five times and then incubated for 15 minutes at 30° C. 10 µL of MR121 substrate solution was added (1 µM final concentration), mixed 30 times and then incubated for 15 minutes at 30° C. Fluorescence was then measured every 2 minutes for 1 hour (Perkin Elmer plate: vision multimode reader); light intensity: 2.5%; exp. time: 1.4 sec, Filter: Fluo_630/690 nm) and $IC_{50}$ values were calculated from these readouts.

| Example | IC50 (µM) |
| --- | --- |
| 1 | 0.008 |
| 1.01 | 0.035 |
| 1.02 | 0.077 |
| 1.03 | 0.025 |
| 1.04 | 0.127 |
| 1.05 | 0.09 |
| 1.06 | 0.255 |
| 1.07 | 1.034 |
| 1.08 | 0.503 |
| 1.09 | 0.009 |
| 1.10 | 0.078 |
| 1.11 | 0.004 |
| 1.12 | 9.26 |
| 1.13 | 0.226 |
| 1.14 | 0.81 |
| 1.15 | 0.001 |
| 1.16 | 0.382 |
| 1.17 | 0.651 |
| 1.18 | 0.01 |

| Example | IC50 (μM) |
|---|---|
| 1.19 | 0.012 |
| 1.20 | 0.083 |
| 1.21 | 0.005 |
| 1.22 | 0.009 |
| 2 | 0.01 |
| 2.01 | 0.005 |
| 2.02 | 0.006 |
| 3 | 0.036 |
| 3.01 | 1.093 |
| 4 | 0.008 |
| 4.01 | 0.041 |
| 4.02 | 0.011 |
| 4.03 | 0.011 |
| 4.04 | 0.046 |
| 4.05 | 0.011 |
| 4.06 | 0.012 |
| 4.07 | 0.016 |
| 4.08 | 0.047 |
| 4.09 | 0.049 |
| 4.10 | 0.004 |
| 4.11 | 0.007 |
| 4.12 | 1.476 |
| 4.13 | 2.907 |
| 4.14 | 4.194 |
| 4.15 | 17.63 |
| 4.16 | 0.398 |
| 4.17 | 0.799 |
| 4.18 | 5.617 |
| 4.19 | 1.583 |
| 4.20 | 0.722 |
| 4.21 | 3.48 |
| 4.22 | 1.381 |
| 4.23 | 0.017 |
| 4.24 | 0.056 |
| 4.25 | 0.122 |
| 4.26 | 0.051 |
| 4.27 | 0.004 |
| 4.28 | 0.123 |
| 4.29 | 0.643 |
| 4.30 | 0.05 |
| 4.31 | 1.817 |
| 4.32 | 3.854 |
| 4.33 | 0.036 |
| 4.34 | 0.019 |
| 4.35 | 0.98 |
| 4.36 | 0.009 |
| 5 | 0.248 |
| 6 | 10.42 |
| 6.01 | 0.077 |
| 6.02 | 2.809 |
| 6.03 | 0.531 |
| 6.04 | 0.282 |
| 6.05 | 0.179 |
| 6.06 | 0.008 |
| 7 | 0.022 |
| 8 | 0.108 |
| 8.01 | 0.002 |
| 8.02 | 0.186 |
| 8.03 | 0.911 |
| 8.04 | 0.192 |
| 8.05 | 0.149 |
| 8.06 | 0.192 |
| 8.07 | 1.845 |
| 9 | 0.709 |
| 9.01 | 0.038 |
| 9.02 | 1.6 |
| 9.03 | 0.042 |
| 9.04 | 0.713 |
| 9.05 | 0.406 |
| 9.06 | 0.247 |
| 9.07 | 0.074 |
| 9.08 | 3.402 |
| 9.09 | 0.162 |
| 10A | 0.036 |
| 10B | 0.118 |
| 11A | 0.022 |
| 11B | 0.009 |
| 12A | 0.011 |
| 12B | 0.005 |
| 13 | 0.057 |
| 14 | 0.926 |
| 15 | 0.026 |
| 15.01 | 1.615 |
| 15.02 | 0.096 |
| 15.03 | 0.362 |
| 15.04 | 2.019 |
| 15.05 | 0.015 |
| 15.06 | 0.012 |
| 15.07 | 0.021 |
| 15.08 | 0.977 |
| 15.09 | 0.042 |
| 15.10 | 0.034 |
| 15.11 | 0.013 |
| 15.12 | 0.006 |
| 15.13 | 0.114 |
| 15.14 | 0.062 |
| 15.15 | 0.156 |
| 15.16 | 5.786 |
| 15.17 | 3.953 |
| 15.18 | 0.02 |
| 15.19 | 0.009 |
| 15.20 | 0.049 |
| 15.21 | 0.005 |
| 15.22 | 0.053 |
| 15.23 | 0.032 |
| 15.24 | 0.01 |
| 15.25 | 0.044 |
| 15.26 | 0.008 |
| 15.27 | 0.002 |
| 15.28 | 4.42 |
| 15.29 | 0.034 |
| 15.30 | 0.014 |
| 15.31 | 0.038 |
| 15.32 | 0.019 |
| 15.33 | 0.328 |
| 15.34 | 0.003 |
| 15.35 | 0.031 |
| 15.36 | 0.003 |
| 15.37 | 0.093 |
| 15.38 | 0.05 |
| 15.39 | 0.005 |
| 15.40 | 0.005 |
| 15.41 | 0.017 |
| 15.42 | 0.006 |
| 15.43 | 0.13 |
| 15.44 | 0.006 |
| 15.45 | 0.039 |
| 15.46 | 0.018 |
| 15.47 | 0.096 |
| 15.48 | 0.006 |
| 15.49 | 0.016 |
| 15.50 | 0.006 |
| 15.51 | 0.006 |
| 15.52 | 0.003 |
| 15.53 | 0.007 |
| 15.54 | 0.28 |
| 15.55 | 0.478 |
| 15.56 | 0.655 |
| 15.57 | 0.494 |
| 15.58 | 0.005 |
| 15.59 | 0.011 |
| 15.60 | 1.037 |
| 15.61 | 0.054 |
| 15.62 | 0.068 |
| 15.63 | 0.012 |
| 15.64 | 0.005 |
| 15.65 | 0.003 |
| 15.66 | 0.013 |
| 15.67 | 0.014 |
| 15.68 | 0.171 |
| 15.69 | 0.008 |
| 15.70 | 0.007 |
| 15.71 | 1.365 |
| 15.72 | 0.015 |

| Example | IC50 (μM) |
|---|---|
| 15.73 | 0.116 |
| 15.74 | 0.012 |
| 15.75 | 0.005 |
| 15.76 | 0.013 |
| 15.77 | 0.008 |
| 15.78 | 0.009 |
| 15.79 | 0.135 |
| 15.80 | 0.06 |
| 15.81 | 0.019 |
| 15.82 | 1.995 |
| 15.83 | 6.859 |
| 15.84 | 0.012 |
| 16 | 0.015 |
| 17 | 0.004 |
| 17.01 | 0.085 |
| 17.02 | 0.101 |
| 17.03 | 0.016 |
| 17.04 | 0.008 |
| 17.05 | 0.006 |
| 17.06 | 0.01 |
| 17.07 | 0.043 |
| 17.08 | 0.016 |
| 17.09 | 0.058 |
| 17.10 | 0.021 |
| 17.11 | 0.028 |
| 17.12 | 0.032 |
| 17.13 | 0.031 |
| 17.14 | 0.464 |
| 18 | 6.735 |
| 1.23 | 0.058 |
| 1.24 | 0.013 |
| 1.25 | 0.114 |
| 1.26 | 0.009 |
| 1.27 | 0.008 |
| 1.28 | 0.006 |
| 1.29 | 0.008 |
| 1.30 | 0.02 |
| 1.31 | 0.021 |
| 1.32 | 0.04 |
| 1.33 | 0.021 |
| 1.34 | 0.013 |
| 1.35 | 0.01 |
| 1.36 | 7.455 |
| 1.37 | 0.025 |
| 1.38 | 0.01 |
| 1.39 | 0.007 |
| 1.40 | 0.007 |
| 1.41 | 0.002 |
| 1.42 | 0.007 |
| 1.43 | 0.014 |
| 1.44 | 0.003 |
| 1.45 | 0.007 |
| 1.46 | 0.002 |
| 1.47 | 0.002 |
| 1.48 | 0.0075 |
| 1.49 | 0.218 |
| 1.50 | 0.017 |
| 1.51 | 0.041 |
| 1.52 | 0.016 |
| 1.53 | 0.052 |
| 1.54 | 0.022 |
| 1.55 | 0.014 |
| 1.56 | 0.2 |
| 1.57 | 0.025 |
| 1.58 | 0.057 |
| 1.59 | 0.006 |
| 1.60 | 0.012 |
| 1.61 | 0.021 |
| 2.03 | 0.005 |
| 2.04 | 0.008 |
| 4.37 | 0.132 |
| 4.38 | 0.024 |
| 4.39 | 0.006 |
| 4.40 | 0.016 |
| 4.41 | 0.009 |
| 4.42 | 0.024 |
| 4.43 | 0.004 |
| 4.44 | 0.006 |
| 4.45 | 0.007 |
| 4.46 | 0.005 |
| 4.47 | 0.004 |
| 4.48 | 0.003 |
| 4.49 | 0.003 |
| 4.50 | 0.006 |
| 4.51 | 0.002 |
| 4.52 | 0.01 |
| 4.53 | 0.005 |
| 4.54 | 0.014 |
| 4.55 | 0.005 |
| 4.56 | 0.009 |
| 4.57 | 0.011 |
| 4.58 | 0.0052 |
| 4.59 | 0.009 |
| 4.60 | 0.005 |
| 4.61 | 0.239 |
| 4.62 | 0.012 |
| 4.63 | 0.037 |
| 4.64 | 0.019 |
| 4.65 | 0.014 |
| 4.66 | 0.04 |
| 4.67 | 0.008 |
| 6.07 | 0.207 |
| 9.10 | 0.007 |
| 15.85 | 0.029 |
| 15.86 | 0.019 |
| 15.87 | 0.103 |
| 15.88 | 0.027 |
| 15.89 | 0.007 |
| 15.90 | 0.007 |
| 15.91 | 0.012 |
| 15.92 | 0.249 |
| 15.93 | 0.921 |
| 15.94 | 1.018 |
| 15.95 | 1.896 |
| 15.96 | 0.074 |
| 15.97 | 0.009 |
| 15.98 | 0.013 |
| 15.99 | 0.012 |
| 17.15 | 0.047 |
| 17.16 | 0.309 |
| 17.17 | 0.004 |
| 17.18 | 0.014 |
| 17.19 | 0.012 |
| 17.20 | 0.002 |
| 19 | 0.007 |
| 19.01 | 0.012 |
| 19.02 | 0.007 |
| 19.03 | 0.008 |
| 19.04 | 1.708 |
| 19.05 | 0.005 |
| 19.06 | 0.25 |
| 19.07 | 0.024 |
| 19.08 | 0.036 |
| 19.09 | 0.01 |
| 19.10 | 0.006 |
| 19.11 | 0.008 |
| 19.12 | 0.01 |
| 19.13 | 0.01 |
| 19.14 | 0.273 |
| 19.15 | 0.02 |
| 19.16 | 0.031 |
| 19.17 | 0.01 |
| 19.18 | 0.011 |
| 19.19 | 0.005 |
| 19.20 | 0.459 |
| 19.21 | 0.003 |
| 19.22 | 0.002 |
| 19.23 | 0.025 |
| 19.24 | 0.007 |
| 19.25 | 0.015 |
| 19.26 | 0.005 |
| 19.27 | 0.006 |
| 19.28 | 0.002 |
| 19.29 | 0.001 |

| Example | IC50 (μM) |
| --- | --- |
| 19.30 | 0.005 |
| 19.31 | 0.002 |
| 19.32 | 0.002 |
| 19.33 | 0.006 |
| 19.34 | 0.003 |
| 19.35 | 0.002 |
| 19.36 | 0.005 |
| 19.37 | 0.015 |
| 19.38 | 0.005 |
| 19.39 | 0.007 |
| 19.40 | 0.1 |
| 19.41 | 0.685 |
| 19.42 | 0.01 |
| 19.43 | 0.014 |
| 20 | 0.029 |
| 20.01 | 0.305 |

Compounds of formula (I) and their pharmaceutically acceptable salts or esters thereof as described herein have $IC_{50}$ values between 0.00001 μM and 1000 μM, particular compounds have $IC_{50}$ values between 0.0005 μM and 500 μM, further particular compounds have $IC_{50}$ values between 0.0005 μM and 50 μM, more particular compounds have $IC_{50}$ values between 0.0005 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragees, hard and soft gelatin capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations aq.=aqueous; CAS-RN=Chemical Abstracts Service Registry Number; e.r.=enantiomeric ratio; HPLC=high performance liquid chromatography; MS=mass spectrum; sat.=saturated

Example 1

(E)-1-[(3aS,8aR)-2-(4,5,6,7-Tetrahydro-1H-benzotriazole-5-carbonyl)-octahydro-pyrrolo[3,4-d]azepin-6-yl]-3-(4-trifluoromethoxy-phenyl)-prop-2-en-1-one

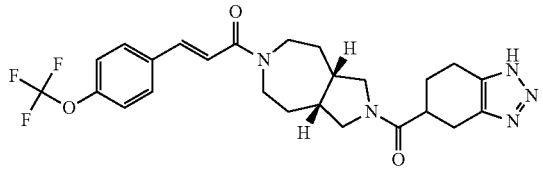 [SMILES: O=C(/C=C/c1ccc(OC(F)(F)F)cc1)N1CC[C@@H]2CN(C(=O)C3CCc4[nH]nnc4C3)C[C@@H]2CC1]

To a solution of (E)-1-((3aR,8aS)-octahydropyrrolo[3,4-d]azepin-6(7H)-yl)-3-(4-(trifluoromethoxy)phenyl)prop-2-en-1-one hydrochloride (intermediate 5; 40 mg, 102 μmol) in N,N-dimethylformamide (2 mL) were added N-methylmorpholine (51.8 mg, 512 μmol), 4,5,6,7-tetrahydro-1H-benzo[d][1,2,3]triazole-5-carboxylic acid (CAS-RN 33062-47-4; 17.1 mg, 102 μmol) and O-(7-azabenzotriazol-1-yl)-N,N,N',N'-tetramethyluronium hexafluoro-phosphate (42.8 mg, 113 μmol) at room temperature, then after 16 h the reaction mixture was partitioned between ethyl acetate and sat. aq. ammonium chloride solution. The organic layer was washed with brine, dried over magnesium sulfate, filtered, and evaporated. Chromatography (silica gel; gradient dichloromethane to dichloromethane/methanol/25% aq. ammonia solution 90:10:0.25) produced the title compound (41 mg, 80%). Colourless gum, MS: 504.7 $(M+H)^+$.

The following examples were prepared according to example 1, replacing (E)-1-((3aR,8aS)-octahydropyrrolo[3,4-d]azepin-6(7H)-yl)-3-(4-(trifluoromethoxy)phenyl)prop-2-en-1-one hydrochloride and 4,5,6,7-tetrahydro-1H-benzo[d][1,2,3]triazole-5-carboxylic acid by the appropriate amine and carboxylic acid reagents, respectively.

| No. | Systematic Name | Amine | Carboxylic acid | MS, m/e |
|---|---|---|---|---|
| 1.01 | 1-((3aR,6aS)-5-(1H-benzo[d][1,2,3]triazole-5-carbonyl)hexahydropyrrolo[3,4-c]pyrrol-2(1H)-yl)-3-(3,5-dichlorophenyl)propan-1-one | 3-(3,5-dichlorophenyl)-1-((3aR,6aS)-hexahydropyrrolo[3,4-c]pyrrol-2(1H)-yl)propan-1-one hydrochloride (intermediate 3) | 1H-benzo[d][1,2,3]triazole-5-carboxylic acid | 458.3 (M + H)⁺ |
| 1.02 | 6-((3aR,6aS)-5-(3-(3,5-dichlorophenyl)propanoyl)octahydro-pyrrolo[3,4-c]pyrrole-2-carbonyl)benzo[d]oxazol-2(3H)-one | 3-(3,5-dichlorophenyl)-1-((3aR,6aS)-hexahydropyrrolo[3,4-c]pyrrol-2(1H)-yl)propan-1-one hydrochloride (intermediate 3) | 2-oxo-2,3-dihydro-benzo[d]-oxazole-6-carboxylic acid | 474.1 (M + H)⁺ |
| 1.03 | (3aR,6aS)-3,5-dichlorobenzyl 5-(1H-benzo[d][1,2,3]triazole-5-carbonyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1) | 1H-benzo[d][1,2,3]triazole-5-carboxylic acid | 460.3 (M + H)⁺ |
| 1.04 | (3aR,6aS)-3,5-dichlorobenzyl 5-(9H-pyrido[3,4-b]indole-3-carbonyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1) | 9H-pyrido[3,4-b]indole-3-carboxylic acid (CAS-RN 74214-63-4) | 509.2 (M + H)⁺ |

-continued

| No. | Systematic Name | Amine | Carboxylic acid | MS, m/e |
|---|---|---|---|---|
| 1.05 | (3aR,6aS)-3,5-dichlorobenzyl 5-(1H-indole-5-carbonyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1) | 1H-indole-5-carboxylic acid | 458.3 (M + H)+ |
| 1.06 | (3aR,6aS)-3,5-dichlorobenzyl 5-(9H-carbazole-3-carbonyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1) | 9H-carbazole-3-carboxylic acid (CAS-RN 51035-17-7) | 508.3 (M + H)+ |
| 1.07 | (3aR,6aS)-3,5-dichlorobenzyl 5-(1H-indazole-5-carbonyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1) | 1H-indazole-5-carboxylic acid | 459.2 (M + H)+ |
| 1.08 | (3aR,6aS)-3,5-dichlorobenzyl 5-(1H-benzo[d]imidazole-5-carbonyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1) | 1H-benzo[d]imidazole-5-carboxylic acid | 459.3 (M + H)+ |

| No. | Systematic Name | Amine | Carboxylic acid | MS, m/e |
|---|---|---|---|---|
| 1.09 | trans-3,5-dichlorobenzyl 2-(1H-benzo[d][1,2,3]triazole-5-carbonyl)hexahydro-1H-pyrrolo[3,4-c]pyridine-5(6H)-carboxylate | trans-3,5-dichlorobenzyl hexahydro-1H-pyrrolo[3,4-c]pyridine-5(6H)-carboxylate hydrochloride (intermediate 1.1) | 1H-benzo[d]-[1,2,3]triazole-5-carboxylic acid | 474.4 (M + H)+ |
| 1.10 | cis-3,5-dichlorobenzyl 2-(1H-benzo[d][1,2,3]triazole-5-carbonyl)hexahydro-1H-pyrrolo[3,4-c]pyridine-5(6H)-carboxylate | cis-3,5-dichlorobenzyl hexahydro-1H-pyrrolo[3,4-c]pyridine-5(6H)-carboxylate hydrochloride (intermediate 1.2) | 1H-benzo[d]-[1,2,3]triazole-5-carboxylic acid | 474.4 (M + H)+ |
| 1.11 | (3aR,8aS)-3,5-dichlorobenzyl 2-(1H-benzo[d][1,2,3]triazole-5-carbonyl)octahydropyrrolo[3,4-d]azepine-6(7H)-carboxylate | (3aR,8aS)-3,5-dichlorobenzyl octahydropyrrolo[3,4-d]azepine-6(7H)-carboxylate hydrochloride (intermediate 1.3) | 1H-benzo[d]-[1,2,3]triazole-5-carboxylic acid | 488.4 (M + H)+ |
| 1.12 | (1H-benzotriazol-5-yl)-{(3aS,6aR)-5-[2-(3-chloro-phenyl)-ethanesulfonyl]-hexahydro-pyrrolo[3,4-c]pyrrol-2-yl}-methanone | (3aR,6aS)-2-(3-chlorophenethyl-sulfonyl)octahydro-pyrrolo[3,4-c]pyrrole (intermediate 21) | 1H-benzo[d]-[1,2,3]triazole-5-carboxylic acid | 460.5 (M + H)+ |

-continued

| No. | Systematic Name | Amine | Carboxylic acid | MS, m/e |
|---|---|---|---|---|
| 1.13 | (3aR,6aS)-3,5-dichlorobenzyl 5-(4,5,6,7-tetrahydro-1H-benzo[d][1,2,3]triazole-5-carbonyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1) | 4,5,6,7-tetrahydro-1H-benzo[d]-[1,2,3]triazole-5-carboxylic acid (CAS-RN 33062-47-4) | 464.5 (M + H)$^+$ |
| 1.14 | 1-((3aR,8aS)-2-(1H-benzo[d][1,2,3]triazole-5-carbonyl)octahydropyrrolo[3,4-d]azepin-6(7H)-yl)-3-(3-chlorophenyl)-2,2-dimethylpropan-1-one | 3-(3-chlorophenyl)-2,2-dimethyl-1-((3aR,8aS)-octahydropyrrolo[3,4-d]azepin-6(7H)-yl)propan-1-one (intermediate 26.02) | 1H-benzo[d]-[1,2,3]triazole-5-carboxylic acid | 480.6 (M + H)$^+$ |
| 1.15 | (E)-1-((3aR,8aS)-2-(1H-benzo[d][1,2,3]triazole-5-carbonyl)octahydropyrrolo[3,4-d]azepin-6(7H)-yl)-3-(3-fluoro-4-(trifluoromethoxy)phenyl)prop-2-en-1-one | (E)-3-(3-fluoro-4-(trifluoromethoxy)-phenyl)-1-((3aR,8aS)-octahydropyrrolo[3,4-d]azepin-6(7H)-yl)prop-2-en-1-one (intermediate 26.03) | 1H-benzo[d]-imidazole-5-carboxylic acid | 518.6 (M + H)$^+$ |

| No. | Systematic Name | Amine | Carboxylic acid | MS, m/e |
|---|---|---|---|---|
| 1.16 | (3aSR,6SR,7aSR)-6-{(3aR,8aS)-6-[(E)-3-(4-trifluoromethoxy-phenyl)-acryloyl]-octahydro-pyrrolo[3,4-d]azepine-2-carbonyl}-hexahydro-benzooxazol-2-one | (E)-1-((3aR,8aS)-octahydropyrrolo[3,4-d]azepin-6(7H)-yl)-3-(4-(trifluoromethoxy)phenyl)prop-2-en-1-one hydrochloride (intermediate 5) | (3aSR,6SR, 7aSR)-2-oxooctahydro-benzo[d]oxazole-6-carboxylic acid (intermediate 29) | 522.7 (M + H)+ |
| 1.17 | (E)-1-[(3aS,8aR)-2-(benzo[c][1,2,5]oxadiazole-5-carbonyl)-octahydro-pyrrolo[3,4-d]azepin-6-yl]-3-(4-trifluoromethoxy-phenyl)-prop-2-en-1-one | (E)-1-((3aR,8aS)-octahydropyrrolo[3,4-d]azepin-6(7H)-yl)-3-(4-(trifluoromethoxy)phenyl)prop-2-en-1-one hydrochloride (intermediate 5) | benzo[c]-[1,2,5]oxa-diazole-5-carboxylic acid | 501.5 (M + H)+ |
| 1.18 | (E)-1-((3aR,8aS)-2-(1H-benzo[d][1,2,3]triazole-5-carbonyl)octahydropyrrolo[3,4-d]azepin-6(7H)-yl)-3-(2-methyl-4-(trifluoromethoxy)phenyl)prop-2-en-1-one | (E)-3-(2-methyl-4-(trifluoromethoxy)phenyl)-1-((3aS,8aS)-octahydropyrrolo[3,4-d]azepin-6(7H)-yl)prop-2-en-1-one (intermediate 26.05) | 1H-benzo[d]-[1,2,3]triazole-5-carboxylic acid | 514.7 (M + H)+ |
| 1.19 | (E)-1-((3aR,8aS)-2-(1H-benzo[d][1,2,3]triazole-5-carbonyl)octahydropyrrolo[3,4-d]azepin-6(7H)-yl)-3-(3-fluoro-4-methoxyphenyl)prop-2-en-1-one | (E)-3-(3-fluoro-4-methoxyphenyl)-1-((3aR,8aS)-octahydropyrrolo[3,4-d]azepin-6(7H)-yl)prop-2-en-1-one (intermediate 26.06) | 1H-benzo[d]-[1,2,3]triazole-5-carboxylic acid | 464.4 (M + H)+ |

| No. | Systematic Name | Amine | Carboxylic acid | MS, m/e |
|---|---|---|---|---|
| 1.20 | (E)-1-[(3aS,8aR)-2-((S)-4,5,6,7-tetrahydro-1H-benzotriazole-5-carbonyl)-octahydro-pyrrolo[3,4-d]azepin-6-yl]-3-(4-trifluoromethoxy-phenyl)-prop-2-en-1-one | (E)-1-((3aR,8aS)-octahydropyrrolo[3,4-d]azepin-6(7H)-yl)-3-(4-(trifluoromethoxy)-phenyl)prop-2-en-1-one hydrochloride (intermediate 5) | (−)-(S)-4,5,6,7-tetrahydro-1H-benzo[d]-[1,2,3]triazole-5-carboxylic acid | 504.6 (M + H)+ |
| 1.21 | (E)-1-[(3aS,8aR)-2-((R)-4,5,6,7-tetrahydro-1H-benzotriazole-5-carbonyl)-octahydro-pyrrolo[3,4-d]azepin-6-yl]-3-(4-trifluoromethoxy-phenyl)-prop-2-en-1-one | (E)-1-((3aR,8aS)-octahydropyrrolo[3,4-d]azepin-6(7H)-yl)-3-(4-(trifluoromethoxy)-phenyl)prop-2-en-1-one hydrochloride (intermediate 5) | (+)-(R)-4,5,6,7-tetrahydro-1H-benzo[d]-[1,2,3]triazole-5-carboxylic acid | 504.6 (M + H)+ |
| 1.22 | (E)-1-[(3aS,8aR)-2-(1H-benzotriazole-5-carbonyl)-octahydro-pyrrolo[3,4-d]azepin-6-yl]-3-(2-isopropyl-phenyl)-prop-2-en-1-one | (E)-3-(2-isopropylphenyl)-1-((3aR,8aS)-octahydropyrrolo[3,4-d]azepin-6(7H)-yl)prop-2-en-1-one (intermediate 26.07) | (+)-(R)-4,5,6,7-tetrahydro-1H-benzo[d]-[1,2,3]triazole-5-carboxylic acid | 458.3 (M + H)+ |
| 1.23 | trans-2-(1H-benzotriazole-5-carbonyl)-octahydro-pyrrolo[3,4-c]pyridine-5-carboxylic acid 3-chloro-5-methanesulfonyl-benzyl ester | trans-octahydro-pyrrolo[3,4-c]pyridine-5-carboxylic acid 3-chloro-5-methanesulfonyl-benzyl ester hydrochloride (intermediate 1.5) | 1H-benzo[d]-[1,2,3]triazole-5-carboxylic acid | 518.6 (M + H)+ |

| No. | Systematic Name | Amine | Carboxylic acid | MS, m/e |
|---|---|---|---|---|
| 1.24 | trans-2-(1H-benzotriazole-5-carbonyl)-octahydro-pyrrolo[3,4-c]pyridine-5-carboxylic acid 4-trifluoromethoxy-benzyl ester | trans-octahydro-pyrrolo[3,4-c]pyridine-5-carboxylic acid 4-trifluoromethoxy-benzyl ester hydrochloride (intermediate 1.4) | 1H-benzo[d][1,2,3]triazole-5-carboxylic acid | 490.6 (M + H)+ |
| 1.25 | 1-[trans-2-(1H-benzotriazole-5-carbonyl)-octahydro-pyrrolo[3,4-c]pyridin-5-yl]-2-(4-trifluoromethoxy-phenoxy)-ethanone | 1-(trans-octahydro-pyrrolo[3,4-c]pyridin-5-yl)-2-(4-(trifluoromethoxy)phenoxy)-ethanone hydrochloride (intermediate 5.4) | 1H-benzo[d][1,2,3]triazole-5-carboxylic acid | 490.6 (M + H)+ |
| 1.26 | (E)-1-[trans-2-(1H-benzotriazole-5-carbonyl)-octahydro-pyrrolo[3,4-c]pyridin-5-yl]-3-(4-trifluoromethoxy-phenyl)-propenone | (E)-1-(trans-octahydro-pyrrolo[3,4-c]pyridin-5-yl)-3-(4-(trifluoromethoxy)phenyl)prop-2-en-1-one hydrochloride (intermediate 5.3) | 1H-benzo[d][1,2,3]triazole-5-carboxylic acid | 486.7 (M + H)+ |
| 1.27 | (E)-1-((3aR,8aS)-2-(1H-benzo[d][1,2,3]triazole-5-carbonyl)octahydropyrrolo[3,4-d]azepin-6(7H)-yl)-3-(3-chloro-5-(trifluoromethyl)phenyl)prop-2-en-1-one | (E)-3-(3-chloro-5-(trifluoromethyl)phenyl)-1-((3aR,8aS)-octahydropyrrolo[3,4-d]azepin-6(7H)-yl)prop-2-en-1-one (intermediate 26.10) | 1H-benzo[d][1,2,3]triazole-5-carboxylic acid | 518.6 (M + H)+ |

-continued

| No. | Systematic Name | Amine | Carboxylic acid | MS, m/e |
|---|---|---|---|---|
| 1.28 | (E)-1-((3aR,8aS)-2-(1H-benzo[d][1,2,3]triazole-5-carbonyl)octahydropyrrolo[3,4-d]azepin-6(7H)-yl)-3-(4-methoxy-2-(trifluoromethyl)phenyl)prop-2-en-1-one | (E)-3-(4-methoxy-2-(trifluoromethyl)phenyl)-1-((3aR,8aS)-octahydropyrrolo[3,4-d]azepin-6(7H)-yl)prop-2-en-1-one (intermediate 26.09) | 1H-benzo[d][1,2,3]triazole-5-carboxylic acid | 514.7 (M + H)+ |
| 1.29 | (E)-1-((3aR,8aS)-2-(1H-benzo[d][1,2,3]triazole-5-carbonyl)octahydropyrrolo[3,4-d]azepin-6(7H)-yl)-3-(2-cyclopropylphenyl)prop-2-en-1-one | (E)-3-(2-cyclopropylphenyl)-1-(trans-octahydropyrrolo[3,4-d]azepin-6(7H)-yl)prop-2-en-1-one (intermediate 26.08) | 1H-benzo[d][1,2,3]triazole-5-carboxylic acid | 456.7 (M + H)+ |
| 1.30 | trans-2-(1H-benzotriazole-5-carbonyl)-octahydro-pyrrolo[3,4-c]pyridine-5-carboxylic acid 4-fluoro-2-trifluoromethyl-benzyl ester | trans-(4-fluoro-2-(trifluoromethyl)-benzyl)hexahydro-1H-pyrrolo[3,4-c]pyridine-5(6H)-carboxylate (intermediate 32.3) | 1H-benzo[d][1,2,3]triazole-5-carboxylic acid | 492.6 (M + H)+ |
| 1.31 | trans-2-(1H-benzotriazole-5-carbonyl)-octahydro-pyrrolo[3,4-c]pyridine-5-carboxylic acid 2-cyclopropyl-4-trifluoromethyl-benzyl ester | trans-(2-cyclopropyl-4-(trifluoromethyl)-benzyl)hexahydro-1H-pyrrolo[3,4-c]pyridine-5(6H)-carboxylate (intermediate 32.2) | 1H-benzo[d][1,2,3]triazole-5-carboxylic acid | 514.6 (M + H)+ |

-continued

| No. | Systematic Name | Amine | Carboxylic acid | MS, m/e |
|---|---|---|---|---|
| 1.32 | 1-[(3aS,8aR)-2-(1H-benzotriazole-5-carbonyl)-octahydro-pyrrolo[3,4-d]azepin-6-yl]-2-(2-trifluoromethoxy-phenoxy)-ethanone | 1-((3aR,8aS)-octahydropyrrolo[3,4-d]azepin-6(7H)-yl)-2-(2-(trifluoromethoxy)-phenoxy)ethanone (intermediate 36.07) | 1H-benzo[d]-[1,2,3]triazole-5-carboxylic acid | 504.2 (M + H)+ |
| 1.33 | trans-2-(1H-benzotriazole-5-carbonyl)-octahydro-pyrrolo[3,4-c]pyridine-5-carboxylic acid 2-methoxy-4-trifluoromethyl-benzyl ester | trans-(2-methoxy-4-(trifluoromethoxy)-benzyl)hexahydro-1H-pyrrolo[3,4-c]pyridine-5(6H)-carboxylate (intermediate 32.1) | 1H-benzo[d]-[1,2,3]triazole-5-carboxylic acid | 520.6 (M + H)+ |
| 1.34 | 4-{2-[(3aS,8aR)-2-(1H-benzotriazole-5-carbonyl)-octahydro-pyrrolo[3,4-d]azepin-6-yl]-2-oxo-ethoxy}-3-trifluoromethyl-benzonitrile | 4-(2-((3aR,8aS)-octahydropyrrolo[3,4-d]azepin-6(7H)-yl)-2-oxoethoxy)-3-(trifluoromethyl)-benzonitrile (intermediate 36.05) | 1H-benzo[d]-[1,2,3]triazole-5-carboxylic acid | 511.1 (M − H)− |
| 1.35 | 1-[(3aS,8aR)-2-(1H-benzotriazole-5-carbonyl)-octahydro-pyrrolo[3,4-d]azepin-6-yl]-2-(4-chloro-2-isopropyl-5-methyl-phenoxy)-ethanone | 2-(4-chloro-2-isopropyl-5-methylphenoxy)-1-((3aR,8aS)-octahydropyrrolo[3,4-d]azepin-6(7H)-yl)ethanone (intermediate 36.06) | 1H-benzo[d]-[1,2,3]triazole-5-carboxylic acid | 510.2 (M + H)+ |

| No. | Systematic Name | Amine | Carboxylic acid | MS, m/e |
|---|---|---|---|---|
| 1.36 | 1-[(3aS,8aR)-2-(1H-benzotriazole-5-carbonyl)-octahydro-pyrrolo[3,4-d]azepin-6-yl]-2-[4-methyl-2-(1-methyl-pyrrolidin-3-yl)-phenoxy]-ethanone | 2-(4-methyl-2-(1-methylpyrrolidin-3-yl)phenoxy)-1-((3aR,8aS)-octahydropyrrolo[3,4-d]azepin-6(7H)-yl)ethanone (intermediate 36.04) | 1H-benzo[d][1,2,3]triazole-5-carboxylic acid | 517.3 (M + H)+ |
| 1.37 | 1-[(3aS,8aR)-2-(1H-benzotriazole-5-carbonyl)-octahydro-pyrrolo[3,4-d]azepin-6-yl]-2-(2-chloro-4-fluoro-phenoxy)-ethanone | 2-(2-chloro-4-fluorophenoxy)-1-((3aR,8aS)-octahydropyrrolo[3,4-d]azepin-6(7H)-yl)ethanone (intermediate 36.03) | 1H-benzo[d][1,2,3]triazole-5-carboxylic acid | 470.1 (M − H)− |
| 1.38 | 1-((3aR,8aS)-2-(1H-benzo[d][1,2,3]triazole-5-carbonyl)octahydropyrrolo[3,4-d]azepin-6(7H)-yl)-2-(2-chloro-4-(trifluoromethyl)phenoxy)ethanone | 2-(2-chloro-4-(trifluoromethyl)-phenoxy)-1-((3aR,8aS)-octahydropyrrolo[3,4-d]azepin-6(7H)-yl)ethanone (intermediate 36.10) | 1H-benzo[d][1,2,3]triazole-5-carboxylic acid | 522.6 (M + H)+ |
| 1.39 | 1-((3aR,8aS)-2-(1H-benzo[d][1,2,3]triazole-5-carbonyl)octahydropyrrolo[3,4-d]azepin-6(7H)-yl)-2-(6-isopropyl-3,3-dimethyl-2,3-dihydro-1H-inden-5-yloxy)ethanone | 2-(6-isopropyl-3,3-dimethyl-2,3-dihydro-1H-inden-5-yloxy)-1-((3aR,8aS)-octahydropyrrolo[3,4-d]azepin-6(7H)-yl)ethanone (intermediate 36.01) | 1H-benzo[d][1,2,3]triazole-5-carboxylic acid | 530.7 (M + H)+ |

-continued

| No. | Systematic Name | Amine | Carboxylic acid | MS, m/e |
|---|---|---|---|---|
| 1.40 | (3aS,8aR)-2-(1H-benzotriazole-5-carbonyl)-octahydro-pyrrolo[3,4-d]azepine-6-carboxylic acid 2-fluoro-4-trifluoromethoxy-benzyl ester | 2-(2-fluoro-4-(trifluoromethoxy)-phenoxy)-1-((3aR,8aS)-octahydropyrrolo[3,4-d]azepin-6(7H)-yl)ethanone | 1H-benzo[d]-[1,2,3]triazole-5-carboxylic acid | 520.6 (M − H)⁻ |
| 1.41 | 1-((3aR,8aS)-2-(1H-benzo[d][1,2,3]triazole-5-carbonyl)octahydropyrrolo[3,4-d]azepin-6(7H)-yl)-2-(5-chloro-2-(trifluoromethyl)phenoxy)ethanone | 2-(5-chloro-2-(trifluoromethyl)-phenoxy)-1-((3aR,8aS)-octahydropyrrolo[3,4-d]azepin-6(7H)-yl)ethanone (intermediate 36) | 1H-benzo[d]-[1,2,3]triazole-5-carboxylic acid | 522.5 (M + H)⁺ |
| 1.42 | 1-[(3aS,8aR)-2-(1H-benzotriazole-5-carbonyl)-1,3,3a,4,5,7,8,8a-octahydropyrrolo[3,4-d]azepin-6-yl]-2-(2-tert-butyl-4-methoxyphenoxy)ethanone | 2-(2-tert-butyl-4-methoxyphenoxy)-1-((3aR,8aS)-octahydropyrrolo[3,4-d]azepin-6(7H)-yl)ethanone (intermediate 36.08) | 1H-benzo[d]-[1,2,3]triazole-5-carboxylic acid | 506.6 (M + H)⁺ |
| 1.43 | 4-[2-[(3aS,8aR)-2-(1H-benzotriazole-5-carbonyl)-1,3,3a,4,5,7,8,8a-octahydropyrrolo[3,4-d]azepin-6-yl]-2-oxoethoxy]-3-propan-2-ylbenzonitrile | 3-isopropyl-4-(2-((3aR,8aS)-octahydropyrrolo[3,4-d]azepin-6(7H)-yl)-2-oxoethoxy)benzonitrile (intermediate 36.09) | 1H-benzo[d]-[1,2,3]triazole-5-carboxylic acid | 487.6 (M + H)⁺ |

| No. | Systematic Name | Amine | Carboxylic acid | MS, m/e |
|---|---|---|---|---|
| 1.44 | 1-[(3aS,8aR)-2-(1H-benzotriazole-5-carbonyl)-1,3,3a,4,5,7,8,8a-octahydropyrrolo[3,4-d]azepin-6-yl]-3-[3-fluoro-4-(2,2,2-trifluoroethoxy)phenyl]propan-1-one | 3-(3-fluoro-4-(2,2,2-trifluoroethoxy)phenyl)-1-((3aR,8aS)-octahydropyrrolo[3,4-d]azepin-6(7H)-yl)propan-1-one (intermediate 35.2) | 1H-benzo[d][1,2,3]triazole-5-carboxylic acid | 532.2 (M + H)+ |
| 1.45 | 1-[(3aS,8aR)-2-(1H-benzotriazole-5-carbonyl)-1,3,3a,4,5,7,8,8a-octahydropyrrolo[3,4-d]azepin-6-yl]-3-[2-fluoro-4-(2,2,2-trifluoroethoxy)phenyl]propan-1-one | 3-(2-fluoro-4-(2,2,2-trifluoroethoxy)phenyl)-1-((3aR,8aS)-octahydropyrrolo[3,4-d]azepin-6(7H)-yl)propan-1-one (intermediate 26.12) | 1H-benzo[d][1,2,3]triazole-5-carboxylic acid | 534.2 (M + H)+ |
| 1.46 | (3aS,8aR)-2-(1H-benzotriazole-5-carbonyl)-octahydro-pyrrolo[3,4-d]azepine-6-carboxylic acid 3-fluoro-4-(2,2,2-trifluoro-ethoxy)-benzyl ester | (3aR,8aS)-3-fluoro-4-(2,2,2-trifluoroethoxy)-benzyl octahydropyrrolo[3,4-d]azepine-6(7H)-carboxylate (intermediate 32.4) | 1H-benzo[d][1,2,3]triazole-5-carboxylic acid | 536.2 (M + H)+ |
| 1.47 | (3aS,8aR)-2-(1H-benzotriazole-5-carbonyl)-octahydro-pyrrolo[3,4-d]azepine-6-carboxylic acid 2-fluoro-4-(2,2,2-trifluoro-ethoxy)-benzyl ester | (3aR,8aS)-2-fluoro-4-(2,2,2-trifluoroethoxy)-benzyl octahydro-pyrrolo[3,4-d]azepine-6(7H)-carboxylate hydrochloride (intermediate 1.7) | 1H-benzo[d][1,2,3]triazole-5-carboxylic acid | 536.6 (M + H)+ |

| No. | Systematic Name | Amine | Carboxylic acid | MS, m/e |
|---|---|---|---|---|
| 1.48 | (3aS,8aR)-2-(1H-benzotriazole-5-carbonyl)-octahydro-pyrrolo[3,4-d]azepine-6-carboxylic acid 4-(2,2,2-trifluoro-ethoxy)-benzyl ester | (3aR,8aS)-4-(2,2,2-trifluoroethoxy)benzyl octahydropyrrolo[3,4-d]azepine-6(7H)-carboxylate hydrochloride (intermediate 1.6) | 1H-benzo[d][1,2,3]triazole-5-carboxylic acid | 518.6 (M + H)+ |
| 1.49 | (3aS,6aS)-5-(3H-[1,2,3]triazolo[4,5-b]pyridine-6-carbonyl)-hexahydro-pyrrolo[3,4-c]pyrrole-2-carboxylic acid 4-trifluoromethoxy-benzyl ester | (3aS,6aS)-4-(trifluoromethoxy)benzyl hexahydropyrrolo[3,4-c]pyrrole-2(1H)-carboxylate hydrochloride (intermediate 1.8) | 3H-1,2,3-triazolo[4,5-b]pyridine-6-carboxylic acid (CAS-RN 1260385-82-7) | 475.5 (M − H)− |
| 1.50 | 1-[(3aR,6aR)-5-(1H-triazolo[4,5-b]pyridine-5-carbonyl)-1,3,3a,4,6,6a-hexahydropyrrolo[3,4-c]pyrrol-2-yl]-3-[4-(trifluoromethoxy)phenyl]-propan-1-one | 1-((3aS,6aS)-hexahydropyrrolo[3,4-c]pyrrol-2(1H)-yl)-3-(4-(trifluoromethoxy)-phenyl)propan-1-one dihydrochloride (intermediate 5.5) | 1H-[1,2,3]triazolo[4,5-b]pyridine-5-carboxylic acid (CAS-RN 1216149-55-1) | 475.4 (M + H)+ |
| 1.51 | (3aS,6aS)-5-(3H-[1,2,3]triazolo[4,5-c]pyridine-6-carbonyl)-hexahydro-pyrrolo[3,4-c]pyrrole-2-carboxylic acid 4-trifluoromethoxy-benzyl ester | (3aS,6aS)-4-(trifluoromethoxy)benzyl hexahydropyrrolo[3,4-c]pyrrole-2(1H)-carboxylate hydrochloride (intermediate 1.8) | 3H-[1,2,3]triazolo[4,5-c]pyridine-6-carboxylic acid (intermediate 45) | 477.4 (M + H)+ |

| No. | Systematic Name | Amine | Carboxylic acid | MS, m/e |
|---|---|---|---|---|
| 1.52 | (3aS,6aS)-5-(4-fluoro-1H-benzotriazole-5-carbonyl)-hexahydro-pyrrolo[3,4-c]pyrrole-2-carboxylic acid 4-trifluoromethoxy-benzyl ester | (3aS,6aS)-4-(trifluoromethoxy)benzyl hexahydropyrrolo[3,4-c]pyrrole-2(1H)-carboxylate hydrochloride (intermediate 1.8) | 4-fluoro-1H-benzo[d]-[1,2,3]triazole-5-carboxylic acid (intermediate 43.2) | 494.4 (M + H)+ |
| 1.53 | (3aS,6aS)-5-(7-fluoro-1H-benzotriazole-5-carbonyl)-hexahydro-pyrrolo[3,4-c]pyrrole-2-carboxylic acid 4-trifluoromethoxy-benzyl ester | (3aS,6aS)-4-(trifluoromethoxy)benzyl hexahydropyrrolo[3,4-c]pyrrole-2(1H)-carboxylate hydrochloride (intermediate 1.8) | 7-fluoro-1H-benzo[d]-[1,2,3]triazole-5-carboxylic acid (intermediate 43.1) | 494.6 (M + H)+ |
| 1.54 | (3aS,6aS)-5-(6-fluoro-1H-benzotriazole-5-carbonyl)-hexahydro-pyrrolo[3,4-c]pyrrole-2-carboxylic acid 4-trifluoromethoxy-benzyl ester | (3aS,6aS)-4-(trifluoromethoxy)-benzyl hexahydro-pyrrolo[3,4-c]pyrrole-2(1H)-carboxylate hydrochloride (intermediate 1.8) | 6-fluoro-1H-benzo[d]-[1,2,3]triazole-5-carboxylic acid (intermediate 43) | 494.5 (M + H)+ |
| 1.55 | (3aS,6aS)-5-(4-chloro-1H-benzotriazole-5-carbonyl)-hexahydro-pyrrolo[3,4-c]pyrrole-2-carboxylic acid 4-trifluoromethoxy-benzyl ester | (3aS,6aS)-4-(trifluoromethoxy)benzyl hexahydropyrrolo[3,4-c]pyrrole-2(1H)-carboxylate hydrochloride (intermediate 1.8) | 4-chloro-1H-benzo[d]-[1,2,3]triazole-5-carboxylic acid (intermediate 43.5) | 510.4 (M + H)+ |

-continued

| No. | Systematic Name | Amine | Carboxylic acid | MS, m/e |
|---|---|---|---|---|
| 1.56 | (3aS,6aS)-5-(6-trifluoromethyl-1H-benzotriazole-5-carbonyl)-hexahydro-pyrrolo[3,4-c]pyrrole-2-carboxylic acid 4-trifluoromethoxy-benzyl ester | (3aS,6aS)-4-(trifluoro-methoxy)benzyl hexahydropyrrolo[3,4-c]pyrrole-2(1H)-carboxylate hydrochloride (intermediate 1.8) | 6-(trifluoro-methyl)-1H-benzo[d][1,2,3]triazole-5-carboxylic acid (intermediate 43.4) | 542.4 (M + H)+ |
| 1.57 | (3aS,6aS)-5-(4-methyl-1H-benzotriazole-5-carbonyl)-hexahydro-pyrrolo[3,4-c]pyrrole-2-carboxylic acid 4-trifluoromethoxy-benzyl ester | (3aS,6aS)-4-(trifluoro-methoxy)benzyl hexahydropyrrolo[3,4-c]pyrrole-2(1H)-carboxylate hydrochloride (intermediate 1.8) | 4-methyl-1H-benzo[d][1,2,3]triazole-5-carboxylic acid (intermediate 43.3) | 488.2 (M − H)− |
| 1.58 | (3aS,6aS)-5-(6-methyl-1H-benzotriazole-5-carbonyl)-hexahydro-pyrrolo[3,4-c]pyrrole-2-carboxylic acid 4-trifluoromethoxy-benzyl ester | (3aS,6aS)-4-(trifluoro-methoxy)benzyl hexahydropyrrolo[3,4-c]pyrrole-2(1H)-carboxylate hydrochloride (intermediate 1.8) | 6-methyl-1H-benzo[d]-[1,2,3]triazole-5-carboxylic acid (intermediate 43.6) | 488.2 (M − H)− |
| 1.59 | 1-[(3aR,6aR)-5-(4-fluoro-1H-benzotriazole-5-carbonyl)-hexahydro-pyrrolo[3,4-c]pyrrol-2-yl]-3-(4-tri-fluoromethoxy-phenyl)-propan-1-one | 1-((3aS,6aS)-hexahydropyrrolo[3,4-c]pyrrol-2(1H)-yl)-3-(4-(trifluoromethoxy)-phenyl)propan-1-one dihydrochloride (intermediate 5.5) | 4-fluoro-1H-benzo[d]-[1,2,3]triazole-5-carboxylic acid (intermediate 43.2) | 492.2 (M + H)+ |

| No. | Systematic Name | Amine | Carboxylic acid | MS, m/e |
|---|---|---|---|---|
| 1.60 | (4-ethoxyquinolin-2-yl)((3aS,6aS)-5-((R)-4,5,6,7-tetrahydro-1H-benzo[d][1,2,3]triazole-5-carbonyl)hexahydropyrrolo[3,4-c]pyrrol-2(1H)-yl)methanone | (4-ethoxyquinolin-2-yl)((3aS,6aS)-hexahydropyrrolo[3,4-c]pyrrol-2(1H)-yl)methanone hydrochloride (intermediate 5.6) | (R)-4,5,6,7-tetrahydro-1H-benzo[d][1,2,3]triazole-5-carboxylic acid (intermediate 30A) | 461.3 (M + H)⁺ |
| 1.61 | (4-ethoxyquinolin-2-yl)((3aS,6aS)-5-(4-fluoro-1H-benzo[d][1,2,3]triazole-5-carbonyl)hexahydropyrrolo[3,4-c]pyrrol-2(1H)-yl)methanone | (4-ethoxyquinolin-2-yl)((3aS,6aS)-hexahydropyrrolo[3,4-c]pyrrol-2(1H)-yl)methanone hydrochloride (intermediate 5.6) | 4-fluoro-1H-benzo[d][1,2,3]triazole-5-carboxylic acid (intermediate 43.2) | 475.3 (M + H)⁺ |

Example 2 trans-3,5-Dichlorobenzyl 2-(2-oxo-2,3-dihydrobenzo[d]oxazole-6-carbonyl)hexahydro-1H-pyrrolo[3,4-c]pyridine-5(6H)-carboxylate

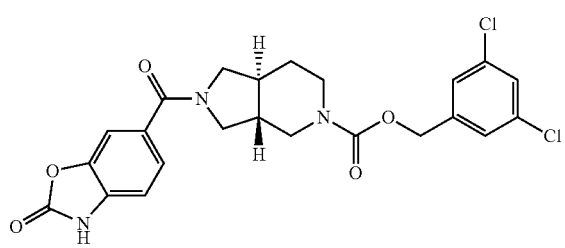 [SMILES: O=C(OCc1cc(Cl)cc(Cl)c1)N1CC[C@@H]2CN(C(=O)c3ccc4[nH]c(=O)oc4c3)C[C@H]2C1]

To a solution of trans-3,5-dichlorobenzyl hexahydro-1H-pyrrolo[3,4-c]pyridine-5(6H)-carboxylate hydrochloride (intermediate 1.1; 50 mg, 137 µmol) in N,N-dimethylformamide (1 mL) were added 4-methylmorpholine (69.1 mg, 684 µmol), 4-amino-3-hydroxybenzoic acid (20.9 mg, 137 µmol) and O-(7-azabenzotriazol-1-yl)-N,N,N',N'-tetramethyluronium hexafluoro-phosphate (62.4 mg, 164 µmol) at room temperature, then after 18 h 1,1'-carbonyldiimidazole (50.3 mg, 301 µmol) was added. After 1 h, the reaction mixture was partitioned between ethyl acetate and 1 M aq. hydrochloric acid solution. The organic layer was washed with brine, dried over magnesium sulfate, filtered and evaporated in vacuo. Chromatography (silica gel, gradient dichloromethane dichloromethane/methanol/25% aq. ammonia solution 90:10:0.25) produced the title compound (35 mg, 52%). Light yellow gum, MS: 490.5 (M+H)⁺.

The following examples were prepared according to example 2, replacing trans-3,5-dichlorobenzyl hexahydro-1H-pyrrolo[3,4-c]pyridine-5(6H)-carboxylate hydrochloride by the appropriate starting material.

| Ex. | Systematic Name | Starting material | MS, m/e |
|---|---|---|---|
| 2.01 | (3aR,6aS)-3,5-dichlorobenzyl 5-(2-oxo-2,3-dihydrobenzo[d]oxazole-6-carbonyl)hexahydropyrrolo[3,4-c]pyrrole-2(1H)-carboxylate | (3aR,6aS)-3,5-dichlorobenzyl hexahydropyrrolo[3,4-c]pyrrole-2(1H)-carboxylate hydrochloride (intermediate 1) | 476.2 (M + H)+ |
| 2.02 | 6-{(3aS,8aR)-6-[(E)-3-(4-trifluoromethoxy-phenyl)-acryloyl]-octahydro-pyrrolo[3,4-d]azepine-2-carbonyl}-3H-benzooxazol-2-one | (E)-1-((3aR,8aS)-octahydropyrrolo[3,4-d]azepin-6(7H)-yl)-3-(4-(trifluoromethoxy)-phenyl)prop-2-en-1-one hydrochloride (intermediate 5) | 514.6 (M − H)− |
| 2.03 | 6-[(3aR,6aR)-2-[3-[4-(trifluoromethoxy)phenyl]propanoyl]-1,3,3a,4,6,6a-hexahydropyrrolo[3,4-c]pyrrole-5-carbonyl]-3H-1,3-benzoxazol-2-one | 1-((3aS,6aS)-hexahydropyrrolo[3,4-c]pyrrol-2(1H)-yl)-3-(4-(trifluoromethoxy)-phenyl)propan-1-one dihydrochloride (intermediate 5.5) | 490.4 (M + H)+ |
| 2.04 | (3aS,6aS)-5-(2-oxo-2,3-dihydro-benzooxazole-6-carbonyl)-hexahydro-pyrrolo[3,4-c]pyrrole-2-carboxylic acid 4-trifluoromethoxy-benzyl ester | (3aS,6aS)-4-(trifluoromethoxy)benzyl hexahydropyrrolo[3,4-c]pyrrole-2(1H)-carboxylate hydrochloride (intermediate 1.8) | 492.6 (M + H)+ |

Example 3

(3aR,5s,6aS)-3,5-Dichlorobenzyl 5-(2-oxo-2,3-dihydrobenzo[d]oxazol-6-yloxy)hexahydrocyclopenta[c]pyrrole-2(1H)-carboxylate

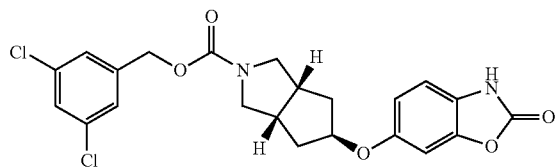 [SMILES: O=C(OCc1cc(Cl)cc(Cl)c1)N1C[C@H]2C[C@H](Oc3ccc4[nH]c(=O)oc4c3)C[C@H]2C1]

A mixture of 4-((3aR,5s,6aS)-2-((3,5-dichlorobenzyloxy)carbonyl)octahydrocyclopenta[c]pyrrol-5-yloxy)-2-hydroxybenzoic acid (intermediate 12.1; 63 mg, 135 µmol), triethylamine (13.7 mg, 135 µmol) and diphenylphosphoryl azide (37.2 mg, 135 µmol) in toluene (2 mL) was heated at 110° C. for 20 h. After evaporation of the solvent, the residue was purified by chromatography (silica gel; heptane-ethyl acetate gradient) to produce the title compound (19 mg, 30%). White solid, MS: 463.2 (M+H)+.

Example 3.01

(3aR,5r,6aS)-3,5-Dichlorobenzyl 5-(2-oxo-2,3-dihydrobenzo[d]oxazol-6-yloxy)hexahydrocyclopenta[c]pyrrole-2(1H)-carboxylate

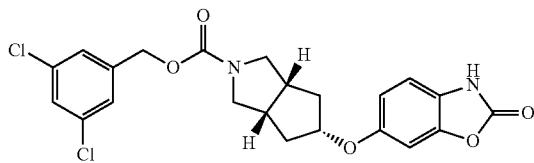 [SMILES: O=C(OCc1cc(Cl)cc(Cl)c1)N1C[C@H]2C[C@@H](Oc3ccc4[nH]c(=O)oc4c3)C[C@H]2C1]

The title compound was produced in analogy to example 3 from 4-((3aR,5r,6aS)-2-((3,5-dichlorobenzyloxy)carbonyl)octahydrocyclopenta[c]pyrrol-5-yloxy)-2-hydroxybenzoic acid (intermediate 12). White solid, MS: 463.2 (M+H)+.

Example 4

(3aS,6aS)-3,5-Dichlorobenzyl 5-(1H-benzo[d][1,2,3]triazole-5-carbonyl)hexahydro-pyrrolo[3,4-c]pyrrole-2(1H)-carboxylate

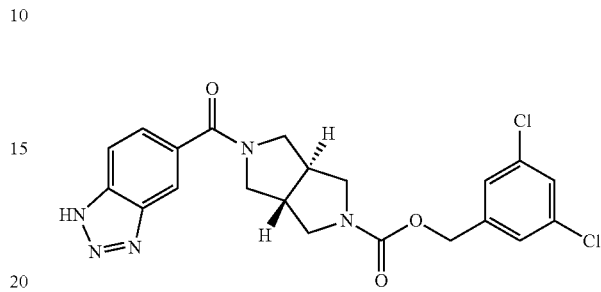

To a solution of (3,5-dichlorophenyl)methanol (21.4 mg, 121 µmol) in acetonitrile (5 mL) was added N,N'-carbonyldiimidazole (20.6 mg, 127 µmol) at room temperature, then after 3 h triethylamine (61.3 mg, 606 µmol) and (1H-benzo[d][1,2,3]triazol-5-yl)((3aR,6aR)-hexahydropyrrolo[3,4-c]pyrrol-2(1H)-yl)methanone dihydrochloride (intermediate 2.4; 40 mg, 121 µmol) were added and the reaction mixture was heated at reflux. After 16 h the reaction mixture was partitioned between ethyl acetate and sat. aq. ammonium chloride, the organic layer was washed with sat. aq. sodium hydrogen carbonate solution and brine, dried over magnesium sulfate, filtered, and evaporated. Chromatography (silica gel; gradient dichloromethane to dichloromethane/methanol/25% aq. ammonia solution 90:10:0.25) produced the title compound (38 mg, 68%). Light yellow foam, MS: 460.4 (M+H)+.

The following compounds were produced in analogy to example 4, replacing (1H-benzo[d][1,2,3]triazol-5-yl)((3aR,6aR)-hexahydropyrrolo[3,4-c]pyrrol-2(1H)-yl)methanone dihydrochloride and (3,5-dichlorophenyl)methanol by the appropriate amine and alcohol precursors, respectively.

| No. | Systematic Name | Amine | Alcohol | MS, m/e |
|---|---|---|---|---|
| 4.01 | trans-5-(1H-benzotriazole-5-carbonyl)-octahydro-pyrrolo[3,4-c]pyridine-2-carboxylic acid 3-methanesulfonyl-5-trifluoromethyl-benzyl ester | (1H-benzotriazol-5-yl)-trans-octahydro-pyrrolo[3,4-c]pyridin-5-yl-methanone; hydrochloride (intermediate 2.1) | (3-(methyl-sulfonyl)-5-(trifluoromethyl)phenyl)-methanol (CAS-RN 1003843-94-4) | 552.5 (M + H)+ |

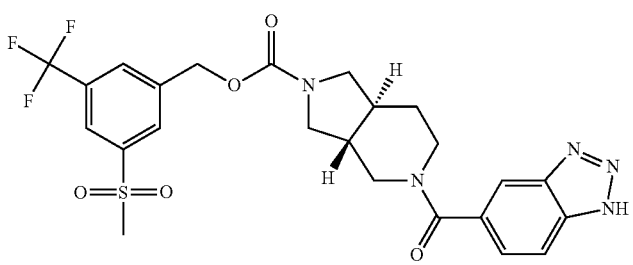 [SMILES: CS(=O)(=O)c1cc(COC(=O)N2C[C@H]3CCN(C(=O)c4ccc5[nH]nnc5c4)C[C@@H]3C2)cc(C(F)(F)F)c1]

| No. | Systematic Name | Amine | Alcohol | MS, m/e |
|---|---|---|---|---|
| 4.02 | (3aR,6aR)-3,5-dichlorobenzyl 5-(1H-benzo[d][1,2,3]triazole-5-carbonyl)hexahydropyrrolo[3,4-c]pyrrole-2(1H)-carboxylate | (1H-benzo[d][1,2,3]triazol-5-yl)((3aS,6aS)-hexahydropyrrolo[3,4-c]pyrrol-2(1H)-yl)methanone dihydrochloride (intermediate 8) | (3,5-dichloro-phenyl)-methanol | 460.5 (M + H)+ |
| 4.03 | (3aS,6aS)-5-(1H-benzotriazole-5-carbonyl)-hexahydro-pyrrolo[3,4-c]pyrrole-2-carboxylic acid 3-chloro-5-methanesulfonyl-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (3-chloro-5-(methyl-sulfonyl)-phenyl)-methanol (intermediate 17) | 504.4 (M + H)+ |
| 4.04 | (3aS,6aR)-5-(1H-benzotriazole-5-carbonyl)-hexahydro-pyrrolo[3,4-c]pyrrole-2-carboxylic acid 3-chloro-5-methanesulfonyl-benzyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | (3-chloro-5-(methyl-sulfonyl)-phenyl)-methanol (intermediate 17) | 504.4 (M + H)+ |
| 4.05 | (3aS,8aR)-2-(1H-benzotriazole-5-carbonyl)-octahydro-pyrrolo[3,4-d]azepine-6-carboxylic acid 3-methanesulfonyl-5-trifluoromethyl-benzyl ester | (1H-benzo[d][1,2,3]triazol-5-yl)((3aR,8aS)-octahydropyrrolo[3,4-d]azepin-2(1H)-yl)methanone (intermediate 6.1) | (3-(methyl-sulfonyl)-5-(trifluoro-methyl)-phenyl)-methanol (CAS-RN 1003843-94-4) | 566.2 (M + H)+ |

-continued

| No. | Systematic Name | Amine | Alcohol | MS, m/e |
|---|---|---|---|---|
| 4.06 | (3aS,8aR)-2-(1H-benzotriazole-5-carbonyl)-octahydro-pyrrolo[3,4-d]azepine-6-carboxylic acid 3-chloro-5-methanesulfonyl-benzyl ester | (1H-benzo[d][1,2,3]triazol-5-yl)((3aR,8aS)-octahydropyrrolo[3,4-d]azepin-2(1H)-yl)methanone (intermediate 6.1) | (3-chloro-5-(methyl-sulfonyl)-phenyl)-methanol (intermediate 17) | 532.3 (M + H)+ |
| 4.07 | (3aS,6aR)-5-(1H-benzotriazole-5-carbonyl)-hexahydro-pyrrolo[3,4-c]pyrrole-2-carboxylic acid 3-methanesulfonyl-5-trifluoromethyl-benzyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | (3-(methyl-sulfonyl)-5-(trifluoro-methyl)-phenyl)-methanol (CAS-RN 1003843-94-4) | 538.4 (M + H)+ |
| 4.08 | cis-3,5-dichlorobenzyl 5-(1H-benzo[d][1,2,3]triazole-5-carbonyl)hexahydro-1H-pyrrolo[3,4-c]pyridine-2(3H)-carboxylate | (1H-benzo[d][1,2,3]triazol-5-yl)(cis-tetrahydro-1H-pyrrolo[3,4-c]pyridin-5(6H,7H,7aH)-yl)methanone hydrochloride (intermediate 2) | (3,5-dichloro-phenyl)-methanol | 474.5 (M + H)+ |
| 4.09 | (3aS,7aR)-5-(1H-benzotriazole-5-carbonyl)-octahydro-pyrrolo[3,4-c]pyridine-2-carboxylic acid 3-chloro-5-methanesulfonyl-benzyl ester | (1H-benzotriazol-5-yl)-trans-octahydro-pyrrolo[3,4-c]pyridin-5-yl-methanone hydrochloride (intermediate 2.1) | (3-chloro-5-(methyl-sulfonyl)-phenyl)-methanol (intermediate 17) | 518.4 (M + H)+ |

| No. | Systematic Name | Amine | Alcohol | MS, m/e |
|---|---|---|---|---|
| 4.10 | trans-3,5-dichlorobenzyl 5-(1H-benzo[d][1,2,3]triazole-5-carbonyl)hexahydro-1H-pyrrolo[3,4-c]pyridine-2(3H)-carboxylate | (1H-benzo[d][1,2,3]triazol-5-yl)(trans-tetrahydro-1H-pyrrolo[3,4-c]pyridin-5(6H,7H,7aH)-yl)methanone hydrochloride (intermediate 2.1) | (3,5-dichloro-phenyl)-methanol | 474.4 (M + H)+ |
| 4.11 | (3aR,8aS)-3,5-dichlorobenzyl 6-(1H-benzo[d][1,2,3]triazole-5-carbonyl)octahydropyrrolo[3,4-d]azepine-2(1H)-carboxylate | (1H-benzo[d][1,2,3]triazol-5-yl)((3aR,8aS)-octahydropyrrolo[3,4-d]azepin-6(7H)-yl)methanone hydrochloride (intermediate 2.3) | (3,5-dichloro-phenyl)-methanol | 486.4 (M + H)+ |
| 4.12 | (3aS,6aR)-5-(1H-benzotriazole-5-carbonyl)-hexahydro-pyrrolo[3,4-c]pyrrole-2-carboxylic acid 1-(3-chloro-phenyl)-cyclopropyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | 1-(3-chloro-phenyl)-cyclopropanol (CAS-RN 43187-67-3) | 452.5 (M + H)+ |
| 4.13 | (3aS,6aR)-5-(1H-benzotriazole-5-carbonyl)-hexahydro-pyrrolo[3,4-c]pyrrole-2-carboxylic acid bicyclo[4.1.0]hept-7-ylmethyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | bicyclo[4.1.0]-heptan-7-ylmethanol | 410.5 (M + H)+ |

| No. | Systematic Name | Amine | Alcohol | MS, m/e |
|---|---|---|---|---|
| 4.14 | (3aS,6aR)-5-(1H-benzotriazole-5-carbonyl)-hexahydro-pyrrolo[3,4-c]pyrrole-2-carboxylic acid adamantan-2-ylmethyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | 2-adamantane-methanol (CAS-RN 22635-61-6) | 450.5 (M + H)+ |
| 4.15 | (3aS,6aR)-5-(1H-benzotriazole-5-carbonyl)-hexahydro-pyrrolo[3,4-c]pyrrole-2-carboxylic acid 1-fluoro-cyclohexylmethyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | (1-fluorocyclo-hexyl)-methanol (CAS-RN 117169-30-9) | 414.4 (M − H)− |
| 4.16 | (3aS,6aR)-5-(1H-benzotriazole-5-carbonyl)-hexahydro-pyrrolo[3,4-c]pyrrole-2-carboxylic acid 2-adamantan-2-yl-ethyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | 2-(2-adamantyl)-ethanol (CAS-NR 39555-28-7) | 464.5 (M + H)+ |
| 4.17 | (3aS,6aR)-5-(1H-benzotriazole-5-carbonyl)-hexahydro-pyrrolo[3,4-c]pyrrole-2-carboxylic acid 2-adamantan-1-yl-ethyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | 1-adamantane-ethanol | 464.5 (M + H)+ |

| No. | Systematic Name | Amine | Alcohol | MS, m/e |
|---|---|---|---|---|
| 4.18 | (3aS,6aR)-5-(1H-benzotriazole-5-carbonyl)-hexahydro-pyrrolo[3,4-c]pyrrole-2-carboxylic acid adamantan-1-ylmethyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | 1-adamantane-methanol | 450.5 (M + H)+ |
| 4.19 | (3aS,6aR)-5-(1H-benzotriazole-5-carbonyl)-hexahydro-pyrrolo[3,4-c]pyrrole-2-carboxylic acid cyclohexyl methyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | cyclohexyl-methanol | 398.5 (M + H)+ |
| 4.20 | cis-5-(1H-benzotriazole-5-carbonyl)-hexahydro-pyrrolo[3,4-c]pyrrole-2-carboxylic acid 3-(2,2,2-trifluoro-1-methoxy-ethyl)-benzyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | (3-(2,2,2-trifluoro-1-methoxy-ethyl)phenyl)-methanol (intermediate 19) | 504.5 (M + H)+ |
| 4.21 | cis-5-(1H-benzotriazole-5-carbonyl)-hexahydro-pyrrolo[3,4-c]pyrrole-2-carboxylic acid 3-(2,2,2-trifluoro-1-hydroxy-ethyl)-benzyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | 2,2,2-trifluoro-1-(3-(hydroxy-methyl)-phenyl)ethanol (intermediate 18) | 490.5 (M + H)+ |

| No. | Systematic Name | Amine | Alcohol | MS, m/e |
|---|---|---|---|---|
| 4.22 | (3aR,6aS)-2-cyclohexylethyl 5-(1H-benzo[d][1,2,3]triazole-5-carbonyl)hexahydropyrrolo[3,4-c]pyrrole-2(1H)-carboxylate | (1H-benzo[d][1,2,3]triazol-5-yl)((3aR,6aS)-hexahydropyrrolo[3,4-c]pyrrol-2(1H)-yl)methanone hydrochloride (intermediate 2.2) | 2-cyclohexyl-ethanol | 412.5 (M + H)+ |
| 4.23 | (3aS,6aR)-5-(1H-benzotriazole-5-carbonyl)-hexahydro-pyrrolo[3,4-c]pyrrole-2-carboxylic acid 3-fluoro-5-trifluoromethoxy-benzyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | (3-fluoro-5-(trifluoro-methoxy)-phenyl)-methanol | 494.4 (M + H)+ |
| 4.24 | (3aR,6aS)-3-chloro-5-cyanobenzyl 5-(1H-benzo[d][1,2,3]triazole-5-carbonyl)hexahydropyrrolo[3,4-c]pyrrole-2(1H)-carboxylate | (1H-benzo[d][1,2,3]triazol-5-yl)((3aR,6aS)-hexahydropyrrolo[3,4-c]pyrrol-2(1H)-yl)methanone hydrochloride (intermediate 2.2) | 3-chloro-5-(hydroxy-methyl)-benzonitrile (CAS-RN 1021871-35-1) | 451.4 (M + H)+ |
| 4.25 | (3aS,6aR)-5-(1H-benzotriazole-5-carbonyl)-hexahydro-pyrrolo[3,4-c]pyrrole-2-carboxylic acid 3-trifluoromethoxy-benzyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | (3-(trifluoro-methoxy)-phenyl)-methanol | 476.4 (M + H)+ |

| No. | Systematic Name | Amine | Alcohol | MS, m/e |
|---|---|---|---|---|
| 4.26 | (3aS,6aR)-5-(1H-benzotriazole-5-carbonyl)-hexahydro-pyrrolo[3,4-c]pyrrole-2-carboxylic acid 3-fluoro-5-trifluoromethyl-benzyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | (3-fluoro-5-(trifluoromethyl)-phenyl)-methanol | 478.5 (M + H)+ |
| 4.27 | (3aS,6aR)-5-(1H-benzotriazole-5-carbonyl)-hexahydro-pyrrolo[3,4-c]pyrrole-2-carboxylic acid 3-chloro-5-trifluoromethoxy-benzyl ester | (1H-benzo[d][1,2,3]triazol-5-yl)((3aR,6aS)-hexahydropyrrolo[3,4-c]pyrrol-2(1H)-yl)methanone hydrochloride (intermediate 2.2) | (3-chloro-5-(trifluoromethoxy)-phenyl)-methanol | 510.4 (M + H)+ |
| 4.28 | (3aS,6aR)-5-(1H-benzotriazole-5-carbonyl)-hexahydro-pyrrolo[3,4-c]pyrrole-2-carboxylic acid 4-fluoro-3-trifluoromethoxy-benzyl ester | (1H-benzo[d][1,2,3]triazol-5-yl)(trans-hexahydropyrrolo[3,4-c]pyrrol-2(1H)-yl)methanone hydrochloride (intermediate 2.2) | (4-fluoro-3-(trifluoromethoxy)-phenyl)-methanol (CAS-RN 86256-18-0) | 494.5 (M + H)+ |
| 4.29 | (3aR,6aS)-3-cyano-5-fluorobenzyl 5-(1H-benzo[d][1,2,3]triazole-5-carbonyl)hexahydropyrrolo[3,4-c]pyrrole-2(1H)-carboxylate | (1H-benzo[d][1,2,3]triazol-5-yl)(trans-hexahydropyrrolo[3,4-c]pyrrol-2(1H)-yl)methanone hydrochloride (intermediate 2.2) | 3-fluoro-5-(hydroxymethyl)-benzonitrile (CAS-RN 1021871-34-0) | 435.4 (M + H)+ |

| No. | Systematic Name | Amine | Alcohol | MS, m/e |
|---|---|---|---|---|
| 4.30 | (3aR,6aS)-3-chloro-5-methoxybenzyl 5-(1H-benzo[d][1,2,3]triazole-5-carbonyl)hexahydropyrrolo[3,4-c]pyrrole-2(1H)-carboxylate | (1H-benzo[d][1,2,3]triazol-5-yl)(trans-hexahydropyrrolo[3,4-c]pyrrol-2(1H)-yl)methanone hydrochloride (intermediate 2.2) | (3-chloro-5-methoxy-phenyl)-methanol (CAS-RN 82477-68-7) | 456.5 (M + H)$^+$ |
| 4.31 | (3aS,6aR)-5-(1H-benzotriazole-5-carbonyl)-hexahydro-pyrrolo[3,4-c]pyrrole-2-carboxylic acid (1S,4R)-3-methyl-bicyclo[2.2.1]hept-2-ylmethyl ester | (1H-benzo[d][1,2,3]triazol-5-yl)(trans-hexahydropyrrolo[3,4-c]pyrrol-2(1H)-yl)methanone hydrochloride (intermediate 2.2) | 2-norbornane-methanol (CAS-RN 6968-75-8) | 423.2 (M + H)$^+$ |
| 4.32 | (3aS,6aR)-5-(1H-benzotriazole-5-carbonyl)-hexahydro-pyrrolo[3,4-c]pyrrole-2-carboxylic acid (1R,4S)-1-bicyclo[2.2.1]hept-2-ylmethyl ester | (1H-benzo[d][1,2,3]triazol-5-yl)(trans-hexahydropyrrolo[3,4-c]pyrrol-2(1H)-yl)methanone hydrochloride (intermediate 2.2) | (1R,4S)-bicyclo[2.2.1]-heptan-2-ylmethanol | 410.2 (M + H)$^+$ |
| 4.33 | (3aR,5s,6aS)-5-[(3H-[1,2,3]triazol-4-ylmethyl)-carbamoyl]-hexahydro-cyclopenta[c]pyrrole-2-carboxylic acid 3,5-dichloro-benzyl ester | (3aR,5s,6aS)-N-((1H-1,2,3-triazol-4-yl)methyl)octahydro-cyclopenta[c]pyrrole-5-carboxamide 2,2,2-trifluoroacetate (intermediate 4) | (3,5-dichloro-phenyl)-methanol | 438.4 (M + H)$^+$ |

| No. | Systematic Name | Amine | Alcohol | MS, m/e |
|---|---|---|---|---|
| 4.34 | (3aS,6aS)-5-(1,4,6,7-tetrahydro-[1,2,3]triazolo[4,5-c]pyridine-5-carbonyl)-hexahydro-pyrrolo[3,4-c]pyrrole-2-carboxylic acid 3-chloro-5-methanesulfonyl-benzyl ester | (6,7-dihydro-1H-[1,2,3]triazolo[4,5-c]pyridin-5(4H)-yl)((3aR,6aR)-hexahydropyrrolo[3,4-c]pyrrol-2(1H)-yl)methanone hydrochloride (intermediate 25) | (3-chloro-5-(methyl-sulfonyl)-phenyl)-methanol (intermediate 17) | 509.5 (M + H)+ |
| 4.35 | (3aS,6aR)-5-[(1H-[1,2,3]triazol-4-ylmethyl)-carbamoyl]-hexahydro-pyrrolo[3,4-c]pyrrole-2-carboxylic acid 3,5-dichloro-benzyl ester | (3aR,6aS)-N-((1H-1,2,3-triazol-4-yl)methyl)hexahydro-pyrrolo[3,4-c]pyrrole-2(1H)-carboxamide 2,2,2-trifluoroacetate (intermediate 20) | (3,5-dichloro-phenyl)-methanol | 440.3 (M + H)+ |
| 4.36 | (3aS,6aS)-5-(1H-benzotriazole-5-carbonyl)-hexahydro-pyrrolo[3,4-c]pyrrole-2-carboxylic acid 4-trifluoromethoxy-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (4-(trifluoro-methoxy)-phenyl)-methanol | 476.5 (M + H)+ |
| 4.37 | (3aS,6aS)-5-(1H-benzotriazole-5-carbonyl)-hexahydro-pyrrolo[3,4-c]pyrrole-2-carboxylic acid 4-cyano-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4-(hydroxy-methyl)-benzonitrile | 415.5 (M − H)− |

| No. | Systematic Name | Amine | Alcohol | MS, m/e |
|---|---|---|---|---|
| 4.38 | (3aS,6aS)-5-(1H-benzotriazole-5-carbonyl)-hexahydro-pyrrolo[3,4-c]pyrrole-2-carboxylic acid 4-(1,1,2,2-tetrafluoro-ethoxy)-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (4-(1,1,2,2-tetrafluoro-ethoxy)-phenyl)-methanol (CAS-RN 773868-39-6) | 508.4 (M + H)$^+$ |
| 4.39 | (3aS,6aS)-5-(1H-benzotriazole-5-carbonyl)-hexahydro-pyrrolo[3,4-c]pyrrole-2-carboxylic acid 4-difluoromethoxy-3-fluoro-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (4-(difluoro-methoxy)-3-fluorophenyl)-methanol (CAS-RN 1242252-59-0) | 476.4 (M + H)$^+$ |
| 4.40 | (3aS,6aS)-5-(1H-[1,2,3]triazolo[4,5-b]pyridine-5-carbonyl)-hexahydro-pyrrolo[3,4-c]pyrrole-2-carboxylic acid 3-fluoro-4-trifluoromethoxy-benzyl ester | (1H-[1,2,3]triazolo[4,5-b]pyridin-5-yl)((3aR,6aR)-hexahydropyrrolo[3,4-c]pyrrol-2(1H)-yl)methanone hydrochloride (intermediate 2.6) | (3-fluoro-4-(trifluoro-methoxy)-phenyl)-methanol (CAS-RN 886498-99-3) | 495.3 (M + H)$^+$ |
| 4.41 | (3aS,6aS)-5-(1H-benzotriazole-5-carbonyl)-hexahydro-pyrrolo[3,4-c]pyrrole-2-carboxylic acid 4-difluoromethoxy-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (4-(difluoro-methoxy)-phenyl)-methanol (CAS-RN 170924-50-2) | 458.6 (M + H)$^+$ |

| No. | Systematic Name | Amine | Alcohol | MS, m/e |
|---|---|---|---|---|
| 4.42 | (3aS,6aS)-5-(1H-[1,2,3]triazolo[4,5-b]pyridine-5-carbonyl)-hexahydro-pyrrolo[3,4-c]pyrrole-2-carboxylic acid 4-trifluoromethoxy-benzyl ester | (1H-[1,2,3]triazolo[4,5-b]pyridin-5-yl)((3aR,6aR)-hexahydropyrrolo[3,4-c]pyrrol-2(1H)-yl)methanone hydrochloride (intermediate 2.6) | (4-(trifluoromethoxy)-phenyl)-methanol | 477.6 (M + H)+ |
| 4.43 | (3aS,6aS)-5-(1H-benzotriazole-5-carbonyl)-hexahydro-pyrrolo[3,4-c]pyrrole-2-carboxylic acid 3-fluoro-4-trifluoromethoxy-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (3-fluoro-4-(trifluoromethoxy)-phenyl)-methanol (CAS-RN 886498-99-3) | 494.4 (M + H)+ |
| 4.44 | (3aS,6aS)-5-(1H-benzotriazole-5-carbonyl)-hexahydro-pyrrolo[3,4-c]pyrrole-2-carboxylic acid 4-(2,2,2-trifluoro-ethoxy)-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (4-(2,2,2-trifluoroethoxy)-phenyl)-methanol (CAS-RN 1020949-12-5) | 490.4 (M + H)+ |
| 4.45 | (3aS,6aS)-5-(1H-benzotriazole-5-carbonyl)-hexahydro-pyrrolo[3,4-c]pyrrole-2-carboxylic acid 5-trifluoromethoxy-pyridin-2-ylmethyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (5-(trifluoromethoxy)-pyridin-2-yl)methanol (CAS-RN 31181-85-8) | 477.4 (M + H)+ |

| No. | Systematic Name | Amine | Alcohol | MS, m/e |
|---|---|---|---|---|
| 4.46 | (3aS,6aS)-5-((R)-4,5,6,7-tetrahydro-1H-benzotriazole-5-carbonyl)-hexahydro-pyrrolo[3,4-c]pyrrole-2-carboxylic acid 4-cyano-2-isopropyl-benzyl ester | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 4-(hydroxy-methyl)-3-isopropyl-benzonitrile (intermediate 41) | 463.5 (M + H)+ |
| 4.47 | (3aS,6aS)-5-((R)-4,5,6,7-tetrahydro-1H-benzotriazole-5-carbonyl)-hexahydro-pyrrolo[3,4-c]pyrrole-2-carboxylic acid 4-cyano-2-isopropyl-5-methyl-benzyl ester | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 4-(hydroxy-methyl)-5-isopropyl-2-methyl-benzonitrile (intermediate 41.1) | 477.5 (M + H)+ |
| 4.48 | (3aS,6aS)-5-((R)-4,5,6,7-tetrahydro-1H-benzotriazole-5-carbonyl)-hexahydro-pyrrolo[3,4-c]pyrrole-2-carboxylic acid 2-fluoro-4-trifluoromethoxy-benzyl ester | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | (2-fluoro-4-(trifluoro-methoxy)-phenyl)-methanol (CAS-RN 1240257-07-1) | 498.4 (M + H)+ |
| 4.49 | (3aS,6aS)-5-(1H-benzotriazole-5-carbonyl)-hexahydro-pyrrolo[3,4-c]pyrrole-2-carboxylic acid 2-fluoro-4-trifluoromethoxy-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (2-fluoro-4-(trifluoro-methoxy)-phenyl)-methanol (CAS-RN 1240257-07-1) | 494.6 (M + H)+ |

| No. | Systematic Name | Amine | Alcohol | MS, m/e |
|---|---|---|---|---|
| 4.50 | (3aS,6aS)-5-(1H-benzotriazole-5-carbonyl)-hexahydro-pyrrolo[3,4-c]pyrrole-2-carboxylic acid 4-cyano-2-ethoxy-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-ethoxy-4-(hydroxy-methyl)-benzonitrile (intermediate 41.2) | 459.6 (M + H)+ |
| 4.51 | (3aS,6aS)-5-((R)-4,5,6,7-tetrahydro-1H-benzotriazole-5-carbonyl)-hexahydro-pyrrolo[3,4-c]pyrrole-2-carboxylic acid 3-fluoro-4-trifluoromethoxy-benzyl ester | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | (3-fluoro-4-(trifluoro-methoxy)-phenyl)-methanol (CAS-RN 886498-99-3) | 496.4 (M − H)− |
| 4.52 | (3aS,6aS)-5-(1H-benzotriazole-5-carbonyl)-hexahydro-pyrrolo[3,4-c]pyrrole-2-carboxylic acid 4-cyano-2-isopropyl-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4-(hydroxy-methyl)-3-isopropyl-benzonitrile (intermediate 41) | 459.5 (M + H)+ |
| 4.53 | (3aS,6aS)-5-(1H-benzotriazole-5-carbonyl)-hexahydro-pyrrolo[3,4-c]pyrrole-2-carboxylic acid 4-cyano-2-isopropyl-5-methyl-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4-(hydroxy-methyl)-5-isopropyl-2-methylbenzo-nitrile (intermediate 41.1) | 473.5 (M + H)+ |

| No. | Systematic Name | Amine | Alcohol | MS, m/e |
|---|---|---|---|---|
| 4.54 | (3aS,6aS)-5-(1,4,6,7-tetrahydro-[1,2,3]triazolo[4,5-c]pyridine-5-carbonyl)-hexahydro-pyrrolo[3,4-c]pyrrole-2-carboxylic acid 4-trifluoromethoxy-benzyl ester | (6,7-dihydro-1H-[1,2,3]triazolo[4,5-c]pyridin-5(4H)-yl)((3aR,6aR)-hexahydropyrrolo[3,4-c]pyrrol-2(1H)-yl)methanone hydrochloride (intermediate 25) | (4-(trifluoro-methoxy)-phenyl)-methanol | 481.6 (M + H)+ |
| 4.55 | (3aR,6aR)-5-(1H-benzotriazole-5-carbonyl)-hexahydro-pyrrolo[3,4-c]pyrrole-2-carboxylic acid 4-trifluoromethoxy-benzyl ester | (1H-benzo[d][1,2,3]triazol-5-yl)((3aS,6aS)-hexahydropyrrolo[3,4-c]pyrrol-2(1H)-yl)methanone dihydrochloride (intermediate 8) | (4-(trifluoro-methoxy)-phenyl)-methanol | 476.4 (M + H)+ |
| 4.56 | (3aS,6aS)-5-(1H-benzotriazole-5-carbonyl)-hexahydro-pyrrolo[3,4-c]pyrrole-2-carboxylic acid 2-fluoro-4-trifluoromethyl-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (2-fluoro-4-(trifluoro-methyl)-phenyl)-methanol | 478.4 (M + H)+ |
| 4.57 | (3aS,6aS)-5-(1H-benzotriazole-5-carbonyl)-hexahydro-pyrrolo[3,4-c]pyrrole-2-carboxylic acid 4-trifluoromethyl-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (4-(trifluoro-methyl)-phenyl)-methanol | 460.5 (M + H)+ |

| No. | Systematic Name | Amine | Alcohol | MS, m/e |
|---|---|---|---|---|
| 4.58 | (3aS,6aS)-5-((R)-4,5,6,7-tetrahydro-1H-benzotriazole-5-carbonyl)-hexahydro-pyrrolo[3,4-c]pyrrole-2-carboxylic acid 4-trifluoromethoxy-benzyl ester | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | (4-(trifluoro-methoxy)-phenyl)-methanol | 480.5 (M + H)+ |
| 4.59 | (3aS,6aS)-5-((R)-4,5,6,7-tetrahydro-1H-benzotriazole-5-carbonyl)-hexahydro-pyrrolo[3,4-c]pyrrole-2-carboxylic acid 4-trifluoromethyl-benzyl ester | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | (4-(trifluoro-methyl)-phenyl)-methanol | 464.5 (M + H)+ |
| 4.60 | (3aS,6aS)-5-((R)-4,5,6,7-tetrahydro-1H-benzotriazole-5-carbonyl)-hexahydro-pyrrolo[3,4-c]pyrrole-2-carboxylic acid 3-chloro-5-methanesulfonyl-benzyl ester | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | (3-chloro-5-(methyl-sulfonyl)-phenyl)-methanol (intermediate 17) | 508.4 (M + H)+ |
| 4.61 | (3aS,6aS)-5-(1H-benzotriazole-5-carbonyl)-hexahydro-pyrrolo[3,4-c]pyrrole-2-carboxylic acid 4-cyano-2-methanesulfonyl-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4-(hydroxymethyl)-3-(methylsulfonyl)benzonitrile (intermediate 48) | 493.2 (M − H)− |

-continued

| No. | Systematic Name | Amine | Alcohol | MS, m/e |
|---|---|---|---|---|
| 4.62 | (3aS,6aS)-5-(1H-benzotriazole-5-carbonyl)-hexahydro-pyrrolo[3,4-c]pyrrole-2-carboxylic acid 4-cyano-2-ethoxy-5-fluoro-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 5-ethoxy-2-fluoro-4-(hydroxy-methyl)-benzonitrile (intermediate 49) | 477.3 (M − H)⁻ |
| 4.63 | (3aS,6aS)-5-(4-methoxy-1H-benzotriazole-5-carbonyl)-hexahydro-pyrrolo[3,4-c]pyrrole-2-carboxylic acid 4-trifluoromethoxy-benzyl ester | (3aS,6aS)-4-(trifluoromethoxy)-benzyl hexahydropyrrolo[3,4-c]pyrrole-2(1H)-carboxylate hydrochloride (intermediate 1.8) | 4-methoxy-1H-benzo[d]-[1,2,3]triazole-5-carboxylic acid (intermediate 45.1) | 504.3 (M − H)⁻ |
| 4.64 | (3aS,6aS)-5-(1H-benzotriazole-5-carbonyl)-hexahydro-pyrrolo[3,4-c]pyrrole-2-carboxylic acid 4-cyano-2-cyclobutoxy-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-cyclobutoxy-4-(hydroxy-methyl)-benzonitrile (intermediate 46) | 487.3 (M + H)⁺ |
| 4.65 | (3aS,6aS)-5-(1H-benzotriazole-5-carbonyl)-hexahydro-pyrrolo[3,4-c]pyrrole-2-carboxylic acid 4-cyano-2-isopropoxy-benzyl ester | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4-(hydroxy-methyl)-3-isopropoxy-benzonitrile (intermediate 46.1) | 475.3 (M + H)⁺ |

| No. | Systematic Name | | Amine | Alcohol | MS, m/e |
|---|---|---|---|---|---|
| 4.66 | (3aS,6aS)-5-(1H-benzotriazole-5-carbonyl)-hexahydro-pyrrolo[3,4-c]pyrrole-2-carboxylic acid 4-cyano-2-(2,2,2-trifluoro-ethoxy)-benzyl ester | | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4-(hydroxy-methyl)-3-(2,2,2-trifluoro-ethoxy)-benzonitrile (intermediate 47.1) | 515.3 (M + H)+ |
| 4.67 | (3aS,6aS)-5-(1H-benzotriazole-5-carbonyl)-hexahydro-pyrrolo[3,4-c]pyrrole-2-carboxylic acid 4-chloro-2-ethoxy-5-fluoro-benzyl ester | | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (4-chloro-2-ethoxy-5-fluorophenyl)methanol (intermediate 47) | 488.2 (M + H)+ |

Example 5

(3aR,5r,6aS)-3,5-Dichlorobenzyl 5-(2-oxo-2,3-dihydrobenzo[d]oxazol-6-ylamino)hexahydrocyclopenta[c]pyrrole-2(1H)-carboxylate

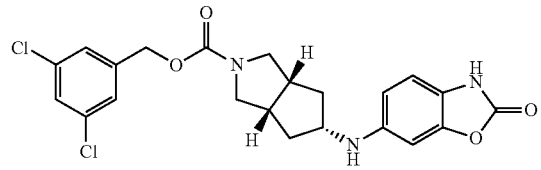 [SMILES: O=C(OCc1cc(Cl)cc(Cl)c1)N1C[C@H]2C[C@@H](Nc3ccc4[nH]c(=O)oc4c3)C[C@H]2C1]

Sodium triacetoxyborohydride (121 mg, 556 µmol) was added at room temperature to a solution of (3aR,6aS)-3,5-dichlorobenzyl 5-oxohexahydrocyclopenta[c]pyrrole-2(1H)-carboxylate (intermediate 13; 128 mg, 371 µmol), 6-aminobenzo[d]oxazol-2(3H)-one (CAS-RN 22876-17-1; 57.3 mg, 371 µmol) and acetic acid (134 mg, 2.22 mmol) in 1,2-dichloroethane (2.5 mL), then after 16 h another portion of sodium triacetoxyborohydride (39.3 mg, 185 µmol) was added. After another 6 h the reaction mixture was partitioned between ethyl acetate and sat. aq. sodium hydrogen carbonate solution. The organic layer was washed with brine, dried over magnesium sulfate, filtered, and evaporated. Chromatography (silica gel; dichloromethane to dichloromethane/methanol/25% aq. ammonia solution 95:5:0.25), followed by HPLC chromatography (Reprosil Chiral-NR, heptane/ethanol 3:2) produced the title compound (70 mg, 41%). White solid, MS: 462.2 (M+H)+.

Example 6

(3aR,6aS)-3,5-Dichlorobenzyl 5-((1H-benzo[d]imidazol-5-yl)methyl)hexahydropyrrolo[3,4-c]pyrrole-2(1H)-carboxylate

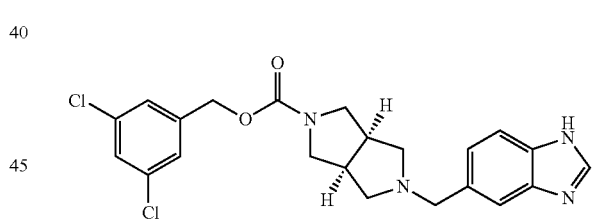

To a white suspension of (3aR,6aS)-3,5-dichlorobenzyl hexahydropyrrolo[3,4-c]pyrrole-2(1H)-carboxylate hydrochloride (intermediate 1; 35 mg, 99.5 µmol) and 1H-benzo[d]imidazole-5-carbaldehyde (15.0 mg, 99.5 µmol) in tetrahydrofuran (2 mL) were added sodium triacetoxyborohydride (31.6 mg, 149 µmol) and acetic acid (9.0 mg, 150 µmol), then after 3 h the reaction mixture was partitioned between ethyl acetate and sat. aq. sodium hydrogen carbonate solution. The organic layer was washed with brine, dried over magnesium sulfate, filtered and evaporated. Chromatography (silica gel; gradient dichloromethane to dichloromethane/methanol/25% aq. ammonia solution 90:10:0.25) produced the title compound (42 mg, 95%). White foam, MS: 445.3 (M+H)+.

The following compounds were produced in analogy to example 6, replacing (3aR,6aS)-3,5-dichlorobenzyl hexahydropyrrolo[3,4-c]pyrrole-2(1H)-carboxylate hydrochloride and 1H-benzo[d]imidazole-5-carbaldehyde by the appropriate amine and aldehyde reagents, respectively.

| No. | Systematic Name | | Amine | Aldehyde | Ms, m/e |
|---|---|---|---|---|---|
| 6.01 | 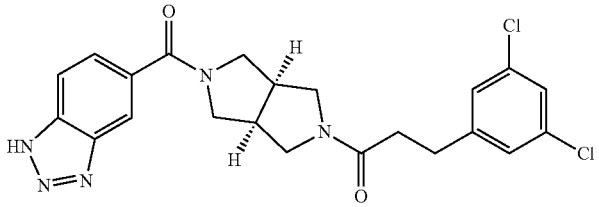<br>1-((3aR,6aS)-5-((1H-benzo[d][1,2,3]triazol-5-yl)methyl)hexahydropyrrolo[3,4-c]pyrrol-2(1H)-yl)-3-(3,5-dichlorophenyl)propan-1-one | | 3-(3,5-dichlorophenyl)-1-((3aR,6aS)-hexahydropyrrolo[3,4-c]pyrrol-2(1H)-yl)propan-1-one hydrochloride (intermediate 3) | 1H-benzo[d]-[1,2,3]triazole-5-carbaldehyde (CAS-RN 70938-42-0) | 444.5 (M + H)+ |
| 6.02 | 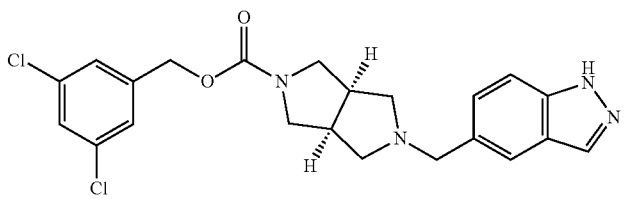<br>(3aR,6aS)-3,5-dichlorobenzyl 5-((1H-indazol-5-yl)methyl)hexahydropyrrolo[3,4-c]pyrrole-2(1H)-carboxylate | | (3aR,6aS)-3,5-dichlorobenzyl hexahydropyrrolo[3,4-c]pyrrole-2(1H)-carboxylate hydrochloride (intermediate 1) | 1H-indazole-5-carbaldehyde | 445.2 (M + H)+ |
| 6.03 | 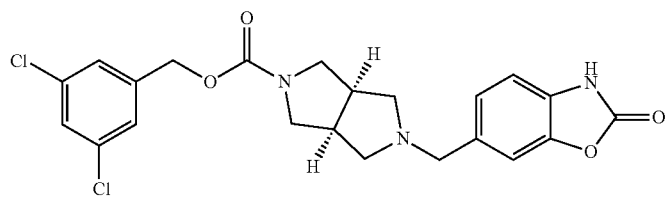<br>(3aR,6aS)-3,5-dichlorobenzyl 5-((2-oxo-2,3-dihydrobenzo[d]oxazol-6-yl)methyl)hexahydropyrrolo[3,4-c]pyrrole-2(1H)-carboxylate | | (3aR,6aS)-3,5-dichlorobenzyl hexahydropyrrolo[3,4-c]pyrrole-2(1H)-carboxylate hydrochloride (intermediate 1) | 2-oxo-2,3-dihydro-benzo[d]oxazole-6-carbaldehyde (CAS-RN 54903-15-0) | 462.2 (M + H)+ |
| 6.04 | 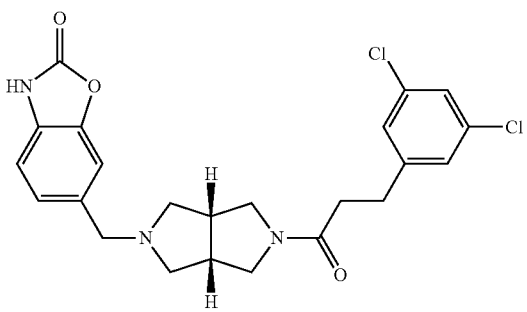<br>6-(((3aR,6aS)-5-(3-(3,5-dichlorophenyl)propanoyl)hexahydropyrrolo[3,4-c]pyrrol-2(1H)-yl)methyl)benzo[d]oxazol-2(3H)-one | | 3-(3,5-dichlorophenyl)-1-((3aR,6aS)-hexahydropyrrolo[3,4-c]pyrrol-2(1H)-yl)propan-1-one hydrochloride (intermediate 3) | 2-oxo-2,3-dihydro-benzo[d]oxazole-6-carbaldehyde (CAS-RN 54903-15-0) | 460.3 (M + H)+ |
| 6.05 | 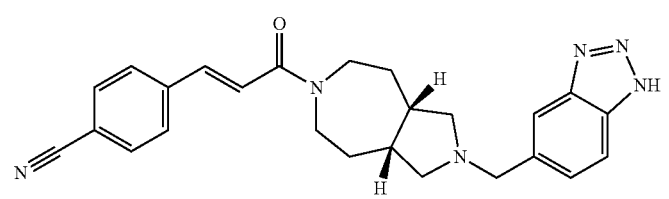<br>4-{(E)-3-[(3aS,8aR)-2-(1H-benzotriazol-5-ylmethyl)-octahydro-pyrrolo[3,4-d]azepin-6-yl]-3-oxo-propenyl}-benzonitrile | | 4-((E)-3-((3aR,8aS)-octahydropyrrolo[3,4-d]azepin-6(7H)-yl)-3-oxoprop-1-enyl)benzonitrile hydrochloride (intermediate 5.1) | 1H-benzo[d]-[1,2,3]triazole-5-carbaldehyde (CAS-RN 70938-42-0) | 427.6 (M + H)+ |

-continued

| No. | Systematic Name | Amine | Aldehyde | Ms, m/e |
|---|---|---|---|---|
| 6.06 | (E)-1-[(3aS,8aR)-2-(1H-benzotriazol-5-ylmethyl)-octahydro-pyrrolo[3,4-d]azepin-6-yl]-3-(4-trifluoromethoxy-phenyl)-prop-2-en-1-one | (E)-1-((3aR,8aS)-octahydropyrrolo[3,4-d]azepin-6(7H)-yl)-3-(4-(trifluoromethoxy)-phenyl)prop-2-en-1-one hydrochloride (intermediate 5) | 1H-benzo[d]-[1,2,3]triazole-5-carbaldehyde (CAS-RN 70938-42-0) | 485.5 (M + H)+ |
| 6.07 | (E)-1-[trans-2-(1H-benzotriazol-5-ylmethyl)-octahydro-pyrrolo[3,4-c]pyridin-5-yl]-3-(4-trifluoromethoxy-phenyl)-propenone | (E)-1-(trans-octahydro-pyrrolo[3,4-c]pyridin-5-yl)-3-(4-(trifluoromethoxy)-phenyl)prop-2-en-1-one hydrochloride (intermediate 5.3) | 1H-benzo[d]-[1,2,3]triazole-5-carbaldehyde (CAS-RN 70938-42-0) | 472.7 (M + H)+ |

Example 7

(3aR,6aS)-3,5-Dichlorobenzyl 5-(2-oxo-2,3-dihydrobenzo[d]oxazol-6-ylsulfonyl)hexahydropyrrolo[3,4-c]pyrrole-2(1H)-carboxylate

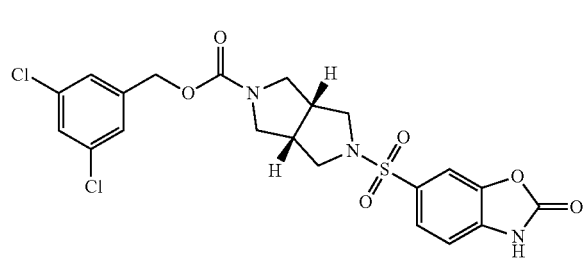 [SMILES: O=C(OCc1cc(Cl)cc(Cl)c1)N1C[C@@H]2CN(S(=O)(=O)c3ccc4[nH]c(=O)oc4c3)C[C@@H]2C1]

To a suspension of (3aR,6aS)-3,5-dichlorobenzyl hexahydropyrrolo[3,4-c]pyrrole-2(1H)-carboxylate hydrochloride (intermediate 1; 40 mg, 114 µmol) and pyridine (45.0 mg, 569 µmol) in acetone (2 mL) was added 2-oxo-2,3-dihydrobenzo[d]oxazole-6-sulfonyl chloride (25.2 mg, 108 µmol) at room temperature, then after 40 h the reaction mixture was partitioned between sat. aq. sodium hydrogencarbonate solution and ethyl acetate. The organic layer was washed with brine, dried over magnesium sulfate, filtered, and evaporated. The residue was dissolved in ethyl acetate, then after 40 min the suspension formed was treated with ethyl acetate/heptane 1:1 and the precipitate was collected by filtration to afford the title compound (24 mg, 41%). White solid, MS: 512.2 (M+H)+.

Example 8

(3aR,6aS)-3,5-Dichlorobenzyl 5-(4,5,6,7-tetrahydro-1H-[1,2,3]triazolo[4,5-c]pyridine-5-carbonyl)hexahydropyrrolo[3,4-c]pyrrole-2(1H)-carboxylate

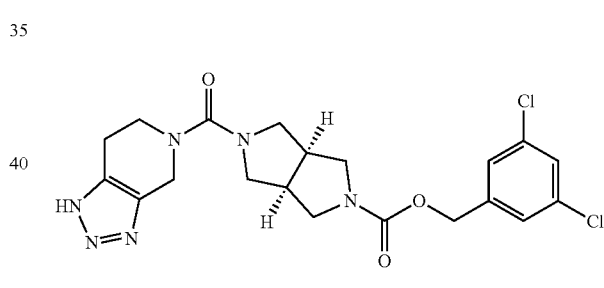

To a suspension of 4,5,6,7-tetrahydro-1H-[1,2,3]triazolo[4,5-c]pyridine (CAS-RN 706757-05-3; 52.5 mg, 423 µmol) in dichloromethane (8 mL) was added a solution of (3aR,6aS)-3,5-dichlorobenzyl 5-(chlorocarbonyl)hexahydropyrrolo[3,4-c]pyrrole-2(1H)-carboxylate (intermediate 9; 168 mg, 423 µmol) in dichloromethane (2 mL) dropwise at room temperature, then after 1 h, N,N-dimethylformamide (1 mL) was added. After 96 h, the reaction mixture was washed with sat. aq. ammonium chloride solution and brine, dried over magnesium sulfate, filtered, and evaporated. Chromatography (silica gel; gradient dichloromethane to dichloromethane/methanol/25% aq. ammonia solution 90:10:0.25) produced the title compound (136 mg, 69%). Colourless oil, MS: 465.5 (M+H)+.

The following examples were produced in analogy to example 8, replacing (3aR,6aS)-3,5-dichlorobenzyl 5-(chlorocarbonyl)hexahydropyrrolo[3,4-c]pyrrole-2(1H)-carboxylate by (3aR,8aS)-6-((E)-3-(4-(trifluoromethoxy)phenyl)acryloyl)octahydropyrrolo[3,4-d]azepine-2(1H)-carbonyl chloride (intermediate 9.1) and 4,5,6,7-tetrahydro-1H-[1,2,3]triazolo[4,5-c]pyridine by the appropriate amine precursor.

| Ex. | Systematic Name | Amine | MS, m/e |
|---|---|---|---|
| 8.01 | 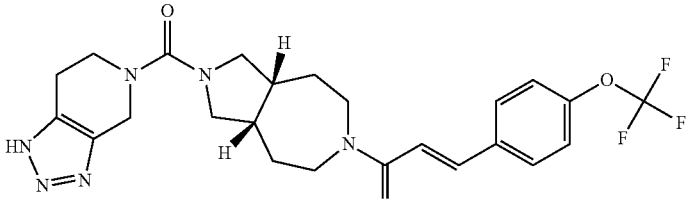<br>(E)-1-[(3aS,8aR)-2-(1,4,6,7-tetrahydro-[1,2,3]triazolo[4,5-c]pyridine-5-carbonyl)-octahydro-pyrrolo[3,4-d]azepin-6-yl]-3-(4-trifluoromethoxy-phenyl)-prop-2-en-1-one | 4,5,6,7-tetrahydro-1H-[1,2,3]triazolo[4,5-c]pyridine (CAS-RN 706757-05-3) | 505.7 (M + H)⁺ |
| 8.02 | 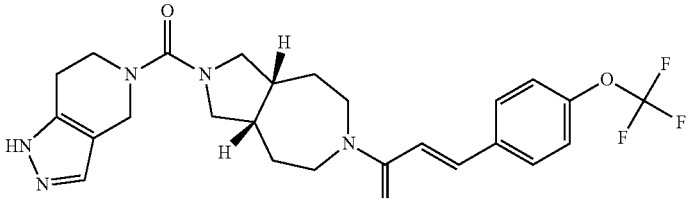<br>(E)-1-[(3aS,8aR)-2-(1,4,6,7-tetrahydro-pyrazolo[4,3-c]pyridine-5-carbonyl)-octahydro-pyrrolo[3,4-d]azepin-6-yl]-3-(4-trifluoromethoxy-phenyl)-prop-2-en-1-one | 4,5,6,7-tetrahydro-1H-pyrazolo[4,3-c]pyridine dihydrochloride (CAS-RN 157327-44-1) | 504.7 (M + H)⁺ |
| 8.03 | 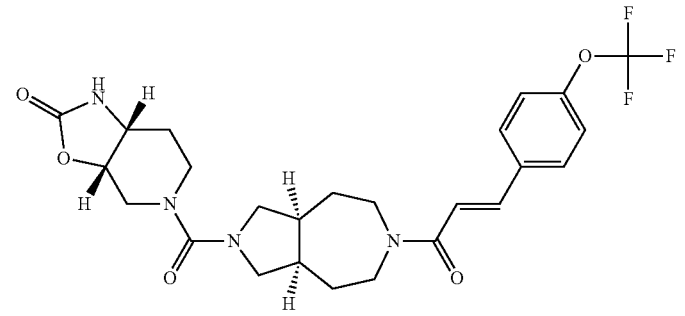<br>cis-5-((3aR,8aS)-6-((E)-3-(4-(trifluoromethoxy)phenyl)acryloyl)decahydro-pyrrolo[3,4-d]azepine-2-carbonyl)-hexahydrooxazolo[5,4-c]pyridin-2(1H)-one | cis-hexahydro-oxazolo[5,4-c]pyridin-2(1H)-one hydrochloride (intermediate 28) | 523.5 (M + H)⁺ |
| 8.04 | 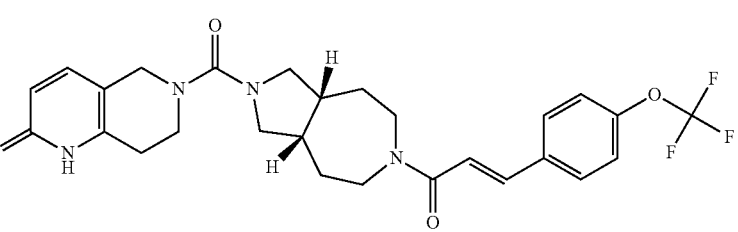<br>6-{(3aS,8aR)-6-[(E)-3-(4-trifluoromethoxy-phenyl)-acryloyl]-octahydro-pyrrolo[3,4-d]azepine-2-carbonyl}-5,6,7,8-tetrahydro-1H-[1,6]naphthyridin-2-one | 5,6,7,8-tetrahydro-1,6-naphthyridin-2(1H)-one hydrochloride (CAS-RN 1211505-91-7) | 531.6 (M + H)⁺ |
| 8.05 | 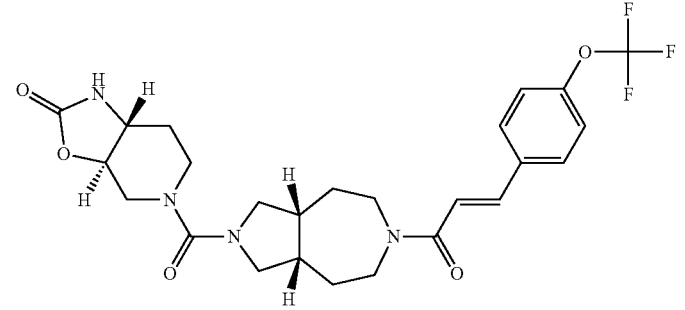<br>(3aR,7aR)-5-{(3aS,8aR)-6-[(E)-3-(4-trifluoromethoxy-phenyl)-acryloyl]-octahydro-pyrrolo[3,4-d]azepine-2-carbonyl}-hexahydro-oxazolo[5,4-c]pyridin-2-one | (3aR,7aR)-hexahydro-oxazolo[5,4-c]pyridin-2(1H)-one hydrochloride (intermediate 27) | 523.6 (M + H)⁺ |

| Ex. | Systematic Name | Amine | MS, m/e |
|---|---|---|---|
| 8.06 | 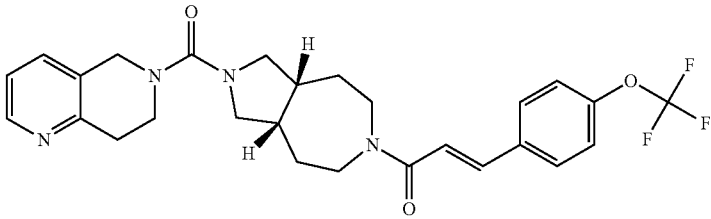<br>(E)-1-[(3aS,8aR)-2-(7,8-dihydro-5H-[1,6]naphthyridine-6-carbonyl)-octahydro-pyrrolo[3,4-d]azepin-6-yl]-3-(4-trifluoromethoxy-phenyl)-prop-2-en-1-one | 5,6,7,8-tetrahydro-1,6-naphthyridine dihydrochloride (CAS-RN 348623-30-3) | 515.5 (M + H)⁺ |
| 8.07 | 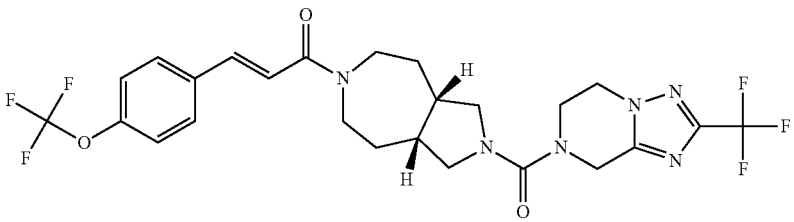<br>(E)-3-(4-trifluoromethoxy-phenyl)-1-[(3aS,8aR)-2-(2-trifluoromethyl-5,6-dihydro-8H-[1,2,4]triazolo[1,5-a]pyrazine-7-carbonyl)-octahydro-pyrrolo[3,4-d]azepin-6-yl]-prop-2-en-1-one | 2-(trifluoromethyl)-5,6,7,8-tetrahydro-[1,2,4]triazolo[1,5-a]pyrazine (CAS-RN 681249-57-0) | 573.7 (M + H)⁺ |

Example 9

(3aR,8aS)—N-((1H-1,2,3-Triazol-5-yl)methyl)-6-((E)-3-(4-(trifluoromethoxy)phenyl)-acryloyl)octahydropyrrolo[3,4-d]azepine-2(1H)-carboxamide

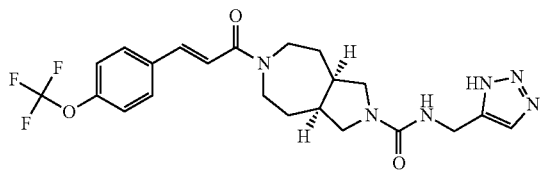 [SMILES: O=C(/C=C/c1ccc(OC(F)(F)F)cc1)N1CC[C@@H]2CN(C(=O)NCc3cnn[nH]3)C[C@@H]2CC1]

A solution of bis(trichloromethyl)-carbonate (73.7 mg, 248 μmol) in ethyl acetate (10 mL) was added dropwise at 0° C. over a period of 5 minutes to a solution of (E)-1-((3aR,8aS)-octahydropyrrolo[3,4-d]azepin-6(7H)-yl)-3-(4-(trifluoromethoxy)phenyl)prop-2-en-1-one (intermediate 5; 176 mg, 497 μmol) in tetrahydrofuran (5 mL). The ice bath was removed, then after 30 min the reaction mixture was heated at reflux for 2 h. After concentration under vacuum, the residue was dissolved in tetrahydrofuran (7 mL), then after addition of (1H-1,2,3-triazol-4-yl)methanamine hydrochloride (66.8 mg, 497 μmol) and triethylamine (251 mg, 2.48 mmol) the reaction mixture was stirred at room temperature for 17 hours and then partitioned between sat. aq. sodium hydrogen carbonate solution and ethyl acetate. The organic layer was washed with brine, dried over sodium sulfate, filtered, and evaporated. Chromatography (silica gel; heptane/ethyl acetate 4:1, then dichloromethane/methanol 95:5) afforded the title compound (68 mg, 28%). White solid, MS: 479.5 (M+H)⁺.

The following examples were produced in analogy to example 8, replacing (E)-1-((3aR,8aS)-octahydropyrrolo[3,4-d]azepin-6(7H)-yl)-3-(4-(trifluoromethoxy)phenyl)prop-2-en-1-one by the appropriate starting material and (1H-1,2,3-triazol-4-yl)methanamine hydrochloride by the appropriate amine reagent.

| Ex. | Systematic Name | Starting material | Amine reagent | MS, m/e |
|---|---|---|---|---|
| 9.01 | 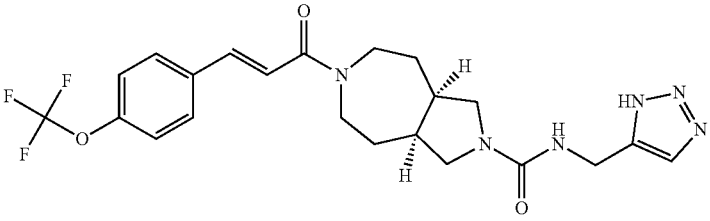<br>(3aR,8aS)-N-((1H-1,2,3-triazol-5-yl)methyl)-6-((E)-3-(4-(trifluoromethoxy)phenyl)acryloyl)-octahydropyrrolo[3,4-d]azepine-2(1H)-carboxamide | (E)-1-((3aR,8aS)-octahydropyrrolo[3,4-d]azepin-6(7H)-yl)-3-(4-(trifluoromethoxy)-phenyl)prop-2-en-1-one (intermediate 5) | (1H-1,2,3-triazol-4-yl)-methanamine hydrochloride | 479.5 (M + H)⁺ |

-continued

| Ex. | Systematic Name | Starting material | Amine reagent | MS, m/e |
|---|---|---|---|---|
| 9.02 | (3aS,6aR)-5-[(E)-3-(4-trifluoromethoxy-phenyl)-acryloyl]-hexahydro-pyrrolo[3,4-c]pyrrole-2-carboxylic acid (1H-[1,2,3]triazol-4-ylmethyl)-amide | (E)-1-((3aR,6aS)-hexahydropyrrolo[3,4-c]pyrrol-2(1H)-yl)-3-(4-(trifluoromethoxy)-phenyl)prop-2-en-1-one (intermediate 26.01) | (1H-1,2,3-triazol-4-yl)-methanamine hydrochloride | 451.5 (M + H)+ |
| 9.03 | (3aR,8aS)-N-((1H-1,2,3-triazol-5-yl)methyl)-6-((E)-3-(3-fluoro-4-(trifluoromethoxy)phenyl)acryloyl)-octahydropyrrolo[3,4-d]azepine-2(1H)-carboxamide | (E)-3-(3-fluoro-4-(trifluoromethoxy)phenyl)-1-((3aR,8aS)-octahydropyrrolo[3,4-d]azepin-6(7H)-yl)prop-2-en-1-one (intermediate 26.03) | (1H-1,2,3-triazol-4-yl)-methanamine hydrochloride | 497.6 (M + H)+ |
| 9.04 | (3aS,8aR)-6-[(E)-3-(4-trifluoromethoxy-phenyl)-acryloyl]-octahydro-pyrrolo[3,4-d]azepine-2-carboxylic acid (4H-[1,2,4]triazol-3-ylmethyl)-amide | (E)-1-((3aR,8aS)-octahydropyrrolo[3,4-d]azepin-6(7H)-yl)-3-(4-(trifluoromethoxy)-phenyl)prop-2-en-1-one hydrochloride (intermediate 5) | 1H-1,2,4-triazole-5-methanamine dihydrochloride (CAS-RN 859791-21-2) | 479.2 (M + H)+ |
| 9.05 | (E)-1-[(3aS,8aR)-2-(6,7-dihydro-4H-[1,2,3]triazolo[1,5-a]pyrazine-5-carbonyl)-octahydro-pyrrolo[3,4-d]azepin-6-yl]-3-(4-trifluoromethoxy-phenyl)-prop-2-en-1-one | (E)-1-((3aR,8aS)-octahydropyrrolo[3,4-d]azepin-6(7H)-yl)-3-(4-(trifluoromethoxy)-phenyl)prop-2-en-1-one hydrochloride (intermediate 5) | 4,5,6,7-tetrahydro-[1,2,3]triazolo[1,5-a]pyrazine hydrochloride (CAS-RN 123308-28-1) | 549.2 (M + HCOO)− |
| 9.06 | (E)-1-[(3aS,8aR)-2-(1,4,6,7-tetrahydro-imidazo[4,5-c]pyridine-5-carbonyl)-octahydro-pyrrolo[3,4-d]azepin-6-yl]-3-(4-trifluoromethoxy-phenyl)-prop-2-en-1-one | (E)-1-((3aR,8aS)-octahydropyrrolo[3,4-d]azepin-6(7H)-yl)-3-(4-(trifluoromethoxy)-phenyl)prop-2-en-1-one hydrochloride (intermediate 5) | 4,5,6,7-tetrahydro-3H-imidazo[4,5-c]pyridine (CAS-RN 6882-74-2) | 504.2 (M + H)+ |

| Ex. | Systematic Name | Starting material | Amine reagent | MS, m/e |
|---|---|---|---|---|
| 9.07 | 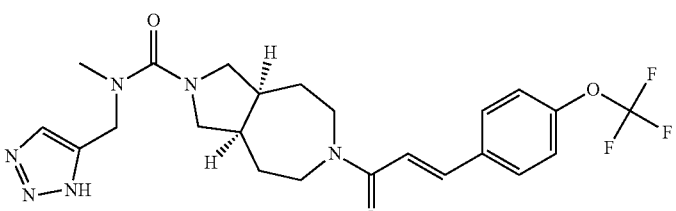<br>(3aR,8aS)-N-((1H-1,2,3-triazol-5-yl)methyl)-N-methyl-6-((E)-3-(4-(trifluoromethoxy)phenyl)acryloyl)-octahydropyrrolo[3,4-d]azepine-2(1H)-carboxamide | (E)-1-((3aR,8aS)-octahydropyrrolo[3,4-d]azepin-6(7H)-yl)-3-(4-(trifluoromethoxy)-phenyl)prop-2-en-1-one (intermediate 5) | N-methyl-1H-1,2,3-triazole-5-methanamine (CAS-RN 1248059-33-7) | 493.7 (M + H)$^+$ |
| 9.08 | 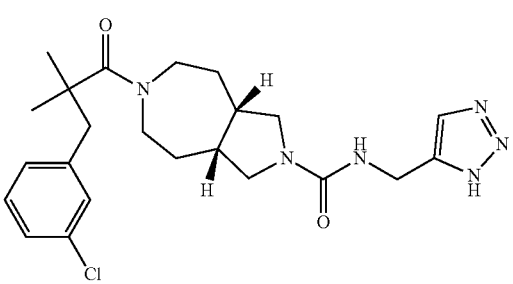<br>(3aS,8aR)-6-[3-(3-chloro-phenyl)-2,2-dimethyl-propionyl]-octahydro-pyrrolo[3,4-d]azepine-2-carboxylic acid (3H-[1,2,3]triazol-4-yl methyl)-amide | 3-(3-chlorophenyl)-2,2-dimethyl-1-((3aR,8aS)-octahydropyrrolo[3,4-d]azepin-6(7H)-yl)propan-1-one (intermediate 26.03) | (1H-1,2,3-triazol-4-yl)-methanamine hydrochloride | 459.5 (M + H)$^+$ |
| 9.09 | 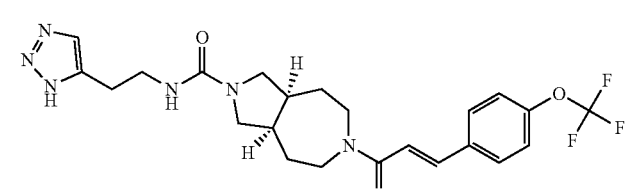<br>(3aR,8aS)-N-(2-(1H-1,2,3-triazol-5-yl)ethyl)-6-((E)-3-(4-(trifluoromethoxy)phenyl)acryloyl)-octahydropyrrolo[3,4-d]azepine-2(1H)-carboxamide | (E)-1-((3aR,8aS)-octahydropyrrolo[3,4-d]azepin-6(7H)-yl)-3-(4-(trifluoromethoxy)-phenyl)prop-2-en-1-one (intermediate 5) | 2-(1H-1,2,3-triazol-5-yl)-ethanamine (CAS-RN 52845-67-7) | 493.6 (M + H)$^+$ |
| 9.10 | 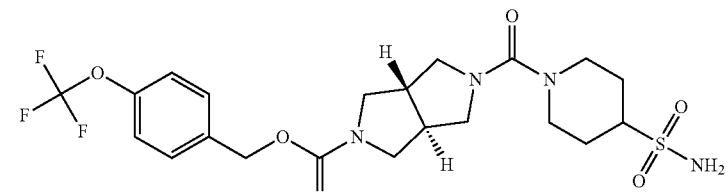<br>(3aS,6aS)-5-(4-sulfamoyl-piperidine-1-carbonyl)-hexahydro-pyrrolo[3,4-c]pyrrole-2-carboxylic acid 4-trifluoromethoxy-benzyl ester | (3aS,6aS)-4-(trifluoromethoxy)-benzyl hexahydro-pyrrolo[3,4-c]pyrrole-2(1H)-carboxylate hydrochloride (intermediate 1.8) | piperidine-4-sulfonamide hydrochloride (CAS-RN 1251923-46-2) | 521.6 (M + H)$^+$ |

Examples 10A and 10B (3aR,7aS)-2-(1H-Benzotriazole-5-carbonyl)-octahydro-pyrrolo[3,4-c]pyridine-5-carboxylic acid 3,5-dichloro-benzyl ester and (3aS,7aR)-2-(1H-benzotriazole-5-carbonyl)-octahydro-pyrrolo[3,4-c]pyridine-5-carboxylic acid 3,5-dichloro-benzyl ester

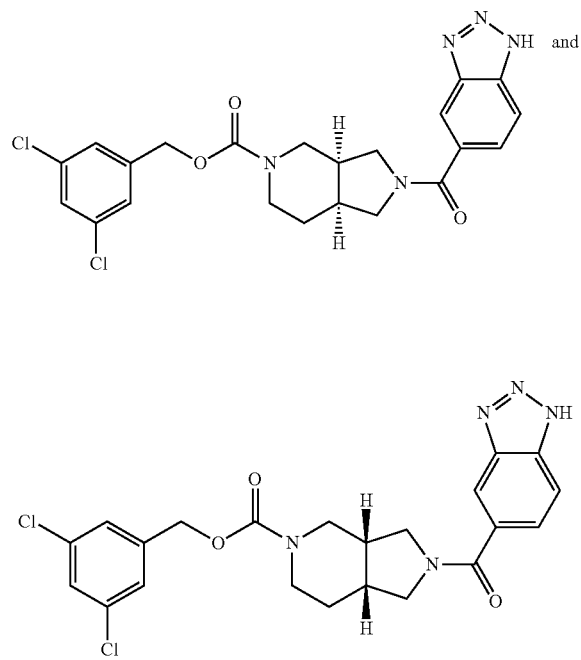

Racemic cis-3,5-dichlorobenzyl 2-(1H-benzo[d][1,2,3]triazole-5-carbonyl)hexahydro-1H-pyrrolo[3,4-c]pyridine-5(6H)-carboxylate (example 1.02; 616 mg, 1.30 mmol) was separated by preparative HPLC using a Reprosil Chiral-NR column as the stationary phase and heptane/ethanol 3:2 as the mobile phase. This produced the faster eluting enantiomer (example 10A; 227 mg, 37%; orange foam, MS: 474.5 (M+H)$^+$), and the slower eluting enantiomer (example 10B; 211 mg, 34%; orange foam, MS: 474.5 (M+H)$^+$).

The following examples were prepared in analogy to examples 10A and 10B by HPLC separation of their racemates:

| No. | Starting material | Optical rotation sign | MS, m/e |
|---|---|---|---|
| 11A | trans-3,5-dichlorobenzyl 2-(1H-benzo[d][1,2,3]triazole-5-carbonyl)-hexahydro-1H-pyrrolo[3,4-c]pyridine-5(6H)-carboxylate (example 1.08) | (+) | 474.4 (M + H)$^+$ |
| 11B | | (−) | 474.4 (M + H)$^+$ |
| 12A | trans-3,5-dichlorobenzyl 5-(1H-benzo[d][1,2,3]triazole-5-carbonyl)-hexahydro-1H-pyrrolo[3,4-c]pyridine-2(3H)-carboxylate (example 4.10) | (+) | 474.5 (M + H)$^+$ |
| 12B | | (−) | 474.5 (M + H)$^+$ |

Example 13

(E)-1-[trans-2-(1H-Benzotriazole-5-carbonyl)-octahydro-pyrrolo[3,4-c]pyridin-5-yl]-3-(3,5-dichlorophenyl)-prop-2-en-1-one

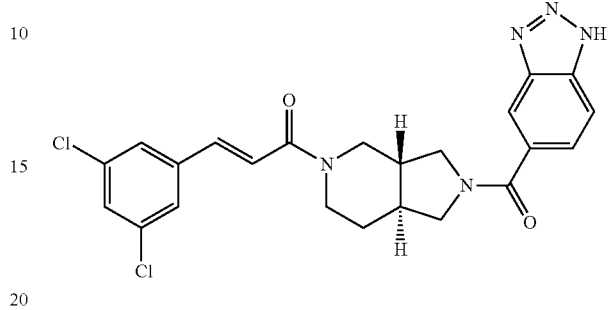

A solution of trans-3,5-dichlorobenzyl 2-(1H-benzo[d][1,2,3]triazole-5-carbonyl)hexahydro-1H-pyrrolo[3,4-c]pyridine-5(6H)-carboxylate (example 1.08; 105 mg, 221 μmol) in ethanol (2 mL) was stirred for 72 h under a hydrogen atmosphere (1 bar) in the presence of palladium (10% on carbon, 100 mg, 94 μmol), then insoluble material was removed by filtration through diatomaceous earth. The filtrate was evaporated, taken up in hydrochloric acid solution (5-6 M in 2-propanol, 1 mL), then after 1 h concentrated in vacuo and the residue was triturated in ethyl acetate to produce an off-white solid (32 mg). This material was dissolved in N,N-dimethylformamide (1 mL), then 4-methylmorpholine (44.8 mg, 443 μmol), 3,5-dichlorocinnamic acid (19.2 mg, 88.5 μmol) and O-(7-azabenzotriazol-1-yl)-N,N,N',N'-tetramethyluronium hexafluoro-phosphate (50.5 mg, 133 μmol) were added at room temperature, then after 18 h the reaction mixture was partitioned between sat. aq. ammonium chloride solution and ethyl acetate. The organic layer was washed with brine, dried over magnesium sulfate, filtered, and evaporated. Chromatography (silica gel, gradient dichlormethane to dichlormethane/methanol/25% aq. ammonia solution 90:10:0.25) produced the title compound (9 mg, 9%). Colourless gum, MS: 470.5 (M+H)$^+$.

Example 14

(1H-Benzotriazol-5-yl)-{trans-2-[5-(4-chloro-phenyl)-[1,3,4]oxadiazol-2-yl]-octahydro-pyrrolo[3,4-c]pyridin-5-yl}-methanone

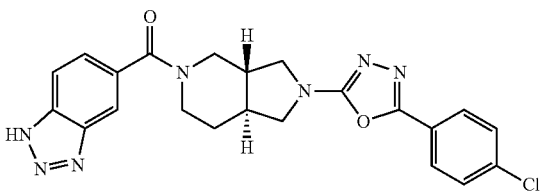 [SMILES: O=C(c1ccc2[nH]nnc2c1)N1CC[C@@H]2CN(c3nnc(-c4ccc(Cl)cc4)o3)C[C@H]2C1]

To a solution of 5-(4-chlorophenyl)-1,3,4-oxadiazol-2(3H)-one (CAS-RN 1711-61-1; 30 mg, 153 μmol) and N,N-diisopropylethylamine (98.6 mg, 763 μmol) in N,N-dimethylformamide (3.00 mL) was added (1H-benzotriazol-5-yl)-trans-octahydro-pyrrolo[3,4-c]pyridin-5-yl-methanone hydrochloride (intermediate 2.1; 51.7 mg, 168 μmol) at room temperature, then after 10 min benzotriazol-1-yl-oxy-tris-(dimethylamino)-phosphonium hexafluorophosphate (75.8 mg, 168 µmol) was added. After 16 h the reaction mixture was partitioned between water and ethyl acetate. The organic layer was washed with sat. aq. ammonium chloride solution and brine, dried over magnesium sulfate, filtered, and evaporated. Chromatography (silica gel; gradient dichloromethane to dichloromethane/methanol/25% aq. ammonia solution 90:10:0.25) produced the title compound (42 mg, 61%). White solid, MS: 450.4 (M+H)⁺.

Example 15

(E)-1-((3aR,6aS)-5-(1H-Benzo[d][1,2,3]triazole-5-carbonyl)hexahydropyrrolo[3,4-c]pyrrol-2(1H)-yl)-3-(4-(trifluoromethoxy)phenyl)prop-2-en-1-one

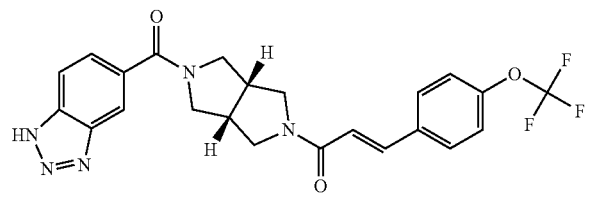 [SMILES: O=C(/C=C/c1ccc(OC(F)(F)F)cc1)N1C[C@@H]2CN(C(=O)c3ccc4[nH]nnc4c3)C[C@@H]2C1]

To a solution of (1H-benzo[d][1,2,3]triazol-5-yl)((3aR,6aS)-hexahydropyrrolo[3,4-c]pyrrol-2(1H)-yl)methanone hydrochloride (intermediate 2.2; 30 mg, 102 µmol), 4-methylmorpholine (51.6 mg, 511 µmol) and (E)-3-(4-(trifluoromethoxy)phenyl)acrylic acid (23.7 mg, 102 µmol) in N,N-dimethylformamide (1.5 mL) was added O-(7-azabenzotriazol-1-yl)-N,N,N',N'-tetramethyluronium hexafluoro-phosphate (38.8 mg, 102 µmol) at 0° C., then the reaction mixture was allowed to reach room temperature over a period of 16 h. After partitioning between ethyl acetate and sat. aq. sodium hydrogen carbonate solution the organic layer was washed with water and brine, dried over magnesium sulfate, filtered, and evaporated. Chromatography (silica gel; gradient dichloromethane to dichloromethane/methanol/25% aq. ammonia solution 90:10:0.25) produced the title compound (38 mg, 79%). White foam, MS: 472.4 (M+H)⁺.

The following compounds were produced in analogy to example 15, replacing (1H-benzo[d][1,2,3]triazol-5-yl)((3aR,6aS)-hexahydropyrrolo[3,4-c]pyrrol-2(1H)-yl)methanone hydrochloride and (E)-3-(4-(trifluoromethoxy)phenyl)acrylic acid by the appropriate amine and carboxylic acid, respectively.

| Ex. | Systematic Name | Amine | Carboxylic acid | MS, m/e |
|---|---|---|---|---|
| 15.01 | (1H-benzotriazol-5-yl)-[(3aR, 6aS)-5-(5-chloro-1H-indole-2-carbonyl)-hexahydro-pyrrolo[3,4-c]pyrrol-2-yl]-methanone | (1H-benzo[d][1,2,3]triazol-5-yl)((3aR,6aS)-hexahydropyrrolo[3,4-c]pyrrol-2(1H)-yl)methanone hydrochloride (intermediate 2.2) | 5-chloro-1H-indole-2-carboxylic acid | 435.5 (M + H)⁺ |
| 15.02 | (E)-1-[(3aR,6aS)-5-(1H-benzotriazole-5-carbonyl)-hexahydro-pyrrolo[3,4-c]pyrrol-2-yl]-3-(3-fluoro-5-trifluoromethyl-phenyl)-prop-2-en-1-one | (1H-benzo[d][1,2,3]triazol-5-yl)((3aR,6aS)-hexahydropyrrolo[3,4-c]pyrrol-2(1H)-yl)methanone hydrochloride (intermediate 2.2) | (E)-3-(3-fluoro-5-(trifluoromethyl)-phenyl(acrylic acid | 472.5 (M − H)⁻ |
| 15.03 | 1-[(3aR,6aS)-5-(1H-benzotriazole-5-carbonyl)-hexahydro-pyrrolo[3,4-c]pyrrol-2-yl]-3-(3-fluoro-5-trifluoromethyl-phenyl)-propan-1-one | (1H-benzo[d][1,2,3]triazol-5-yl)((3aR,6aS)-hexahydropyrrolo[3,4-c]pyrrol-2(1H)-yl)methanone hydrochloride (intermediate 2.2) | 3-(3-fluoro-5-(trifluoromethyl)-phenyl)-propanoic acid | 474.5 (M − H)⁻ |

-continued

| Ex. | Systematic Name | Amine | Carboxylic acid | MS, m/e |
|---|---|---|---|---|
| 15.04 | (1H-benzotriazol-5-yl)-[(3aR, 6aS)-5-(6-chloro-1H-indole-2-carbonyl)-hexahydro-pyrrolo[3,4-c]pyrrol-2-yl]-methanone | (1H-benzo[d][1,2,3]triazol-5-yl)((3aR,6aS)-hexahydropyrrolo[3,4-c]pyrrol-2(1H)-yl)methanone hydrochloride (intermediate 2.2) | 6-chloro-1H-indole-2-carboxylic acid | 435.5 (M + H)+ |
| 15.05 | (E)-1-((3aR,8aS)-2-(1H-benzo[d][1,2,3]triazole-5-carbonyl)octahydropyrrolo[3,4-d]azepin-6(7H)-yl)-3-(4-(trifluoromethylsulfonyl)phenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(4-(trifluoro-methyl-sulfonyl)-phenyl)acrylic acid (CAS-RN 910654-44-3) | 548.4 (M + H)+ |
| 15.06 | (E)-1-((3aR,8aS)-2-(1H-benzo[d][1,2,3]triazole-5-carbonyl)octahydropyrrolo[3,4-d]azepin-6(7H)-yl)-3-(4-chlorophenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(4-chlorophenyl)-acrylic acid | 450.4 (M + H)+ |
| 15.07 | (E)-1-((3aR,8aS)-2-(1H-benzo[d][1,2,3]triazole-5-carbonyl)octahydropyrrolo[3,4-d]azepin-6(7H)-yl)-3-p-tolylprop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-p-tolylacrylic acid | 430.5 (M + H)+ |
| 15.08 | 4-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)-N,N-dimethylbenzenesulfonamide | (1H-benzo[d][1,2,3]triazol-5-yl)((3aR,8aS)-octahydropyrrolo[3,4-d]azepin-2(1H)-yl)methanone (intermediate 6.1) | (E)-3-(4-(N,N-dimethyl-sulfamoyl)-phenyl)acrylic acid | 523.4 (M + H)+ |

-continued

| Ex. | Systematic Name | Amine | Carboxylic acid | MS, m/e |
|---|---|---|---|---|
| 15.09 | (E)-1-((3aR,8aS)-2-(1H-benzo[d][1,2,3]triazole-5-carbonyl)octahydropyrrolo[3,4-d]azepin-6(7H)-yl)-3-(4-methoxyphenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(4-methoxy-phenyl)acrylic acid | 446.6 (M + H)+ |
| 15.10 | (E)-1-((3aR,8aS)-6-(1H-benzo[d][1,2,3]triazole-5-carbonyl)octahydropyrrolo[3,4-d]azepin-2(1H)-yl)-3-(4-(trifluoromethoxy)phenyl)prop-2-en-1-one | (1H-benzo[d][1,2,3]triazol-5-yl)((3aR,8aS)-octahydropyrrolo[3,4-d]azepin-6(7H)-yl)methanone hydrochloride (intermediate 2.3) | (E)-3-(4-(trifluoro-methoxy)-phenyl)acrylic acid | 500.4 (M + H)+ |
| 15.11 | 4-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)benzonitrile | (1H-benzo[d][1,2,3]triazol-5-yl)((3aR,8aS)-octahydropyrrolo[3,4-d]azepin-2(1H)-yl)methanone (intermediate 6.1) | (E)-3-(4-cyanophenyl)-acrylic acid | 441.5 (M + H)+ |
| 15.12 | (E)-1-((3aR,6aR)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(4-(trifluoro-methoxy)-phenyl)acrylic acid | 472.5 (M + H)+ |
| 15.13 | 1-((3aR,6aS)-5-(1H-benzo[d][1,2,3]triazole-5-carbonyl)hexahydropyrrolo[3,4-c]pyrrol-2(1H)-yl)-3-(4-(trifluoromethoxy)phenyl)propan-1-one | (1H-benzo[d][1,2,3]triazol-5-yl)((3aR,6aS)-hexahydropyrrolo[3,4-c]pyrrol-2(1H)-yl)methanone hydrochloride (intermediate 2.2) | 3-(4-(trifluoro-methoxy)-phenyl)-propanoic acid | 474.4 (M + H)+ |

-continued

| Ex. | Systematic Name | Amine | Carboxylic acid | MS, m/e |
|---|---|---|---|---|
| 15.14 | 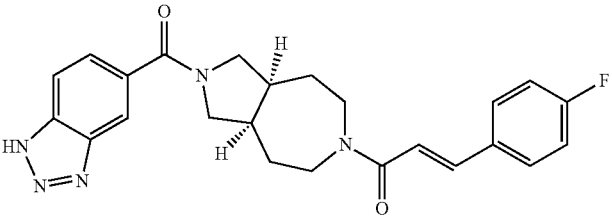<br>(E)-1-((3aR,8aS)-2-(1H-benzo[d][1,2,3]triazole-5-carbonyl)octahydropyrrolo[3,4-d]azepin-6(7H)-yl)-3-(4-fluorophenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(4-fluorophenyl)-acrylic acid | 434.4 (M + H)+ |
| 15.15 | 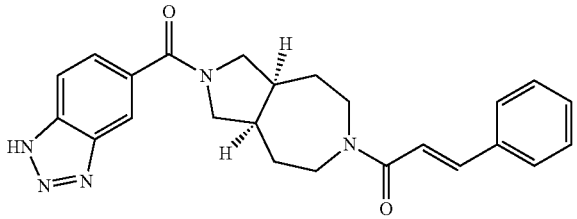<br>(E)-1-((3aR,8aS)-2-(1H-benzo[d][1,2,3]triazole-5-carbonyl)octahydropyrrolo[3,4-d]azepin-6(7H)-yl)-3-phenylprop-2-en-1-one | (1H-benzo[d][1,2,3]triazol-5-yl)((3aR,8aS)-octahydropyrrolo[3,4-d]azepin-2(1H)-yl)methanone (intermediate 6.1) | cinnamic acid | 416.5 (M + H)+ |
| 15.16 | 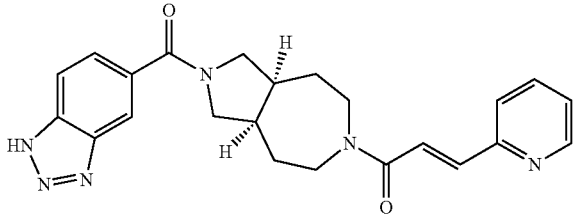<br>(E)-1-((3aR,8aS)-2-(1H-benzo[d][1,2,3]triazole-5-carbonyl)octahydropyrrolo[3,4-d]azepin-6(7H)-yl)-3-(pyridin-2-yl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(pyridin-2-yl)acrylic acid | 417.5 (M + H)+ |
| 15.17 | 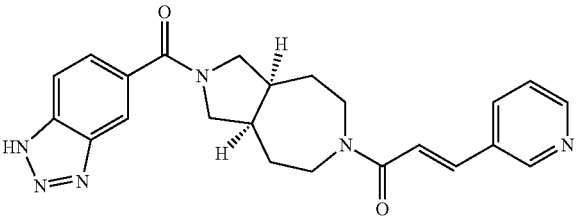<br>(E)-1-((3aR,8aS)-2-(1H-benzo[d][1,2,3]triazole-5-carbonyl)octahydropyrrolo[3,4-d]azepin-6(7H)-yl)-3-(pyridin-3-yl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(pyridin-3-yl)acrylic acid | 417.5 (M + H)+ |
| 15.18 | 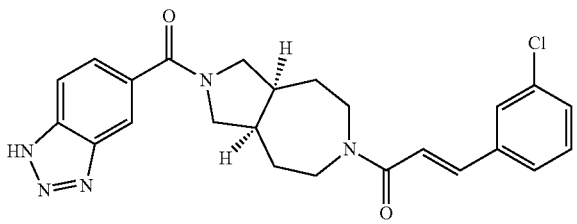<br>(E)-1-((3aR,8aS)-2-(1H-benzo[d][1,2,3]triazole-5-carbonyl)octahydropyrrolo[3,4-d]azepin-6(7H)-yl)-3-(3-chlorophenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(3-chlorophenyl)-acrylic acid | 448.4 (M − H)− |

-continued

| Ex. | Systematic Name | Amine | Carboxylic acid | MS, m/e |
|---|---|---|---|---|
| 15.19 | (E)-1-((3aR,8aS)-6-(1H-benzo[d][1,2,3]triazole-5-carbonyl)octahydropyrrolo[3,4-d]azepin-2(1H)-yl)-3-(4-chlorophenyl)prop-2-en-1-one | (1H-benzo[d][1,2,3]triazol-5-yl)((3aR,8aS)-octahydropyrrolo[3,4-d]azepin-6(7H)-yl)methanone hydrochloride (intermediate 2.3) | (E)-3-(4-chlorophenyl)-acrylic acid | 450.4 (M + H)+ |
| 15.20 | (E)-1-((3aR,8aS)-6-(1H-benzo[d][1,2,3]triazole-5-carbonyl)octahydropyrrolo[3,4-d]azepin-2(1H)-yl)-3-(3-(trifluoromethoxy)phenyl)prop-2-en-1-one | (1H-benzo[d][1,2,3]triazol-5-yl)((3aR,8aS)-octahydropyrrolo[3,4-d]azepin-6(7H)-yl)methanone hydrochloride (intermediate 2.3) | (E)-3-(3-(trifluoromethoxy)-phenyl)acrylic acid | 500.4 (M + H)+ |
| 15.21 | (E)-1-((3aR,8aS)-2-(1H-benzo[d][1,2,3]triazole-5-carbonyl)octahydropyrrolo[3,4-d]azepin-6(7H)-yl)-3-(4-(difluoromethoxy)phenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | 3-(4-(difluoromethoxy)-phenyl)acrylic acid | 482.4 (M + H)+ |
| 15.22 | (E)-1-((3aR,6aR)-5-(1H-benzo[d][1,2,3]triazole-5-carbonyl)hexahydropyrrolo[3,4-c]pyrrol-2(1H)-yl)-3-(3-(trifluoromethoxy)phenyl)prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(4-(trifluoromethoxy)-phenyl)acrylic acid | 470.6 (M − H)− |
| 15.23 | 4-((E)-3-((3aR,6aR)-5-(1H-benzo[d][1,2,3]triazole-5-carbonyl)hexahydropyrrolo[3,4-c]pyrrol-2(1H)-yl)-3-oxoprop-1-enyl)benzonitrile | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(4-cyanophenyl)-acrylic acid | 413.6 (M + H)+ |

| Ex. | Systematic Name | Amine | Carboxylic acid | MS, m/e |
|---|---|---|---|---|
| 15.24 | 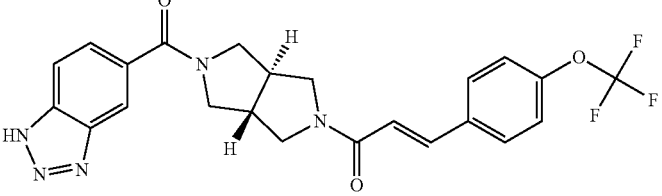<br>(E)-1-((3aS,6aS)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one | (1H-benzo[d][1,2,3]triazol-5-yl)((3aS,6aS)-hexahydropyrrolo[3,4-c]pyrrol-2(1H)-yl)methanone dihydrochloride (intermediate 8) | (E)-3-(4-(trifluoromethoxy)phenyl)acrylic acid | 472.5 (M + H)+ |
| 15.25 | 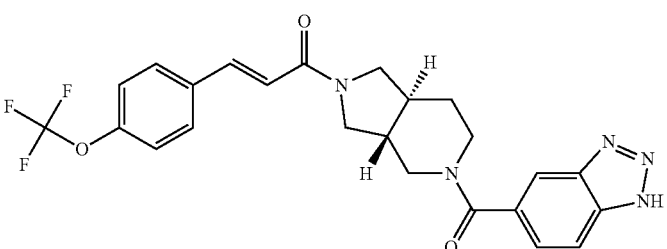<br>(-)-(E)-1-[trans-5-(1H-benzotriazole-5-carbonyl)-octahydro-pyrrolo[3,4-c]pyridin-2-yl]-3-(4-trifluoromethoxy-phenyl)-prop-2-en-1-one | (1H-benzo[d][1,2,3]triazol-5-yl)(trans-tetrahydro-1H-pyrrolo[3,4-c]pyridin-5(6H,7H,7aH)-yl)methanone hydrochloride, enantiomer A (intermediate 7A) | (E)-3-(4-(trifluoromethoxy)phenyl)acrylic acid | 486.4 (M + H)+ |
| 15.26 | 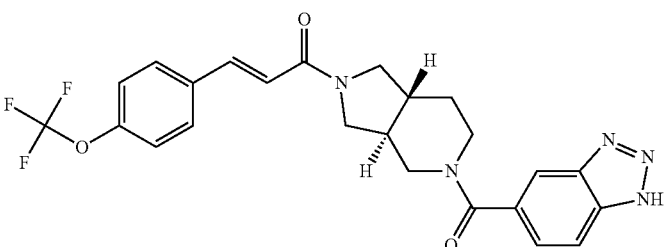<br>(+)-(E)-1-[trans-5-(1H-benzotriazole-5-carbonyl)-octahydro-pyrrolo[3,4-c]pyridin-2-yl]-3-(4-trifluoromethoxy-phenyl)-prop-2-en-1-one | (1H-benzo[d][1,2,3]triazol-5-yl)((3aS,7aS)-tetrahydro-1H-pyrrolo[3,4-c]pyridin-5(6H,7H,7aH)-yl)methanone hydrochloride, enantiomer B (intermediate 7B) | (E)-3-(4-(trifluoromethoxy)phenyl)acrylic acid | 486.4 (M + H)+ |
| 15.27 | 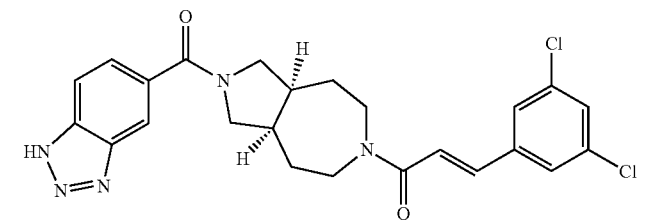<br>(E)-1-((3aR,8aS)-2-(1H-benzo[d][1,2,3]triazole-5-carbonyl)octahydropyrrolo[3,4-d]azepin-6(7H)-yl)-3-(3,5-dichlorophenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(3,5-dichlorophenyl)acrylic acid | 484.5 (M + H)+ |
| 15.28 | 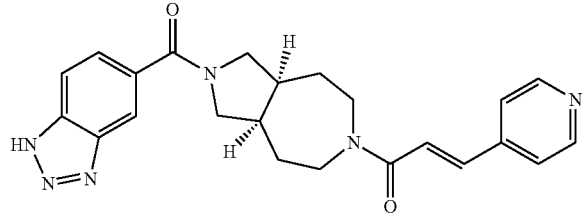<br>(E)-1-((3aR,8aS)-2-(1H-benzo[d][1,2,3]triazole-5-carbonyl)octahydropyrrolo[3,4-d]azepin-6(7H)-yl)-3-(pyridin-4-yl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(pyridin-4-yl)acrylic acid | 417.5 (M + H)+ |

-continued

| Ex. | Systematic Name | Amine | Carboxylic acid | MS, m/e |
|---|---|---|---|---|
| 15.29 | 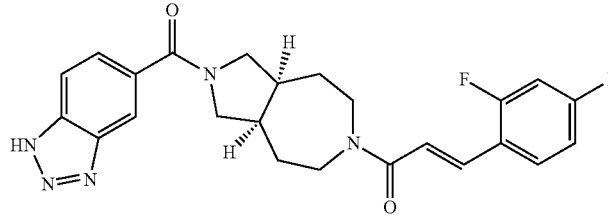<br>(E)-1-((3aR,8aS)-2-(1H-benzo[d][1,2,3]triazole-5-carbonyl)octahydropyrrolo[3,4-d]azepin-6(7H)-yl)-3-(2,4-difluorophenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(2,4-difluorophenyl)acrylic acid | 452.6 (M + H)+ |
| 15.30 | 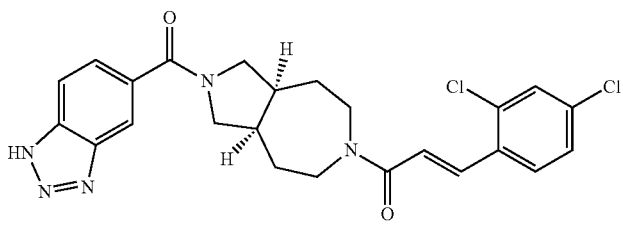<br>(E)-1-((3aR,8aS)-2-(1H-benzo[d][1,2,3]triazole-5-carbonyl)octahydropyrrolo[3,4-d]azepin-6(7H)-yl)-3-(2,4-dichlorophenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(2,4-dichlorophenyl)acrylic acid | 484.5 (M + H)+ |
| 15.31 | 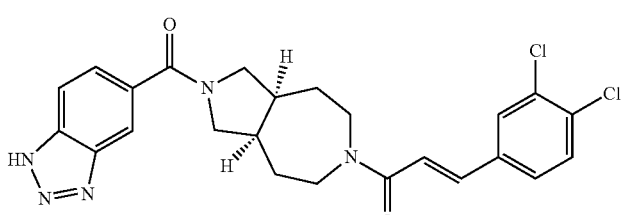<br>(E)-1-((3aR,8aS)-2-(1H-benzo[d][1,2,3]triazole-5-carbonyl)octahydropyrrolo[3,4-d]azepin-6(7H)-yl)-3-(3,4-dichlorophenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(3,4-dichlorophenyl)acrylic acid | 484.3 (M + H)+ |
| 15.32 | 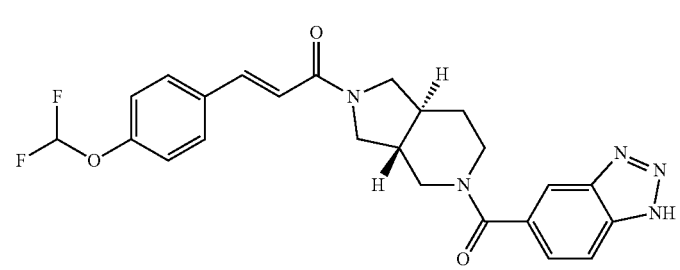<br>(E)-1-[trans-5-(1H-benzotriazole-5-carbonyl)-octahydro-pyrrolo[3,4-c]pyridin-2-yl]-3-(4-difluoromethoxy-phenyl)-prop-2-en-1-one, enantiomer B | (1H-benzotriazol-5-yl)-trans-octahydro-pyrrolo[3,4-c]pyridin-5-yl-methanone; hydrochloride, enantiomer B (intermediate 7B) | (E)-3-(4-(difluoromethoxy)-phenyl)acrylic acid | 468.4 (M + H)+ |
| 15.33 | 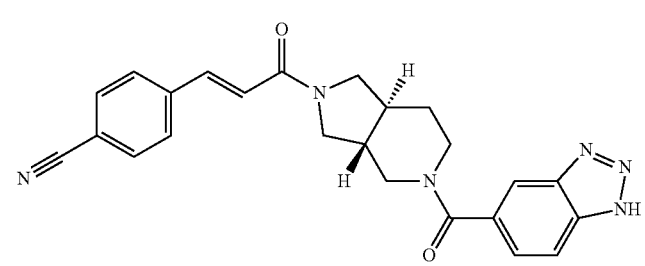<br>4-{(E)-3-[trans-5-(1H-benzotriazole-5-carbonyl)-octahydro-pyrrolo[3,4-c]pyridin-2-yl]-3-oxo-propenyl}-benzonitrile, enantiomer B | (1H-benzotriazol-5-yl)-trans-octahydro-pyrrolo[3,4-c]pyridin-5-yl-methanone; hydrochloride, enantiomer B (intermediate 7B) | (E)-3-(4-cyanophenyl)-acrylic acid | 427.6 (M + H)+ |

-continued

| Ex. | Systematic Name | Amine | Carboxylic acid | MS, m/e |
|---|---|---|---|---|
| 15.34 | 4-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)-3-fluorobenzonitrile | (1H-benzo[d][1,2,3]triazol-5-yl)((3aR,8aS)-octahydropyrrolo[3,4-d]azepin-2(1H)-yl)methanone (intermediate 6.1) | (E)-3-(4-cyano-2-fluorophenyl)-acrylic acid (CAS-RN 669002-88-4) | 459.6 (M + H)+ |
| 15.35 | 4-((E)-3-((3aR,6aR)-5-(1H-benzo[d][1,2,3]triazole-5-carbonyl)hexahydropyrrolo[3,4-c]pyrrol-2(1H)-yl)-3-oxoprop-1-enyl)-3-fluorobenzonitrile | (1H-benzo[d][1,2,3]triazol-5-yl)((3aR,8aS)-octahydropyrrolo[3,4-d]azepin-2(1H)-yl)methanone (intermediate 6.1) | (E)-3-(4-cyano-2-fluorophenyl)-acrylic acid (CAS-RN 669002-88-4) | 431.5 (M + H)+ |
| 15.36 | (E)-1-((3aR,6aR)-5-(1H-benzo[d][1,2,3]triazole-5-carbonyl)hexahydropyrrolo[3,4-c]pyrrol-2(1H)-yl)-3-(4-(difluoromethoxy)phenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(4-(difluoromethoxy)phenyl)acrylic acid | 454.6 (M + H)+ |
| 15.37 | (E)-1-[cis-2-(1H-benzotriazole-5-carbonyl)-octahydro-pyrrolo[3,4-c]pyridin-5-yl]-3-(4-trifluoromethoxy-phenyl)-prop-2-en-1-one | (1H-benzotriazol-5-yl)-cis-octahydro-pyrrolo[3,4-c]pyridin-2-yl-methanone (intermediate 6) | (E)-3-(4-(trifluoromethoxy)phenyl)acrylic acid | 486.3 (M + H)+ |
| 15.38 | 3-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)benzonitrile | (1H-benzo[d][1,2,3]triazol-5-yl)((3aR,8aS)-octahydropyrrolo[3,4-d]azepin-2(1H)-yl)methanone (intermediate 6.1) | (E)-3-(3-cyanophenyl)-acrylic acid | 441.6 (M + H)+ |

-continued

| Ex. | Systematic Name | Amine | Carboxylic acid | MS, m/e |
|---|---|---|---|---|
| 15.39 | 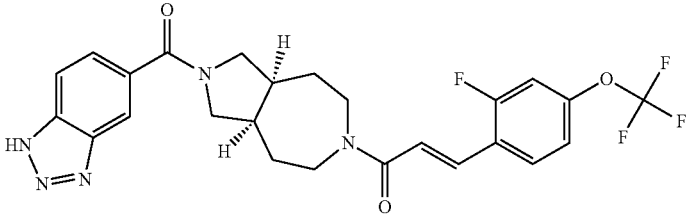<br>(E)-1-((3aR,8aS)-2-(1H-benzo[d][1,2,3]triazole-5-carbonyl)octahydropyrrolo[3,4-d]azepin-6(7H)-yl)-3-(2-fluoro-4-(trifluoromethoxy)phenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(2-fluoro-4-(trifluoromethoxy)phenyl)acrylic acid (CAS-RN 1240261-81-7) | 518.5 (M + H)+ |
| 15.40 | 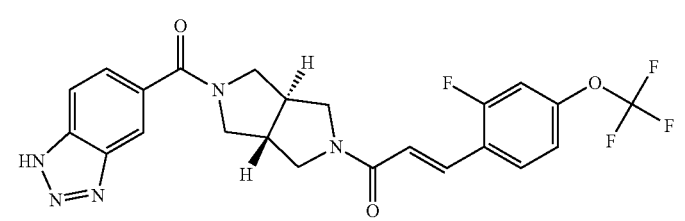<br>(E)-1-((3aR,6aR)-5-(1H-benzo[d][1,2,3]triazole-5-carbonyl)hexahydropyrrolo[3,4-c]pyrrol-2(1H)-yl)-3-(2-fluoro-4-(trifluoromethoxy)phenyl)prop-2-en-1-one | (1H-benzo[d][1,2,3]triazol-5-yl)((3aR,6aR)-hexahydropyrrolo(3,4-c]pyrrol-2(1H)-yl)methanone dihydrochloride (intermediate 2.4) | (E)-3-(2-fluoro-4-(trifluoromethoxy)phenyl)acrylic acid (CAS-RN 1240261-81-7) | 490.2 (M + H)+ |
| 15.41 | 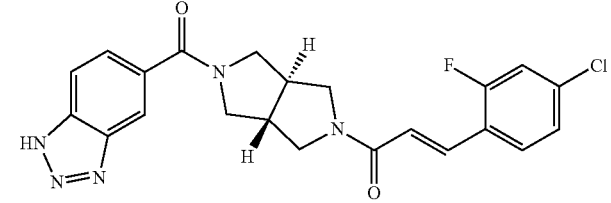<br>(E)-1-((3aR,6aR)-5-(1H-benzo[d][1,2,3]triazole-5-carbonyl)hexahydropyrrolo[3,4-c]pyrrol-2(1H)-yl)-3-(4-chloro-2-fluorophenyl)prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(4-chloro-2-fluorophenyl)-acrylic acid | 440.1 (M + H)+ |
| 15.42 | 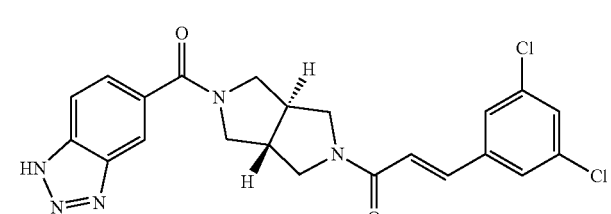<br>(E)-1-((3aR,6aR)-5-(1H-benzo[d][1,2,3]triazole-5-carbonyl)hexahydropyrrolo[3,4-c]pyrrol-2(1H)-yl)-3-(3,5-dichlorophenyl)prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(3,5-dichlorophenyl)acrylic acid | 456.1 (M + H)+ |
| 15.43 | 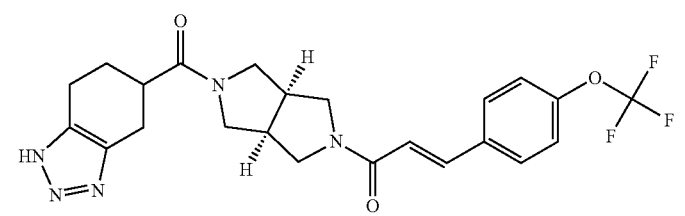<br>(E)-1-((3aR,6aS)-5-(4,5,6,7-tetrahydro-1H-benzo[d][1,2,3]triazole-5-carbonyl)hexahydro-pyrrolo[3,4-c]pyrrol-2(1H)-yl)-3-(4-(trifluoromethoxy)phenyl)prop-2-en-1-one | ((3aR,6aS)-hexahydropyrrolo[3,4-c]pyrrol-2(1H)-yl)(4,5,6,7-tetrahydro-1H-benzo[d][1,2,3]triazol-5-yl)methanone (intermediate 6.3) | (E)-3-(4-(trifluoromethoxy)phenyl)acrylic acid | 476.4 (M + H)+ |

-continued

| Ex. | Systematic Name | Amine | Carboxylic acid | MS, m/e |
|---|---|---|---|---|
| 15.44 | 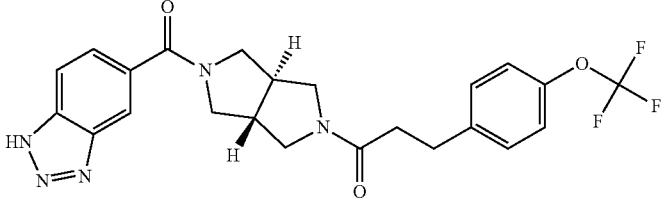<br>1-[(3aR,6aR)-5-(1H-benzotriazole-5-carbonyl)-hexahydro-pyrrolo[3,4-c]pyrrol-2-yl]-3-(4-trifluoromethoxy-phenyl)-propan-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(4-(trifluoromethoxy)-phenyl)-propanoic acid | 474.6 (M + H)+ |
| 15.45 | 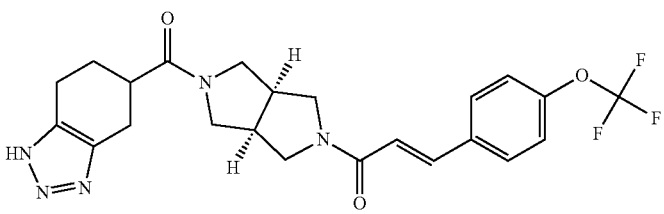<br>(E)-1-[(3aS,6aR)-5-(1,4,6,7-tetrahydro-[1,2,3]triazolo[4,5-c]pyridine-5-carbonyl)-hexahydro-pyrrolo[3,4-c]pyrrol-2-yl]-3-(4-trifluoromethoxy-phenyl)-prop-2-en-1-one | (6,7-dihydro-1H-[1,2,3]triazolo[4,5-c]pyridin-5(4H)-yl)((3aR,6aS)-hexahydropyrrolo[3,4-c]pyrrol-2(1H)-yl)methanone (intermediate 6.2) | (E)-3-(4-(trifluoromethoxy)-phenyl)acrylic acid | 477.5 (M + H)+ |
| 15.46 | 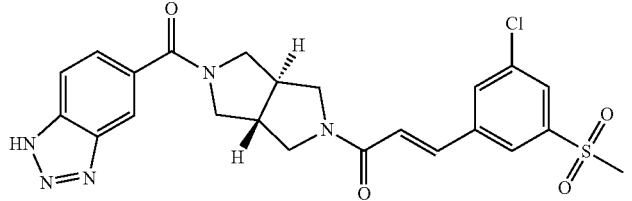<br>(E)-1-[(3aR,6aR)-5-(1H-benzotriazole-5-carbonyl)-hexahydro-pyrrolo[3,4-c]pyrrol-2-yl]-3-(3-chloro-5-methanesulfonyl-phenyl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(3-chloro-5-(methylsulfonyl)-phenyl)acrylic acid (intermediate 23) | 500.5 (M + H)+ |
| 15.47 | 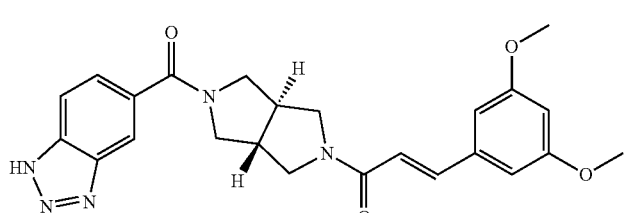<br>(E)-1-[(3aR,6aR)-5-(1H-benzotriazole-5-carbonyl)-hexahydro-pyrrolo[3,4-c]pyrrol-2-yl]-3-(3,5-dimethoxy-phenyl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(3,5-dimethoxy-phenyl)acrylic acid | 448.5 (M + H)+ |
| 15.48 | 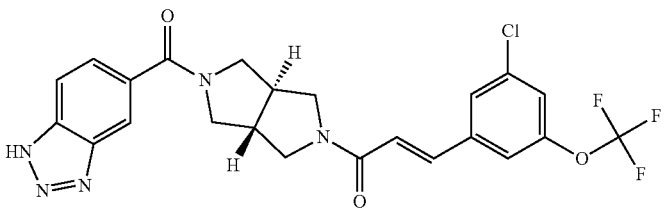<br>(E)-1-[(3aR,6aR)-5-(1H-benzotriazole-5-carbonyl)-hexahydro-pyrrolo[3,4-c]pyrrol-2-yl]-3-(3-chloro-5-trifluoromethoxy-phenyl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(3-chloro-5-(trifluoromethoxy)-phenyl)acrylic acid | 506.4 (M + H)+ |

-continued

| Ex. | Systematic Name | Amine | Carboxylic acid | MS, m/e |
|---|---|---|---|---|
| 15.49 | 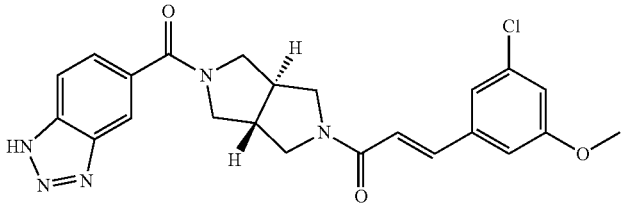<br>(E)-1-[(3aR,6aR)-5-(1H-benzotriazole-5-carbonyl)-hexahydro-pyrrolo[3,4-c]pyrrol-2-yl]-3-(3-chloro-5-methoxy-phenyl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(3-chloro-5-methoxy-phenyl)acrylic acid (intermediate 23.1) | 452.5 (M + H)⁺ |
| 15.50 | 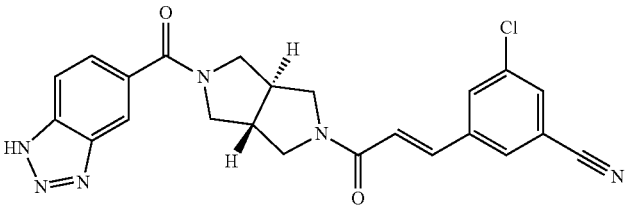<br>3-{(E)-3-[(3aR,6aR)-5-(1H-benzotriazole-5-carbonyl)-hexahydro-pyrrolo[3,4-c]pyrrol-2-yl]-3-oxo-propenyl}-5-chloro-benzonitrile | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(3-chloro-5-cyanophenyl)acrylic acid (intermediate 24.1) | 447.5 (M + H)⁺ |
| 15.51 | 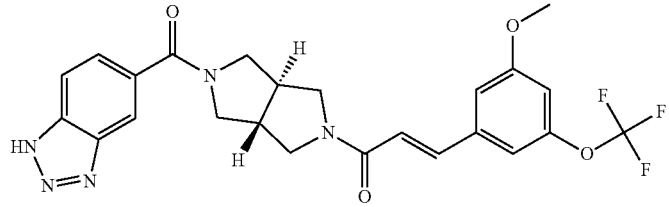<br>(E)-1-[(3aR,6aR)-5-(1H-benzotriazole-5-carbonyl)-hexahydro-pyrrolo[3,4-c]pyrrol-2-yl]-3-(3-methoxy-5-trifluoromethoxy-phenyl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(3-methoxy-5-(trifluoromethoxy)phenyl)acrylic acid (intermediate 24) | 502.5 (M + H)⁺ |
| 15.52 | 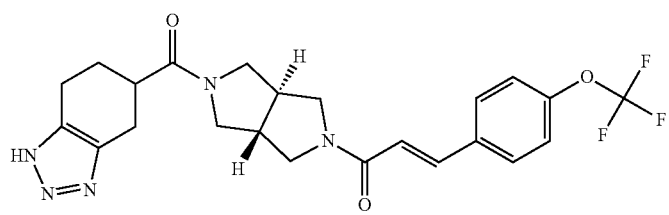<br>(E)-1-[(3aR,6aR)-5-(1,4,6,7-tetrahydro-[1,2,3]triazolo[4,5-c]pyridine-5-carbonyl)-hexahydro-pyrrolo[3,4-c]pyrrol-2-yl]-3-(4-trifluoromethoxy-phenyl)-prop-2-en-1-one | (6,7-dihydro-1H-[1,2,3]triazolo[4,5-c]pyridin-5(4H)-yl)((3aR,6aR)-hexahydropyrrolo[3,4-c]pyrrol-2(1H)-yl)methanone hydrochloride (intermediate 25) | (E)-3-(4-(trifluoromethoxy)phenyl)acrylic acid | 477.6 (M + H)⁺ |
| 15.53 | 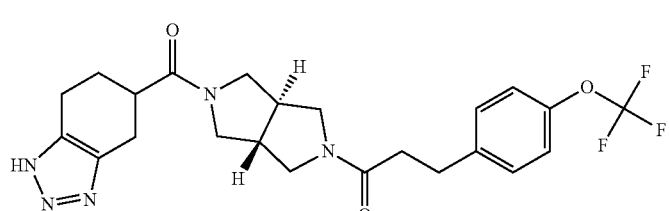<br>1-[(3aR,6aR)-5-(1,4,6,7-tetrahydro-[1,2,3]triazolo[4,5-c]pyridine-5-carbonyl)-hexahydro-pyrrolo[3,4-c]pyrrol-2-yl]-3-(4-trifluoromethoxy-phenyl)-propan-1-one | (6,7-dihydro-1H-[1,2,3]triazolo[4,5-c]pyridin-5(4H)-yl)((3aR,6aR)-hexahydropyrrolo[3,4-c]pyrrol-2(1H)-yl)methanone hydrochloride (intermediate 25) | 3-(4-(trifluoromethoxy)-phenyl)-propanoic acid | 479.6 (M + H)⁺ |

| Ex. | Systematic Name | Amine | Carboxylic acid | MS, m/e |
|---|---|---|---|---|
| 15.54 | (3aR,7aR)-5-{(3aR,6aR)-5-[(E)-3-(4-trifluoromethoxy-phenyl)-acryloyl]-hexahydro-pyrrolo[3,4-c]pyrrole-2-carbonyl}-hexahydro-oxazolo[5,4-c]pyridin-2-one | (3aR,7aR)-5-((3aR,6aR)-octahydropyrrolo[3,4-c]pyrrole-2-carbonyl)hexahydro-oxazolo[5,4-c]pyridin-2(1H)-one hydrochloride (intermediate 25.1) | (E)-3-(4-(trifluoro-methoxy)-phenyl)acrylic acid | 495.6 (M + H)+ |
| 15.55 | (3aR,7aR)-5-{(3aR,6aR)-5-[3-(4-trifluoromethoxy-phenyl)-propionyl]-hexahydro-pyrrolo[3,4-c]pyrrole-2-carbonyl}-hexahydro-oxazolo[5,4-c]pyridin-2-one | (3aR,7aR)-5-((3aR,6aR)-octahydropyrrolo[3,4-c]pyrrole-2-carbonyl)hexahydro-oxazolo[5,4-c]pyridin-2(1H)-one hydrochloride (intermediate 25.1) | 3-(4-(trifluoro-methoxy)-phenyl)-propanoic acid | 497.7 (M + H)+ |
| 15.56 | (E)-1-[(3aR,6aR)-5-(1H-benzotriazole-5-carbonyl)-hexahydro-pyrrolo[3,4-c]pyrrol-2-yl]-3-phenyl-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | cinnamic acid | 388.6 (M + H)+ |
| 15.57 | 1-[(3aR,6aR)-5-(1H-benzotriazole-5-carbonyl)-hexahydro-pyrrolo[3,4-c]pyrrol-2-yl]-3-phenyl-propan-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-phenyl-propanoic acid | 390.6 (M + H)+ |
| 15.58 | (E)-1-[(3aR,6aR)-5-(1H-benzotriazole-5-carbonyl)-hexahydro-pyrrolo[3,4-c]pyrrol-2-yl]-3-(4-trifluoromethyl-phenyl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(4-(trifluoro-methyl)-phenyl)acrylic acid | 456.7 (M + H)+ |

-continued

| Ex. | Systematic Name | Amine | Carboxylic acid | MS, m/e |
|---|---|---|---|---|
| 15.59 | 1-[(3aR,6aR)-5-(1H-benzotriazole-5-carbonyl)-hexahydro-pyrrolo[3,4-c]pyrrol-2-yl]-3-(4-trifluoromethyl-phenyl)-propan-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(4-(trifluoromethyl)-phenyl)-propanoic acid | 458.7 (M + H)+ |
| 15.60 | (3aR,6aS)-N-((1H-1,2,3-triazol-5-yl)methyl)-N-methyl-5-(3-(4-(trifluoromethoxy)phenyl)propanoyl)hexahydropyrrolo[3,4-c]pyrrole-2(1H)-carboxamide | (3aR,6aS)-N-((1H-1,2,3-triazol-5-yl)methyl)-N-methylhexahydropyrrolo[3,4-c]pyrrole-2(1H)-carboxamide 2,2,2-trifluoroacetate (intermediate 20.1) | 3-(4-(trifluoromethoxy)-phenyl)-propanoic acid | 467.6 (M + H)+ |
| 15.61 | (3aR,8aS)-N-((1H-1,2,3-triazol-5-yl)methyl)-6-((E)-3-(3-fluoro-4-(trifluoromethoxy)phenyl)acryloyl)-N-methyloctahydropyrrolo[3,4-d]azepine-2(1H)-carboxamide | (E)-3-(3-fluoro-4-(trifluoromethoxy)-phenyl)-1-((3aR,8aS)-octahydropyrrolo[3,4-d]azepin-6(7H)-yl)prop-2-en-1-one (intermediate 26.03) | N-methyl-1-(1H-1,2,3-triazol-4-yl)methan-amine (CAS-RN 1248059-33-7) | 511.6 (M + H)+ |
| 15.62 | 1-[(3aR,6aR)-5-(1H-benzotriazole-5-carbonyl)-hexahydro-pyrrolo[3,4-c]pyrrol-2-yl]-3-(6-trifluoromethyl-pyridin-3-yl)-propan-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(6-(trifluoromethyl)-pyridin-3-yl(propanoic acid (CAS-RN 539855-70-4) | 459.5 (M + H)+ |
| 15.63 | 1-[(3aS,6aS)-5-(1H-benzotriazole-5-carbonyl)-hexahydro-pyrrolo[3,4-c]pyrrol-2-yl]-2-(4-trifluoromethoxy-phenoxy)-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(4-(trifluoromethoxy)-phenoxy)acetic acid | 476.5 (M + H)+ |

-continued

| Ex. | Systematic Name | Amine | Carboxylic acid | MS, m/e |
|---|---|---|---|---|
| 15.64 | 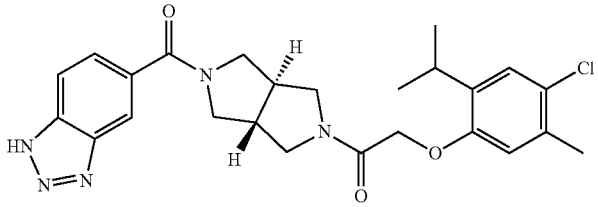<br>1-[(3aS,6aS)-5-(1H-benzotriazole-5-carbonyl)-hexahydro-pyrrolo[3,4-c]pyrrol-2-yl]-2-(4-chloro-2-isopropyl-5-methyl-phenoxy)-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(4-chloro-2-isopropyl-5-methylphenoxy)acetic acid (CAS-RN 5411-11-0) | 482.6 (M + H)+ |
| 15.65 | 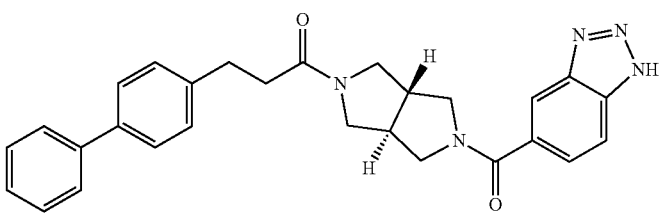<br>1-[(3aR,6aR)-5-(1H-benzotriazole-5-carbonyl)-hexahydro-pyrrolo[3,4-c]pyrrol-2-yl]-3-biphenyl-4-yl-propan-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(biphenyl-4-yl)propanoic acid | 466.6 (M + H)+ |
| 15.66 | 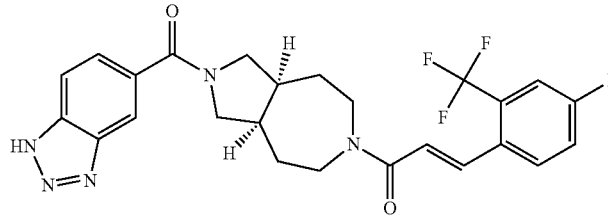<br>(E)-1-((3aR,8aS)-2-(1H-benzo[d][1,2,3]triazole-5-carbonyl)octahydropyrrolo[3,4-d]azepin-6(7H)-yl)-3-(4-fluoro-2-(trifluoromethyl)phenyl)prop-2-en-1-one | (E)-3-(4-fluoro-2-(trifluoromethyl)phenyl)-1-((3aR,8aS)-octahydropyrrolo[3,4-d]azepin-6(7H)-yl)prop-2-en-1-one (intermediate 26.04) | 1H-benzo[d]-[1,2,3]triazole-5-carboxylic acid | 502.6 (M + H)+ |
| 15.67 | 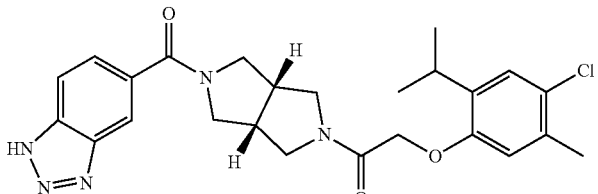<br>1-[(3aS,6aR)-5-(1H-benzotriazole-5-carbonyl)-hexahydro-pyrrolo[3,4-c]pyrrol-2-yl]-2-(4-chloro-2-isopropyl-5-methyl-phenoxy)-ethanone | 2-(4-chloro-2-isopropyl-5-methylphenoxy)-1-((3aR,6aS)-hexahydropyrrolo[3,4-c]pyrrol-2(1H)-yl)ethanone hydrochloride (intermediate 5.2) | 1H-benzo[d]-[1,2,3]triazole-5-carboxylic acid | 482.7 (M + H)+ |
| 15.68 | 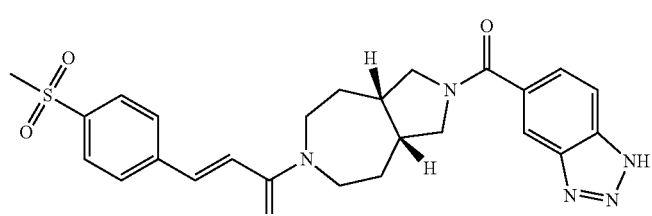<br>(E)-1-((3aR,8aS)-2-(1H-benzo[d][1,2,3]triazole-5-carbonyl)-octahydropyrrolo[3,4-d]azepin-6(7H)-yl)-3-(4-(methylsulfonyl)phenyl)-prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(4-(methylsulfonyl)-phenyl)acrylic acid | 494.4 (M + H)+ |

-continued

| Ex. | Systematic Name | Amine | Carboxylic acid | MS, m/e |
|---|---|---|---|---|
| 15.69 | 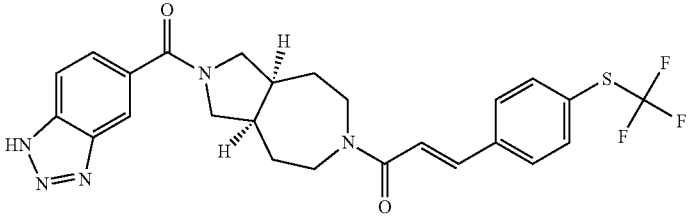<br>(E)-1-((3aR,8aS)-2-(1H-benzo[d][1,2,3]triazole-5-carbonyl)octahydropyrrolo[3,4-d]azepin-6(7H)-yl)-3-(4-(trifluoromethylthio)phenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(4-(trifluoromethylthio)phenyl)acrylic acid | 516.4 (M + H)$^+$ |
| 15.70 | 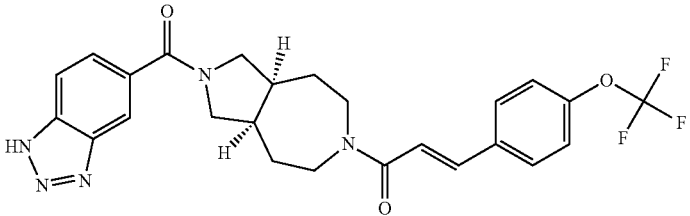<br>(E)-1-((3aR,8aS)-2-(1H-benzo[d][1,2,3]triazole-5-carbonyl)-octahydropyrrolo[3,4-d]azepin-6(7H)-yl)-3-(4-(trifluoromethoxy)-phenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(4-(trifluoromethoxy)-phenyl)acrylic acid | 500.4 (M + H)$^+$ |
| 15.71 | 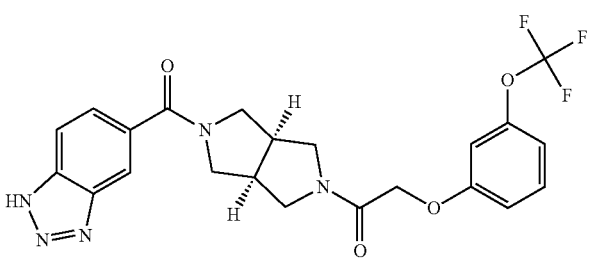<br>1-((3aR,6aS)-5-(1H-benzo[d][1,2,3]triazole-5-carbonyl) hexahydropyrrolo[3,4-c]pyrrol-2(1H)-yl)-2-(3-(trifluoromethoxy)phenoxy)ethanone | (1H-benzo[d][1,2,3]triazol-5-yl)(trans-hexahydropyrrolo[3,4-c]pyrrol-2(1H)-yl)methanone hydrochloride (intermediate 2.2) | 2-(3-(trifluoromethoxy)-phenoxy)acetic acid (CAS-RN 836-33-9) | 476.5 (M + H)$^+$ |
| 15.72 | 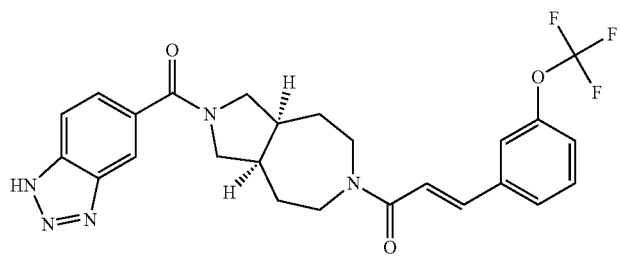<br>(E)-1-((3aR,8aS)-2-(1H-benzo[d][1,2,3]triazole-5-carbonyl)octahydropyrrolo[3,4-d]azepin-6(7H)-yl)-3-(3-(trifluoromethoxy)phenyl)prop-2-en-1-one | (1H-benzo[d][1,2,3]triazol-5-yl)((3aR,8aS)-octahydropyrrolo[3,4-d]azepin-2(1H)-yl)methanone (intermediate 6.1) | (E)-3-(3-(trifluoromethoxy)-phenyl)acrylic acid | 500.4 (M + H)$^+$ |

-continued

| Ex. | Systematic Name | | Amine | Carboxylic acid | MS, m/e |
|---|---|---|---|---|---|
| 15.73 | 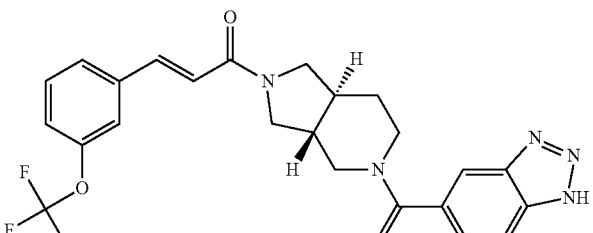<br>(E)-1-[trans-5-(1H-benzotriazole-5-carbonyl)-octahydro-pyrrolo[3,4-c]pyridin-2-yl]-3-(3-trifluoromethoxy-phenyl)-prop-2-en-1-one | | (1H-benzotriazol-5-yl)-trans-octahydro-pyrrolo[3,4-c]pyridin-5-yl-methanone; hydrochloride (intermediate 2.1) | (E)-3-(3-(trifluoro-methoxy)-phenyl)acrylic acid | 486.4 (M + H)+ |
| 15.74 | 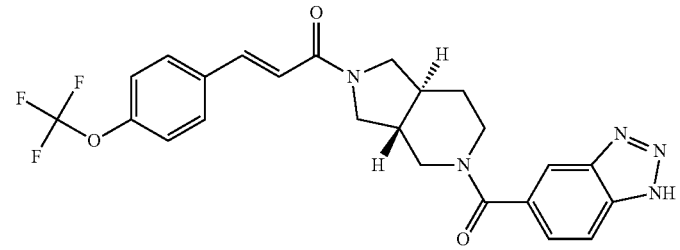<br>(E)-1-[trans-5-(1H-benzotriazole-5-carbonyl)-octahydro-pyrrolo[3,4-c]pyridin-2-yl]-3-(4-trifluoromethoxy-phenyl)-prop-2-en-1-one | | (1H-benzotriazol-5-yl)-trans-octahydro-pyrrolo[3,4-c]pyridin-5-yl-methanone; hydrochloride (intermediate 2.1) | (E)-3-(4-(trifluoro-methoxy)-phenyl)acrylic acid | 486.5 (M + H)+ |
| 15.75 | 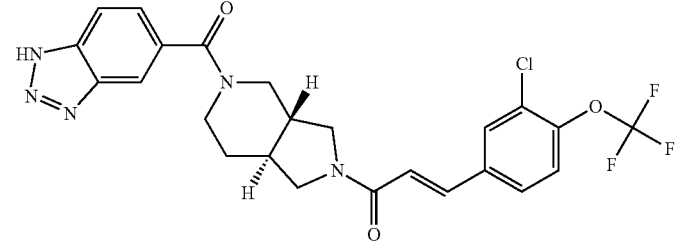<br>(E)-1-[trans-5-(1H-benzotriazole-5-carbonyl)-octahydro-pyrrolo[3,4-c]pyridin-2-yl]-3-(3-chloro-5-trifluoromethoxy-phenyl)-prop-2-en-1-one | | (1H-benzotriazol-5-yl)-trans-octahydro-pyrrolo[3,4-c]pyridin-5-yl-methanone; hydrochloride (intermediate 2.1) | (E)-3-(3-chloro-5-(trifluoro-methoxy)-phenyl)acrylic acid | 520.4 (M + H)+ |
| 15.76 | 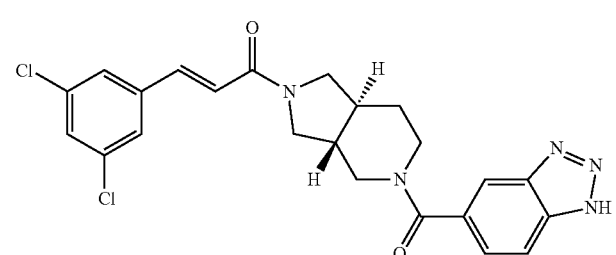<br>(E)-1-[trans-5-(1H-benzotriazole-5-carbonyl)-octahydro-pyrrolo[3,4-c]pyridin-2-yl]-3-(3,5-dichloro-phenyl)-prop-2-en-1-one | | (1H-benzotriazol-5-yl)-trans-octahydro-pyrrolo[3,4-c]pyridin-5-yl-methanone; hydrochloride (intermediate 2.1) | (E)-3-(3,5-dichloro-phenyl)acrylic acid | 470.4 (M + H)+ |
| 15.77 | 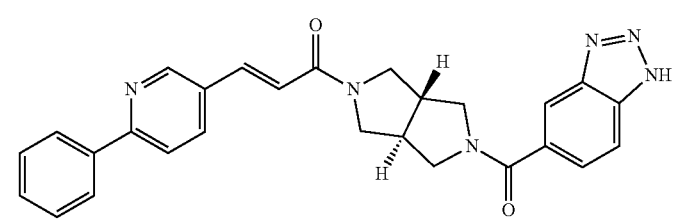<br>(E)-1-[(3aR,6aR)-5-(1H-benzotriazole-5-carbonyl)-hexahydro-pyrrolo[3,4-c]pyrrol-2-yl]-3-(6-phenyl-pyridin-3-yl)-prop-2-en-1-one | | (1H-benzo[d][1,2,3]triazol-5-yl)((3aR,6aR)-hexahydropyrrolo[3,4-c]pyrrol-2(1H)-yl)methanone dihydrochloride (intermediate 2.04) | (E)-3-(6-phenylpyridin-3-yl)acrylic acid (intermediate 23.05) | 465.5 (M + H)+ |

-continued

| Ex. | Systematic Name | Amine | Carboxylic acid | MS, m/e |
|---|---|---|---|---|
| 15.78 | (E)-1-[(3aR,6aR)-5-(1H-benzotriazole-5-carbonyl)-hexahydro-pyrrolo[3,4-c]pyrrol-2-yl]-3-(5-trifluoromethyl-pyridin-2-yl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.04) | (E)-3-(5-(trifluoro-methyl)-pyridin-2-yl)acrylic acid (CAS-RN 910654-24-9) | 457.5 (M + H)+ |
| 15.79 | (E)-1-[(3aR,6aR)-5-(1H-benzotriazole-5-carbonyl)-hexahydro-pyrrolo[3,4-c]pyrrol-2-yl]-3-(4-pyridin-4-yl-phenyl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(4-(pyridin-4-yl)phenyl)-acrylic acid (intermediate 23.07) | 465.6 (M + H)+ |
| 15.80 | (E)-1-[(3aR,6aR)-5-(1H-benzotriazole-5-carbonyl)-hexahydro-pyrrolo[3,4-c]pyrrol-2-yl]-3-(4-pyridin-3-yl-phenyl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(4-(pyridin-3-yl)phenyl)-acrylic acid (intermediate 23.08) | 465.6 (M + H)+ |
| 15.81 | (E)-1-[(3aR,6aR)-5-(1H-benzotriazole-5-carbonyl)-hexahydro-pyrrolo[3,4-c]pyrrol-2-yl]-3-(4-pyridin-2-yl-phenyl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(4-(pyridin-2-yl)phenyl)-acrylic acid (intermediate 23.09) | 465.6 (M + H)+ |
| 15.82 | 1-[(3aS,6aR)-5-(1H-benzotriazole-5-carbonyl)-hexahydro-pyrrolo[3,4-c]pyrrol-2-yl]-2-(4-chloro-3-methyl-phenoxy)-ethanone | 2-(4-chloro-3-methylphenoxy)-1-((3aR,6aS)-hexahydropyrrolo[3,4-c]pyrrol-2(1H)-yl)ethanone hydrochloride (intermediate 31.1) | 1H-benzo[d]-[1,2,3]triazole-5-carboxylic acid | 440.7 (M + H)+ |

-continued

| Ex. | Systematic Name | Amine | Carboxylic acid | MS, m/e |
|---|---|---|---|---|
| 15.83 | 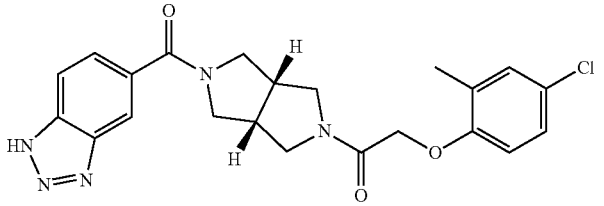<br>1-[(3aS,6aR)-5-(1H-benzotriazole-5-carbonyl)-hexahydro-pyrrolo[3,4-c]pyrrol-2-yl]-2-(4-chloro-2-methyl-phenoxy)-ethanone | 2-(4-chloro-2-methylphenoxy)-1-((3aR,6aS)-hexahydropyrrolo[3,4-c]pyrrol-2(1H)-yl)ethanone hydrochloride (intermediate 31) | 1H-benzo[d]-[1,2,3]triazole-5-carboxylic acid | 440.7 (M + H)+ |
| 15.84 | 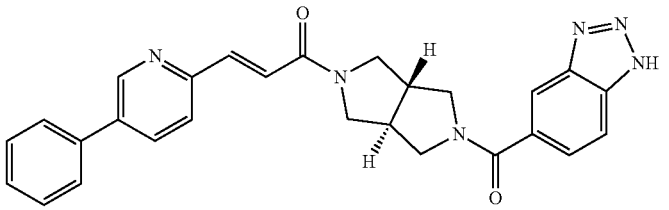<br>(E)-1-[(3aR,6aR)-5-(1H-benzotriazole-5-carbonyl)-hexahydro-pyrrolo[3,4-c]pyrrol-2-yl]-3-(5-phenyl-pyridin-2-yl)-prop-2-en-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | (E)-3-(5-phenylpyridin-2-yl)acrylic acid (intermediate 23.06) | 465.5 (M + H)+ |
| 15.85 | 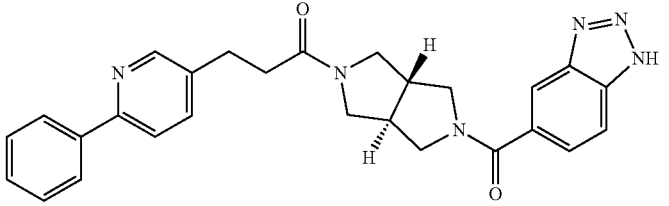<br>1-[(3aR,6aR)-5-(1H-benzotriazole-5-carbonyl)-hexahydro-pyrrolo[3,4-c]pyrrol-2-yl]-3-(6-phenyl-pyridin-3-yl)-propan-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(6-phenylpyridin-3-yl)propanoic acid (intermediate 35.1) | 467.6 (M + H)+ |
| 15.86 | 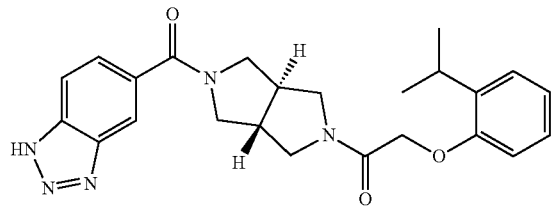<br>1-[(3aS,6aS)-5-(1H-benzotriazole-5-carbonyl)-hexahydro-pyrrolo[3,4-c]pyrrol-2-yl]-2-(2-isopropyl-phenoxy)-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-isopropylphenoxy)acetic acid | 434.6 (M + H)+ |
| 15.87 | 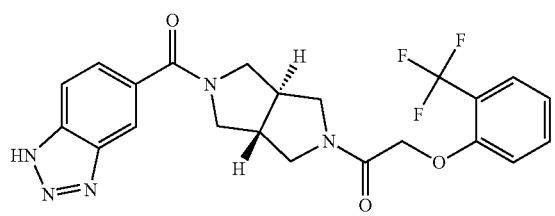<br>1-[(3aS,6aS)-5-(1H-benzotriazole-5-carbonyl)-hexahydro-pyrrolo[3,4-c]pyrrol-2-yl]-2-(2-trifluoromethyl-phenoxy)-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-(trifluoromethyl)-phenoxy)acetic acid | 460.5 (M + H)+ |

-continued

| Ex. | Systematic Name | Amine | Carboxylic acid | MS, m/e |
|---|---|---|---|---|
| 15.88 | 1-[(3aS,6aS)-5-(1H-benzotriazole-5-carbonyl)-hexahydro-pyrrolo[3,4-c]pyrrol-2-yl]-2-(biphenyl-2-yloxy)-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(biphenyl-2-yloxy)acetic acid | 468.5 (M + H)+ |
| 15.89 | (E)-1-[(3aS,6aS)-5-((R)-4,5,6,7-tetrahydro-1H-benzotriazole-5-carbonyl)-hexahydro-pyrrolo[3,4-c]pyrrol-2-yl]-3-(4-trifluoromethoxy-phenyl)-propenone | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | (E)-3-(4-(trifluoro-methoxy)-phenyl)acrylic acid | 476.6 (M + H)+ |
| 15.90 | 1-((3aR,6aR)-5-((R)-4,5,6,7-tetrahydro-1H-benzo[d]-[1,2,3]triazole-5-carbonyl)hexahydro-pyrrolo[3,4-c]pyrrol-2(1H)-yl)-3-(4-(trifluoromethoxy)phenyl)propan-1-one | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 3-(4-(trifluoro-methoxy)-phenyl)-propanoic acid | 478.5 (M + H)+ |
| 15.91 | 1-[(3aS,6aS)-5-(1H-benzotriazole-5-carbonyl)-hexahydro-pyrrolo[3,4-c]pyrrol-2-yl]-2-(2-chloro-4-trifluoromethoxy-phenoxy)-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-chloro-4-(trifluoro-methoxy)-phenoxy)acetic acid (intermediate 33.3) | 510.6 (M + H)+ |
| 15.92 | 1-[(3aS,6aS)-5-(1H-benzotriazole-5-carbonyl)-hexahydro-pyrrolo[3,4-c]pyrrol-2-yl]-2-(2-pyrrol-1-yl-phenoxy)-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-(1H-pyrrol-1-yl)phenoxy)-acetic acid (intermediate 33.2) | 457.6 (M + H)+ |

| Ex. | Systematic Name | Amine | Carboxylic acid | MS, m/e |
|---|---|---|---|---|
| 15.93 | 4-{2-[(3aS,6aS)-5-(1H-benzotriazole-5-carbonyl)-hexahydro-pyrrolo[3,4-c]pyrrol-2-yl]-2-oxo-ethoxy}-3-methoxy-benzonitrile | (1H-benzo[d]-[1,2,3]triazol-5-yl)((3aR,6aR)-hexahydropyrrolo[3,4-c]pyrrol-2(1H)-yl)methanone dihydrochloride (intermediate 2.4) | 2-(4-cyano-2-methoxy-phenoxy)acetic acid (CAS-RN 115109-49-4) | 447.5 (M + H)+ |
| 15.94 | 4-{2-[(3aS,6aS)-5-(1H-benzotriazole-5-carbonyl)-hexahydro-pyrrolo[3,4-c]pyrrol-2-yl]-2-oxo-ethoxy}-benzonitrile | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(4-cyano-phenoxy)acetic acid | 417.5 (M + H)+ |
| 15.95 | 1-[(3aS,6aS)-5-(1H-benzotriazole-5-carbonyl)-hexahydro-pyrrolo[3,4-c]pyrrol-2-yl]-2-phenoxy-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-phenoxyacetic acid | 392.6 (M + H)+ |
| 15.96 | 2-{2-[(3aS,6aS)-5-(1H-benzotriazole-5-carbonyl)-hexahydro-pyrrolo[3,4-c]pyrrol-2-yl]-2-oxo-ethoxy}-5-trifluoromethoxy-benzonitrile | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-cyano-4-(trifluoro-methoxy)-phenoxy)acetic acid (intermediate 34.2) | 501.5 (M + H)+ |
| 15.97 | 1-((3aR,8aS)-2-(1H-benzo[d][1,2,3]triazole-5-carbonyl)octahydropyrrolo[3,4-d]azepin-6(7H)-yl)-2-(2-isopropyl-5-methylphenoxy)ethanone | 2-(2-isopropyl-5-methylphenoxy)-1-((3aR,8aS)-octahydropyrrolo[3,4-d]azepin-6(7H)-yl)ethanone (intermediate 36.02) | 1H-benzo[d]-[1,2,3]triazole-5-carboxylic acid | 476.7 (M + H)+ |

-continued

| Ex. | Systematic Name | Amine | Carboxylic acid | MS, m/e |
|---|---|---|---|---|
| 15.98 | 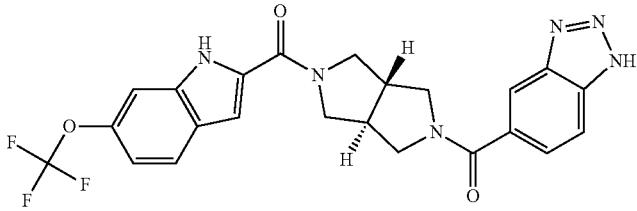<br>(1H-benzotriazol-5-yl)-[(3aS,6aS)-5-(6-trifluoromethoxy-1H-indole-2-carbonyl)-hexahydro-pyrrolo[3,4-c]pyrrol-2-yl]-methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 6-(trifluoromethoxy)-1H-indole-2-carboxylic acid | 485.4 (M + H)⁺ |
| 15.99 | 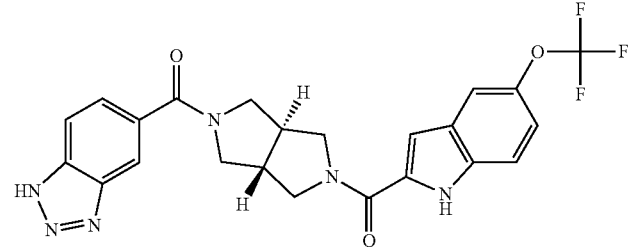<br>(1H-benzotriazol-5-yl)-[(3aS,6aS)-5-(5-trifluoromethoxy-1H-indole-2-carbonyl)-hexahydro-pyrrolo[3,4-c]pyrrol-2-yl]-methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 5-(trifluoromethoxy)-1H-indole-2-carboxylic acid | 485.4 (M + H)⁺ |

Example 16

(E)-1-((3aR,8aS)-2-(1H-benzo[d][1,2,3]triazole-5-carbonyl)octahydropyrrolo[3,4-d]azepin-6(7H)-yl)-3-(4-(trifluoromethylsulfinyl)phenyl)prop-2-en-1-one

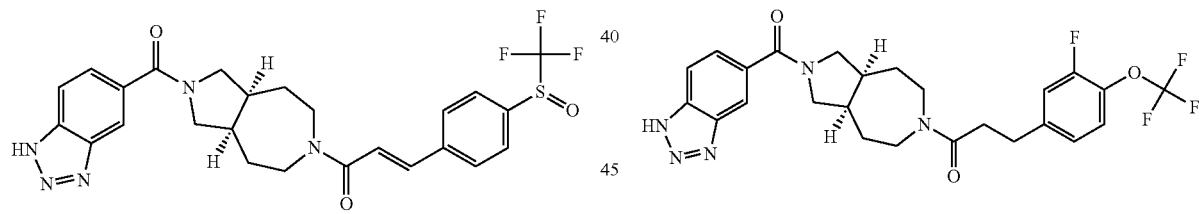

To solution of (E)-1-((3aR,8aS)-2-(1H-benzo[d][1,2,3]triazole-5-carbonyl)octahydropyrrolo[3,4-d]azepin-6(7H)-yl)-3-(4-(trifluoromethylthio)phenyl)prop-2-en-1-one (example 15.69; 25 mg, 48.5 µmol) in acetic acid (1 mL) was added 35% aq. hydrogen peroxide solution (9.43 mg, 97.0 µmol). The reaction mixture was heated at 95° C., then after 3 h another portion of 35% aq. hydrogen peroxide solution (18.9 mg, 194 µmol) was added. After another 15 h the reaction mixture was partitioned between ethyl acetate and sat. aq. sodium hydrogencarbonate solution. The organic layer was washed with brine, dried over magnesium sulfate, filtered, and evaporated. Chromatography (silica gel; gradient dichloromethane to dichloromethane/methanol/25% aq. ammonia solution 90:10:0.25) produced the title compound (11 mg, 43%). White foam, MS: 532.4 (M+H)⁺.

Example 17

1-((3aR,8aS)-2-(1H-Benzo[d][1,2,3]triazole-5-carbonyl)octahydropyrrolo[3,4-d]azepin-6(7H)-yl)-3-(3-fluoro-4-(trifluoromethoxy)phenyl)propan-1-one A solution of (E)-1-((3aR,8aS)-2-(1H-benzo[d][1,2,3]triazole-5-carbonyl)octahydropyrrolo[3,4-d]azepin-6(7H)-yl)-3-(3-fluoro-4-(trifluoromethoxy)phenyl)prop-2-en-1-one (example 1.15; 63 mg, 122 µmol) in methanol (4 mL) was stirred at room temperature under a hydrogen atmosphere (1 bar) in the presence of palladium (10% on activated charcoal, 39 mg, 0.37 mmol), then after 18 h insoluble material was removed by filtration through diatomaceous earth. The filtrate was evaporated and purified by chromatography (silica gel; heptane-ethyl acetate gradient) to produce the title compound (48 mg, 74%). White foam, MS: 520.7 (M+H)⁺.

The following examples were produced in analogy to example 17, replacing of (E)-1-((3aR,8aS)-2-(1H-benzo[d][1,2,3]triazole-5-carbonyl)octahydropyrrolo[3,4-d]azepin-6(7H)-yl)-3-(3-fluoro-4-(trifluoromethoxy)phenyl)prop-2-en-1-one by the appropriate starting material.

| Ex. | Systematic Name | Starting material | MS |
|---|---|---|---|
| 17.01 | (3aR,8aS)-N-((1H-1,2,3-triazol-5-yl)methyl)-N-methyl-6-(3-(4-(trifluoromethoxy)phenyl)-propanoyl)octahydropyrrolo[3,4-d]azepine-2(1H)-carboxamide | (3aR,8aS)-N-((1H-1,2,3-triazol-5-yl)methyl)-N-methyl-6-((E)-3-(4-(trifluoromethoxy)phenyl)-acryloyl)octahydro-pyrrolo[3,4-d]azepine-2(1H)-carboxamide (example 9.07) | 495.6 (M + H)+ |
| 17.02 | (3aR,8aS)-N-((1H-1,2,3-triazol-5-yl)methyl)-6-(3-(3-fluoro-4-(trifluoromethoxy)phenyl)-propanoyl)-N-methyloctahydropyrrolo[3,4-d]azepine-2(1H)-carboxamide | (3aR,8aS)-N-((1H-1,2,3-triazol-5-yl)methyl)-6-((E)-3-(3-fluoro-4-(trifluoromethoxy)phenyl)-acryloyl)-N-methyloctahydro-pyrrolo[3,4-d]azepine-2(1H)-carboxamide (example 15.61) | 513.6 (M + H)+ |
| 17.03 | 1-[(3aR,6aR)-5-(1H-benzotriazole-5-carbonyl)-hexahydro-pyrrolo[3,4-c]pyrrol-2-yl]-3-(4-difluoromethoxy-phenyl)-propan-1-one | (E)-1-((3aR,6aR)-5-(1H-benzo[d][1,2,3]triazole-5-carbonyl)hexahydro-pyrrolo[3,4-c]pyrrol-2(1H)-yl)-3-(4-(difluoromethoxy)phenyl)-prop-2-en-1-one (example 15.36) | 465.5 (M + H)+ |
| 17.04 | 1-[(3aR,6aR)-5-(1H-benzotriazole-5-carbonyl)-hexahydro-pyrrolo[3,4-c]pyrrol-2-yl]-3-(2-fluoro-4-trifluoromethoxy-phenyl)-propan-1-one | (E)-1-((3aR,6aR)-5-(1H-benzo[d][1,2,3]triazole-5-carbonyl)hexahydro-pyrrolo[3,4-c]pyrrol-2(1H)-yl)-3-(2-fluoro-4-(trifluoromethoxy)phenyl)-prop-2-en-1-one (example 15.40) | 492.7 (M + H)+ |

-continued

| Ex. | Systematic Name | Starting material | MS |
|---|---|---|---|
| 17.05 | 1-((3aR,8aS)-2-(1H-benzo[d][1,2,3]triazole-5-carbonyl)octahydropyrrolo[3,4-d]azepin-6(7H)-yl)-3-(4-fluoro-2-(trifluoromethyl)phenyl)propan-1-one | (E)-1-((3aR,8aS)-2-(1H-benzo[d][1,2,3]triazole-5-carbonyl)octahydro-pyrrolo[3,4-d]azepin-6(7H)-yl)-3-(4-fluoro-2-(trifluoromethyl)phenyl)-prop-2-en-1-one (example 15.66) | 504.6 (M + H)+ |
| 17.06 | 1-((3aR,8aS)-2-(1H-benzo[d][1,2,3]triazole-5-carbonyl)octahydropyrrolo[3,4-d]azepin-6(7H)-yl)-3-(2-methyl-4-(trifluoromethoxy)phenyl)-propan-1-one | (E)-1-((3aR,8aS)-2-(1H-benzo[d][1,2,3]triazole-5-carbonyl)octahydro-pyrrolo[3,4-d]azepin-6(7H)-yl)-3-(2-methyl-4-(trifluoromethoxy)phenyl)-prop-2-en-1-one (example 1.18) | 516.7 (M + H)+ |
| 17.07 | 1-((3aR,8aS)-2-(1H-benzo[d][1,2,3]triazole-5-carbonyl)octahydropyrrolo[3,4-d]azepin-6(7H)-yl)-3-(3-fluoro-4-methoxyphenyl)propan-1-one | (E)-1-((3aR,8aS)-2-(1H-benzo[d][1,2,3]triazole-5-carbonyl)octahydro-pyrrolo[3,4-d]azepin-6(7H)-yl)-3-(3-fluoro-4-methoxyphenyl)prop-2-en-1-one (example 1.19) | 466.7 (M + H)+ |
| 17.08 | 1-[(3aS,8aR)-2-(1H-benzotriazole-5-carbonyl)-octahydro-pyrrolo[3,4-d]azepin-6-yl]-3-(2-isopropyl-phenyl)-propan-1-one | (E)-1-[(3aS,8aR)-2-(1H-benzotriazole-5-carbonyl)-octahydro-pyrrolo[3,4-d]azepin-6-yl]-3-(2-isopropyl-phenyl)-prop-2-en-1-one (example 1.22) | 460.7 (M + H)+ |

-continued

| Ex. | Systematic Name | Starting material | MS |
|---|---|---|---|
| 17.09 | 1-[(3aR,6aR)-5-(1H-benzotriazole-5-carbonyl)-hexahydro-pyrrolo[3,4-c]pyrrol-2-yl]-3-(5-trifluoromethyl-pyridin-2-yl)-propan-1-one | (E)-1-[(3aR,6aR)-5-(1H-benzotriazole-5-carbonyl)-hexahydro-pyrrolo[3,4-c]pyrrol-2-yl]-3-(5-trifluoromethyl-pyridin-2-yl)-prop-2-en-1-one (example 15.78) | 459.5 (M + H)+ |
| 17.10 | 1-[(3aR,6aR)-5-(1H-benzotriazole-5-carbonyl)-hexahydro-pyrrolo[3,4-c]pyrrol-2-yl]-3-(5-phenyl-pyridin-2-yl)-propan-1-one | (E)-1-[(3aR,6aR)-5-(1H-benzotriazole-5-carbonyl)-hexahydro-pyrrolo[3,4-c]pyrrol-2-yl]-3-(5-phenyl-pyridin-2-yl)-prop-2-en-1-one (example 15.84) | 467.6 (M + H)+ |
| 17.11 | 1-[(3aR,6aR)-5-(1H-benzotriazole-5-carbonyl)-hexahydro-pyrrolo[3,4-c]pyrrol-2-yl]-3-(4-pyridin-4-yl-phenyl)-propan-1-one | (E)-1-[(3aR,6aR)-5-(1H-benzotriazole-5-carbonyl)-hexahydro-pyrrolo[3,4-c]pyrrol-2-yl]-3-(4-pyridin-4-yl-phenyl)-prop-2-en-1-one (example 15.79) | 467.5 (M + H)+ |
| 17.12 | 1-[(3aR,6aR)-5-(1H-benzotriazole-5-carbonyl)-hexahydro-pyrrolo[3,4-c]pyrrol-2-yl]-3-(4-pyridin-3-yl-phenyl)-propan-1-one | (E)-1-[(3aR,6aR)-5-(1H-benzotriazole-5-carbonyl)-hexahydro-pyrrolo[3,4-c]pyrrol-2-yl]-3-(4-pyridin-3-yl-phenyl)-prop-2-en-1-one (example 15.80) | 467.6 (M + H)+ |
| 17.13 | 1-[(3aR,6aR)-5-(1H-benzotriazole-5-carbonyl)-hexahydro-pyrrolo[3,4-c]pyrrol-2-yl]-3-(4-pyridin-2-yl-phenyl)-propan-1-one | (E)-1-[(3aR,6aR)-5-(1H-benzotriazole-5-carbonyl)-hexahydro-pyrrolo[3,4-c]pyrrol-2-yl]-3-(4-pyridin-2-yl-phenyl)-prop-2-en-1-one (example 15.81) | 467.5 (M + H)+ |

-continued

| Ex. | Systematic Name | Starting material | MS |
|---|---|---|---|
| 17.14 | (3aS,8aR)-6-[3-(4-trifluoromethoxy-phenyl)-propionyl]-octahydro-pyrrolo[3,4-d]azepine-2-carboxylic acid [2-(3H-[1,2,3]triazol-4-yl)-ethyl]-amide | (3aR,8aS)-N-(2-(1H-1,2,3-triazol-5-yl)ethyl)-6-((E)-3-(4-(trifluoromethoxy)-phenyl)acryloyl)octa-hydropyrrolo[3,4-d]azepine-2(1H)-carboxamide (example 9.09) | 495.2 (M + H)+ |
| 17.15 | 1-[trans-2-(1H-benzotriazole-5-carbonyl)-octahydro-pyrrolo[3,4-c]pyridin-5-yl]-3-(4-trifluoromethoxy-phenyl)-propan-1-one | (E)-1-[trans-2-(1H-benzotriazole-5-carbonyl)-octahydro-pyrrolo[3,4-c]pyridin-5-yl]-3-(4-trifluoromethoxy-phenyl)-propenone (example 1.26) | 488.7 (M + H)+ |
| 17.16 | 1-[trans-2-(1H-benzotriazol-5-ylmethyl)-octahydro-pyrrolo[3,4-c]pyridin-5-yl]-3-(4-trifluoromethoxy-phenyl)-propan-1-one | (E)-1-[trans-2-(1H-benzotriazol-5-ylmethyl)-octahydro-pyrrolo[3,4-c]pyridin-5-yl]-3-(4-trifluoromethoxy-phenyl)-propenone (example 6.07) | 474.4 (M + H)+ |
| 17.17 | 1-((3aR,8aS)-2-(1H-benzo[d][1,2,3]triazole-5-carbonyl)octahydropyrrolo[3,4-d]azepin-6(7H)-yl)-3-(3-chloro-5-(trifluoromethyl)phenyl)propan-1-one | (E)-1-((3aR,8aS)-2-(1H-benzo[d][1,2,3]triazole-5-carbonyl)octahydropyrrolo[3,4-d]azepin-6(7H)-yl)-3-(3-chloro-5-(trifluoromethyl)phenyl)prop-2-en-1-one (example 1.27) | 520.6 (M + H)+ |

| Ex. | Systematic Name | Starting material | MS |
|---|---|---|---|
| 17.18 | 1-((3aR,8aS)-2-(1H-benzo[d][1,2,3]triazole-5-carbonyl)octahydropyrrolo[3,4-d]azepin-6(7H)-yl)-3-(4-methoxy-2-(trifluoromethyl)phenyl)propan-1-one | (E)-1-((3aR,8aS)-2-(1H-benzo[d][1,2,3]triazole-5-carbonyl)octahydropyrrolo[3,4-d]azepin-6(7H)-yl)-3-(4-methoxy-2-(trifluoromethyl)phenyl)prop-2-en-1-one (example 1.28) | 516.7 (M + H)⁺ |
| 17.19 | 1-((3aR,8aS)-2-(1H-benzo[d][1,2,3]triazole-5-carbonyl)octahydropyrrolo[3,4-d]azepin-6(7H)-yl)-3-(2-cyclopropylphenyl)propan-1-one | (E)-1-((3aR,8aS)-2-(1H-benzo[d][1,2,3]triazole-5-carbonyl)octahydropyrrolo[3,4-d]azepin-6(7H)-yl)-3-(2-cyclopropylphenyl)prop-2-en-1-one (example 1.29) | 458.7 (M + H)⁺ |
| 17.20 | 1-[(3aR,6aR)-5-(1H-benzotriazole-5-carbonyl)-1,3,3a,4,6,6a-hexahydropyrrolo[3,4-c]pyrrol-2-yl]-3-[3-methoxy-5-(trifluoromethoxy)phenyl]propan-1-one | (E)-1-[(3aR,6aR)-5-(1H-benzotriazole-5-carbonyl)-hexahydro-pyrrolo[3,4-c]pyrrol-2-yl]-3-(3-methoxy-5-trifluoromethoxy-phenyl)-prop-2-ene-1-one (example 15.51) | 504.4 (M + H)⁺ |

Example 18

(E)-3-[4-(Trifluoro-methoxy)-phenyl]-1-[(3aS,8aR)-2-((S)-4,5,6,7-tetrahydro-1H-imidazo[4,5-c]pyridine-6-carbonyl)-octahydro-pyrrolo[3,4-d]azepin-6-yl]-prop-2-en-1-one hydrochloride

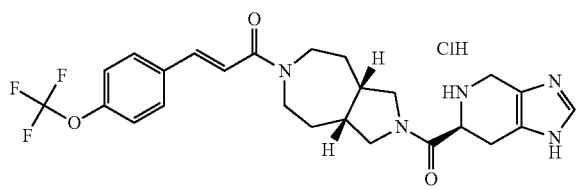 [SMILES: O=C(/C=C/c1ccc(OC(F)(F)F)cc1)N1CC[C@@H]2CN(C(=O)[C@@H]3Cc4[nH]cnc4CN3)C[C@@H]2CC1 ; Cl]

Step 1: (S)-Di-tert-butyl 6-((3aR,8aS)-6-((E)-3-(4-(trifluoromethoxy)phenyl)acryloyl)-decahydropyrrolo[3,4-d]azepine-2-carbonyl)-6,7-dihydro-1H-imidazo[4,5-c]pyridine-1,5(4H)-dicarboxylate The title compound was produced in analogy to example 15 from (E)-1-((3aR,8aS)-octahydropyrrolo[3,4-d]azepin-6(7H)-yl)-3-(4-(trifluoromethoxy)phenyl)prop-2-en-1-one hydrochloride (intermediate 5) and (S)-1,5-bis(tert-butoxycarbonyl)-4,5,6,7-tetrahydro-1H-imidazo[4,5-c]pyridine-6-carboxylic acid (CAS-RN 175289-42-6). White foam, MS: 704.3 (M+H)⁺.

Step 2: (E)-3-[4-(Trifluoro-methoxy)-phenyl]-1-[(3aS,8aR)-2-((S)-4,5,6,7-tetrahydro-1H-imidazo[4,5-c]pyridine-6-carbonyl)-octahydro-pyrrolo[3,4-d]azepin-6-yl]-prop-2-en-1-one hydrochloride The title compound was produced in analogy to intermediate 1, step 2 from (S)-di-tert-butyl 6-((3aR,8aS)-6-((E)-3-(4-(trifluoromethoxy)phenyl)acryloyl)decahydropyrrolo[3, 4-d]azepine-2-carbonyl)-6,7-dihydro-1H-imidazo[4,5-c]pyridine-1,5(4H)-dicarboxylate. White solid, MS: 504.2 (M+H)⁺.

Example 19

1-[(3aS,6aS)-5-(1H-benzotriazole-5-carbonyl)-hexahydro-pyrrolo[3,4-c]pyrrol-2-yl]-2-(2-isopropyl-5-methyl-phenoxy)-ethanone

To a suspension of (1H-benzo[d][1,2,3]triazol-5-yl)((3aR,6aR)-hexahydropyrrolo[3,4-c]pyrrol-2(1H)-yl)methanone hydrochloride (intermediate 2.04; 25 mg, 85.1 µmol, Eq: 1.00), N-methylmorpholine (43.0 mg, 426 µmol) and 2-(2-isopropyl-5-methylphenoxy)acetic acid (17.7 mg, 85.1 µmol) in N,N-dimethylformamide (4 mL) was added O-(7-azabenzotriazol-1-yl)-N,N,N',N'-tetramethyluronium hexafluoro-phosphate (32.4 mg, 85.1 µmol) at 0° C., then the reaction mixture was allowed to reach room temperature over a period of 16 h. After partitioning between ethyl acetate and sat. aq. sodium hydrogen carbonate solution the organic layer was washed with water and brine, dried over magnesium sulfate, filtered, and evaporated. Chromatography (silica gel; gradient dichloromethane to dichloromethane/methanol/25% aq. ammonia solution 90:10:0.25) produced the title compound (37 mg, 97%). White foam, MS: 448.6 (M+H)⁺.

The following compounds were produced in analogy to example 19, replacing (1H-benzo[d][1,2,3]triazol-5-yl)((3aR,6aR)-hexahydropyrrolo[3,4-c]pyrrol-2(1H)-yl)methanone hydrochloride and 2-(2-isopropyl-5-methylphenoxy)acetic acid by the appropriate amine and carboxylic acid, respectively.

| Ex. | Systematic Name | Amine | Carboxylic acid | MS, m/e |
|---|---|---|---|---|
| 19.01 | 1-[(3aS,6aS)-5-(1H-benzotriazole-5-carbonyl)-hexahydro-pyrrolo[3,4-c]pyrrol-2-yl]-2-(2-bromo-4-trifluoromethoxy-phenoxy)-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-bromo-4-(trifluoro-methoxy)-phenoxy)acetic acid (intermediate 33.1) | 554.3 (M + H)⁺ |
| 19.02 | (1H-benzotriazol-5-yl)-[(3aR,6aR)-5-(4'-chloro-biphenyl-4-carbonyl)-hexahydro-pyrrolo[3,4-c]pyrrol-2-yl]-methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4'-chlorobiphenyl-4-carboxylic acid | 472.5 (M + H)⁺ |
| 19.03 | 4-{2-[(3aS,6aS)-5-(1H-benzotriazole-5-carbonyl)-hexahydro-pyrrolo[3,4-c]pyrrol-2-yl]-2-oxo-ethoxy}-3-isopropyl-benzonitrile | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(4-cyano-2-isopropyl-phenoxy)acetic acid (intermediate 34.1) | 459.6 (M + H)⁺ |

-continued

| Ex. | Systematic Name | Amine | Carboxylic acid | MS, m/e |
|---|---|---|---|---|
| 19.04 | 2-(2-acetyl-phenoxy)-1-[(3aS,6aS)-5-(1H-benzotriazole-5-carbonyl)-hexahydro-pyrrolo[3,4-c]pyrrol-2-yl]-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-acetyl-phenoxy)acetic acid (CAS-RN 1878-62-2) | 434.6 (M + H)+ |
| 19.05 | 4-{2-[(3aS,6aS)-5-(1H-benzotriazole-5-carbonyl)-hexahydro-pyrrolo[3,4-c]pyrrol-2-yl]-2-oxo-ethoxy}-5-isopropyl-2-methyl-benzonitrile | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(4-cyano-2-isopropyl-5-methyl-phenoxy)acetic acid (intermediate 34) | 473.7 (M + H)+ |
| 19.06 | (1H-benzotriazol-5-yl)-[(3aR,6aR)-5-(naphthalene-2-carbonyl)-hexahydro-pyrrolo[3,4-c]pyrrol-2-yl]-methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-naphthoic acid | 410.6 (M − H)− |
| 19.07 | (1H-benzotriazol-5-yl)-[(3aS,6aS)-5-(4-methoxy-naphthalene-2-carbonyl)-hexahydro-pyrrolo[3,4-c]pyrrol-2-yl]-methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4-methoxy-2-naphthoic acid (CAS-RN 5773-93-3) | 442.6 (M + H)+ |

-continued

| Ex. | Systematic Name | Amine | Carboxylic acid | MS, m/e |
|---|---|---|---|---|
| 19.08 | 4-{2-[(3aS,6aS)-5-(1H-benzotriazole-5-carbonyl)-hexahydro-pyrrolo[3,4-c]pyrrol-2-yl]-2-oxo-ethoxy}-3-ethoxy-benzonitrile 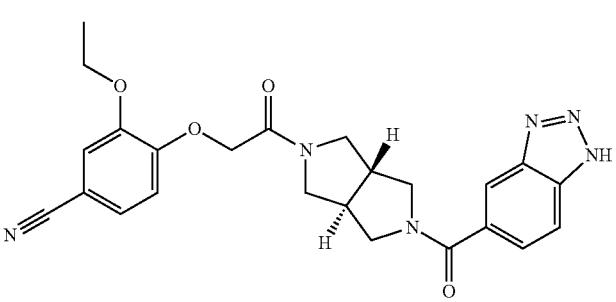 [SMILES: CCOc1cc(C#N)ccc1OCC(=O)N1C[C@@H]2CN(C(=O)c3ccc4[nH]nnc4c3)C[C@H]2C1] | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(4-cyano-2-ethoxy-phenoxy)acetic acid (CAS-RN 835888-68-1) | 461.7 (M + H)+ |
| 19.09 | 1-[(3aR,6aR)-5-(1H-benzotriazole-5-carbonyl)-hexahydro-pyrrolo[3,4-c]pyrrol-2-yl]-3-(3-fluoro-4-trifluoromethoxy-phenyl)-propan-1-one 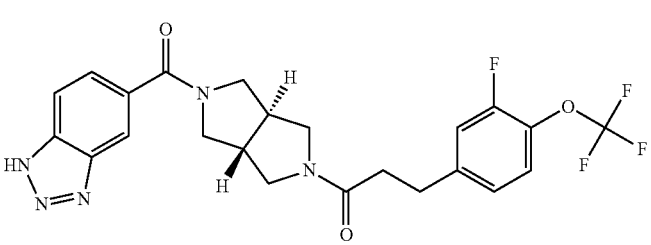 [SMILES: O=C(CCc1ccc(OC(F)(F)F)c(F)c1)N1C[C@@H]2CN(C(=O)c3ccc4[nH]nnc4c3)C[C@H]2C1] | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(3-fluoro-4-(trifluoromethoxy)-phenyl)-propanoic acid (intermediate 35) | 492.4 (M + H)+ |
| 19.10 | 1-[(3aS,6aS)-5-(1H-benzotriazole-5-carbonyl)-hexahydro-pyrrolo[3,4-c]pyrrol-2-yl]-2-(4-chloro-2-isopropyl-phenoxy)-ethanone 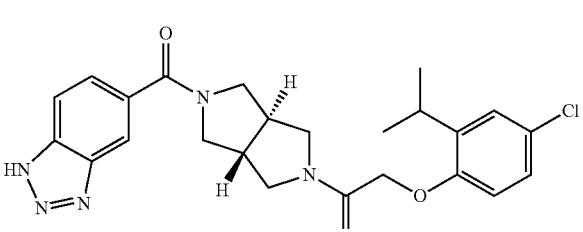 | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(4-chloro-2-isopropyl-phenoxy)acetic acid (CAS-RN 109042-01-5) | 468.5 (M + H)+ |
| 19.11 | [(3aS,6aS)-5-(4'-chloro-biphenyl-4-carbonyl)-hexahydro-pyrrolo[3,4-c]pyrrol-2-yl]-(R)-4,5,6,7-tetrahydro-1H-benzotriazol-5-yl-methanone 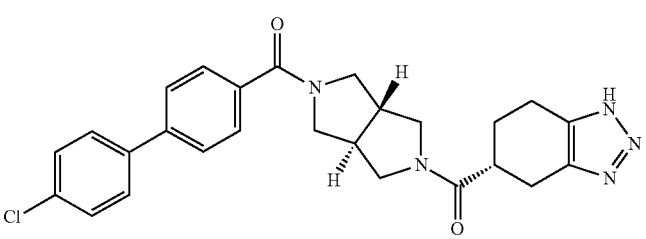 [SMILES: O=C(c1ccc(-c2ccc(Cl)cc2)cc1)N1C[C@@H]2CN(C(=O)[C@@H]3CCc4[nH]nnc4C3)C[C@H]2C1] | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 4'-chlorobi-phenyl-4-carboxylic acid | 476.5 (M + H)+ |

-continued

| Ex. | Systematic Name | Amine | Carboxylic acid | MS, m/e |
|---|---|---|---|---|
| 19.12 | 1-[(3aS,6aS)-5-(1H-benzotriazole-5-carbonyl)-hexahydro-pyrrolo[3,4-c]pyrrol-2-yl]-3-(4-trifluoromethoxy-phenyl)-propan-1-one | (1H-benzo[d][1,2,3]triazol-5-yl)((3aS,6aS)-hexahydropyrrolo[3,4-c]pyrrol-2(1H)-yl)methanone dihydrochloride (intermediate 8) | 3-(4-(trifluoro-methoxy)-phenyl)-propanoic acid | 474.4 (M + H)+ |
| 19.13 | (1H-benzotriazol-5-yl)-[(3aS,6aS)-5-(4'-chloro-biphenyl-4-carbonyl)-hexahydro-pyrrolo[3,4-c]pyrrol-2-yl]-methanone | (1H-benzo[d][1,2,3]triazol-5-yl)((3aS,6aS)-hexahydropyrrolo[3,4-c]pyrrol-2(1H)-yl)methanone dihydrochloride (intermediate 8) | 4'-chloro-biphenyl-4-carboxylic acid | 472.6 (M + H)+ |
| 19.14 | 1-[(3aS,6aS)-5-(1H-benzotriazole-5-carbonyl)-hexahydro-pyrrolo[3,4-c]pyrrol-2-yl]-2-[2-(tetrahydro-furan-2-yl)-phenoxy]-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-(tetrahydro-furan-2-yl)-phenoxy)acetic acid (intermediate 33) | 462.5 (M + H)+ |
| 19.15 | (1H-benzotriazol-5-yl)-[(3aR,6aR)-5-(4-methoxy-naphthalene-2-carbonyl)-hexahydro-pyrrolo[3,4-c]pyrrol-2-yl]-methanone | (1H-benzo[d][1,2,3]triazol-5-yl)((3aS,6aS)-hexahydropyrrolo[3,4-c]pyrrol-2(1H)-yl)methanone dihydrochloride (intermediate 8) | 4-methoxy-2-naphthoic acid (CAS-RN 5773-93-3) | 442.6 (M + H)+ |

-continued

| Ex. | Systematic Name | Amine | Carboxylic acid | MS, m/e |
|---|---|---|---|---|
| 19.16 | 1-[(3aS,6aS)-5-(1H-benzotriazole-5-carbonyl)-hexahydro-pyrrolo[3,4-c]pyrrol-2-yl]-2-(2-tert-butyl-phenoxy)-ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-tert-butyl-phenoxy)acetic acid (CAS-RN 19271-90-0) | 448.5 (M + H)$^+$ |
| 19.17 | [(3aR,6aR)-5-(1H-benzotriazole-5-carbonyl)-hexahydro-pyrrolo[3,4-c]pyrrol-2-yl]-[trans-4-(4-chloro-phenyl)-cyclohexyl]-methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | trans-4-(4-chlorophenyl)-cyclohexane-carboxylic acid | 478.2 (M + H)$^+$ |
| 19.18 | 1-[(3aR,6aR)-5-(1H-benzotriazole-5-carbonyl)-hexahydro-pyrrolo[3,4-c]pyrrol-2-yl]-3-(3-fluoro-4-trifluoromethyl-phenyl)-propan-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(3-fluoro-4-(trifluoro-methyl)-phenyl)-propanoic acid | 474.5 (M − H)$^-$ |
| 19.19 | 1-[(3aR,6aR)-5-(1H-benzotriazole-5-carbonyl)-hexahydro-pyrrolo[3,4-c]pyrrol-2-yl]-3-(2-fluoro-4-trifluoromethyl-phenyl)-propan-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(2-fluoro-4-(trifluoro-methyl)-phenyl)-propanoic acid | 474.5 (M − H)$^-$ |

-continued

| Ex. | Systematic Name | Amine | Carboxylic acid | MS, m/e |
|---|---|---|---|---|
| 19.20 | 1-[(3aS,6aS)-5-(1H-benzotriazole-5-carbonyl)-1,3,3a,4,6,6a-hexahydropyrrolo[3,4-c]pyrrol-2-yl]-2-(2-pyridin-3-ylphenoxy)ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-(pyridin-3-yl)phenoxy)-acetic acid (intermediate 34.3) | 467.6 (M − H)⁻ |
| 19.21 | 4-[3-[(3aR,6aR)-5-(1H-benzotriazole-5-carbonyl)-1,3,3a,4,6,6a-hexahydropyrrolo[3,4-c]pyrrol-2-yl]-3-oxopropyl]-2-methyl-5-propan-2-ylbenzonitrile | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(4-cyano-2-isopropyl-5-methyl-phenyl)-propanoic acid (intermediate 42.1) | 471.7 (M + H)⁺ |
| 19.22 | 4-[3-[(3aR,6aR)-5-(1H-benzotriazole-5-carbonyl)-1,3,3a,4,6,6a-hexahydropyrrolo[3,4-c]pyrrol-2-yl]-3-oxopropyl]-3-propan-2-ylbenzonitrile | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(4-cyano-2-isopropyl-phenyl)-propanoic acid (intermediate 42) | 457.7 (M + H)⁺ |
| 19.23 | [(3aR,6aR)-5-[1-(4-chlorophenyl)piperidine-4-carbonyl]-1,3,3a,4,6,6a-hexahydropyrrolo[3,4-c]pyrrol-2-yl]-(1H-benzotriazol-5-yl)methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 1-(4-chlorophenyl)-piperidine-4-carboxylic acid (CAS-RN 845645-46-7) | 479.6 (M + H)⁺ |

-continued

| Ex. | Systematic Name | Amine | Carboxylic acid | MS, m/e |
|---|---|---|---|---|
| 19.24 | [(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-(4-propan-2-yloxynaphthalen-2-yl)methanone | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 4-isopropoxy-2-naphthoic acid (CAS-RN 1368865-02-4) | 474.5 (M + H)+ |
| 19.25 | [(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-(4-propan-2-yloxyquinolin-2-yl)methanone | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 4-isopropoxy-quinoline-2-carboxylic acid (CAS-RN 1406553-19-2) | 475.5 (M + H)+ |
| 19.26 | 1-[(3aR,6aR)-5-[(5R)-4,5,6,7-tetrahydro-1H-benzotriazole-5-carbonyl]-1,3,3a,4,6,6a-hexahydro-pyrrolo[3,4-c]pyrrol-2-yl]-3-[2-fluoro-4-(trifluoromethoxy)phenyl]-propan-1-one | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 3-(2-fluoro-4-(trifluoro-methoxy)-phenyl)-propanoic acid (intermediate 35.4) | 496.4 (M + H)+ |
| 19.27 | 4-[2-[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-2-oxoethoxy]-2-methyl-5-propan-2-ylbenzonitrile | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 2-(4-cyano-2-isopropyl-5-methyl-phenoxy)acetic acid (intermediate 34) | 477.5 (M + H)+ |

-continued

| Ex. | Systematic Name | Amine | Carboxylic acid | MS, m/e |
|---|---|---|---|---|
| 19.28 | [(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-[1-(2,2,2-trifluoroethoxy)isoquinolin-3-yl]methanone | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 1-(2,2,2-trifluoro-ethoxy)-isoquinoline-3-carboxylic acid (CAS-RN 1096982-79-4) | 515.4 (M + H)+ |
| 19.29 | 1-[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-2-(4-bromo-2-tert-butylphenoxy)ethanone | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 2-(4-bromo-2-tert-butyl-phenoxy)acetic acid (CAS-RN 425372-86-7) | 530.4 (M + H)+ |
| 19.30 | 1-[(3aS,6aS)-5-(1H-benzotriazole-5-carbonyl)-1,3,3a,4,6,6a-hexahydropyrrolo[3,4-c]pyrrol-2-yl]-2-(4-bromo-2-tert-butylphenoxy)ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(4-bromo-2-tert-butyl-phenoxy)acetic acid (CAS-RN 425372-86-7) | 526.6 (M + H)+ |
| 19.31 | 4-[2-[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-2-oxoethoxy]-3-tert-butylbenzonitrile | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 2-(2-tert-butyl-4-cyano-phenoxy)acetic acid (intermediate 40) | 477.7 (M + H)+ |

-continued

| Ex. | Systematic Name | Amine | Carboxylic acid | MS, m/e |
|---|---|---|---|---|
| 19.32 | 4-[2-[(3aS,6aS)-5-(1H-benzotriazole-5-carbonyl)-1,3,3a,4,6,6a-hexahydropyrrolo[3,4-c]pyrrol-2-yl]-2-oxoethoxy]-3-tert-butylbenzonitrile | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-tert-butyl-4-cyano-phenoxy)acetic acid (intermediate 40) | 471.7 (M − H)⁻ |
| 19.33 | [(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl][1-methyl-5-(trifluoromethoxy)indol-2-yl]methanone | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 1-methyl-5-(trifluoromethoxy)-1H-indole-2-carboxylic acid (CAS-RN 1257122-42-1) | 501.5 (M − H)⁻ |
| 19.34 | 1-[(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-2-[4-(trifluoromethoxy)phenoxy]ethanone | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 2-(4-(trifluoromethoxy)phenoxy)acetic acid | 487.5 (M − H)⁻ |
| 19.35 | [(3aS,6aS)-5-[(5R)-4,5,6,7-tetrahydro-1H-benzotriazole-5-carbonyl]-1,3,3a,4,6,6a-hexahydropyrrolo[3,4-c]pyrrol-2-yl]-(1-ethoxyisoquinolin-3-yl)methanone | ((3aR,6aR)-hexahydropyrrolo[3,4-c]pyrrol-2(1H)-yl)((R)-4,5,6,7-tetrahydro-1H-benzo[d][1,2,3]triazol-5-yl)methanone hydrochloride (intermediate 2.5) | 1-ethoxy-isoquinoline-3-carboxylic acid (CAS-RN 1094758-39-0) | 461.5 (M + H)⁺ |

-continued

| Ex. | Systematic Name | Amine | Carboxylic acid | MS, m/e |
|---|---|---|---|---|
| 19.36 | 1-[(3aS,6aS)-5-(1H-benzotriazole-5-carbonyl)-1,3,3a,4,6,6a-hexahydropyrrolo[3,4-c]pyrrol-2-yl]-2-(2-tert-butyl-4-methoxyphenoxy)ethanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 2-(2-tert-butyl-4-methoxy-phenoxy)acetic acid | 476.5 (M + H)+ |
| 19.37 | ((3aS,6aS)-5-(1H-benzo[d][1,2,3]triazole-5-carbonyl)hexahydropyrrolo[3,4-c]pyrrol-2(1H)-yl)(4-ethoxyquinolin-2-yl)methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4-ethoxy-quinoline-2-carboxylic acid (CAS-RN 40609-78-7) | 457.6 (M + H)+ |
| 19.38 | ((3aS,6aS)-5-(1H-benzo[d][1,2,3]triazole-5-carbonyl)hexahydro-pyrrolo[3,4-c]pyrrol-2(1H)-yl)(4-(2,2,2-trifluoroethoxy)quinolin-2-yl)methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 4-(2,2,2-trifluoro-ethoxy)-quinoline-2-carboxylic acid (CAS-RN 1281584-65-3) | 511.6 (M + H)+ |
| 19.39 | ((3aS,6aS)-5-(1H-benzo[d][1,2,3]triazole-5-carbonyl)hexahydro-pyrrolo[3,4-c]pyrrol-2(1H)-yl)(6-cyclobutoxy-5-(trifluoromethyl)-pyridin-3-yl)methanone | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 6-cyclobutoxy-5-(trifluoro-methyl)-nicotinic acid | 501.2 (M + H)+ |

-continued

| Ex. | Systematic Name | Amine | Carboxylic acid | MS, m/e |
|---|---|---|---|---|
| 19.40 | ((3aS,6aS)-5-(1H-benzo[d][1,2,3]triazole-5-carbonyl)hexahydropyrrolo[3,4-c]pyrrol-2(1H)-yl)(5-bromo-6-(2-methoxyethoxy)pyridin-3-yl)methanone 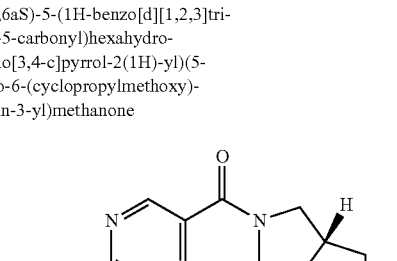 | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 5-bromo-6-(2-methoxy-ethoxy)-nicotinic acid (CAS-RN 912454-34-3) | 515.2 (M + H)⁺ |
| 19.41 | ((3aS,6aS)-5-(1H-benzo[d][1,2,3]triazole-5-carbonyl)hexahydropyrrolo[3,4-c]pyrrol-2(1H)-yl)(5-bromo-6-(cyclopropylmethoxy)-pyridin-3-yl)methanone 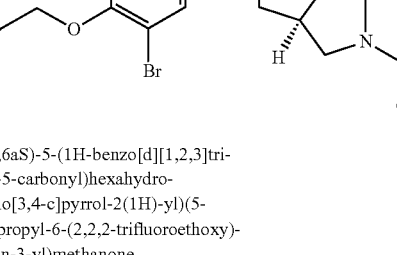 | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 5-bromo-6-(cyclopropyl-methoxy)-nicotinic acid (CAS-RN 912454-38-7) | 511.1 (M + H)⁺ |
| 19.42 | ((3aS,6aS)-5-(1H-benzo[d][1,2,3]triazole-5-carbonyl)hexahydropyrrolo[3,4-c]pyrrol-2(1H)-yl)(5-cyclopropyl-6-(2,2,2-trifluoroethoxy)-pyridin-3-yl)methanone 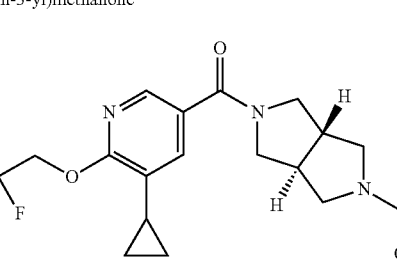 | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 5-cyclopropyl-6-(2,2,2-trifluoro-ethoxy)-nicotinic acid (CAS-RN 1427064-90-1) | 501.5 (M + H)⁺ |
| 19.43 | ((3aS,6aS)-5-(1H-benzo[d][1,2,3]triazole-5-carbonyl)hexahydropyrrolo[3,4-c]pyrrol-2(1H)-yl)(6-(2,2,2-trifluoroethoxy)-5-(trifluoromethyl)pyridin-3-yl)methanone 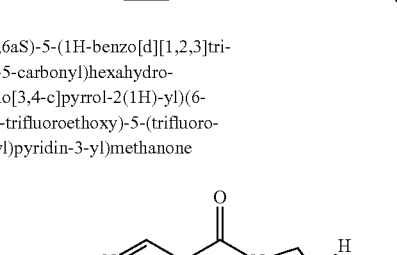 | (1H-benzo[d][1,2,3]triazol-5-yl)((3aR,6aR)-hexahydropyrrolo[3,4-c]pyrrol-2(1H)-yl)methanone dihydrochloride (intermediate 2.4) | 6-(2,2,2-trifluoro-ethoxy)-5-(trifluoro-methyl)-nicotinic acid | 529.5 (M + H)⁺ |

Example 20

(1H-Benzotriazol-5-yl)-{(3aS,6aS)-5-[4-(4-chloro-phenyl)-piperidine-1-carbonyl]-hexahydro-pyrrolo[3,4-c]pyrrol-2-yl}-methanone

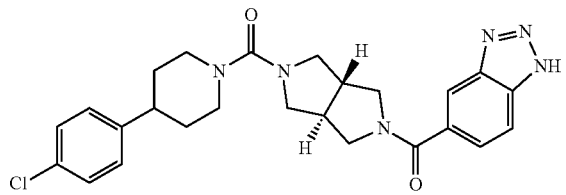 [SMILES: O=C(c1ccc2[nH]nnc2c1)N1C[C@H]2CN(C(=O)N3CCC(c4ccc(Cl)cc4)CC3)C[C@@H]2C1]

To a white suspension of (1H-benzo[d][1,2,3]triazol-5-yl)((3aR,6aR)-hexahydropyrrolo[3,4-c]pyrrol-2(1H)-yl)methanone hydrochloride (intermediate 2.4; 40 mg, 136 μmol) and triethylamine (68.9 mg, 681 μmol) in dichloromethane (4 mL) was added a solution of 4-(4-chlorophenyl)piperidine-1-carbonyl chloride (intermediate 9.3; 44.9 mg, 163 μmol) in dichloromethane (2 mL) at room temperature, then after 19 the reaction mixture was partitioned between sat. aq. sodium hydrogencarbonate solution and dichloromethane. The organic layer was washed with brine, dried over magnesium sulfate, filtered, and evaporated. Chromatography (silica gel; gradient dichloromethane to dichloromethane/methanol/25% aq. ammonia solution 90:10:0.25) produced the title compound (50 mg, 77%). White foam, MS: 479.6 (M+H)$^+$.

The following example was produced in analogy to example 20, replacing 4-(4-chlorophenyl)piperidine-1-carbonyl chloride by the appropriate reagent.

| Ex. | Systematic Name | Reagent | MS |
|---|---|---|---|
| 20.01 | (1H-benzotriazol-5-yl)-{(3aS,6aS)-5-[4-(4-chloro-phenyl)-piperazine-1-carbonyl]-hexahydro-pyrrolo[3,4-c]pyrrol-2-yl}-methanone | 4-(4-chlorophenyl)piperazine-1-carbonyl chloride (CAS-RN 64985-84-8) | 480.4 (M + H)$^+$ |

Intermediates

Intermediate 1

(3aR,6aS)-3,5-Dichlorobenzyl hexahydropyrrolo[3,4-c]pyrrole-2(1H)-carboxylate hydrochloride Step 1: (3aR,6aS)-2-tert-Butyl 5-(3,5-dichlorobenzyl) tetrahydropyrrolo[3,4-c]pyrrole-2,5(1H,3H)-dicarboxylate To a light brown solution of (3,5-dichlorophenyl)methanol (425 mg, 2.35 mmol) in dichloromethane (7 mL) was added N,N'-carbonyldiimidazole (401 mg, 2.47 mmol). The solution was stirred at room temperature for 3 h, then (3aR,6aS)-tert-butyl hexahydropyrrolo[3,4-c]pyrrole-2(1H)-carboxylate (CAS-RN 250275-15-1; 526 mg, 2.35 mmol) was added, then after 15 h the reaction mixture was partitioned between 1 M aq. hydrochloric acid solution and dichloromethane. The organic layer was washed with brine, dried over magnesium sulfate, filtered and evaporated to afford the title compound (972 mg, 99%). Light brown viscous oil, MS: 359.2 (M+H-isobutene)$^+$.

Step 2: (3aR,6aS)-3,5-Dichlorobenzyl hexahydropyrrolo[3,4-c]pyrrole-2(1H)-carboxylate hydrochloride To a solution of (3aR,6aS)-2-tert-butyl 5-(3,5-dichlorobenzyl) tetrahydropyrrolo[3,4-c]pyrrole-2,5(1H,3H)-dicarboxylate (962 mg, 2.32 mmol) in 2-propanol (4 mL) was added hydrochloric acid (5-6 M in 2-propanol) (11.6 mL, 57.9 mmol), then after 3 h the reaction mixture was evaporated. The residue was taken up in ethyl acetate and a few drops of ethanol, then the precipitate was collected by filtration to produce the title compound (738 mg, 91%). White solid, MS: 315.3 (M+H)$^+$.

The following intermediates were prepared according to intermediate 1, replacing (3aR,6aS)-tert-butyl hexahydropyrrolo[3,4-c]pyrrole-2(1H)-carboxylate and (3,5-dichlorophenyl)methanol by the appropriate amine and alcohol, respectively.

µmol) in N,N-dimethylformamide (1 mL) were added 4-methylmorpholine (84.9 mg, 840 µmol), 1H-benzo[d][1,2,3]triazole-5-carboxylic acid (36.0 mg, 220 µmol) and O-(7-azabenzotriazol-1-yl)-N,N,N',N'-tetramethyluronium hexafluoro-phosphate (120 mg, 315 µmol) at room temperature, then after 16 h the reaction mixture was partitioned between ethyl acetate and sat. aq. ammonium chloride solution. The organic layer was washed with brine, dried over magnesium sulfate, filtered, and evaporated. Chromatography (silica gel; gradient dichloromethane to dichloromethane/methanol/25% aq. ammonia solution 90:10:0.25) produced the title compound (52 mg, 67%). Light yellow gum, MS: 370.5 (M–H)$^-$.

| No. | Systematic Name | Amine | Alcohol | MS, m/e |
|---|---|---|---|---|
| 1.1 | (3aS,7aS)-3,5-dichlorobenzyl hexahydro-1H-pyrrolo[3,4-c]pyridine-5(6H)-carboxylate hydrochloride | trans-tert-butyl hexahydro-1H-pyrrolo[3,4-c]pyridine-2(3H)-carboxylate (CAS-RN 1251014-37-5) | (3,5-dichlorophenyl)methanol | 329.4 (M + H)$^+$ |
| 1.2 | cis-3,5-dichlorobenzyl hexahydro-1H-pyrrolo[3,4-c]pyridine-5(6H)-carboxylate hydrochloride | cis-tert-butyl hexahydro-1H-pyrrolo[3,4-c]pyridine-2(3H)-carboxylate (intermediate 14) | (3,5-dichlorophenyl)methanol | 329.4 (M + H)$^+$ |
| 1.3 | (3aR,8aS)-3,5-dichlorobenzyl octahydropyrrolo[3,4-d]azepine-6(7H)-carboxylate hydrochloride | cis-octahydro-pyrrolo[3,4-d]azepine-2-carboxylic acid tert-butyl ester (CAS-RN 1251013-07-6) | (3,5-dichlorophenyl)methanol | 343.4 (M + H)$^+$ |
| 1.4 | trans-octahydro-pyrrolo[3,4-c]pyridine-5-carboxylic acid 4-trifluoromethoxy-benzyl ester hydrochloride | trans-tert-butyl hexahydro-1H-pyrrolo[3,4-c]pyridine-2(3H)-carboxylate (CAS-RN 1251014-37-5) | (4-(trifluoromethoxy)phenyl)methanol | 345.6 (M + H)$^+$ |
| 1.5 | trans-octahydro-pyrrolo[3,4-c]pyridine-5-carboxylic acid 3-chloro-5-methanesulfonyl-benzyl ester hydrochloride | trans-tert-butyl hexahydro-1H-pyrrolo[3,4-c]pyridine-2(3H)-carboxylate (CAS-RN 1251014-37-5) | (3-chloro-5-(methylsulfonyl)phenyl)methanol (intermediate 17) | 373.6 (M + H)$^+$ |
| 1.6 | (3aR,8aS)-4-(2,2,2-trifluoroethoxy)benzyl octahydropyrrolo[3,4-d]azepine-6(7H)-carboxylate hydrochloride | cis-octahydro-pyrrolo[3,4-d]azepine-2-carboxylic acid tert-butyl ester (CAS-RN 1251013-07-6) | (4-(2,2,2-trifluoroethoxy)-phenyl)methanol (CAS-RN 1020949-12-5) | n.a. |
| 1.7 | (3aR,8aS)-2-fluoro-4-(2,2,2-trifluoroethoxy)benzyl octahydropyrrolo[3,4-d]azepine-6(7H)-carboxylate hydrochloride | cis-octahydro-pyrrolo[3,4-d]azepine-2-carboxylic acid tert-butyl ester (CAS-RN 1251013-07-6) | (2-fluoro-4-(2,2,2-trifluoroethoxy)-phenyl)methanol (intermediate 38) | n.a. |
| 1.8 | (3aS,6aS)-4-(trifluoromethoxy)benzyl hexahydropyrrolo[3,4-c]pyrrole-2(1H)-carboxylate hydrochloride | (3aR,6aR)-tert-butyl hexahydropyrrolo[3,4-c]pyrrole-2(1H)-carboxylate (intermediate 15.1) | (4-(trifluoromethoxy)phenyl)methanol | 331.5 (M + H)$^+$ |

Intermediate 2

(1H-Benzotriazol-5-yl)-cis-octahydro-pyrrolo[3,4-c]pyridin-5-yl-methanone hydrochloride Step 1: cis-tert-Butyl 5-(1H-benzo[d][1,2,3]triazole-5-carbonyl)hexahydro-1H-pyrrolo[3,4-c]pyridine-2 (3H)-carboxylate To a solution of cis-tert-butyl hexahydro-1H-pyrrolo[3,4-c]pyridine-2(3H)-carboxylate (intermediate 14; 50 mg, 210

Step 2: (1H-Benzotriazol-5-yl)-cis-octahydro-pyrrolo[3,4-c]pyridin-5-yl-methanone; hydrochloride The title compound was produced in analogy to intermediate 1, step 2 from (3aS,7aS)-tert-butyl 5-(1H-benzo[d][1,2,3]triazole-5-carbonyl)hexahydro-1H-pyrrolo[3,4-c]pyridine-2(3H)-carboxylate. White solid, MS: 272.5 (M+H)$^+$.

The following intermediates were prepared according to intermediate 2, replacing (3aR,6aS)-tert-butyl hexahydropyrrolo[3,4-c]pyrrole-2(1H)-carboxylate and 1H-benzo[d][1,2,3]triazole-5-carboxylic acid by the appropriate amine and carboxylic acid, respectively.

| No. | Systematic Name | Amine | Carboxylic acid | MS, m/e |
|---|---|---|---|---|
| 2.1 | (1H-benzotriazol-5-yl)-trans-octahydro-pyrrolo[3,4-c]pyridin-5-yl-methanone; hydrochloride | trans-tert-butyl hexahydro-1H-pyrrolo[3,4-c]pyridine-2(3H)-carboxylate (CAS-RN 1251014-37-5) | 1H-benzo[d]-[1,2,3]triazole-5-carboxylic acid | 272.5 (M + H)$^+$ |
| 2.2 | (1H-benzo[d]-[1,2,3]triazol-5-yl)(trans-hexahydropyrrolo[3,4-c]pyrrol-2(1H)-yl)methanone hydrochloride | (3aR,6aS)-tert-butyl hexahydropyrrolo[3,4-c]pyrrole-2(1H)-carboxylate (CAS-RN 250275-15-1) | 1H-benzo[d]-[1,2,3]triazole-5-carboxylic acid | 258.5 (M + H)$^+$ |
| 2.3 | (1H-benzo[d]-[1,2,3]triazol-5-yl)-((3aR,8aS)-octahydro-pyrrolo[3,4-d]azepin-6(7H)-yl)methanone hydrochloride | cis-octahydro-pyrrolo[3,4-d]azepine-2-carboxylic acid tert-butyl ester (CAS-RN 1251013-07-6) | 1H-benzo[d]-[1,2,3]triazole-5-carboxylic acid | 286.5 (M + H)$^+$ |
| 2.4 | (1H-benzo[d]-[1,2,3]triazol-5-yl)((3aR,6aR)-hexahydro-pyrrolo[3,4-c]pyrrol-2(1H)-yl)methanone dihydrochloride | (3aS,6aS)-tert-butyl hexahydropyrrolo[3,4-c]pyrrole-2(1H)-carboxylate (intermediate 15) | 1H-benzo[d]-[1,2,3]triazole-5-carboxylic acid | 258.5 (M + H)$^+$ |
| 2.5 | ((3aR,6aR)-hexahydro-pyrrolo[3,4-c]pyrrol-2(1H)-yl)((R)-4,5,6,7-tetrahydro-1H-benzo[d]-[1,2,3]triazol-5-yl)-methanone hydrochloride | (3aS,6aS)-tert-butyl hexahydropyrrolo[3,4-c]pyrrole-2(1H)-carboxylate (intermediate 15) | (+)-(R)-4,5,6,7-tetrahydro-1H-benzo[d]-[1,2,3]triazole-5-carboxylic acid (intermediate 30A) | 262.6 (M + H)$^+$ |
| 2.6 | (1H-[1,2,3]triazolo[4,5-b]pyridin-5-yl)((3aR,6aR)-hexahydropyrrolo[3,4-c]pyrrol-2(1H)-yl)methanone hydrochloride | (3aS,6aS)-tert-butyl hexahydropyrrolo[3,4-c]pyrrole-2(1H)-carboxylate (intermediate 15) | 1H-[1,2,3]triazolo[4,5-b]pyridine-5-carboxylic acid (CAS-RN 1216149-55-1) | 257.5 (M − H)$^−$ |

Intermediate 3

3-(3,5-Dichlorophenyl)-1-((3aR,6aS)-hexahydropyrrolo[3,4-c]pyrrol-2(1H)-yl)propan-1-one hydrochloride Step 1: (3aR,6aS)-tert-Butyl 5-(3-(3,5-dichlorophenyl)propanoyl)hexahydropyrrolo[3,4-c]pyrrole-2(1H)-carboxylate To a solution of 3-(3,5-dichlorophenyl)propanoic acid (103 mg, 470 µmol), (3aR,6aS)-tert-butyl hexahydropyrrolo[3,4-c]pyrrole-2(1H)-carboxylate (CAS-RN 250275-15-1; 100 mg, 471 µmol) and 4-methylmorpholine (238 mg, 2.35 mmol) in N,N-dimethylformamide (1 mL) was added O-(7-azabenzotriazol-1-yl)-N,N,N',N'-tetramethyluronium hexafluoro-phosphate (268 mg, 705 mol) at room temperature, then after 16 h the reaction mixture was partitioned between ethyl acetate and sat. aq. sodium hydrogencarbonate solution. The organic layer was washed with brine, dried over magnesium sulfate, filtered, and evaporated. Chromatography (silica gel; heptane-ethyl acetate gradient) afforded the title compound (161 mg, 83%). Colourless oil, MS: 357.1 (M-isobutene+H)$^+$.

Step 2: 3-(3,5-Dichlorophenyl)-1-((3aR,6aS)-hexahydropyrrolo[3,4-c]pyrrol-2(1H)-yl)propan-1-one hydrochloride The title compound was produced in analogy to intermediate 1, step 2 from (3aR,6aS)-tert-butyl 5-(3-(3,5-dichlorophenyl)propanoyl)hexahydropyrrolo[3,4-c]pyrrole-2(1H)-carboxylate. White solid, MS: 313.1 (M+H)$^+$.

Intermediate 4

(3aR,5s,6aS)—N-((1H-1,2,3-Triazol-4-yl)methyl)octahydrocyclopenta[c]pyrrole-5-carboxamide 2,2,2-trifluoroacetate Step 1: (3aR,5s,6aS)-tert-butyl 5-((1H-1,2,3-triazol-4-yl)methylcarbamoyl)hexahydro-cyclopenta[c]pyrrole-2(1H)-carboxylate To a solution of (3aR,5s,6aS)-2-(tert-butoxycarbonyl)octahydrocyclopenta[c]pyrrole-5-carboxylic acid (WuXi AppTec (Wuhan) Co., Ltd.; catalogue No. WX110047; 100 mg, 392 mol) and (1H-1,2,3-triazol-4-yl)methanamine hydrochloride (52.7 mg, 392 µmol) in dichloromethane (2 mL) were added at 0° C. diisopropylethylamine (127 mg, 979 µmol) and benzotriazol-1-yl-oxy-tris-(dimethylamino)-phosphonium hexafluorophosphate (182 mg, 411 mol), then after 15 h at room temperature the reaction mixture was evaporated and the residue partitioned between ethyl acetate and water. The organic layer was dried over magnesium sulfate, filtered, and evaporated. Chromatography (silica gel, ethyl acetate-methanol gradient) produced the title compound (100 mg, 75%). White foam, MS: 334.5 (M−H)⁻.

Step 2: (3aR,5s,6aS)—N-((1H-1,2,3-Triazol-4-yl)methyl)octahydrocyclopenta[c]pyrrole-5-carboxamide 2,2,2-trifluoroacetate Trifluoroacetic acid (340 mg, 2.98 mmol) was added at room temperature to a solution of (3aR,5s,6aS)-tert-butyl 5-((1H-1,2,3-triazol-4-yl)methylcarbamoyl)hexahydrocyclopenta[c]pyrrole-2(1H)-carboxylate (100 mg, 298 μmol) in dichloromethane, then after 4 h the reaction mixture was evaporated to produce the title compound, which was used directly in the next step. Light yellow oil, MS: 236.5 (M+H)⁺.

Intermediate 5

(E)-1-((3aR,8aS)-Octahydropyrrolo[3,4-d]azepin-6(7H)-yl)-3-(4-(trifluoromethoxy)-phenyl)prop-2-en-1-one hydrochloride Step 1: (3aR,8aS)-tert-Butyl 6-((E)-3-(4-(trifluoromethoxy)phenyl)acryloyl)octahydro-pyrrolo[3,4-d]azepine-2(1H)-carboxylate To a solution of (3aR,8aS)-tert-butyl octahydropyrrolo[3,4-d]azepine-2(1H)-carboxylate hydrochloride (CAS-RN 1251013-07-6; 1.50 g, 5.42 mmol), 4-methylmorpholine (2.19 g, 21.7 mmol) and (E)-3-(4-(trifluoromethoxy)phenyl)acrylic acid (1.26 g, 5.42 mmol) in N,N-dimethylformamide (30 mL) was added added O-(7-azabenzotriazol-1-yl)-N,N,N',N'-tetramethyluronium hexafluoro-phosphate (2.06 g, 5.42 mmol) at 0° C. After 60 min the ice bath was removed, then after 16 h the reaction mixture was partitioned between ethyl acetate and sat. aq. sodium hydrogencarbonate solution. The organic layer was washed with sat. aq. ammonium chloride solution, water, and brine, dried over magnesium sulfate, filtered, and evaporated. The residue was triturated in heptane/ethyl acetate 9:1 to produce the title compound (2.20 g, 89%). White solid, MS: 399.5 (M+H-isobutene)⁺.

Step 2: (E)-1-((3aR,8aS)-Octahydropyrrolo[3,4-d]azepin-6(7H)-yl)-3-(4-(trifluoromethoxy)-phenyl)prop-2-en-1-one hydrochloride The title compound was produced in analogy to intermediate 1, step 2 from (3aR,8aS)-tert-butyl 6-((E)-3-(4-(trifluoromethoxy)phenyl)acryloyl)octahydropyrrolo[3,4-d]azepine-2(1H)-carboxylate. White solid, MS: 355.5 (M+H)⁺.

The following intermediates were produced according to intermediate 5, replacing (3aR,8aS)-tert-butyl octahydropyrrolo[3,4-d]azepine-2(1H)-carboxylate hydrochloride and (E)-3-(4-(trifluoromethoxy)phenyl)acrylic acid by the appropriate amine and carboxylic acid precursors, respectively.

| No. | Systematic Name | Amine | Carboxylic acid | MS |
| --- | --- | --- | --- | --- |
| 5.1 | 4-((E)-3-((3aR,8aS)-octahydropyrrolo[3,4-d]azepin-6(7H)-yl)-3-oxoprop-1-enyl)benzonitrile hydrochloride | (3aR,8aS)-tert-butyl octahydropyrrolo[3,4-d]azepine-2(1H)-carboxylate hydrochloride (CAS-RN 1251013-07-6) | (E)-3-(4-cyanophenyl)-acrylic acid | 296.5 (M + H)⁺ |
| 5.2 | 2-(4-chloro-2-isopropyl-5-methylphenoxy)-1-((3aR,6aS)-hexahydro-pyrrolo[3,4-c]pyrrol-2(1H)-yl)ethanone hydrochloride | (3aR,6aS)-tert-butyl hexahydropyrrolo[3,4-c]pyrrole-2(1H)-carboxylate (CAS-RN 250275-15-1) | 2-[4-chloro-5-methyl-2-(1-methylethyl)-phenoxy]-acetic acid (CAS-RN 5411-11-0) | 337.6 (M + H)⁺ |
| 5.3 | (E)-1-(trans-octahydro-pyrrolo[3,4-c]pyridin-5-yl)-3-(4-(trifluoromethoxy)-phenyl)prop-2-en-1-one hydrochloride | trans-tert-butyl hexahydro-1H-pyrrolo[3,4-c]pyridine-2(3H)-carboxylate (CAS-RN 1251014-37-5) | (E)-3-(4-(trifluoro-methoxy)-phenyl)acrylic acid | 341.6 (M + H)⁺ |
| 5.4 | 1-(trans-octahydro-pyrrolo[3,4-c]pyridin-5-yl)-2-(4-(trifluoromethoxy)-phenoxy)ethanone hydrochloride | trans-tert-butyl hexahydro-1H-pyrrolo[3,4-c]pyridine-2(3H)-carboxylate (CAS-RN 1251014-37-5) | 2-(4-(trifluoro-methoxy)-phenoxy)acetic acid | 345.6 (M + H)⁺ |
| 5.5 | 1-((3aS,6aS)-hexahydropyrrolo[3,4-c]pyrrol-2(1H)-yl)-3-(4-(trifluoromethoxy)-phenyl)propan-1-one dihydrochloride | (3aR,6aR)-tert-butyl hexahydropyrrolo[3,4-c]pyrrole-2(1H)-carboxylate (intermediate 15.1) | 3-(4-(trifluoro-methoxy)-phenyl)propanoic acid | 329.5 (M + H)+ |
| 5.6 | (4-ethoxyquinolin-2-yl)((3aS,6aS)-hexahydropyrrolo[3,4-c]pyrrol-2(1H)-yl)methanone hydrochloride | (3aR,6aR)-tert-butyl hexahydropyrrolo[3,4-c]pyrrole-2(1H)-carboxylate (intermediate 15.1) | 4-ethoxy-quinoline-2-carboxylic acid (CAS-RN 40609-78-7) | 329.5 (M + H)+ |

Intermediate 6 cis-3,5-Dichlorobenzyl 2-(1H-benzo[d][1,2,3]triazole-5-carbonyl)hexahydro-1H-pyrrolo[3,4-c]pyridine-5(6H)-carboxylate A solution of cis-3,5-dichlorobenzyl 2-(1H-benzo[d][1,2,3]triazole-5-carbonyl)hexahydro-1H-pyrrolo[3,4-c]pyridine-5(6H)-carboxylate (example 1.02; 100 mg, 211 µmol) in methanol (3 mL) was stirred for 20 h at 100° C. under a hydrogen atmosphere (10 bar) in the presence of palladium (10% on carbon, 10 mg), then insoluble material was removed by filtration through diatomaceous earth and the filtrate was evaporated to produce the title compound (62 mg), which was used directly in the next step. Light yellow foam, MS: 272.5 (M+H)$^+$.

The following intermediates were prepared according to intermediate 6, replacing cis-3,5-dichlorobenzyl 2-(1H-benzo[d][1,2,3]triazole-5-carbonyl)hexahydro-1H-pyrrolo[3,4-c]pyridine-5(6H)-carboxylate by the appropriate starting material.

| No. | Systematic Name | Starting material | MS, m/e |
|---|---|---|---|
| 6.1 | (1H-benzo[d][1,2,3]triazol-5-yl)((3aR,8aS)-octahydropyrrolo[3,4-d]azepin-2(1H)-yl)methanone | (3aR,8aS)-3,5-dichlorobenzyl 2-(1H-benzo[d][1,2,3]triazole-5-carbonyl)octahydropyrrolo[3,4-d]azepine-6(7H)-carboxylate (example 1.04) | 286.5 (M + H)$^+$ |
| 6.2 | (6,7-dihydro-1H-[1,2,3]triazolo[4,5-c]pyridin-5(4H)-yl)((3aR,6aS)-hexahydropyrrolo[3,4-c]pyrrol-2(1H)-yl)methanone | (3aR,6aS)-3,5-dichlorobenzyl 5-(4,5,6,7-tetrahydro-1H-[1,2,3]triazolo[4,5-c]pyridine-5-carbonyl)hexahydropyrrolo[3,4-c]pyrrole-2(1H)-carboxylate (example 8) | 263.5 (M + H)$^+$ |
| 6.3 | ((3aR,6aS)-hexahydropyrrolo[3,4-c]pyrrol-2(1H)-yl)(4,5,6,7-tetrahydro-1H-benzo[d][1,2,3]triazol-5-yl)methanone | (3aR,6aS)-3,5-dichlorobenzyl 5-(4,5,6,7-tetrahydro-1H-benzo[d][1,2,3]triazole-5-carbonyl)hexahydropyrrolo[3,4-c]pyrrole-2(1H)-carboxylate (example 1.01) | 262.4 (M + H)$^+$ |

Intermediate 7A

(1H-Benzotriazol-5-yl)-trans-octahydro-pyrrolo[3,4-c]pyridin-5-yl-methanone hydrochloride, enantiomer A

Step 1: trans-tert-Butyl 5-(1H-benzo[d][1,2,3]triazole-5-carbonyl)hexahydro-1H-pyrrolo[3,4-c]pyridine-2(3H)-carboxylate The title compound was produced in analogy to intermediate 2, step 1 from trans-tert-butyl hexahydro-1H-pyrrolo[3,4-c]pyridine-2(3H)-carboxylate (CAS-RN 1251014-37-5) and 1H-benzo[d][1,2,3]triazole-5-carboxylic acid. Light yellow foam, MS: 370.4 (M–H)$^-$.

Step 2: (–)-trans-tert-Butyl 5-(1H-benzo[d][1,2,3]triazole-5-carbonyl)hexahydro-1H-pyrrolo[3,4-c]pyridine-2(3H)-carboxylate and (+)-trans-tert-butyl 5-(1H-benzo[d][1,2,3]triazole-5-carbonyl)hexahydro-1H-pyrrolo[3,4-c]pyridine-2(3H)-carboxylate HPLC separation of racemic trans-tert-butyl 5-(1H-benzo[d][1,2,3]triazole-5-carbonyl)hexahydro-1H-pyrrolo[3,4-c]pyridine-2(3H)-carboxylate (668 mg, 1.80 mmol) using a Reprosil Chiral-NR column as the stationary phase and heptane/ethanol 3:2 as the eluent produced the faster eluting (–)-enantiomer (251 mg, 37%; colourless gum, MS: 370.6 (M–H)$^-$), followed by the slower eluting (+)-enantiomer (212 mg, 32%; colourless gum, MS: 370.6 (M–H)$^-$).

Step 3: (1H-Benzotriazol-5-yl)-trans-octahydro-pyrrolo[3,4-c]pyridin-5-yl-methanone hydrochloride enantiomer A The title compound was produced in analogy to intermediate 1, step 2 from (–)-trans-tert-butyl 5-(1H-benzo[d][1,2,3]triazole-5-carbonyl)hexahydro-1H-pyrrolo[3,4-c]pyridine-2(3H)-carboxylate. White solid, MS: 272.5 (M+H)$^+$.

Intermediate 7B

(1H-Benzotriazol-5-yl)-trans-octahydro-pyrrolo[3,4-c]pyridin-5-yl-methanone hydrochloride, enantiomer B The following intermediate was prepared according to intermediate 7A, step 3 from (+)-trans-tert-butyl 5-(1H-benzo[d][1,2,3]triazole-5-carbonyl)hexahydro-1H-pyrrolo[3,4-c]pyridine-2(3H)-carboxylate (intermediate 7A, step 2). White solid, MS: 272.5 (M+H)$^+$.

Intermediate 8

(1H-Benzo[d][1,2,3]triazol-5-yl)((3aS,6aS)-hexahydropyrrolo[3,4-c]pyrrol-2(1H)-yl)methanone dihydrochloride

Step 1: trans-tert-Butyl 5-(1H-benzo[d][1,2,3]triazole-5-carbonyl)hexahydropyrrolo[3,4-c]pyrrole-2(1H)-carboxylate The title compound was produced in analogy to intermediate 2, step 1 from trans-tert-butyl hexahydropyrrolo[3,4-c]pyrrole-2(1H)-carboxylate (intermediate 16) and 1H-benzo[d][1,2,3]triazole-5-carboxylic acid. Light yellow foam, MS: 358.5 (M+H)$^+$.

Step 2: (+)-(3aR,6aR)-tert-Butyl 5-(1H-benzo[d][1,2,3]triazole-5-carbonyl)hexahydropyrrolo[3,4-c]pyrrole-2(1H)-carboxylate and (–)-(3aS,6aS)-tert-butyl 5-(1H-benzo[d][1,2,3]triazole-5-carbonyl)hexahydropyrrolo[3,4-c]pyrrole-2(1H)-carboxylate HPLC separation of racemic trans-tert-butyl 5-(1H-benzo[d][1,2,3]triazole-5-carbonyl)hexahydropyrrolo[3,4-c]pyrrole-2(1H)-carboxylate (790 mg, 2.21 mmol) using a Chiralpak AD column as the stationary phase and heptane/ethanol 7:3 as the eluent produced the faster eluting (+)-(R,R)-enantiomer (350 mg, 44%; light yellow foam, MS: 358.5 (M+H)$^+$; e. r. 100:0), followed by the slower eluting (−)-(S,S)-enantiomer (388 mg, 49%; light yellow foam, MS: 358.5 (M+H)$^+$; e. r. 4:96).

Step 3: (1H-Benzo[d][1,2,3]triazol-5-yl)((3aS,6aS)-hexahydropyrrolo[3,4-c]pyrrol-2(1H)-yl)methanone dihydrochloride The title compound was produced in analogy to intermediate 1, step 2 from (3aR,6aR)-tert-butyl 5-(1H-benzo[d][1,2,3]triazole-5-carbonyl)hexahydropyrrolo[3,4-c]pyrrole-2(1H)-carboxylate. White solid, MS: 258.5 (M+H)$^+$.

Intermediate 9

(3aR,6aS)-3,5-Dichlorobenzyl 5-(chlorocarbonyl)hexahydropyrrolo[3,4-c]pyrrole-2(1H)-carboxylate To a colourless solution of (3aR,6aS)-3,5-dichlorobenzyl hexahydropyrrolo[3,4-c]pyrrole-2(1H)-carboxylate hydrochloride (intermediate 1; 152 mg, 432 µmol) and pyridine (106 mg, 1.34 mmol) in dichloromethane (2 mL) was added dropwise a solution of triphosgene (57.7 mg, 195 µmol) in dichloromethane (2 mL) at 0° C., then after 30 min the ice bath was removed. After 16 h the reaction mixture was partitioned between 1 M aq. hydrochloric acid solution and dichloromethane. The organic layer was washed with water and brine, dried over magnesium sulfate, filtered and evaporated to afford the title compound (172 mg), which was used directly in the next step. Colourless oil, MS: 401.3 (M+Na)$^+$.

The following intermediates were prepared according to intermediate 9, replacing (3aR,6aS)-3,5-dichlorobenzyl hexahydropyrrolo[3,4-c]pyrrole-2(1H)-carboxylate hydrochloride by the appropriate starting material.

| No. | Systematic Name | Starting material | MS, m/e |
|---|---|---|---|
| 9.1 | (3aR,8aS)-6-((E)-3-(4-(trifluoromethoxy)phenyl)acryloyl)octahydropyrrolo[3,4-d]azepine-2(1H)-carbonyl chloride | (E)-1-((3aR,8aS)-octahydropyrrolo[3,4-d]azepin-6(7H)-yl)-3-(4-(trifluoromethoxy)phenyl)prop-2-en-1-one hydrochloride (intermediate 5) | 416 (M)$^+$ |
| 9.2 | (3aR,6aR)-tert-butyl 5-(chlorocarbonyl)hexahydropyrrolo[3,4-c]pyrrole-2(1H)-carboxylate | (3aS,6aS)-tert-butyl hexahydropyrrolo[3,4-c]pyrrole-2(1H)-carboxylate (intermediate 15) | 274 (M)$^+$ |
| 9.3 | 4-(4-chlorophenyl)piperidine-1-carbonyl chloride | 4-(4-chlorophenyl)piperidine hydrochloride | 257.0 (M)$^+$ | methanol was removed under reduced pressure. The reaction mixture was partitioned between ethyl acetate and brine. The organic layer was dried over magnesium sulfate, filtered and evaporated to produce the title compound (4.38 g, 100%). Off-white solid, MS: 228.3 (M+H)$^+$.

Step 2: (3aR,5r,6aS)-Octahydrocyclopenta[c]pyrrol-5-ol hydrochloride (3aR,5r,6aS)-tert-butyl 5-hydroxyhexahydrocyclopenta[c]pyrrole-2(1H)-carboxylate (4.37 g, 19.0 mmol) was combined with hydrochloric acid solution (5-6 M in 2-propanol) (49 mL, 245 mmol), then after 2 h the reaction mixture was evaporated and the residue was triturated in ethyl acetate to afford the title compound as an off-white solid (2.84 g, 91%).

Step 3: (3aR,5r,6aS)-3,5-Dichlorobenzyl 5-hydroxyhexahydrocyclopenta[c]pyrrole-2(1H)-carboxylate To a solution of (3,5-dichlorophenyl)methanol (541 mg, 3.06 mmol) in dichloromethane (10 mL) was added 1,1'-carbonyldiimidazole (520 mg, 3.21 mmol) at room temperature. Then after 3 h (3aR,5r,6aS)-octahydrocyclopenta[c]pyrrol-5-ol hydrochloride (500 mg, 3.06 mmol) and triethylamine (309 mg, 3.06 mmol) were added, then after 18 h the reaction mixture was partitioned between dichloromethane and water. The organic layer was washed with brine, dried over magnesium sulfate, filtered and evaporated. Chromatography (silica gel; heptane-ethyl acetate gradient) produced the title compound (847 mg, 84%). Colourless oil, MS: 330.1 (M+H)$^+$.

Intermediate 10

(3aR,5r,6aS)-3,5-Dichlorobenzyl 5-hydroxyhexahydrocyclopenta[c]pyrrole-2(1H)-carboxylate Step 1: (3aR,5r,6aS)-tert-Butyl 5-hydroxyhexahydrocyclopenta[c]pyrrole-2(1H)-carboxylate To a solution of (3aR,6aS)-tert-butyl 5-oxohexahydrocyclopenta[c]pyrrole-2(1H)-carboxylate (CAS-RN 146231-54-1; 4.3 g, 19.1 mmol) in methanol (100 mL) was added sodium borohydride (1.44 g, 38.2 mmol) at 0° C., then after 1 h the reaction mixture was treated with ice water and the Intermediate 11

(3aR,5s,6aS)-3,5-Dichlorobenzyl 5-hydroxyhexahydrocyclopenta[c]pyrrole-2(1H)-carboxylate Step 1: (3aR,5s,6aS)-3,5-Dichlorobenzyl 5-(4-nitrobenzoyloxy)hexahydrocyclopenta[c]pyrrole-2(1H)-carboxylate Diethyl azodicarboxylate solution (40% in toluene; 168 µL, 424 µmol) was added at room temperature to a solution of (3aR,5r,6aS)-3,5-dichlorobenzyl 5-hydroxyhexahydrocyclopenta[c]pyrrole-2(1H)-carboxylate (intermediate 10; 140 mg, 424 µmol), 4-nitrobenzoic acid (85.0 mg, 509 µmol), and triphenylphosphine (111 mg, 424 µmol) in toluene (10 mL), then after 16 h another portion of triphenylphosphine (33.4 mg, 127 µmol) and diethyl azodicarboxylate solution (40% in toluene; 50 µL, 127 µmol) was added. The reaction mixture was stirred for another 5 h at room temperature, evaporated and the residue was purified by chromatography (silica gel; heptane-ethyl acetate gradient) to produce the title compound (167 mg, 82%). Colourless oil, MS 479.0 (M+H)$^+$.

Step 2: (3aR,5s,6aS)-3,5-Dichlorobenzyl 5-hydroxyhexahydrocyclopenta[c]pyrrole-2(1H)-carboxylate A mixture of (3aR,5s,6aS)-3,5-dichlorobenzyl 5-(4-nitrobenzoyloxy)hexahydrocyclopenta[c]pyrrole-2(1H)-carboxylate (163 mg, 340 µmol) and 2 M aq. sodium hydroxide solution (1 mL, 2 mmol) in tetrahydrofuran (2 mL) was stirred at room temperature for 6 h. After evaporation of volatile material the residue was partitioned between 1 M aq. hydrochloric acid solution and ethyl acetate. The organic layer was washed with brine, dried over magnesium sulfate, filtered and evaporated in vacuo to give the title compound (109 mg, 97%). Colourless oil, MS: 330.1 (M+H)$^+$.

Intermediate 12

4-((3aR,5r,6aS)-2-((3,5-Dichlorobenzyloxy)carbonyl)octahydrocyclopenta[c]pyrrol-5-yloxy)-2-hydroxybenzoic acid

Step 1: (3aR,5r,6aS)-3,5-Dichlorobenzyl 5-(3-hydroxy-4-(methoxycarbonyl)phenoxy)-hexahydrocyclopenta[c]pyrrole-2(1H)-carboxylate Diethyl azodicarboxylate solution (40% in toluene, 157 µL, 398 µmol) was added at room temperature to a solution of (3aR,5s,6aS)-3,5-dichlorobenzyl 5-hydroxyhexahydrocyclopenta[c]pyrrole-2(1H)-carboxylate (101 mg, 306 µmol), methyl 2,4-dihydroxybenzoate (68.9 mg, 398 µmol), and triphenylphosphine (104 mg, 398 µmol) in toluene (2 mL). Then after 18 h the reaction mixture was concentrated and the residue purified by chromatography (silica gel; heptane-ethyl acetate gradient) to produce the title compound (144 mg, 98%). Colourless gum, MS: 480.1 (M+H+).

Step 2: 4-((3aR,5r,6aS)-2-((3,5-Dichlorobenzyloxy)carbonyl)octahydrocyclopenta[c]pyrrol-5-yloxy)-2-hydroxybenzoic acid The title compound was produced in analogy to intermediate 11, step 2 from (3aR,5r,6aS)-3,5-dichlorobenzyl 5-(3-hydroxy-4-(methoxycarbonyl)phenoxy)hexahydrocyclopenta[c]pyrrole-2(1H)-carboxylate. Colourless gum, MS: 466.2 (M+H)$^+$.

Intermediate 12.1

4-((3aR,5s,6aS)-2-((3,5-Dichlorobenzyloxy)carbonyl)octahydrocyclopenta[c]pyrrol-5-yloxy)-2-hydroxybenzoic acid The title compound was produced in analogy to intermediate 12 from (3aR,5r,6aS)-3,5-dichlorobenzyl 5-hydroxyhexahydrocyclopenta[c]pyrrole-2(1H)-carboxylate (intermediate 10). Colourless gum, MS: 466.2 (M+H)$^+$.

Intermediate 13

(3aR,6aS)-3,5-Dichlorobenzyl 5-oxohexahydrocyclopenta[c]pyrrole-2(1H)-carboxylate To a stirred solution of (3aR,5r,6aS)-3,5-dichlorobenzyl 5-hydroxyhexahydrocyclopenta[c]pyrrole-2(1H)-carboxylate (intermediate 10; 144 mg, 436 µmol) in dichloromethane (3 mL) was added 1,1,1-triacetoxy-1,1-dihydro-1,2-benziodoxol-3(1H)-one solution (15% in dichloromethane; 1.48 g, 523 µmol) at 0° C. Then after 2.5 h solid sodium bicarbonate (256 mg, 3.05 mmol) was added and the reaction mixture was stirred for another 5 min and was then filtered through diatomaceous earth. The filtrate was evaporated and purified by chromatography (silica gel; heptane-ethyl acetate gradient) to produce the title compound (132 mg, 88%). Colourless oil, MS': 328.2 (M+H)$^+$.

Intermediate 14 cis-tert-Butyl hexahydro-1H-pyrrolo[3,4-c]pyridine-2(3H)-carboxylate

Step 1: cis-tert-Butyl 6-oxohexahydropyrano[3,4-c]pyrrole-2(1H)-carboxylate (3aR,6aS)-tert-Butyl 5-oxohexahydrocyclopenta[c]pyrrole-2(1H)-carboxylate (CAS-RN 146231-54-1; 5.00 g, 17.8 mmol) was dissolved in dry dichloromethane (250 mL) and then disodium hydrogen phosphate (63.0 g, 444 mmol) and 3-chloroperbenzoic acid (10.9 g, 44.4 mmol) were added. The suspension was stirred at room temperature for 72 h, then 2 M aq. sodium sulfite solution (200 mL) was added. After stirring for another 30 min, the organic layer was washed with sat. aq. sodium hydrogencarbonate solution, dried over magnesium sulfate, filtered, and evaporated to produce a mixture (4.66 g) containing the title compound (MS: 264.5 (M+Na)$^+$) as the main product, along with some unreacted starting material.

Step 2: cis-tert-Butyl 3-(2-hydroxyethyl)-4-(hydroxymethyl)pyrrolidine-1-carboxylate cis-tert-Butyl 6-oxohexahydropyrano[3,4-c]pyrrole-2 (1H)-carboxylate (crude mixture from step 1; 4.46 g) was dissolved in ethanol (300 mL), then freshly powdered anhydrous calcium chloride (3.69 g, 33.3 mmol) was added at once, then sodium borohydride (2.52 g, 66.5 mmol) was added portionwise at room temperature. After 1 h, the reaction was poured onto ice water (800 mL) and ethyl acetate (800 mL). The two phases were saturated with solid sodium chloride and stirred for 15 min, then the organic layer was separated, washed with brine, dried over magnesium sulfate, filtered, and evaporated. Chromatography (silica gel; heptane-ethyl acetate gradient) produced the title compound (2.57 g, ca. 60% yield over 2 steps). Colourless oil, MS: 268.5 (M+Na)$^+$.

Step 3: cis-tert-Butyl 3-(2-(methylsulfonyloxy)ethyl)-4-((methylsulfonyloxy)methyl)pyrrolidine-1-carboxylate A solution of methanesulfonyl chloride (3.60 g, 31.4 mmol) in dichloromethane (5 mL) was added at 0° C. to a solution of cis-tert-butyl 3-(2-hydroxyethyl)-4-(hydroxymethyl)pyrrolidine-1-carboxylate (2.57 g, 10.5 mmol) and N,N-diisopropylethylamine (8.12 g, 62.9 mmol) in dichloromethane (70 mL), then after 1 h the mixture was partitioned between ethyl acetate and sat. aq. ammonium chloride solution. The organic layer was washed with sat. aq. sodium hydrogencarbonate solution, dried over magnesium sulfate, filtered, and evaporated. Chromatography (silica gel, heptane-ethyl acetate gradient afforded the title compound (3.47 g, 83%). Light yellow oil, MS: 424.5 (M+Na)$^+$.

Step 4: cis-tert-Butyl 5-benzylhexahydro-1H-pyrrolo[3,4-c]pyridine-2(3H)-carboxylate To a solution of cis-tert-butyl 3-(2-(methylsulfonyloxy)ethyl)-4-((methylsulfonyloxy)-methyl)pyrrolidine-1-carboxylate (3.05 g, 7.60 mmol) in acetonitrile (100 mL) were added phenylmethanamine (2.44 g, 22.8 mmol) and potassium carbonate (5.25 g, 38.0 mmol). The reaction mixture was heated at 95° C. for 22 h and was then partitioned between ethyl acetate and water. The organic layer was washed with sat. aq. ammonium chloride solution and brine, dried over magnesium sulfate, filtered, and evaporated. Chromatography (silica gel, gradient dichloromethane to dichloromethane/methanol/25% aq. ammonia solution 95:5:0.25) produced the title compound (1.63 g, 64%). Light yellow oil, MS: 317.6 (M+H)$^+$.

Step 5: cis-tert-Butyl hexahydro-1H-pyrrolo[3,4-c]pyridine-2(3H)-carboxylate

To a solution of cis-tert-butyl 5-benzylhexahydro-1H-pyrrolo[3,4-c]pyridine-2(3H)-carboxylate (1.63 g, 4.89 mmol) in methanol (33 mL) was added palladium (10% on carbon; 260 mg, 245 mol), and the reaction mixture was stirred under a hydrogen atmosphere (1 bar) at room temperature for 24 h, then insoluble material was removed by filtration through diatomaceous earth. The filtrate was concentrated and the residue was chromatographed (silica gel, gradient dichloromethane to dichloromethane/methanol/25% aq. ammonia solution 95:5:0.25) to produce the title compound (895 mg, 81%). Light yellow oil, MS: 227.5 (M+H)$^+$.

Intermediate 15

(3aS,6aS)-tert-Butyl hexahydropyrrolo[3,4-c]pyrrole-2(1H)-carboxylate

Step 1: (3R,4R)-tert-Butyl 3,4-bis((methyl sulfonyloxy)methyl)pyrrolidine-1-carboxylate The title compound was produced in analogy to intermediate 14, step 3 from (3R,4R)-3,4-bis-hydroxymethyl-pyrrolidine-1-carboxylic acid tert-butyl ester (CAS-RN 895245-32-6). Light yellow oil, MS: 332.4 (M-isobutene+H)$^+$.

Step 2: (3aS,6aS)-tert-Butyl 5-benzylhexahydropyrrolo[3,4-c]pyrrole-2(1H)-carboxylate The title compound was produced in analogy to intermediate 14, step 4 from (3R,4R)-tert-butyl 3,4-bis((methylsulfonyloxy)methyl)pyrrolidine-1-carboxylate. Light yellow solid, MS: 303.5 (M+H)$^+$.

Step 3: (3aS,6aS)-tert-Butyl hexahydropyrrolo[3,4-c]pyrrole-2(1H)-carboxylate

To a solution of (3aS,6aS)-tert-butyl 5-benzylhexahydropyrrolo[3,4-c]pyrrole-2(1H)-carboxylate (2.22 g, 7.34 mmol) in methanol (20 mL) was added palladium (10% on carbon, 220 mg, 7.34 mmol), and the reaction mixture was stirred under a hydrogen atmosphere (1 bar) at room temperature for 24 h, then insoluble material was removed by filtration through diatomaceous earth. The filtrate was concentrated to produce the title compound (1.60 g, 100%). White waxy solid, MS: 213.5 (M+H)$^+$.

Intermediate 15.1

(3aR,6aR)-tert-Butyl hexahydropyrrolo[3,4-c]pyrrole-2(1H)-carboxylate

The title compound was produced in analogy to intermediate 15, replacing (3R,4R)-3,4-bis-hydroxymethyl-pyrrolidine-1-carboxylic acid tert-butyl ester by (3S,4S)-3,4-bis-hydroxymethyl-pyrrolidine-1-carboxylic acid tert-butyl ester (CAS-RN 895245-30-4). White waxy solid, MS: 213.3 (M+H)$^+$.

Intermediate 16 trans-tert-Butyl hexahydropyrrolo[3,4-c]pyrrole-2(1H)-carboxylate

The title compound was produced in analogy to intermediate 15 from trans-3,4-bis(hydroxymethyl)pyrrolidine-1-carboxylic acid tert-butyl ester (CAS-RN 895245-31-5). White waxy solid, MS: 213.5 (M+H)$^+$.

Intermediate 17

(3-Chloro-5-(methylsulfonyl)phenyl)methanol

To a solution of 3-chloro-5-(methylsulfonyl)benzoic acid (CAS-RN 151104-63-1; 500 mg, 2.13 mmol) in tetrahydrofuran (5 mL) was added slowly borane-tetrahydrofuran complex solution (1 M solution in tetrahydrofuran, 5.33 mL, 5.33 mmol) at 0° C., then after 3 h the ice-bath was removed and the reaction mixture was stirred at room temperature overnight. The mixture was then carefully treated with methanol (3 mL) and evaporated. The residue was partitioned between ethyl acetate and water. The organic layer was washed with brine, dried over magnesium sulfate, filtered, and evaporated. Chromatography (silica gel; heptane-ethyl acetate gradient afforded the title compound (428 mg, 91%). White solid, MS: 221.3 (M+H)$^+$.

The following intermediate was produced according to intermediate 17, replacing 3-chloro-5-(methylsulfonyl)benzoic acid with the appropriate carboxylic acid

| No. | Systematic Name | Starting material | MS, m/e |
|---|---|---|---|
| 17.1 | (2-cyclopropyl-4-(trifluoromethyl)phenyl)methanol | 2-cyclopropyl-4-trifluoromethyl-benzoic acid (CAS-RN 1236303-04-0) | 216.0 (M)$^+$ |

Intermediate 18

2,2,2-Trifluoro-1-(3-(hydroxymethyl)phenyl)ethanol

Lithium borohydride solution (2 M in tetrahydrofuran, 1.15 mL, 2.31 mmol) was added dropwise at 0° C. to a solution of methyl 3-(2,2,2-trifluoro-1-hydroxyethyl)benzoate (CAS-RN 1188323-28-5; 180 mg, 769 μmol) in tetrahydrofuran (6 mL), then after 15 min the ice bath was removed and the reaction mixture was heated at reflux for 21 h. Then another portion of lithium borohydride solution (2 M in tetrahydrofuran, 0.77 mL, 1.54 mmol) was added and the reaction mixture was heated at reflux for another 5 h. After cooling, the reaction mixture was partitioned between 1 M aq. hydrochloric acid solution and ethyl acetate. The organic layer was washed with brine, dried over sodium sulfate, filtered, and evaporated. Chromatography (silica gel; heptane-ethyl acetate gradient afforded the title compound (86 mg, 53%). White solid, MS: 206.0 (M+).

Intermediate 19

(3-(2,2,2-Trifluoro-1-methoxyethyl)phenyl)methanol

Step 1: Methyl 3-(2,2,2-trifluoro-1-methoxyethyl)benzoate

Sodium hydride dispersion (60% in mineral oil, 93.2 mg, 2.33 mmol) was added at −5° C. to a solution of methyl 3-(2,2,2-trifluoro-1-hydroxyethyl)benzoate (303 mg, 1.29 mmol) in tetrahydrofuran (8 mL), then after 30 min iodomethane (643 mg, 4.53 mmol) was added dropwise over a period of 5 min. After 1 h, the ice bath was removed and the reaction mixture was stirred for another 90 min. The reaction mixture was then partitioned between ethyl acetate and water, the organic layer was washed with brine, dried over sodium sulfate, filtered, and evaporated to produce the title compound (purity ca. 90%; 263 mg, 74%). Light yellow liquid, MS: 248.0 (M+).

Step 2: (3-(2,2,2-Trifluoro-1-methoxyethyl)phenyl)methanol

The title compound was produced in analogy to intermediate 18 from methyl 3-(2,2,2-trifluoro-1-methoxyethyl)benzoate. Colourless liquid, MS: 220.0 (M+).

Intermediate 20

(3aR,6aS)—N-((1H-1,2,3-Triazol-4-yl)methyl)hexahydropyrrolo[3,4-c]pyrrole-2(1H)-carboxamide 2,2,2-trifluoroacetate

Step 1: (3aR,6aS)-tert-Butyl 5-((1H-1,2,3-triazol-4-yl)methylcarbamoyl)hexahydropyrrolo[3,4-c]pyrrole-2(1H)-carboxylate A solution of triphosgene (140 mg, 471 μmol) in ethyl acetate (12 mL) was added at 0° C. to a solution of (3aR,6aS)-tert-butyl hexahydropyrrolo[3,4-c]pyrrole-2(1H)-carboxylate (CAS-RN 250275-15-1; 200 mg, 942 μmol) in tetrahydrofuran (5 mL). The ice bath was removed, then after 30 min the reaction mixture was heated at reflux for 2 h and was then concentrated in vacuo. The residue was taken up in tetrahydrofuran (20 mL), then after the addition of triethylamine (286 mg, 2.83 mmol) and (1H-1,2,3-triazol-4-yl)methanamine hydrochloride (127 mg, 942 μmol) the reaction mixture was stirred at room temperature for 15 h. After partitioning between water and ethyl acetate, the organic layer was dried over sodium sulfate, filtered, and evaporated. Chromatography (silica gel; dichloromethane-methanol gradient) produced the title compound (110 mg, 34%). White foam, MS: MS: 337.5 (M+H)+.

Step 2: (3aR,6aS)—N-((1H-1,2,3-Triazol-4-yl)methyl)hexahydropyrrolo[3,4-c]pyrrole-2(1H)-carboxamide 2,2,2-trifluoroacetate The title compound was produced in analogy to intermediate 4, step 2 from (3aR,6aS)-tert-butyl 5-((1H-1,2,3-triazol-4-yl)methylcarbamoyl)hexahydropyrrolo[3,4-c]pyrrole-2(1H)-carboxylate. Light yellow oil, MS: 237.5 (M+H)+.

The following intermediate was produced according to intermediate 20, replacing (1H-1,2,3-triazol-4-yl)methanamine hydrochloride by the appropriate amine.

| No. | Systematic Name | Starting material | MS, m/e |
|---|---|---|---|
| 20.1 | (3aR,6aS)-N-((1H-1,2,3-triazol-5-yl)methyl)-N-methylhexahydropyrrolo[3,4-c]pyrrole-2(1H)-carboxamide 2,2,2-trifluoroacetate | N-methyl-1H-1,2,3-triazole-5-methanamine (CAS-RN 1248059-33-7) | 251.5 (M + H)+ |

Intermediate 21

(3aR,6aS)-2-(3-Chlorophenethylsulfonyl)octahydropyrrolo[3,4-c]pyrrole

Step 1: (3aR,6aS)-tert-Butyl 5-(3-chlorophenethylsulfonyl)hexahydropyrrolo[3,4-c]pyrrole-2(1H)-carboxylate To a solution of (3aR,6aS)-tert-butyl hexahydropyrrolo[3,4-c]pyrrole-2(1H)-carboxylate (CAS-RN 250275-15-1; 300 mg, 1.34 mmol) in N,N-dimethylformamide (5 mL) was added 2-(3-chlorophenyl)ethanesulfonyl chloride (321 mg, 1.34 mmol) triethylamine (291 mg, 2.87 mmol), and 4-(dimethylamino)pyridine, then after 16 h the reaction mixture was concentrated in vacuo. The residue was partitioned between sat. aq. sodium hydrogencarbonate solution and ethyl acetate. The organic layer was washed with brine, dried over magnesium sulfate, filtered, and evaporated to produce the title compound (520 mg, 93%), which was directly used in the next step.

Step 2: (3aR,6aS)-2-(3-Chlorophenethylsulfonyl)octahydropyrrolo[3,4-c]pyrrole To a solution of (3aR,6aS)-tert-butyl 5-(3-chlorophenethylsulfonyl)hexahydropyrrolo[3,4-c]pyrrole-2(1H)-carboxylate (520 mg, 1.25 mmol) in methanol (10 mL) was added hydrogen chloride solution (4 M in 1,4-dioxane, 6.3 mL), then after 1 h a few drops of 37% aq. hydrochloric acid solution were added, then after another 2 h the reaction mixture was concentrated to ⅓ of the volume. This was basified to pH 7 with 2 M aq. sodium hydroxide solution and was extracted with ethyl acetate. The organic layer was washed with brine and was dried over magnesium sulfate to produce the title compound (320 mg, 81%). Colourless oil, MS: 315.4 (M+H)$^+$.

Intermediate 22

3-Chloro-5-(methylsulfonyl)benzaldehyde

To a clear colourless solution of (3-chloro-5-(methylsulfonyl)phenyl)methanol (intermediate 17; 505 mg, 2.29 mmol) in dichloromethane (10 mL) was added 1,1,1-triacetoxy-1,1-dihydro-1,2-benziodoxol-3(1H)-one solution (15% in dichlomethane; 5.7 mL, 2.75 mmol) at 0° C., then after 1 h the reaction mixture was allowed to reach room temperature over 1 h. After partitioning between dichloromethane and 1 M aq. sodium thiosulfate solution, the organic layer was washed with water and brine, dried over magnesium sulfate, filtered, and evaporated. Chromatography (silica gel; dichloromethane) afforded the title compound (376 mg, 75%). White solid, MS: 218 (M$^+$).

The following intermediate was produced according to intermediate 20, replacing (1H-1,2,3-triazol-4-yl)methanamine hydrochloride by the appropriate amine.

| No. | Systematic Name | Starting material | MS, m/e |
|---|---|---|---|
| 22.1 | 4-formyl-3-isopropylbenzonitrile | 4-(hydroxymethyl)-3-isopropylbenzonitrile (intermediate 41) | 173 (M)$^+$ |
| 22.2 | 4-formyl-5-isopropyl-2-methylbenzonitrile | 4-(hydroxymethyl)-5-isopropyl-2-methylbenzonitrile (intermediate 41.1) | 187 (M)$^+$ |

Intermediate 23

(E)-3-(3-chloro-5-(methylsulfonyl)phenyl)acrylic acid

To a clear yellow solution of 3-chloro-5-(methylsulfonyl)benzaldehyde (intermediate 22; 370 mg, 1.69 mmol) and malonic acid (352 mg, 3.38 mmol) in pyridine (3 mL) was added piperidine (28.8 mg, 338 μmol) and the reaction mixture was heated at reflux for 2 h. After cooling, the reaction mixture was treated with 4 M aq. hydrochloric acid solution. The precipitate was collected by filtration, washed with water, and dried to afford the title compound (352 mg, 78%). White solid, MS: 259.5 (M−H)$^-$.

The following intermediates were prepared according to intermediate 23, replacing 3-chloro-5-(methylsulfonyl)benzaldehyde by the appropriate aldehyde.

| No. | Systematic Name | Aldehyde | MS, m/e |
|---|---|---|---|
| 23.01 | (E)-3-(3-chloro-5-methoxyphenyl)acrylic acid | 3-chloro-5-methoxybenzaldehyde (CAS-RN 164650-68-4) | 211.1 (M + H)$^+$ |
| 23.02 | (E)-3-(2-fluoro-4-(trifluoromethoxy)phenyl)acrylic acid | 2-fluoro-4-(trifluoromethoxy)benzaldehyde (CAS-RN 1227628-83-2) | 249.1 (M − H)$^-$ |
| 23.03 | (E)-3-(3-fluoro-4-(trifluoromethoxy)phenyl)acrylic acid | 3-fluoro-4-(trifluoromethoxy)benzaldehyde (CAS-RN 473917-15-6) | 249.5 (M − H)$^-$ |
| 23.04 | (E)-3-(4-fluoro-2-(trifluoromethyl)phenyl)acrylic acid | 4-fluoro-2-(trifluoromethyl)benzaldehyde | 224.3 (M − H)$^-$ |
| 23.05 | (E)-3-(6-phenylpyridin-3-yl)acrylic acid | 6-phenylnicotinaldehyde | 224.3 (M − H)$^-$ |
| 23.06 | (E)-3-(5-phenylpyridin-2-yl)acrylic acid | 5-phenylpicolinaldehyde | 224.3 (M − H)$^-$ |
| 23.07 | (E)-3-(4-(pyridin-4-yl)phenyl)acrylic acid | 4-(pyridin-4-yl)benzaldehyde | 224.3 (M − H)$^-$ |
| 23.08 | (E)-3-(4-(pyridin-3-yl)phenyl)acrylic acid | 4-(pyridin-3-yl)benzaldehyde | 224.3 (M − H)$^-$ |
| 23.09 | (E)-3-(4-(pyridin-2-yl)phenyl)acrylic acid | 4-(pyridin-2-yl)benzaldehyde | 224.3 (M − H)$^-$ |
| 23.10 | (E)-3-(2-cyclopropylphenyl)acrylic acid | 2-cyclopropylbenzaldehyde | 187.4 (M − H)$^-$ |
| 23.11 | (E)-3-(2-fluoro-4-(2,2,2-trifluoroethoxy)phenyl)acrylic acid | 2-fluoro-4-(2,2,2-trifluoroethoxy)benzaldehyde | 263.0 (M − H)$^-$ |

Intermediate 24

(E)-3-(3-Methoxy-5-(trifluoromethoxy)phenyl) acrylic acid

Step 1 (E)-tert-Butyl 3-(3-methoxy-5-(trifluoromethoxy)phenyl)acrylate

To a colourless solution of 1-bromo-3-methoxy-5-(trifluoromethoxy)benzene (CAS-RN 1330750-28-1; 1.00 g, 3.62 mmol) in N,N-dimethylformamide (10 mL) was added triethylamine (1.1 g, 10.8 mmol), tert-butyl acrylate (567 mg, 4.34 mmol), palladium(II) acetate (16.2 mg, 72.3 mol) and tri-o-tolylphosphine (88 mg, 289 µmol). The light yellow reaction mixture was evacuated and backfilled with argon, three times. The reaction mixture was heated at 120° C., then after 16 h partitioned between ethyl acetate and sat. aq. sodium hydrogencarbonate solution. The organic layer was washed with water, sat. aq. ammonium chloride solution, and brine, dried over magnesium sulfate, filtered, and evaporated. Chromatography (silica gel; heptane-ethyl acetate gradient) afforded the title compound (984 mg, 85%). Colourless oil, MS: 318 (M+).

Step 2: (E)-3-(3-Methoxy-5-(trifluoromethoxy)phenyl)acrylic acid

To a solution of (E)-tert-butyl 3-(3-methoxy-5-(trifluoromethoxy)phenyl)acrylate (966 mg, 3.03 mmol) in dichloromethane (9 mL) was added trifluoroacetic acid (3.5 mL), then after 2 h the reaction mixture was concentrated in vacuo. The residue was triturated in heptane to afford the title compound (752 mg, 95%). White solid, MS: 261.2 (M−H)⁻.

The following intermediate was prepared according to intermediate 24, replacing 1-bromo-3-methoxy-5-(trifluoromethoxy)benzene by the appropriate starting material.

| No. | Systematic Name | Starting material | MS, m/e |
|---|---|---|---|
| 24.1 | (E)-3-(3-chloro-5-methoxyphenyl)acrylic acid | 3-chloro-5-iodobenzonitrile (CAS-RN 289039-30-1) | 206.1 (M − H)⁻ |

Intermediate 25

(6,7-Dihydro-1H-[1,2,3]triazolo[4,5-c]pyridin-5(4H)-yl)((3aR,6aR)-hexahydropyrrolo[3,4-c]pyrrol-2(1H)-yl)methanone hydrochloride

Step 1: (3aS,6aS)-tert-Butyl 5-(4,5,6,7-tetrahydro-1H-[1,2,3]triazolo[4,5-c]pyridine-5-carbonyl)hexahydropyrrolo[3,4-c]pyrrole-2(1H)-carboxylate To a colourless solution of 4,5,6,7-tetrahydro-1H-[1,2,3]triazolo[4,5-c]pyridine (CAS-RN 706757-05-3; 102 mg, 819 µmol) and N,N-diisopropylethylamine (222 mg, 1.72 mmol) in N,N-dimethylformamide (4 mL) was added a solution of (3aR,6aR)-tert-butyl 5-(chlorocarbonyl)hexahydropyrrolo[3,4-c]pyrrole-2(1H)-carboxylate (intermediate 9.2; 225 mg, 819 µmol) in dichloromethane (8 mL), then after 70 h the reaction mixture was partitioned between dichloromethane and sat. aq. ammonium chloride solution. The organic layer was washed with brine, dried over magnesium sulfate, filtered, and evaporated. Chromatography (silica gel; gradient dichloromethane to dichloromethane/methanol/25% aq. ammonia solution 90:10:0.25) produced the title compound (225 mg, 76%). White foam, MS: 363.6 (M+H)⁺.

Step 2: (6,7-Dihydro-1H-[1,2,3]triazolo[4,5-c]pyridin-5(4H)-yl)((3aR,6aR)-hexahydropyrrolo[3,4-c]pyrrol-2(1H)-yl)methanone hydrochloride The title compound was produced in analogy to intermediate 1, step 2 from (3aS,6aS)-tert-butyl 5-(4,5,6,7-tetrahydro-1H-[1,2,3]triazolo[4,5-c]pyridine-5-carbonyl)hexahydropyrrolo[3,4-c]pyrrole-2(1H)-carboxylate. White solid, MS: 263.5 (M+H)⁺.

The following intermediate was produced according to intermediate 25, replacing 4,5,6,7-tetrahydro-1H-[1,2,3]triazolo[4,5-c]pyridine by the appropriate amine:

| No. | Systematic Name | Amine | MS, m/e |
|---|---|---|---|
| 25.1 | (3aR,7aR)-5-((3aR,6aR)-octahydropyrrolo[3,4-c]pyrrole-2-carbonyl)hexahydrooxazolo[5,4-c]pyridin-2(1H)-one hydrochloride | (3aR,7aR)-hexahydrooxazolo[5,4-c]pyridin-2(1H)-one hydrochloride (intermediate 27) | 281.1 (M + H)⁺ |

Intermediate 26

(E)-1-((3aR,8aS)-Octahydropyrrolo[3,4-d]azepin-6(7H)-yl)-3-(3-(trifluoromethoxy)-phenyl)prop-2-en-1-one

Step 1: from (3aR,8aS)-tert-butyl 6-((E)-3-(3-(trifluoromethoxy)phenyl)acryloyl)-octahydropyrrolo[3,4-d]azepine-2(1H)-carboxylate To a solution of (3aR,8aS)-tert-butyl octahydropyrrolo[3,4-d]azepine-2(1H)-carboxylate (CAS-RN 1251013-07-6; 353 mg, 1.47 mmol) and (E)-3-(3-(trifluoromethoxy)phenyl)acrylic acid (341 mg, 1.47 mmol) in N,N-dimethylformamide (10 mL) were added N-ethyldiisopropylamine (570 mg, 4.41 mmol) dropwise over a period of 2 minutes at room temperature under an argon atmosphere. The mixture was cooled down to 0° C. and O-(7-azabenzotriazol-1-yl)-N,N,N',N'-tetramethyluronium hexafluoro-phosphate (563 mg, 1.47 mmol) was added, then after 1 h the ice bath was removed. The reaction mixture was stirred for 16 h at room temperature, then partitioned between ethyl acetate and sat. aq. sodium hydrogencarbonate solution. The organic layer was washed with brine, dried over sodium sulfate, filtered, and evaporated. Chromatography (silica gel; heptane-ethyl acetate gradient) produced the title compound (768 mg, 87%). White foam, MS: 399.5 (M+H-isobutene)⁺.

Step 2: (E)-1-((3aR,8aS)-Octahydropyrrolo[3,4-d]
azepin-6(7H)-yl)-3-(3-(trifluoromethoxy)phenyl)
prop-2-en-1-one Trifluoroacetic acid (1.1 mL, 15 mmol) was added over 5 min to a solution of (3aR,8aS)-tert-butyl 6-((E)-3-(3-(trifluoromethoxy)phenyl)acryloyl)octahydropyrrlo[3,4-d]azepine-2(1H)-carboxylate (768 mg, 1.49 mmol) in dichloromethane (12 mL) at room temperature, then after 5 h the reaction mixture was poured onto ice water, basified to pH 10 with 2 M aq. sodium hydroxide solution, and extracted with chloroform. The organic layer was washed with brine, dried over sodium sulfate, filtered, and evaporated. Chromatography (silica gel; dichloromethane/methanol 9:1) produced the title compound (526 mg, 95%). Yellow gum, MS: 355.5 (M+H)$^+$.

The following intermediate was prepared according to intermediate 26, replacing (3aR,8aS)-tert-butyl octahydropyrrolo[3,4-d]azepine-2(1H)-carboxylate by the appropriate amine and (E)-3-(3-(trifluoromethoxy)phenyl)acrylic acid by the appropriate carboxylic acid.

| No. | Systematic Name | Amine | Carboxylic acid | MS, m/e |
|---|---|---|---|---|
| 26.01 | (E)-1-((3aR,6aS)-hexahydropyrrolo[3,4-c]pyrrol-2(1H)-yl)-3-(4-(trifluoromethoxy)phenyl)prop-2-en-1-one | (3aR,6aS)-tert-butyl hexahydropyrrolo[3,4-c]pyrrole-2(1H)-carboxylate (CAS-RN 250275-15-1) | (E)-3-(4-(trifluoromethoxy)phenyl)acrylic acid | 327.5 (M + H)$^+$ |
| 26.02 | 3-(3-chlorophenyl)-2,2-dimethyl-1-((3aR,8aS)-octahydropyrrolo[3,4-d]azepin-6(7H)-yl)propan-1-one | cis-octahydro-pyrrolo[3,4-d]azepine-2-carboxylic acid tert-butyl ester hydrochloride (CAS-RN 1251013-07-6) | 3-(3-chlorophenyl)-2,2-dimethylpropanoic acid (CAS-RN 1225505-29-2) | 335.6 (M + H)$^+$ |
| 26.03 | (E)-3-(3-fluoro-4-(trifluoromethoxy)phenyl)-1-((3aR,8aS)-octahydropyrrolo[3,4-d]azepin-6(7H)-yl)prop-2-en-1-one | cis-octahydro-pyrrolo[3,4-d]azepine-2-carboxylic acid tert-butyl ester hydrochloride (CAS-RN 1251013-07-6) | (E)-3-(3-fluoro-4-(trifluoromethoxy)phenyl)acrylic acid (intermediate 23.3) | 373.6 (M + H)$^+$ |
| 26.04 | (E)-3-(4-fluoro-2-(trifluoromethyl)phenyl)-1-((3aR,8aS)-octahydropyrrolo[3,4-d]azepin-6(7H)-yl)prop-2-en-1-one | cis-octahydro-pyrrolo[3,4-d]azepine-2-carboxylic acid tert-butyl ester hydrochloride (CAS-RN 1251013-07-6) | (E)-3-(4-fluoro-2-(trifluoromethyl)phenyl)acrylic acid (intermediate 23.4) | 357.6 (M + H)$^+$ |
| 26.05 | (E)-3-(2-methyl-4-(trifluoromethoxy)phenyl)-1-((3aR,8aS)-octahydropyrrolo[3,4-d]azepin-6(7H)-yl)prop-2-en-1-one | cis-octahydro-pyrrolo[3,4-d]azepine-2-carboxylic acid tert-butyl ester hydrochloride (CAS-RN 1251013-07-6) | (E)-3-(2-methyl-4-(trifluoromethoxy)phenyl)acrylic acid (CAS-RN 1262012-31-6) | 369.6 (M + H)$^+$ |
| 26.06 | (E)-3-(3-fluoro-4-methoxyphenyl)-1-((3aR,8aS)-octahydropyrrolo[3,4-d]azepin-6(7H)-yl)prop-2-en-1-one | cis-octahydro-pyrrolo[3,4-d]azepine-2-carboxylic acid tert-butyl ester hydrochloride (CAS-RN 1251013-07-6) | (E)-3-(3-fluoro-4-methoxyphenyl)acrylic acid (CAS-RN 147906-08-9) | 319.6 (M + H)$^+$ |
| 26.07 | (E)-3-(2-isopropyl-phenyl)-1-(3aS,8aR)-octahydro-pyrrolo[3,4-d]azepin-6-yl-prop-2-en-1-one | cis-octahydro-pyrrolo[3,4-d]azepine-2-carboxylic acid tert-butyl ester hydrochloride (CAS-RN 1251013-07-6) | (E)-3-(2-isopropyl-phenyl)-acrylic acid (CAS-RN 1379383-70-6) | 313.2 (M + H)$^+$ |
| 26.08 | (E)-3-(2-cyclopropylphenyl)-1-(trans-octahydropyrrolo[3,4-d]azepin-6(7H)-yl)prop-2-en-1-one | cis-octahydro-pyrrolo[3,4-d]azepine-2-carboxylic acid tert-butyl ester hydrochloride (CAS-RN 1251013-07-6) | (E)-3-(2-cyclopropyl-phenyl)acrylic acid (intermediate 23.10) | 311.6 (M + H)$^+$ |
| 26.09 | (E)-3-(4-methoxy-2-(trifluoromethyl)phenyl)-1-((3aR,8aS)-octahydropyrrolo[3,4-d]azepin-6(7H)-yl)prop-2-en-1-one | cis-octahydro-pyrrolo[3,4-d]azepine-2-carboxylic acid tert-butyl ester hydrochloride (CAS-RN 1251013-07-6) | (E)-3-(4-methoxy-2-(trifluoromethyl)phenyl)-acrylic acid (CAS-RN 773131-66-1) | 369.6 (M + H)$^+$ |
| 26.10 | (E)-3-(3-chloro-5-(trifluoromethyl)phenyl)-1-((3aR,8aS)-octahydropyrrolo[3,4-d]azepin-6(7H)-yl)prop-2-en-1-one | cis-octahydro-pyrrolo[3,4-d]azepine-2-carboxylic acid tert-butyl ester hydrochloride (CAS-RN 1251013-07-6) | (E)-3-(3-chloro-5-(trifluoromethyl)phenyl)acrylic acid (CAS-RN 886761-69-9) | 373.6 (M + H)$^+$ |
| 26.11 | 3-(3-fluoro-4-(2,2,2-trifluoroethoxy)phenyl)-1-((3aR,8aS)-octahydropyrrolo[3,4-d]azepin-6(7H)-yl)propan-1-one | cis-octahydro-pyrrolo[3,4-d]azepine-2-carboxylic acid tert-butyl ester hydrochloride (CAS-RN 1251013-07-6) | 3-(3-fluoro-4-(2,2,2-trifluoroethoxy)phenyl)-propanoic acid | 389.2 (M + H)$^+$ |

-continued

| No. | Systematic Name | Amine | Carboxylic acid | MS, m/e |
|---|---|---|---|---|
| 26.12 | 3-(2-fluoro-4-(2,2,2-trifluoroethoxy)phenyl)-1-((3aR,8aS)-octahydropyrrolo[3,4-d]azepin-6(7H)-yl)propan-1-one | cis-octahydro-pyrrolo[3,4-d]azepine-2-carboxylic acid tert-butyl ester (CAS-RN 1251013-07-6) | 3-(2-fluoro-4-(2,2,2-trifluoro-ethoxy)-phenyl)propanoic acid (intermediate 35.3) | 389.2 (M + H)$^+$ |

Intermediate 27

(3aR,7aR)-Hexahydrooxazolo[5,4-c]pyridin-2(1H)-one hydrochloride

Step 1: (3aR,7aR)-tert-butyl 2-oxohexahydrooxazolo[5,4-c]pyridine-5(6H)-carboxylate To a solution of (3R,4R)-tert-butyl 4-amino-3-hydroxypiperidine-1-carboxylate (CAS-RN 1007596-95-3; 500 mg, 2.31 mmol) in N,N-dimethylformamide (5.00 mL) was added imidazole (157 mg, 2.31 mmol) and 1,1'-carbonyldiimidazole (375 mg, 2.31 mmol) at room temperature, then after 18 h the reaction mixture was partitioned between ethyl acetate and water. The organic layer was washed with brine, dried over magnesium sulfate, filtered and evaporated.

The residue was chromatographed (silica gel; gradient dichloromethane to dichloromethane/methanol/25% aq. ammonia solution 95:5:0.25) to produce the title compound (401 mg, 72%) as a white solid.

Step 2: (3aR,7aR)-Hexahydrooxazolo[5,4-c]pyridin-2(1H)-one hydrochloride

The title compound was produced in analogy to intermediate 1, step 2 from (3aR,7aR)-tert-butyl 2-oxohexahydrooxazolo[5,4-c]pyridine-5(6H)-carboxylate. White solid, MS: 143.2 (M+H)$^+$.

Intermediate 28 cis-Hexahydrooxazolo[5,4-c]pyridin-2(1H)-one hydrochloride

Step 1: cis-tert-butyl 2-oxohexahydrooxazolo[5,4-c]pyridine-5(6H)-carboxylate

To a light yellow solution of 1-(tert-butoxycarbonyl)-3-hydroxypiperidine-4-carboxylic acid (CAS-RN 1260876-51-4; 196 mg, 799 µmol) in toluene (2 mL) was added triethylamine (97 mg, 0.96 mmol) and diphenylphosphoryl azide (269 mg, 959 µmol). The reaction mixture was heated at reflux for 18 h and was then partitioned between ethyl acetate and sat. aq. sodium hydrogen carbonate solution. The organic layer was washed with water and brine, dried over magnesium sulfate, filtered and evaporated. Chromatography (silica gel; ethyl acetate-methanol gradient) produced the title compound (66 mg, 34%). White solid, MS: 241.4 (M−H)$^−$.

Step 2: cis-Hexahydrooxazolo[5,4-c]pyridin-2(1H)-one hydrochloride

The title compound was produced in analogy to intermediate 1, step 2 from cis-tert-butyl 2-oxohexahydrooxazolo[5,4-c]pyridine-5(6H)-carboxylate. White solid, MS: 142.1 (M$^+$).

Intermediate 29

(3aSR,6SR,7aSR)-2-Oxooctahydrobenzo[d]oxazole-6-carboxylic acid

Step 1: (1SR,3 SR,4RS)-Methyl 4-bromo-3-(phenoxycarbonyloxy)cyclohexanecarboxylate To a solution of (1 SR,3 SR,4RS)-methyl 4-bromo-3-hydroxycyclohexanecarboxylate (CAS 38361-11-4; 500 mg, 2.11 mmol) and pyridine (175 mg, 2.21 mmol) in dichloromethane (8 mL) was added a solution of phenyl carbonochloridate (347 mg, 2.21 mmol) in dichloromethane (1 mL) at −5° C., then after 1 h the reaction mixture was partitioned between dichloromethane and water. The organic layer was washed with sat. aq. ammonium chloride solution and brine, dried over magnesium sulfate, filtered, and evaporated. Chromatography (silica gel; heptane-ethyl acetate gradient) produced the title compound (545 mg, 72%). Colourless oil, MS: 357.4 (M+H)$^+$.

Step 2: (1SR,3 SR,4SR)-Methyl 4-azido-3-(phenoxycarbonyloxy)cyclohexanecarboxylate To a solution of (1SR,3 SR,4RS)-methyl 4-bromo-3-(phenoxycarbonyloxy)cyclohexanecarboxylate (533 mg, 1.49 mmol) and 15-crown-5 (23.0 mg, 104 µmol) in N,N-dimethylformamide (4 mL) was added sodium azide (437 mg, 6.71 mmol). The reaction mixture was heated at 75° C. for 72 h and was then partitioned between water and ethyl acetate. The organic layer was washed with brine, dried over magnesium sulfate, filtered, and evaporated. Chromatography (silica gel; dichloromethane) produced the title compound (60 mg, 13%). Colourless oil, MS: 337.2 (M+NH$_4$)$^+$.

Step 3: (3aSR,6SR,7aSR)-Methyl 2-oxooctahydrobenzo[d]oxazole-6-carboxylate

To a colourless solution of (1R,3R,4R)-methyl 4-azido-3-(phenoxycarbonyloxy)cyclohexanecarboxylate (56 mg, 175 µmol) in tetrahydrofuran (2 mL) and water (50 µL) was added triphenylphosphine (138 mg, 526 µmol). The solution was heated to 50° C. for 3 h and was then partitioned between ethyl acetate and brine. The organic layer was dried over magnesium sulfate, filtered, and evaporated. Chromatography (silica gel; gradient dichloromethane to dichloromethane/methanol/25% aq. ammonia solution 95:5:0.25 produced the title compound (49 mg), which contained triphenylphosphine oxide as an inseparable impurity.

Step 4: (3aSR,6SR,7aSR)-2-Oxooctahydrobenzo[d]oxazole-6-carboxylic acid

The title compound was produced in analogy to intermediate 11, step 2 from (3aSR,6SR,7aSR)-methyl 2-oxooctahydrobenzo[d]oxazole-6-carboxylate. White solid, MS: 184.3 (M−H)$^−$.

Intermediate 30A and 30B (+)-(R)-4,5,6,7-Tetrahydro-1H-benzo[d][1,2,3]triazole-5-carboxylic acid and (−)-(S)-4,5,6,7-tetrahydro-1H-benzo[d][1,2,3]triazole-5-carboxylic acid Racemic 4,5,6,7-tetrahydro-1H-benzo[d][1,2,3]triazole-5-carboxylic acid (CAS-RN 33062-47-4; 1.10 g, 6.58 mmol) was separated by preparative HPLC using a Chiralpak AD column as the stationary phase and heptane/ethanol 3:2 as the mobile phase. This produced the faster eluting (+)-(R)-enantiomer (452 mg, 41%), followed by the slower eluting (−)-(S)-enantiomer (381 mg, 35%).

Intermediate 31

2-(4-Chloro-2-methylphenoxy)-1-((3aR,6aS)-hexahydropyrrolo[3,4-c]pyrrol-2(1H)-yl)ethanone hydrochloride

Step 1: (3aR,6aS)-tert-Butyl 5-(2-bromoacetyl)hexahydropyrrolo[3,4-c]pyrrole-2(1H)-carboxylate To a solution of (3aR,6aS)-tert-butyl hexahydropyrrolo[3,4-c]pyrrole-2(1H)-carboxylate (CAS-RN 250275-15-1; 400 mg, 1.88 mmol) and triethylamine (191 mg, 1.88 mmol) was added 2-bromoacetyl chloride (297 mg, 1.88 mmol) at −40° C., then after 2 h the reaction mixture was washed with water at 0° C. The organic layer was dried over magnesium sulfate, filtered, and evaporated to produce the title compound (628 mg, 100%), which was directly used in the next step.

Step 2: (3aR,6aS)-tert-Butyl 5-(2-(4-chloro-2-methylphenoxy)acetyl)hexahydropyrrolo[3,4-c]pyrrole-2(1H)-carboxylate To a solution of (3aR,6aS)-tert-butyl 5-(2-bromoacetyl)hexahydropyrrolo[3,4-c]pyrrole-2(1H)-carboxylate (100.6 mg, 302 μmol) and 4-chloro-2-methylphenol (64.6 mg, 453 μmol) in N,N-dimethylformamide (5 mL) was added caesium carbonate (197 mg, 604 μmol) at room temperature, then after 16 h the reaction mixture was partitioned between water and ethyl acetate. The organic layer was washed with brine, dried over sodium sulfate, filtered, and concentrated in vacuo. Chromatography (silica gel; heptane-ethyl acetate gradient) produced the title compound (57 mg, 48%). Colourless oil, MS: 339.5 (M+H-isobutene)⁺.

Step 3: 2-(4-Chloro-2-methylphenoxy)-1-((3aR,6aS)-hexahydropyrrolo[3,4-c]pyrrol-2(1H)-yl)ethanone hydrochloride The title compound was produced in analogy to intermediate 1, step 2 from (3aR,6aS)-tert-butyl 5-(2-(4-chloro-2-methylphenoxy)acetyl)hexahydropyrrolo[3,4-c]pyrrole-2(1H)-carboxylate. Light brown solid, MS: 295.5 (M+H)⁺.

The following intermediate was produced in analogy to intermediate 31, replacing 4-chloro-2-methylphenol in step 2 by the appropriate phenol.

| No. | Systematic Name | Phenol | MS, m/e |
|---|---|---|---|
| 31.1 | 2-(4-chloro-3-methylphenoxy)-1-((3aR,6aS)-hexahydropyrrolo[3,4-c]pyrrol-2(1H)-yl)ethanone hydrochloride | 4-chloro-3-methylphenol | 295.5 (M + H)⁺ |

Intermediate 32

(3aR,8aS)-2-Fluoro-4-(trifluoromethoxy)benzyl octahydropyrrolo[3,4-d]azepine-6(7H)-carboxylate

Step 1: (3aR,8aS)-2-tert-Butyl 6-(2-fluoro-4-(trifluoromethoxy)benzyl) hexahydropyrrolo[3,4-d]azepine-2,6(1H,7H)-dicarboxylate The title compound was produced in analogy to intermediate 1, step 1 from cis-octahydro-pyrrolo[3,4-d]azepine-2-carboxylic acid tert-butyl ester hydrochloride (CAS-RN 1251013-07-6) and (2-fluoro-4-(trifluoromethoxy)phenyl)methanol (CAS-RN 1240257-07-1).

Step 2: (3aR,8aS)-2-Fluoro-4-(trifluoromethoxy)benzyl octahydropyrrolo[3,4-d]azepine-6(7H)-carboxylate The title compound was produced in analogy to intermediate 4, step 2 from (3aR,8aS)-2-tert-butyl 6-(2-fluoro-4-(trifluoromethoxy)benzyl) hexahydropyrrolo[3,4-d]azepine-2,6(1H,7H)-dicarboxylate. Light brown gum, MS: 377.6 (M+H)⁺.

The following intermediates were produced according to intermediate 32, replacing cis-octahydro-pyrrolo[3,4-d]azepine-2-carboxylic acid tert-butyl ester hydrochloride and (2-fluoro-4-(trifluoromethoxy)phenyl)methanol by the appropriate amine and alcohol, respectively.

| No. | Systematic Name | Amine | Alcohol | MS, m/e |
|---|---|---|---|---|
| 32.1 | trans-(2-methoxy-4-(trifluoromethoxy)benzyl) hexahydro-1H-pyrrolo[3,4-c]pyridine-5(6H)-carboxylate | trans-tert-butyl hexahydro-1H-pyrrolo[3,4-c]pyridine-2(3H)-carboxylate (CAS-RN 1251014-37-5) | (2-methoxy-4-(trifluoromethoxy)phenyl)methanol (CAS-RN 886500-30-7) | 375.6 (M + H)⁺ |
| 32.2 | trans-(2-cyclopropyl-4-(trifluoromethyl)benzyl) hexahydro-1H-pyrrolo[3,4-c]pyridine-5(6H)-carboxylate | trans-tert-butyl hexahydro-1H-pyrrolo[3,4-c]pyridine-2(3H)-carboxylate (CAS-RN 1251014-37-5) | (2-cyclopropyl-4-(trifluoromethyl)phenyl)methanol (intermediate 17.1) | 369.3 (M + H)⁺ |

| No. | Systematic Name | Amine | Alcohol | MS, m/e |
|---|---|---|---|---|
| 32.3 | trans-(4-fluoro-2-(trifluoromethyl)benzyl) hexahydro-1H-pyrrolo[3,4-c]pyridine-5(6H)-carboxylate | trans-tert-butyl hexahydro-1H-pyrrolo[3,4-c]pyridine-2(3H)-carboxylate (CAS-RN 1251014-37-5) | (4-fluoro-2-(trifluoromethyl)-phenyl)methanol | 347.6 (M + H)+ |
| 32.4 | (3aR,8aS)-3-fluoro-4-(2,2,2-trifluoroethoxy)benzyl octahydropyrrolo[3,4-d]azepine-6(7H)-carboxylate | cis-octahydro-pyrrolo[3,4-d]azepine-2-carboxylic acid tert-butyl ester (CAS-RN 1251013-07-6) | [3-fluoro-4-(2,2,2-trifluoroethoxy)-phenyl]methanol (CAS-RN 1039931-47-9 | 390.2 (M+) |

Intermediate 33

2-(2-(Tetrahydrofuran-2-yl)phenoxy)acetic acid

Step 1: Ethyl 2-(2-(tetrahydrofuran-2-yl)phenoxy)acetate

To a solution of 2-(tetrahydrofuran-2-yl)phenol (CAS-RN 40324-49-0; 510 mg, 3.11 mmol) in acetone (4 mL) were added potassium carbonate (859 mg, 6.21 mmol) and ethyl 2-bromoacetate (545 mg, 3.26 mmol) at room temperature, then after 3 h the reaction mixture was partitioned between ethyl acetate and water. The organic layer was washed with brine, dried over magnesium sulfate, filtered, and evaporated to produce the title compound (754 mg, 97%). Light yellow oil, MS: 251.5 (M+H)+.

Step 2: 2-(2-(Tetrahydrofuran-2-yl)phenoxy)acetic acid

To a solution of ethyl 2-(2-(tetrahydrofuran-2-yl)phenoxy)acetate (754 mg, 3.01 mmol) in methanol (2.5 mL) and tetrahydrofuran (12 mL) was added 1 M aq. lithium hydroxide solution (5.12 mL, 5.12 mmol), then after 90 min the reaction mixture was acidified with 2 M aq. hydrochloric acid solution and extracted with ethyl acetate. The organic layer was washed with brine, dried over magnesium sulfate, filtered, and evaporated to produce the title compound (650 mg, 97%). White solid, MS: 221.2 (M−H)−.

The following intermediates were produced according to intermediate 33, replacing 2-(tetrahydrofuran-2-yl)phenol by the appropriate phenol.

| No. | Systematic Name | Phenol | MS, m/e |
|---|---|---|---|
| 33.1 | 2-(2-bromo-4-(trifluoromethoxy)-phenoxy)acetic acid | 2-bromo-4-(trifluoromethoxy)-phenol (CAS-RN 200956-13-4) | 313.3 (M − H)− |
| 33.2 | 2-(2-(1H-pyrrol-1-yl)phenoxy)acetic acid | 2-(1H-pyrrol-1-yl)phenol (CAS-RN 32277-91-1) | 216.5 (M − H)− |
| 33.3 | 2-(2-chloro-4-(trifluoromethoxy)phenoxy)acetic acid | 2-chloro-4-(trifluoromethoxy)phenol (CAS-RN 70783-75-4) | 269.5 (M − H)− |

Intermediate 34

2-(4-Cyano-2-isopropyl-5-methylphenoxy)acetic acid

Step 1: tert-Butyl 2-(4-cyano-2-isopropyl-5-methylphenoxy)acetate

To a solution of 4-hydroxy-5-isopropyl-2-methylbenzonitrile (CAS-RN 858026-56-9; 156 mg, 890 μmol) in acetone (4 mL) were added potassium carbonate (246 mg, 1.78 mmol) and tert-butyl 2-bromoacetate (188 mg, 935 μmol) at room temperature, then after 3 h the reaction mixture was partitioned between ethyl acetate and water. The organic layer was washed with brine, dried over magnesium sulfate, filtered, and evaporated to produce the title compound (253 mg 98%). White solid, MS: 290.5 (M+H)+.

Step 2: 2-(4-Cyano-2-isopropyl-5-methylphenoxy)acetic acid

To a colourless solution of tert-butyl 2-(4-cyano-2-isopropyl-5-methylphenoxy)acetate (248 mg, 857 μmol) in dichloromethane (3 mL) was added trifluoroacetic acid (1.95 g, 17.1 mmol), then after 3 h the reaction mixture was concentrated and the residue triturated in heptane. The crude product was purified by chromatography (silica gel; dichloromethane-methanol gradient) to afford the title compound (179 mg, 90%). White solid, MS: 232.5 (M−H)−. The following intermediates were produced according to intermediate 34, replacing 4-hydroxy-5-isopropyl-2-methylbenzonitrile by the appropriate phenol.

| No. | Systematic Name | Phenol | MS, m/e |
|---|---|---|---|
| 34.1 | 2-(4-cyano-2-isopropyl-phenoxy)acetic acid | 3-isopropyl-4-hydroxy-benzonitrile (CAS-RN 46057-54-9) | 218.3 (M − H)− |
| 34.2 | 2-(2-cyano-4-(trifluoromethoxy)phenoxy)acetic acid | 2-hydroxy-5-(trifluoromethoxy)-benzonitrile | 260.5 (M − H)− |
| 34.3 | 2-(2-(pyridin-3-yl)phenoxy)acetic acid | 2-(3-pyridinyl)-phenol (CAS-RN 54168-07-9) | 230.2 (M + H)+ |

Intermediate 35

3-(3-Fluoro-4-(trifluoromethoxy)phenyl)propanoic acid

A solution of (E)-3-(3-fluoro-4-(trifluoromethoxy)phenyl)acrylic acid (intermediate 23.3; 500 mg, 2.00 mmol) in methanol (7 mL) was stirred under a hydrogen atmosphere (1 bar) in the presence of palladium (10% on activated charcoal; 50 mg), then after 20 h insoluble material was removed by filtration through diatomaceous earth. The filtrate was concentrated to produce the title compound (485 mg, 96%). White solid, MS: 251.2 (M−H)−.

The following intermediates were produced according to intermediate 35, replacing (E)-3-(3-fluoro-4-(trifluoromethoxy)phenyl)acrylic acid by the appropriate starting material.

| No. | Systematic Name | Starting material | MS, m/e |
|---|---|---|---|
| 35.1 | 3-(6-phenylpyridin-3-yl)propanoic acid | (E)-3-(6-phenylpyridin-3-yl)acrylic acid (intermediate 23.05) | 226.3 (M − H)⁻ |
| 35.2 | 3-(3-fluoro-4-(2,2,2-trifluoro-ethoxy)phenyl)propanoic acid | (E)-3-(3-fluoro-4-(2,2,2-trifluoro-ethoxy)phenyl)acrylic acid (CAS-RN 1087780-94-6) | 265.1 (M − H)⁻ |
| 35.3 | 3-(2-fluoro-4-(2,2,2-trifluoro-ethoxy)phenyl)propanoic acid | (E)-3-(2-fluoro-4-(2,2,2-trifluoro-ethoxy)phenyl)acrylic acid (intermediate 23.11) | 265.1 (M − H)⁻ |
| 35.4 | 3-(2-fluoro-4-(trifluoromethoxy)-phenyl)propanoic acid | (E)-3-(2-fluoro-4-(trifluoro-methoxy)phenyl)acrylic acid (intermediate 23.02) | 251.2 (M − H)⁻ |

Intermediate 36

2-(5-Chloro-2-(trifluoromethyl)phenoxy)-1-((3aR, 8aS)-octahydropyrrolo[3,4-d]azepin-6(7H)-yl)ethanone Step 1: (3aR,8aS)-tert-butyl 6-(2-(5-chloro-2-(trifluoromethyl)phenoxy)acetyl)octahydropyrrolo[3,4-d]azepine-2(1H)-carboxylate Caesium carbonate (132 mg, 404 µmol) was added to a solution of 5-chloro-2-(trifluoromethyl)phenol (47.7 mg, 242 µmol) and (3aR,8aS)-tert-butyl 6-(2-bromoacetyl)octahydropyrrolo[3,4-d]azepine-2(1H)-carboxylate (intermediate 37; 73 mg, 202 mol) in N,N-dimethylformamide (5 mL) at room temperature, then after 18 h the reaction mixture was partitioned between ice water and ethyl acetate. The organic layer was washed with brine, dried over sodium sulfate, filtered, and evaporated. Chromatography (silica gel; heptane-ethyl acetate gradient) produced the title compound (82 mg, 83%). White foam, MS: 421.5 (M+H-isobutene)⁺.

Step 2: 2-(5-Chloro-2-(trifluoromethyl)phenoxy)-1-((3aR,8aS)-octahydropyrrolo[34-d]azepin-6(7H)-yl)ethanone The title compound was produced in analogy to intermediate 26, step 2 from (3aR,8aS)-tert-butyl 6-(2-(5-chloro-2-(trifluoromethyl)phenoxy)acetyl)octahydropyrrolo[3,4-d]azepine-2(1H)-carboxylate. Light yellow foam, MS: 377.5 (M+H)⁺.

The following intermediates were produced according to intermediate 36, replacing 5-chloro-2-(trifluoromethyl)phenol by the appropriate phenol.

| No. | Systematic Name | Phenol | MS, m/e |
|---|---|---|---|
| 36.01 | 2-(6-isopropyl-3,3-dimethyl-2,3-dihydro-1H-inden-5-yloxy)-1-((3aR,8aS)-octahydropyrrolo[3,4-d]azepin-6(7H)-yl)ethanone | 6-isopropyl-3,3-dimethyl-2,3-dihydro-1H-inden-5-ol | 385.7 (M + H)⁺ |
| 36.02 | 2-(2-isopropyl-5-methylphenoxy)-1-((3aR,8aS)-octahydropyrrolo[3,4-d]azepin-6(7H)-yl)ethanone | 2-isopropyl-5-methylphenol | 331.6 (M + H)⁺ |
| 36.03 | 2-(2-chloro-4-fluorophenoxy)-1-((3aR,8aS)-octahydropyrrolo[3,4-d]azepin-6(7H)-yl)ethanone | 2-chloro-4-fluorophenol | 327.1 (M + H)⁺ |
| 36.04 | 2-(4-methyl-2-(1-methylpyrrolidin-3-yl)phenoxy)-1-((3aR,8aS)-octahydropyrrolo[3,4-d]azepin-6(7H)-yl)ethanone | 4-methyl-2-(1-methylpyrrolidin-3-yl)phenol | 372.3 (M + H)⁺ |
| 36.05 | 4-(2-((3aR,8aS)-octahydropyrrolo[3,4-d]azepin-6(7H)-yl)-2-oxoethoxy)-3-(trifluoromethyl)benzonitrile | 4-hydroxy-3-(trifluoro-methyl)benzo-nitrile | 368.1 (M + H)⁺ |
| 36.06 | 2-(4-chloro-2-isopropyl-5-methylphenoxy)-1-((3aR,8aS)-octahydropyrrolo[3,4-d]azepin-6(7H)-yl)ethanone | 4-chloro-2-isopropyl-5-methylphenol | 365.2 (M + H)⁺ |
| 36.07 | 1-(3aS,8aR)-octahydro-pyrrolo[3,4-d]azepin-6-yl-2-(2-trifluoromethoxy-phenoxy)-ethanone | 2-(trifluoro-methoxy)phenol | 359.6 (M + H)⁺ |
| 36.08 | 2-(2-tert-butyl-4-methoxyphenoxy)-1-((3aR,8aS)-octahydropyrrolo[3,4-d]azepin-6(7H)-yl)ethanone | 2-tert-butyl-4-methoxyphenol | 361.6 (M + H)⁺ |
| 36.09 | 3-isopropyl-4-(2-((3aR,8aS)-octahydropyrrolo[3,4-d]azepin-6(7H)-yl)-2-oxoethoxy)benzonitrile | 4-hydroxy-3-isopropyl-benzonitrile (CAS-RN CAS-RN 46057-54-9) | 342.6 (M + H)⁺ |
| 36.10 | 2-(2-chloro-4-(trifluoromethyl)phenoxy)-1-((3aR,8aS)-octahydropyrrolo[3,4-d]azepin-6(7H)-yl)ethanone | 2-chloro-4-(trifluoro-methyl)phenol | n.a. |

Intermediate 37

(3aR,8aS)-tert-Butyl 6-(2-bromoacetyl)octahydropyrrolo[3,4-d]azepine-2(1H)-carboxylate To a suspension of (3aR,8aS)-tert-butyl octahydropyrrolo[3,4-d]azepine-2(1H)-carboxylate hydrochloride (CAS-RN 1251013-07-6; 600 mg, 2.17 mmol) and triethylamine (439 mg, 4.34 mmol) in dichloromethane (40 mL) was added 2-bromoacetyl chloride (341 mg, 2.17 mmol) dropwise at −40° C., then the reaction mixture was allowed to reach room temperature over 2 h and partitioned between water and dichloromethane. The organic layer was dried over sodium sulfate, filtered, and evaporated to produce the title compound (600 mg, 69%; brown oil), which was directly used in the next step.

Intermediate 38

[2-Fluoro-4-(2,2,2-trifluoroethoxy)phenyl]methanol

Sodium borohydride was added portionwise at 0° C. to a solution of 2-fluoro-4-(2,2,2-trifluoroethoxy)benzaldehyde (intermediate 39; 500 mg, 2.25 mmol) in methanol (3 mL), then the reaction mixture was allowed to reach room temperature over 3 h. After addition of water (5 mL) and evaporation of methanol, the reaction mixture was partitioned between ethyl acetate and water. The organic layer was dried over sodium sulfate, filtered, and evaporated to produce the title compound (450 mg, 87%). Colourless oil, MS: 224 (M⁺).

Intermediate 39

2-Fluoro-4-(2,2,2-trifluoroethoxy)benzaldehyde

To a solution of 2-fluoro-4-hydroxybenzaldehyde (1.00 g, 7.14 mmol) in N,N-dimethylformamide (6 mL) were added potassium carbonate (1.48 g, 10.7 mmol) and 2,2,2-trifluoroethyl trifluoromethanesulfonate (1.99 g, 8.56 mmol) at room temperature. The reaction mixture was heated at 50° C. for 2 h, then partitioned between ethyl acetate and water. The organic layer was dried over sodium sulfate, filtered, and evaporated to produce the title compound (1.30 g, 80%). White solid, MS: 222 (M+).

Intermediate 40

2-(2-tert-Butyl-4-cyanophenoxy)acetic acid

A mixture of 2-(4-bromo-2-tert-butylphenoxy)acetic acid (CAS-RN 425372-86-7; 453 mg, 1.58 mmol), 1,1'-bis(diphenylphosphino)ferrocene (26.2 mg, 47.3 μmol), tris(dibenzylideneacetone)dipalladium(0) (14.4 mg, 15.8 μmol), zinc cyanide (102 mg, 868 μmol), zinc powder (4.13 mg, 63.1 μmol) and zinc acetate (11.6 mg, 63.1 μmol), N,N-dimethylformamide (4.5 mL) and water (45 μl) was heated at 180° C. for 15 min under microwave irradiation, then evaporated under vacuum. The residue was taken up in ethyl acetate, then insoluble material was removed by filtration through diatomaceous earth. The filtrate was evaporated and the residue purified by chromatography (silica gel; ethyl acetate-methanol gradient, then dichloromethane-methanol gradient) to produce the title compound (64 mg, 22%). Dark brown solid. MS: 232.5 (M–H)⁻.

Intermediate 41

4-(Hydroxymethyl)-3-isopropylbenzonitrile

Step 1: 4-Cyano-2-isopropylphenyl trifluoromethanesulfonate

To a solution of pyridine (895 mg, 11.3 mmol) in dichloromethane (70 mL) was added trifluoromethanesulfonic anhydride (2.93 g, 10.4 mmol) at 0° C., then after 10 min a solution of 4-hydroxy-3-isopropylbenzonitrile (CAS-RN 46057-54-9; 1.52 g, 9.43 mmol) in dichloromethane (40 mL) was added dropwise to the white suspension that had formed. The ice bath was removed, then after 75 min the reaction mixture was partitioned between dichloromethane and water. The organic layer was washed with brine, dried over magnesium sulfate, filtered, and evaporated. Chromatography (silica gel; heptane-dichloromethane gradient) produced the title compound (2.63 g, 95%). Yellow liquid, MS: 292.1 (M–H)⁻.

Step 2: Methyl 4-cyano-2-isopropylbenzoate

A solution of 4-cyano-2-isopropylphenyl trifluoromethanesulfonate (2.62 g, 8.93 mmol), triethylamine (2.26 g, 22.3 mmol), and bis(diphenylphosphino)ferrocene-palladium(II) dichloride dichloromethane complex (365 mg, 447 μmol) was stirred for 20 h under a carbon monoxide atmosphere (50 bar) at 110° C. After cooling the reaction mixture was evaporated and the residue was purified by chromatography (silica gel; dichloromethane/heptane 1:1) to produce the title compound (1.40 g, 77%). Light yellow oil, MS: 218.5 (M+H)⁺.

Step 3: 4-(Hydroxymethyl)-3-isopropylbenzonitrile

Lithium borohydride solution (2 M in tetrahydrofuran, 9.06 mL, 18.1 mmol) was added at room temperature to a solution of methyl 4-cyano-2-isopropylbenzoate (1.227 g, 6.04 mmol) in tetrahydrofuran (15 mL). The reaction mixture was heated at reflux for 1 h, then partitioned between ethyl acetate and water. The organic layer was washed with brine, dried over magnesium sulfate, filtered, and evaporated. Chromatography (silica gel; gradient dichloromethane to dichloromethane/methanol/25% aq. ammonia solution 95:5:0.25) afforded the title compound (802 mg, 76%). Light yellow oil, MS: 176.2 (M+H)⁺.

The following intermediates were produced according to intermediate 41, replacing 4-hydroxy-3-isopropylbenzonitrile by the appropriate phenol.

| No. | Systematic Name | Phenol | MS, m/e |
|---|---|---|---|
| 41.1 | 4-(hydroxymethyl)-5-isopropyl-2-methylbenzonitrile | 4-hydroxy-5-isopropyl-2-methyl-benzonitrile (CAS-RN 858026-56-9) | 190.3 (M + H)⁺ |
| 41.2 | 3-ethoxy-4-(hydroxymethyl)benzonitrile | 3-ethoxy-4-hydroxy-benzonitrile (CAS-RN 60758-79-4) | 177 (M)⁺ |

Intermediate 42

3-(4-Cyano-2-isopropylphenyl)propanoic acid

Triethylamine (1.22 g, 12.1 mmol) was added dropwise to formic acid (1.36 g, 29.6 mmol) at 0° C. This was added to 4-formyl-3-isopropylbenzonitrile (190 mg, 1.1 mmol) and 2,2-dimethyl-1,3-dioxane-4,6-dione (158 mg, 1.1 mmol). The solution was stirred at room temperature for 3 h, then poured upon ice water, acidified with 4 M aq. hydrochloric acid solution, and extracted with ethyl acetate. The organic layer was washed with brine, dried over magnesium sulfate, filtered, and evaporated to afford crude 4-[(2,2-dimethyl-4,6-dioxo-1,3-dioxan-5-yl)methyl]-3-isopropyl-benzonitrile (334 mg) as a light yellow foam, MS: 302.4 (M+H)⁺. This was dissolved in acetonitrile/water 100:1 (2 mL) and heated at 100° C. for 30 min under microwave irradiation, then concentrated in vacuo. The residue was partitioned between 2 M hydrochloric acid solution and ethyl acetate. The organic layer was washed with brine, dried over magnesium sulfate, filtered, and evaporated to afford the title compound (240 mg), which was used directly in the next step. Yellow oil, MS: 216.3 (M+H)⁺.

The following intermediate was produced according to intermediate 42, replacing 4-formyl-3-isopropylbenzonitrile by the appropriate aldehyde.

| No. | Systematic Name | Phenol | MS, m/e |
|---|---|---|---|
| 42.1 | 3-(4-cyano-2-isopropyl-5-methylphenyl)propanoic acid | 4-formyl-5-isopropyl-2-methyl-benzonitrile (intermediate 22.2) | 230.2 (M – H)⁻ |

Intermediate 43

6-Fluoro-1H-benzo[d][1,2,3]triazole-5-carboxylic acid

Step 1: Methyl 6-fluoro-1H-benzo[d][1,2,3]triazole-5-carboxylate

A solution of 5-bromo-6-fluoro-1H-benzo[d][1,2,3]triazole (CAS-RN 1242336-69-1; 492 mg, 2.28 mmol), triethylamine (576 mg, 5.69 mmol), and 1,1'-bis(diphenylphosphino)ferrocene-palladium(II) dichloride dichloromethane complex (74.4 mg, 91.1 µmol), in methanol (6 mL) was stirred at 110° C. under a carbon monoxide atmosphere (70 bar) for 18 h. After cooling insoluble material was separated by filtration through diatomaceous earth. The filtrate was evaporated and purified by chromatography (silica gel; dichloromethane-methanol gradient) to produce the title compound (281 mg, 63%). Light red solid, MS: 194.2 (M−H)⁻.

Step 2: 6-Fluoro-1H-benzo[d][1,2,3]triazole-5-carboxylic acid

To a solution of methyl 6-fluoro-1H-benzo[d][1,2,3]triazole-5-carboxylate (276 mg, 1.41 mmol) in tetrahydrofuran (3 mL) and methanol (1.5 mL) was added 1 M aq. lithium hydroxide solution 1 M in water (4.24 mL, 4.24 mmol). After 5 h most of the organic solvents were removed by concentration under reduced pressure, then the aqueous solution was acidified with 1 M aq. hydrochloric acid solution. The precipitate was collected by filtration and dried to afford the title compound (266 mg, 100%). Off-white solid, MS: 180.2 (M−H)⁻.

The following intermediates were produced according to intermediate 43, replacing 5-bromo-6-fluoro-1H-benzo[d][1,2,3]triazole by the appropriate starting material.

| No. | Systematic Name | Starting material | MS, m/e |
|---|---|---|---|
| 43.1 | 7-fluoro-1H-benzo[d][1,2,3]triazole-5-carboxylic acid | 5-bromo-7-fluoro-1H-benzo[d][1,2,3]triazole (intermediate 44) | 180.2 (M − H)⁻ |
| 43.2 | 4-fluoro-1H-benzo[d][1,2,3]triazole-5-carboxylic acid | 5-bromo-4-fluoro-1H-benzo[d][1,2,3]triazole (intermediate 44.1) | 180.2 (M − H)⁻ |
| 43.3 | 4-methyl-1H-benzo[d][1,2,3]triazole-5-carboxylic acid | 5-bromo-4-methyl-1H-benzo[d][1,2,3]triazole (CAS-RN 1372795-26-0) | 176.2 (M − H)⁻ |
| 43.4 | 6-(trifluoromethyl)-1H-benzo[d][1,2,3]triazole-5-carboxylic acid | 5-bromo-6-(trifluoromethyl)-1H-benzo[d][1,2,3]triazole (CAS-RN 157590-65-3) | 230.1 (M − H)⁻ |
| 43.5 | 4-chloro-1H-benzo[d][1,2,3]triazole-5-carboxylic acid | 5-bromo-4-chloro-1H-benzo[d][1,2,3]triazole (CAS-RN 1388044-33-4) | 196.2 (M − H)⁻ |
| 43.6 | 6-methyl-1H-benzo[d][1,2,3]triazole-5-carboxylic acid | 5-bromo-6-methyl-1H-benzo[d][1,2,3]triazole (CAS-RN 1388070-91-4) | 176.4 (M − H)⁻ |

Example 44

5-bromo-7-fluoro-1H-benzo[d][1,2,3]triazole

A solution of sodium nitrite (185 mg, 2.68 mmol) in water (0.5 mL) was added dropwise at room temperature to a solution of 5-bromo-3-fluorobenzene-1,2-diamine (500 mg, 2.44 mmol) in water (5 mL) and acetic acid (1.8 mL). The reaction mixture was stirred at room temperature for 1 h, then heated at 85° C. for another hour, then partitioned between water and ethyl acetate. The organic layer was washed with brine, dried over magnesium sulfate, filtered, and evaporated to produce the title compound (498 mg, 94%). Light brown solid, MS: 214.1 (M−H)⁻.

The following intermediate was produced according to intermediate 44, replacing 5-bromo-6-fluoro-1H-benzo[d][1,2,3]triazole by the appropriate starting material.

| No. | Systematic Name | Starting material | MS, m/e |
|---|---|---|---|
| 44.1 | 5-bromo-4-fluoro-1H-benzo[d][1,2,3]triazole | 4-bromo-3-fluorobenzene-1,2-diamine | 214.1 (M − H)⁻ |

Intermediate 45

3H-[1,2,3]triazolo[4,5-c]pyridine-6-carboxylic acid

Step 1: Methyl 3H-[1,2,3]triazolo[4,5-c]pyridine-6-carboxylate

A solution of sodium nitrite (413 mg, 5.99 mmol) in water (1.5 mL) was added dropwise at 0° C. to a solution of methyl 4,5-diaminopicolinate (CAS-RN 850689-13-3; 910 mg, 5.44 mmol) in water (10 mL) and acetic acid (2 mL) at 0° C., then after 1 h acetic acid (2 mL) was added to the suspension formed. The reaction mixture was stirred for 1 h at 85° C. and filtered hot. The precipitate was triturated in methanol to produce the title compound (758 mg, 78%). Red solid, MS: 177.2 (M−H)⁻.

Step 2: 3H-[1,2,3]Triazolo[4,5-c]pyridine-6-carboxylic acid

The title compound was produced in analogy to intermediate 43, step 2 from ethyl 3H-[1,2,3]triazolo[4,5-c]pyridine-6-carboxylate. Light brown solid, MS: 163.1 (M−H)⁻.

The following intermediate was produced according to intermediate 45, replacing methyl 4,5-diaminopicolinate by the appropriate starting material.

| No. | Systematic Name | Starting material | MS, m/e |
|---|---|---|---|
| 45.1 | 4-methoxy-1H-benzo[d][1,2,3]triazole-5-carboxylic acid | methyl 3,4-diamino-2-methoxy-benzoate (CAS-RN 538372-37-1) | 192.3 (M − H)⁻ |

Intermediate 46

3-Cyclobutoxy-4-(hydroxymethyl)benzonitrile

Step 1: 4-Cyano-2-cyclobutoxybenzoic acid

To a suspension of sodium hydride (60% dispersion in mineral oil, 545 mg, 13.6 mmol) in N,N-dimethylformamide (20 mL) was added cyclobutanol (1.05 g, 13.9 mmol) dropwise below 30° C. The clear solution obtained was stirred for 2 h, then a solution of 4-cyano-2-fluorobenzoic acid (1.00 g, 6.06 mmol) in N,N-dimethylformamide (15 mL) was added dropwise below 35° C. The light yellow suspension was stirred for 66 h at room temperature, then partitioned between water and heptane. The aqueous layer was separated and acidified to pH 2.5 with 3 M aq. hydrochloric acid solution to pH 2.5. The precipitate was collected by filtration, washed with water and dried to afford the title compound (1.03 g, 79%). White foam, MS: 216.2 (M−H)⁻.

Step 2:
3-Cyclobutoxy-4-(hydroxymethyl)benzonitrile

Borane dimethyl sulfide complex (429 mg, 5.64 mmol) was added at 0° C. to a solution of 4-cyano-2-cyclobutoxybenzoic acid (613 mg, 2.82 mmol) in tetrahydrofuran (8 mL). After 30 min the ice bath was removed, then after 3 h the reaction was stopped by careful addition of water. The reaction mixture was extracted with ethyl acetate, the organic layer was washed with sat. aq. ammonium chloride solution and brine, dried over magnesium sulfate, filtered, and evaporated. Chromatography (silica gel; dichloromethane) afforded the title compound (452 mg, 79%). White solid, MS: 203 (M$^+$).

The following intermediate was produced according to intermediate 46, replacing cyclobutanol by the appropriate alcohol.

| No. | Systematic Name | Alcohol | MS, m/e |
|---|---|---|---|
| 46.1 | 4-(hydroxymethyl)-3-isopropoxybenzonitrile | 2-propanol | 191 (M$^+$) |

Intermediate 47

(4-Chloro-2-ethoxy-5-fluorophenyl)methanol

Step 1: Ethyl 4-chloro-2-ethoxy-5-fluorobenzoate

To a solution of methyl 4-chloro-2,5-difluorobenzoate (CAS-RN 1214361-01-9; 848 mg, 4.11 mmol) in N,N-dimethylformamide (8 mL) was added a freshly prepared sodium ethoxide solution (94.4 mg/4.11 mmol sodium in 2 mL ethanol) at 0° C. The reaction mixture was allowed to reach room temperature over 30 min, then partitioned between ethyl acetate and 1 M hydrochloric acid solution. The organic layer was washed with water and brine, dried over magnesium sulfate, filtered, and evaporated. Chromatography (silica gel; heptane-ethyl acetate gradient) afforded the title compound (484 mg, 48%) and methyl 4-chloro-2-ethoxy-5-fluorobenzoate (192 mg, 20%). White solid, MS: 247.2 (M+H)$^+$.

Step 2:
(4-Chloro-2-ethoxy-5-fluorophenyl)methanol

The title compound was produced in analogy to intermediate 41, step 3 from ethyl 4-chloro-2-ethoxy-5-fluorobenzoate. White solid, MS: 204 (M$^+$).

The following intermediate was produced according to intermediate 47, replacing methyl 4-chloro-2,5-difluorobenzoate tert-butyl ester hydrochloride and ethanol by the appropriate ester and alcohol, respectively.

| No. | Systematic Name | Ester | Alcohol | MS, m/e |
|---|---|---|---|---|
| 47.1 | 4-(hydroxymethyl)-3-(2,2,2-trifluoroethoxy)benzonitrile | methyl 4-cyano-2-fluorobenzoate | 2,2,2-trifluoroethanol | 231 (M$^+$) |

Intermediate 48

4-(Hydroxymethyl)-3-(methylsulfonyl)benzonitrile

Step 1: 4-Cyano-2-(methylthio)benzoate

To a solution of methyl 4-cyano-2-fluorobenzoate (500 mg, 2.79 mmol) in N,N-dimethylformamide (5 mL) was added sodium thiomethoxide (293 mg, 4.19 mmol, Eq: 1.5) at 0° C. After 2 h the reaction mixture was partitioned between sat. aq sodium hydrogen carbonate solution and ethyl acetate 3 times. The organic layer was washed with water and brine, dried over magnesium sulfate, filtered and evaporated to afford the title compound (434 mg, 75%). White solid, MS: 207 (M$^+$).

Step 2: 4-Cyano-2-(methyl sulfonyl)benzoate

To a of methyl 4-cyano-2-(methylthio)benzoate (420 mg, 2.03 mmol) in dichloromethane (10 mL) was added a suspension of 3-chloroperoxybenzoic acid (1.82 g, 8.11 mmol) in dichloromethane (15 mL) portionwise at 0° C. The reaction mixture was stirred at 0° C. for 45 min and at room temperature for 45 min, then partitioned between dichloromethane and 1 M sodium sulfite solution. The organic layer was washed with sat. aq. sodium hydrogen carbonate solution and brine, dried over magnesium sulfate, filtered, and evaporated. The residue was triturated in heptane/ethyl acetate 7:3 to afford the title compound (453 g, 93%). White solid, MS: 239 (M$^+$).

Step 3:
4-(Hydroxymethyl)-3-(methylsulfonyl)benzonitrile

A solution of calcium chloride (390 mg, 3.51 mmo) in ethanol (10 mL) was added at room temperature to a solution of methyl 4-cyano-2-(methylsulfonyl)benzoate (420 mg, 1.76 mmol) in tetrahydrofuran (10 mL). Then sodium borohydride (266 mg, 7.02 mmol) was added portionwise over 20 min. After 2 h the reaction mixture was partitioned between sat aq. ammonium chloride solution and ethyl acetate. The organic layer was washed with brine, dried over magnesium sulfate, filtered, and evaporated. Chromatography (silica gel, dichloromethane/ethanol 19:1) afforded the title compound (123 mg, 33%). White solid, MS: 211 (M$^+$).

Intermediate 49

5-Ethoxy-2-fluoro-4-(hydroxymethyl)benzonitrile

Step 1: Ethyl 4-bromo-2-ethoxy-5-fluorobenzoate

The title compound was produced in analogy to intermediate 47, step 1 from methyl 4-bromo-2,5-difluorobenzoate (CAS-RN 1193162-21-8). White solid, MS: 290 (M$^+$).

Step 2: Ethyl 4-cyano-2-ethoxy-5-fluorobenzoate

A mixture of ethyl 4-bromo-2-ethoxy-5-fluorobenzoate (50 mg, 172 μmol), zinc cyanide (11.1 mg, 94.5 μmol), zinc powder (0.4 mg, 7 μmol, Eq: 0.04), zinc acetate (1.3 mg, 7 μmol, Eq: 0.04) 1,1'-bis(diphenylphosphino)ferrocene (2.9 mg, 5.2 μmol), and tris(dibenzylideneacetone)dipalladium(0) (1.6 mg, 1.8 μmol) in N,N-dimethylformamide (500 μl) and water (5 μl) was heated at 120° C. for 15 min under microwave irradiation, then insoluble material was removed by filtration through diatomaceous earth and the filtrate was evaporated. The residue was purified by chromatography (silica gel; heptane-dichloromethane gradient) to produce the title compound (41 mg, quant.). White solid. MS: 237 (M$^+$).

Step 3:
5-Ethoxy-2-fluoro-4-(hydroxymethyl)benzonitrile

The title compound was produced in analogy to intermediate 41, step 3 from ethyl 4-cyano-2-ethoxy-5-fluorobenzoate. White solid. MS: 195 (M+).

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (I)

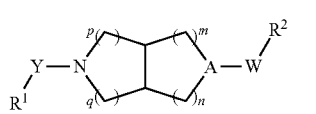

wherein
$R^1$ is alkyl, haloalkyl, substituted cycloalkyl, substituted cycloalkylalkyl, substituted piperazinyl, substituted piperidinyl, substituted indanyloxyalkyl, substituted phenyl, substituted phenyl alkyl, substituted phenoxyalkyl, substituted phenylcycloalkyl, substituted phenylalkenyl, substituted phenylalkynyl, substituted pyridinyl, substituted pyridinylalkyl, substituted pyridinylalkenyl, substituted pyridinylalkynyl substituted thiophenyl, substituted thiophenylalkyl, substituted thiophenylalkenyl, substituted thiophenylalkynyl, naphthyl, substituted naphthyl, quinolyl, substituted quinolinyl, isoquinolyl, substituted isoquinolinyl, substituted 2,3-dihydro-1H-isoindol-2-yl, substituted 1H-indol-2-yl, or substituted benzofuran-2-yl, wherein substituted cycloalkyl, substituted cycloalkylalkyl, substituted piperazinyl, substituted piperidinyl, substituted indanyloxyalkyl, substituted phenyl, substituted phenyl alkyl, substituted phenylalkynyl, substituted phenoxyalkyl, substituted phenylcycloalkyl, substituted phenylalkenyl, substituted pyridinyl, substituted pyridinyl alkyl, substituted pyridinylalkenyl, substituted pyridinylalkynyl, substituted thiophenyl, substituted thiophenylalkyl, substituted thiophenylalkenyl, substituted thiophenylalkynyl, substituted naphthyl, substituted quinolinyl, substituted isoquinolinyl, substituted 2,3-dihydro-1H-isoindol-2-yl, substituted 1H-indol-2-yl, and substituted benzofuran-2-yl are substituted with $R^8$, $R^9$, and $R^{10}$;

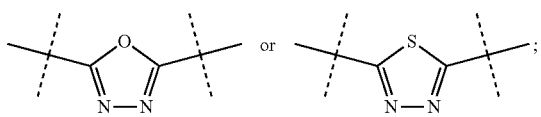

Y is -OC(O)-, -NR$^7$C(O)-, -C(O)-, -S(O)$_2$-,
A is -N- or CR$^5$-;
W is -O-, -S-, -NR$^6$-, -C(O)-, -S(O)$_2$-, -C(O)-NR$^6$-, or -CR$^3$R$^4$-;
$R^3$ and $R^4$ are independently selected from H, halogen, alkyl, and cycloalkyl;
$R^5$, $R^6$, and $R^7$ are independently selected from H, alkyl, and cycloalkyl;
$R^8$, $R^9$, and $R_{10}$ are independently selected from H, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, phenyl, substituted phenyl, pyridinyl, substituted pyridinyl, pyrrolyl, substituted pyrrolyl, pyrrolidinyl, substituted pyrrolidinyl, tetrahydrofuranyl, substituted tetrahydrofuranyl, halogen, hydroxy, cyano, alkylsulfanyl, haloalkylsulfanyl, cycloalkylsulfanyl, alkylsulfinyl, haloalkylsulfinyl, cycloalkylsulfinyl, alkylcarbonyl, haloalkylcarbonyl, cycloalkylcarbonyl, alkyl sulfonyl, haloalkylsulfonyl, cycloalkylsulfonyl, substituted aminosulfonyl, substituted amino and substituted aminoalkyl, wherein substituted aminosulfonyl, substituted amino, and substituted aminoalkyl are substituted on the nitrogen atom with one to two sub stituents independently selected from H, alkyl, cycloalkyl, cycloalkylalkyl, hydroxyalkyl, alkoxyalkyl, alkylcarbonyl, and cycloalkylcarbonyl, and wherein substituted phenyl, substituted pyrrolyl, substituted pyrrolidinyl, substituted tetrahydrofuranyl, and substituted pyridinyl are substituted with one to three substituents independently selected from alkyl, halogen, haloalkyl, alkoxy, and haloalkoxy;
m, n, p, and q are independently selected from 1 and 2; and
$R^2$ is

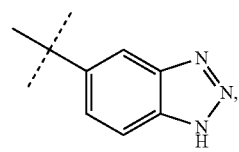

or a pharmaceutically acceptable salt thereof.

2. A compound according to claim 1, wherein $R^1$ is alkyl, haloalkyl, substituted cycloalkyl, substituted cycloalkylalkyl, substituted phenyl, substituted phenylalkyl, substituted phenoxyalkyl, substituted phenyl cycloalkyl, substituted phenyl alkenyl, substituted phenylalkynyl, substituted pyridinyl, substituted pyridinylalkyl, substituted pyridinylalkenyl, substituted pyridinylalkynyl, substituted thiophenyl, substituted thiophenyl alkyl, substituted thiophenylalkenyl, substituted thiophenylalkynyl, substituted 2,3-dihydro-1H-isoindol-2-yl, substituted 1H-indol-2-yl, or substituted benzofuran-2-yl, wherein substituted cycloalkyl, substituted cycloalkylalkyl, substituted phenyl, substituted phenylalkyl, substituted phenylalkynyl, substituted phenoxyalkyl, substituted phenyl cycl oalkyl, substituted phenylalkenyl, substituted pyridinyl, substituted pyridinylalkyl, substituted pyridinylalkenyl, substituted pyridinylalkynyl, substituted thiophenyl, substituted thiophenylalkyl, substituted thiophenylalkenyl, substituted thiophenylalkynyl, substituted 2,3-dihydro-1H-isoindol-2-yl, substituted 1H-indol-2-yl, and substituted benzofuran-2-yl are substituted with $R^8$, $R^9$, and $R^{10}$;

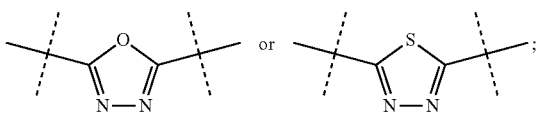

Y is -OC(O)-, -NR$^7$C(O)-, -C(O)-, -S(O)$_2$-,

A is -N- or CR$^5$-;

W is -O-, -S-, -NR$^6$-, -C(O)-, -S(O)$_2$-, -C(O)-NR$^6$-, or -CR$^3$R$^4$-;

$R^3$ and $R^4$ are independently selected from H, halogen, alkyl, and cycloalkyl;

$R^5$, $R^6$ and $R^7$ are independently selected from H, alkyl, and cycloalkyl;

$R^8$, $R^9$ and $R^{10}$ are independently selected from H, alkyl, hydroxyalkyl, haloalkyl, hydroxyhaloalkyl, cycloalkyl, cycloalkylalkyl, cycloalkylalkoxy, cycloalkoxy, cycloalkoxyalkyl, cycloalkylalkoxyalkyl, alkoxy, alkoxyalkyl, haloalkoxy, alkoxyhaloalkyl, alkoxyalkoxy, alkoxyalkoxyalkyl, phenyl, substituted phenyl, pyridinyl, substituted pyridinyl, halogen, hydroxy, cyano, alkylsulfanyl, haloalkylsulfanyl, cycloalkylsulfanyl, alkyl sulfinyl, haloalkylsulfinyl, cycloalkylsulfinyl, alkyl sulfonyl, haloalkylsulfonyl, cycloalkylsulfonyl, substituted aminosulfonyl, substituted amino and substituted aminoalkyl, wherein substituted aminosulfonyl, substituted amino, and substituted aminoalkyl are substituted on the nitrogen atom with one to two substituents independently selected from H, alkyl, cycloalkyl, cycloalkylalkyl, hydroxyalkyl, alkoxyalkyl, alkylcarbonyl, and cycloalkylcarbonyl, and wherein substituted phenyl and substituted pyridinyl are optionally substituted with one to three substituents independently selected from alkyl, halogen, haloalkyl, alkoxy, and haloalkoxy;

m, n, p, and q are independently selected from 1 and 2; and $R^2$ is

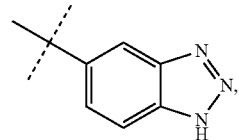

or a pharmaceutically acceptable salt thereof.

3. A compound according to claim 1, or a pharmaceutically acceptable salt thereof, wherein $R^1$ is substituted cycloalkylalkyl, substituted piperazinyl, substituted piperidinyl, substituted indanyloxyalkyl, substituted phenyl, substituted phenyl alkyl, substituted phenoxyalkyl, substituted phenylcycloalkyl, substituted phenyl alkenyl, substituted pyridinyl alkyl, substituted pyridinylalkenyl, naphthyl, substituted naphthyl, substituted quinolinyl, substituted isoquinolinyl, or substituted 1H-indol-2-yl, wherein substituted cycloalkyl alkyl, substituted piperazinyl, substituted piperidinyl, substituted indanyloxyalkyl, substituted phenyl, substituted phenyl alkyl, substituted phenoxyalkyl, substituted phenylcycloalkyl, substituted phenylalkenyl, substituted pyridinylalkyl, substituted pyridinylalkenyl, substituted naphthyl, substituted quinolinyl, substituted isoquinolinyl, and substituted 1H-indol-2-yl are substituted with $R^8$, $R^9$, and $R^{10}$.

4. A compound according to claim 1, or a pharmaceutically acceptable salt thereof, wherein $R^1$ is substituted cycloalkylalkyl, substituted phenyl, substituted phenylalkyl, substituted phenoxyalkyl, substituted phenylcycloalkyl, substituted phenylalkenyl, substituted pyridinylalkyl, substituted pyridinylalkenyl, or substituted 1H-indol-2-yl, wherein substituted cycloalkylalkyl, substituted phenyl, substituted phenylalkyl, substituted phenoxyalkyl, substituted phenylcycloalkyl, substituted phenylalkenyl, substituted pyridinylalkyl, substituted pyridinylalkenyl, and substituted 1H-indol-2-yl are substituted with $R^8$, $R^9$, and $R^{10}$.

5. A compound according to claim 1, or a pharmaceutically acceptable salt thereof, wherein $R^1$ is substituted phenylalkyl or substituted phenylalkenyl, wherein substituted phenylalkyl and substituted phenylalkenyl are substituted with $R^8$, $R^9$, and $R^{10}$.

6. A compound according to claim 1, or a pharmaceutically acceptable salt thereof, wherein $R^1$ is phenylalkyl substituted with $R^8$, $R^9$, and $R^{10}$.

7. A compound according to claim 1, or a pharmaceutically acceptable salt thereof, wherein Y is -OC(O)-, -C(O)-, -S(O)$_2$-, or

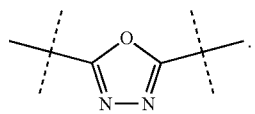

8. A compound according to claim 1, or a pharmaceutically acceptable salt thereof, wherein Y is -OC(O)- or -C(O)-.

9. A compound according to claim 1, or a pharmaceutically acceptable salt thereof, wherein Y is -OC(O)-.

10. A compound according to claim 1, or a pharmaceutically acceptable salt thereof, wherein Y is -C(O)-.

11. A compound according to claim 1, or a pharmaceutically acceptable salt thereof, wherein A is -N-.

12. A compound according to claim 1, or a pharmaceutically acceptable salt thereof, wherein W is -O-, -NR$^6$-, -C(O)-, -S(O)$_2$-, -C(O)-NR$^6$-, or -CR$^3$R$^4$-.

13. A compound according to claim 1, or a pharmaceutically acceptable salt thereof, wherein W is -C(O)-, -C(O)-NR$^6$-, or -CR$^3$R$^4$-.

14. A compound according to claim 1, or a pharmaceutically acceptable salt thereof, wherein W is -C(O)-.

15. A compound according to claim 1, or a pharmaceutically acceptable salt thereof, wherein R$^3$ and R$^4$ are H.

16. A compound according to claim 1, or a pharmaceutically acceptable salt thereof, wherein R$^5$ is H.

17. A compound according to claim 1, or a pharmaceutically acceptable salt thereof, wherein R$^6$ is H or alkyl.

18. A compound according to claim 1, or a pharmaceutically acceptable salt thereof, wherein R$^8$, R$^9$, and R$^{10}$ are independently selected from H, alkyl, haloalkyl, hydroxyhaloalkyl, alkoxy, haloalkoxy, alkoxyhaloalkyl, phenyl, pyridinyl, halogen, cyano, haloalkylsulfanyl, haloalkylsulfinyl, alkylsulfonyl, haloalkylsulfonyl, pyrrolyl substituted with one alkyl, pyrrolidinyl, tetrahydrofuranyl, alkylcarbonyl, and aminosulfonyl substituted on the nitrogen atom with one to two substituents independently selected from H, alkyl, cycloalkyl, cycloalkylalkyl, hydroxyalkyl, alkoxyalkyl, alkylcarbonyl, and cycloalkylcarbonyl.

19. A compound according to claim 1, or a pharmaceutically acceptable salt thereof, wherein R$^8$, R$^9$, and R$^{10}$ are independently selected from H, alkyl, haloalkyl, hydroxyhaloalkyl, alkoxy, haloalkoxy, alkoxyhaloalkyl, phenyl, pyridinyl, halogen, cyano, haloalkylsulfanyl, haloalkylsulfinyl, alkylsulfonyl, haloalkylsulfonyl, and aminosulfonyl substituted on the nitrogen atom with one to two substituents independently selected from H, alkyl, cycloalkyl, cycloalkylalkyl, hydroxyalkyl, alkoxyalkyl, alkylcarbonyl, and cycloalkylcarbonyl.

20. A compound according to claim 1, or a pharmaceutically acceptable salt thereof, wherein R$^8$, R$^9$, and R$^{10}$ are independently selected from H, alkyl, haloalkyl, hydroxyhaloalkyl, alkoxy, haloalkoxy, alkoxyhaloalkyl, phenyl, pyridinyl, halogen, cyano, haloalkylsulfanyl, haloalkylsulfinyl, alkylsulfonyl, haloalkylsulfonyl, and aminosulfonyl substituted on the nitrogen atom with two alkyl substituents.

21. A compound according to claim 1, or a pharmaceutically acceptable salt thereof, wherein R$^8$, R$^9$, and R$^{10}$ are independently selected from H, alkyl, haloalkyl, haloalkoxy, halogen, and alkylsulfonyl.

22. A compound according claim 1, or a pharmaceutically acceptable salt thereof, wherein R$^8$ is H, alkyl, haloalkyl, hydroxyhaloalkyl, alkoxy, haloalkoxy, alkoxyhaloalkyl, phenyl, pyridinyl, halogen, cyano, haloalkylsulfanyl, haloalkylsulfinyl, alkyl sulfonyl, haloalkyl sulfonyl, pyrrolyl substituted with one alkyl, pyrrolidinyl, tetrahydrofuranyl, alkylcarbonyl, or aminosulfonyl substituted on the nitrogen atom with two alkyl substituents.

23. A compound according to claim 1, or a pharmaceutically acceptable salt thereof, wherein R$^8$ is haloalkyl, haloalkoxy, halogen, or alkylsulfonyl.

24. A compound according to claim 1, or a pharmaceutically acceptable salt thereof, wherein R$^8$ is haloalkoxy or halogen.

25. A compound according to claim 1, or a pharmaceutically acceptable salt thereof, wherein R$^8$ is halogen.

26. A compound according to claim 1, or a pharmaceutically acceptable salt thereof, wherein R$^9$ is H, alkyl, haloalkyl, cycloalkyl, cycloalkoxy, alkoxy, haloalkoxy, alkoxyalkoxy, cyano, or halogen.

27. A compound according to claim 1, or a pharmaceutically acceptable salt thereof, wherein R$^9$ is H, alkyl, haloalkyl, alkoxy, or halogen.

28. A compound according to claim 1, or a pharmaceutically acceptable salt thereof, wherein R$^9$ is H, alkyl, or halogen.

29. A compound according to claim 1, or a pharmaceutically acceptable salt thereof, wherein R$^8$ and R$^9$ are halogen.

30. A compound according to claim 1, or a pharmaceutically acceptable salt thereof, wherein R$^{10}$ is H, alkyl, alkoxy, or halogen.

31. A compound according to claim 1, or a pharmaceutically acceptable salt thereof, wherein R$^{10}$ is H or alkyl.

32. A compound according to claim 1, or a pharmaceutically acceptable salt thereof, wherein R$^{10}$ is H.

33. A compound according to claim 1, or a pharmaceutically acceptable salt thereof, wherein m is 1.

34. A compound according to claim 1, or a pharmaceutically acceptable salt thereof, wherein n is 1.

35. A compound according to claim 1, or a pharmaceutically acceptable salt thereof, wherein m and n are 1.

36. A compound according to claim 1, or a pharmaceutically acceptable salt thereof wherein p and q are 1.

37. A compound according to claim 1, or a pharmaceutically acceptable salt thereof, wherein m, n, p, and q are 1.

38. A compound according to claim 1, selected from
1-((3aR,6aS)-5-(1H-benzo[d][1,2,3]triazole-5-carbonyl)hexahydropyrrolo[3,4-c]pyrrol-2(1H)-yl)-3-(3,5-dichlorophenyl)propan-1-one;
(3aR,6aS)-3,5-dichlorobenzyl 5-(1H-benzo[d][1,2,3]triazole-5-carbonyl)hexahydropyrrolo[3,4-c]pyrrole-2(1H)-carboxylate;
(3aR,6aS)-3,5-dichlorobenzyl 5-(1H-benzo[d]imidazole-5-carbonyl)hexahydropyrrolo[3,4-c]pyrrole-2(1H)-carboxylate;
trans-3, 5-dichlorobenzyl 2-(1H-benzo[d][1,2,3]triazole-5-carbonyl)hexahydro -1H-pyrrolo[3,4-c]pyridine-5(6H)-carboxylate;
cis-3,5-dichlorobenzyl 2-(1H-benzo[d][1,2,3]triazole-5-carbonyl)hexahydro-1H-pyrrolo[3,4-c]pyridine-5(6H)-carboxylate;
(3aR,8aS)-3,5-dichlorobenzyl 2-(1H-benzo[d][1,2,3]triazole-5-carbonyl)octahydropyrrolo[3,4-d]azepine-6(7H)-carboxylate;
(1H-benzotriazol-5-yl)-{(3aS,6aR)-5-[2-(3-chloro-phenyl)-ethanesulfonyl]-hexahydro-pyrrolo[3 ,4-c]pyrrol-2-yl}-methanone;
1-((3aR,8aS)-2-(1H-benzo[d][1,2,3]triazole-5-carbonyl)octahydropyrrolo[3,4-d]azepin-6(7H)-yl)-3-(3-chlorophenyl)-2,2-dimethylpropan-1-one;
(E)-1-((3aR,8aS)-2-(1H-benzo[d][1,2,3]triazole-5-carbonyl)octahydropyrrolo[3,4-d]azepin-6(7H)-yl)-3-(3-fluoro-4-(trifluoromethoxy)phenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(2-methyl-4-(trifluoromethoxy)phenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(3-fluoro-4-methoxyphenyl)prop-2-en-1-one;
(E)-1-[(3aS,8aR)-2-(1H-benzotriazole-5-carbonyl)-octahydro-pyrrolo[3,4-d]azepin-6-yl]-3-(2-isopropyl-phenyl)-prop-2-ene-1-one;

(3aS,6aS)-3,5-dichlorobenzyl 5-(1H-benzo[d][1,2,3]triazole-5-carbonyl)hexahydropyrrolo[3,4-c]pyrrole-2(1H)-carboxylate;

trans-5-(1H-benzotriazole-5-carbonyl)-octahydro-pyrrolo[3,4-c]pyridine-2-carboxylic acid 3-methanesulfonyl-5-trifluoromethyl-benzyl ester;

(3aR,6aR)-3,5-dichlorobenzyl 5-(1H-benzo[d][1,2,3]triazole-5-carbonyl)hexahydropyrrolo[3,4-c]pyrrole-2(1H)-carboxylate;

(3aS,6aS)-5-(1H-benzotriazole-5-carbonyl)-hexahydropyrrolo[3,4-c]pyrrole-2-carboxylic acid 3-chloro-5-methanesulfonyl-benzyl ester;

(3aS,6aR)-5-(1H-benzotriazole-5-carbonyl)-hexahydropyrrolo[3,4-c]pyrrole-2-carboxylic acid 3-chloro-5-methanesulfonyl-benzyl ester;

(3aS,8aR)-2-(1H-benzotriazole-5-carbonyl)-octahydropyrrolo[3,4-d]azepine-6-carboxylic acid 3-methanesulfonyl-5-trifluoromethyl-benzyl ester;

(3aS,8aR)-2-(1H-benzotriazole-5-carbonyl)-octahydropyrrolo[3,4-d]azepine-6-carboxylic acid 3-chloro-5-methanesulfonyl-benzyl ester;

(3aS,6aR)-5-(1H-benzotriazole-5-carbonyl)-hexahydropyrrolo[3,4-c]pyrrole-2-carboxylic acid 3-methanesulfonyl-5-trifluoromethyl-benzyl ester;

cis-3,5-dichlorobenzyl 5-(1H-benzo[d][1,2,3]triazole-5-carbonyl)hexahydro-1H-pyrrolo[3,4-c]pyridine-2(3H)-carboxylate;

(3aS,7aR)-5-(1H-benzotriazole-5-carbonyl)-octahydropyrrolo[3,4-c]pyridine-2-carboxylic acid 3-chloro-5-methanesulfonyl-benzyl ester;

trans-3,5-dichlorobenzyl 5-(1H-benzo[d][1,2,3]triazole-5-carbonyl)hexahydro-1H-pyrrolo[3,4-c]pyridine-2(3H)-carboxylate;

(3aR,8aS)-3,5-dichlorobenzyl 6-(1H-benzo[d][1,2,3]triazole-5-carbonyl)octahydropyrrolo[3,4-d]azepine-2(1H)-carboxylate;

(3aS,6aR)-5-(1H-benzotriazole-5-carbonyl)-hexahydropyrrolo[3,4-c]pyrrole-2-carboxylic acid 1-(3-chlorophenyl)-cyclopropyl ester;

(3aS,6aR)-5-(1H-b enzotriazole-5-carbonyl)-hexahydropyrrolo[3,4-c]pyrrole-2-carboxylic acid bicyclo[4.1.0]hept-7-ylmethyl ester;

(3aS,6aR)-5-(1H-benzotriazole-5-carbonyl)-hexahydropyrrolo[3,4-c]pyrrole-2-carboxylic acid adamantan-2-ylmethyl ester;

(3aS,6aR)-5-(1H-benzotriazole-5-carbonyl)-hexahydropyrrolo[3,4-c]pyrrole-2-carboxylic acid 1-fluoro-cyclohexylmethyl ester;

(3aS,6aR)-5-(1H-benzotriazole-5-carbonyl)-hexahydropyrrolo[3,4-c]pyrrole-2-carboxylic acid 2-adamantan-2-yl-ethyl ester;

(3aS,6aR)-5-(1H-benzotriazole-5-carbonyl)-hexahydropyrrolo[3,4-c]pyrrole-2-carboxylic acid 2-adamantan-1-yl-ethyl ester;

(3aS,6aR)-5-(1H-benzotriazole-5-carbonyl)-hexahydropyrrolo[3,4-c]pyrrole-2-carboxylic acid adamantan-1-ylmethyl ester;

(3aS,6aR)-5-(1H-benzotriazole-5-carbonyl)-hexahydropyrrolo[3,4-c]pyrrole-2-carboxylic acid cyclohexylmethyl ester;

cis-5-(1H-benzotriazole-5-carbonyl)-hexahydro-pyrrolo[3,4-c]pyrrole-2-carboxylic acid 3-(2,2,2-trifluoro-1-methoxy-ethyl)-benzyl ester;

cis-5-(1H-benzotriazole-5-carbonyl)-hexahydro-pyrrolo[3,4-c]pyrrole-2-carboxylic acid 3-(2,2,2-trifluoro-1-hydroxy-ethyl)-benzyl ester;

(3aR,6aS)-2-cyclohexylethyl 5-(1H-benzo[d][1,2,3]triazole-5-carbonyl)hexahydropyrrolo[3,4-c]pyrrole-2(1H)-carboxylate;

(3aS,6aR)-5-(1H-benzotriazole-5-carbonyl)-hexahydropyrrolo[3,4-c]pyrrole-2-carboxylic acid 3-fluoro-5-trifluoromethoxy-benzyl ester;

(3aR,6aS)-3-chloro-5-cyanobenzyl 5-(1H-benzo[d][1,2,3]triazole-5-carbonyl)hexahydropyrrolo[3,4-c]pyrrole-2(1H)-carboxylate;

(3aS,6aR)-5-(1H-benzotriazole-5-carbonyl)-hexahydropyrrolo[3,4-c]pyrrole-2-carboxylic acid 3-trifluoromethoxy-benzyl ester;

(3aS,6aR)-5-(1H-benzotriazole-5-carbonyl)-hexahydropyrrolo[3,4-c]pyrrole-2-carboxylic acid 3-fluoro-5-trifluoromethyl-benzyl ester;

(3aS,6aR)-5-(1H-benzotriazole-5-carbonyl)-hexahydropyrrolo[3,4-c]pyrrole-2-carboxylic acid 3-chloro-5-trifluoromethoxy-benzyl ester;

(3aS,6aR)-5-(1H-benzotriazole-5-carbonyl)-hexahydropyrrolo[3,4-c]pyrrole-2-carboxylic acid 4-fluoro-3-trifluoromethoxy-benzyl ester;

(3aR,6aS)-3-cyano-5-fluorobenzyl 5-(1H-benzo[d][1,2,3]triazole-5-carbonyl)hexahydropyrrolo[3,4-c]pyrrole-2(1H)-carboxylate;

(3aR,6aS)-3-chloro-5-methoxybenzyl 5-(1H-benzo[d][1,2,3]triazole-5-carbonyl)hexahydropyrrolo[3,4-c]pyrrole-2(1H)-carboxylate;

(3aS,6aR)-5-(1H-benzotriazole-5-carbonyl)-hexahydropyrrolo[3,4-c]pyrrole-2-carboxylic acid (1S,4R)-3-methyl-bicyclo[2.2.1]hept-2-ylmethyl ester;

(3aS,6aR)-5-(1H-benzotriazole-5-carbonyl)-hexahydropyrrolo[3,4-c]pyrrole-2-carboxylic acid (1R,4S)-1-bicyclo[2.2.1]hept-2-ylmethyl ester;

(3aS,6aS)-5-(1H-benzotriazole-5-carbonyl)-hexahydropyrrolo[3,4-c]pyrrole-2-carboxylic acid 4-trifluoromethoxy-benzyl ester;

1-((3aR,6aS)-5-((1H-benzo[d][1,2,3]triazol-5-yl)methyl)hexahydropyrrolo[3,4-c]pyrrol-2(1H)-yl)-3-(3,5-dichlorophenyl)propan-1-one;

4-{ (E)-3 -[(3aS, 8aR)-2-(1H-benzotriazol-5-ylmethyl)-octahydro-pyrrolo[3 ,4-d]azepin-6-yl]-3 -oxo-propenyl -benzonitrile;

(E)-1-[(3aS,8aR)-2-(1H-benzotriazol-5-ylmethyl)-octahydro-pyrrolo[3,4-d]azepin-6-yl]-3-(4-trifluoromethoxy-phenyl)-prop-2-ene-1-one;

(3aR,7aS)-2-(1H-benzotriazole-5-carbonyl)-octahydropyrrolo[3,4-c]pyridine-5-carboxylic acid 3,5-dichlorobenzyl ester;

(3aS,7aR)-2-(1H-benzotriazole-5-carbonyl)-octahydropyrrolo[3,4-c]pyridine-5-carboxylic acid 3,5-dichlorobenzyl ester;

(+)-trans-3,5-dichlorobenzyl 2-(1H-benzo[d][1,2,3]triazole-5-carbonyl)hexahydro-1H-pyrrolo[3,4-c]pyridine-5(6H)-carboxylate;

(−)-trans-3,5-dichlorobenzyl 2-(1H-benzo[d][1,2,3]triazole-5-carbonyl)hexahydro-1H-pyrrolo[3,4-c]pyridine-5(6H)-carboxylate;

(−)-trans-3,5-dichlorobenzyl 5-(1H-benzo[d][1,2,3]triazole-5-carbonyl)hexahydro-1H-pyrrolo[3,4-c]pyridine-2(3H)-carboxylate;

(+)-trans-3,5-dichlorobenzyl 5-(1H-benzo[d][1,2,3]triazole-5-carbonyl)hexahydro-1H-pyrrolo[3,4-c]pyridine-2(3H)-carboxylate;

(E)-1-[trans-2-(1H-benzotriazole-5-carbonyl)-octahydropyrrolo[3,4-c]pyridin-5-yl]-3-(3,5-dichloro-phenyl)-prop-2-en-1-one;

(1H-benzotriazol-5-yl)-{trans-2-[5-(4-chloro-phenyl)1,3, 4]oxadiazol-2-yl]-octahydro-pyrrolo[3,4-c]pyridin-5-yl}-methanone;

(E)- 1-((3aR,6aS)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one;

(1H-benzotriazol-5-yl)-[(3aR,6aS)-5-(5-chloro-1H-indole-2-carbonyl)-hexahydro-pyrrolo[3,4-c]pyrrol-2-yl]-methanone;

(E)-1-[(3aR,6aS)-5-(1H-benzotriazole-5-carbonyl)-hexahydro-pyrrolo[3,4-c]pyrrol-2-yl]-3-(3-fluoro-5-trifluoromethyl-phenyl)-prop-2-ene-1-one;

1-[(3 aR, 6aS)-5 -(1H-benzotriazole-5 -carbonyl)-hexahydro-pyrrolo[3,4-c]pyrrol-2-yl]-3-(3-fluoro-5-trifluoromethyl-phenyl)-propan-1-one;

(1H-benzotriazol-5-yl)-[(3aR, 6aS)-5-(6-chloro-1H-indole-2-carbonyl)-hexahydro-pyrrolo[3,4-c]pyrrol-2-yl]-methanone;

(E)-1-((3aR,8aS)-2-(1H-benzo[d][1,2,3]triazole-5-carbonyl)octahydropyrrolo[3,4-d]azepin-6(7H)-yl)-3-(4-(trifluoromethylsulfonyl)phenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(4-chlorophenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3 -p-tolylprop-2-en-1-one;

4-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)-N,N-dimethylbenzenesulfonamide;

(E)-1-((3aR,8aS)-2-(1H-benzo[d][1,2,3]triazole-5-carbonyl)octahydropyrrolo[3,4-d]azepin-6(7H)-yl)-3-(4-methoxyphenyl)prop-2-en-1-one;

(E)-1-((3aR,8aS)-6-(1H-benzo[d][1,2,3]triazole-5-carbonyl)octahydropyrrolo[3,4-d]azepin-2(1H)-yl)-3-(4-(trifluoromethoxy)phenyl)prop-2-en-1-one;

4-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)benzonitrile;

(E)-1-((3aR,6aR)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one;

1-((3aR,6aS)-5-(1H-benzo[d][1,2,3]triazole-5-carbonyl)hexahydropyrrolo[3,4-c]pyrrol-2(1H)-yl)-3-(4-(trifluoromethoxy)phenyl)propan-1-one;

(E)-1-((3aR,8aS)-2-(1H-benzo[d][1,2,3]triazole-5-carbonyl)octahydropyrrolo[3,4-d]azepin-6(7H)-yl)-3-(4-fluorophenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-phenylprop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(pyridin-2-yl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(pyridin-3-yl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(3-chlorophenyl)prop-2-en-1-one;

(E)-1-((3aR,8aS)-6-(1H-benzo[d][1,2,3]triazole-5-carbonyl)octahydropyrrolo[3,4-d]azepin-2(1H)-yl)-3-(4-chlorophenyl)prop-2-en-1-one;

(E)-1-((3aR,8aS)-6-(1H-benzo[d][1,2,3]triazole-5-carbonyl)octahydropyrrolo[3,4-d]azepin-2(1H)-yl)-3-(3-(trifluoromethoxy)phenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(4-(difluoromethoxy)phenyl)prop-2-en-1-one;

(E)-1-((3aR,6aR)-5-(1H-benzo[d][1,2,3]triazole-5-carbonyl)hexahydropyrrolo[3,4-c]pyrrol-2(1H)-yl)-3-(3-(trifluoromethoxy)phenyl)prop-2-en-1-one;

4-((E)-3-((3aR,6aR)-5-(1H-benzo[d][1,2,3]triazole-5-carbonyl)hexahydropyrrolo[3,4-c]pyrrol-2(1H)-yl)-3-oxoprop-1-enyl)benzonitrile;

(E)-1-((3aS,6aS)-5-(1H-benzo[d][1,2,3]triazole-5-carbonyl)hexahydropyrrolo[3,4-c]pyrrol-2(1H)-yl)-3-(4-(trifluoromethoxy)phenyl)prop-2-en-1-one;

(−)-(E)- 1-[trans-5-(1H-benzotriazole-5-carbonyl)-octahydro-pyrrolo[3,4-c]pyridin-2-yl]-3-(4-trifluoromethoxy-phenyl)-3-prop-2-ene-1-one;

(+)-(E)- 1-[trans-5 -(1H-benzotriazole-5-carbonyl)-octahydro-pyrrolo[3,4-c]pyridin-2-yl]-3-(4-trifluoromethoxy-phenyl)-prop-2-ene-1-one;

(E)-1-((3aR,8aS)-2-(1H-benzo[d][1,2,3]triazole-5-carbonyl)octahydropyrrolo[3,4-d]azepin-6(7H)-yl)-3-(3,5-dichlorophenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(pyridin-4-yl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(2,4-difluorophenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(2,4-dichlorophenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(3,4-dichlorophenyl)prop-2-en-1-one;

(E)-1-[(3aS,7aS)-5-(1H-benzotriazole-5-carbonyl)-octahydro-pyrrolo[3,4-c]pyridin-2-yl]-3-(4-difluoromethoxy-phenyl)-prop-2-ene-1-one;

4-{(E)-3-[(3aS,7aS)-5-(1H-benzotriazole-5-carbonyl)-octahydro-pyrrolo[3,4-c]pyridin-2-yl]-3-oxo-propenyl}-benzonitrile;

4-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)-3-fluorobenzonitrile;

4-((E)-3-((3aR,6aR)-5-(1H-benzo[d][1,2,3]triazole-5-carbonyl)hexahydropyrrolo[3,4-c]pyrrol-2(1H)-yl)-3-oxoprop-1-enyl)-3-fluorobenzonitrile;

(E)-1-((3aR,6aR)-5-(1H-benzo[d][1,2,3]triazole-5-carbonyl)hexahydropyrrolo[3,4-c]pyrrol-2(1H)-yl)-3-(4-(difluoromethoxy)phenyl)prop-2-en-1-one;

(E)-1-[cis-2-(1H-benzotriazole-5-carbonyl)-octahydro-pyrrolo[3,4-c]pyridin-5-yl]-3-(4-trifluoromethoxy-phenyl)-prop-2-ene-1-one;

3-((E)-3-((3aR,8aS)-2-(1H-benzo[d][1,2,3]triazole-5-carbonyl)octahydropyrrolo[3,4-d]azepin-6(7H)-yl)-3-oxoprop-1-enyl)benzonitrile;

(E)-1-((3aR,8aS)-2-(1H-benzo[d][1,2,3]triazole-5-carbonyl)octahydropyrrolo[3,4-d]azepin-6(7H)-yl)-3-(2-fluoro-4-(trifluoromethoxy)phenyl)prop-2-en-1-one;

(E)-1-((3aR,6aR)-5-(1H-benzo[d][1,2,3]triazole-5-carbonyl)hexahydropyrrolo[3,4-c]pyrrol-2(1H)-yl)-3-(2-fluoro-4-(trifluoromethoxy)phenyl)prop-2-en-1-one;

(E)1((3aR,6aR)-5-(1H-benzo[d][1,2,3]triazole-5-carbonyl)hexahydropyrrolo[3,4-c]pyrrol-2(1H)-yl)-3-(4-chloro-2-fluorophenyl)prop-2-en-1-one;

(E)-1-((3aR,6aR)-5-(1H-benzo[d][1,2,3]triazole-5-carbonyl)hexahydropyrrolo[3,4-c]pyrrol-2(1H)-yl)-3-(3,5-dichlorophenyl)prop-2-en-1-one;

1-[(3aR,6aR)-5-(1H-benzotriazole-5-carbonyl)-hexahydro-pyrrolo[3,4-c]pyrrol-2-yl]-3-(4-trifluoromethoxy-phenyl)-propan-1-one;

(E)-1-[(3aR, 6aR)-5-(1H-benzotriazole-5-carbonyl)-hexahydro-pyrrolo[3,4-c]pyrrol-2-yl]-3-(3-chloro-5-methanesulfonyl-phenyl)-prop-2-ene-1-one;

(E)-1-[(3aR,6aR)-5-(1H-benzotriazole-5-carbonyl)-hexahydro-pyrrolo[3,4-c]pyrrol-2-yl]-3-(3,5-dimethoxy-phenyl)-prop-2-ene- 1-one;

(E)-1-[(3aR,6aR)-5-(1H-benzotriazole-5-carbonyl)-hexahydro-pyrrolo[3,4-c]pyrrol-2-yl]-3-(3-chloro-5-trifluoromethoxy-phenyl)-prop-2-ene-1-one;

(E)-1-[(3aR,6aR)-5-(1H-benzotriazole-5-carbonyl)-hexahydro-pyrrolo[3,4-c]pyrrol-2-yl]-3-(3-chloro-5-methoxy-phenyl)-prop-2-ene-1-one;

3-{(E)-3-[(3aR,6aR)-5-(1H-benzotriazole-5-carbonyl)-hexahydro-pyrrolo[3,4-c]pyrrol-2-yl]-3-oxo-propenyl}-5-chloro-benzonitrile;

(E)-1-[(3aR,6aR)-5-(1H-benzotriazole-5-carbonyl)-hexahydro-pyrrolo[3,4-c]pyrrol-2-yl]-3-(3-methoxy-5-trifluoromethoxy-phenyl)-prop-2-ene-1-one;

(E)-1-[(3aR, 6aR)-5-(1H-benzotriazole-5-carbonyl)-hexahydro-pyrrolo[3,4-c]pyrrol-2-yl]-3-phenyl-prop-2-ene-1-one;

1-[(3aR,6aR)-5-(1H-benzotriazole-5-carbonyl)-hexahydro-pyrrolo[3,4-c]pyrrol-2-yl]-3-phenyl-propan-1-one;

(E)-1-[(3aR,6aR)-5-(1H-benzotriazole-5-carbonyl)-hexahydro-pyrrolo[3,4-c]pyrrol-2-yl]-3-(4-trifluoromethyl-phenyl)-prop-2-ene-1-one;

1-[(3aR,6aR)-5-(1H-benzotriazole-5-carbonyl)-hexahydro-pyrrolo[3,4-c]pyrrol-2-yl]-3-(4-trifluoromethyl-phenyl)-propan-1-one;

1-[(3aR,6aR)-5-(1H-benzotriazole-5-carbonyl)-hexahydro-pyrrolo[3,4-c]pyrrol-2-yl]-3-(6-trifluoromethyl-pyridin-3-yl)-propan-1-one;

1-[(3aS,6aS)-5-(1H-benzotriazole-5-carbonyl)-hexahydro-pyrrolo[3,4-c]pyrrol-2-yl]-2-(4-trifluoromethoxy-phenoxy)-ethanone;

1-[(3aS,6aS)-5-(1H-benzotriazole-5-carbonyl)-hexahydro-pyrrolo[3,4-c]pyrrol-2-yl]-2-(4-chloro-2-isopropyl-5-methyl-phenoxy)-ethanone;

1-[(3aR,6aR)-5-(1H-benzotriazole-5-carbonyl)-hexahydro-pyrrolo[3,4-c]pyrrol-2-yl]-3-biphenyl-4-yl-propan-1-one;

(E)-1-((3aR,8aS)-2-(1H-benzo[d][1,2,3]triazole-5-carbonyl)octahydropyrrolo[3,4-d]azepin-6(7H)-yl)-3-(4-fluoro-2-(trifluoromethyl)phenyl)prop-2-en-1-one;

1-[(3aS,6aR)-5-(1H-Benzotriazole-5-carbonyl)-hexahydro-pyrrolo[3,4-c]pyrrol-2-yl]-2-(4-chloro-2-isopropyl-5-methyl-phenoxy)-ethanone;

(E)-1-((3aR,8aS)-2-(1H-benzo[d][1,2,3]triazole-5-carbonyl)octahydropyrrolo[3,4-d]azepin-6(7H)-yl)-3-(4-(methylsulfonyl)phenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(4-(trifluoromethylthio)phenyl)prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(4-(trifluoromethoxy)phenyl)prop-2-en-1-one;

1-((3aR,6aS)-5-(1H-benzo[d][1,2,3]triazole-5-carbonyl)hexahydropyrrolo[3,4-c]pyrrol-2(1H)-yl)-2-(3-(trifluoromethoxy)phenoxy)ethanone;

(E)-1-((3aR,8aS)-2-(1H-benzo[d][1,2,3]triazole-5-carbonyl)octahydropyrrolo[3,4-d]azepin-6(7H)-yl)-3-(3-(trifluoromethoxy)phenyl)prop-2-en-1-one;

(E)-1-[trans-5-(1H-benzotriazole-5-carbonyl)-octahydropyrrolo[3,4-c]pyridin-2-yl]-3-(3-trifluoromethoxy-phenyl)-prop-2-en-1-one;

(E)-1-[trans-5-(1H-benzotriazole-5-carbonyl)-octahydropyrrolo[3,4-c]pyridin-2-yl]-3-(4-trifluoromethoxy-phenyl)-prop-2-en-1-one;

(E)-1-[trans-5-(1H-benzotriazole-5-carbonyl)-octahydropyrrolo[3,4-c]pyridin-2-yl]-3-(3-chloro-5-trifluoromethoxy-phenyl)-prop-2-en-1-one;

(E)-1-[trans-5-(1H-benzotriazole-5-carbonyl)-octahydropyrrolo[3,4-c]pyridin-2-yl]-3-(3,5-dichloro-phenyl)-prop-2-en-1-one;

(E)-1-[(3aR,6aR)-5-(1H-benzotriazole-5-carbonyl)-hexahydro-pyrrolo[3,4-c]pyrrol-2-yl]-3-(6-phenyl-pyridin-3-yl)-prop-2-en-1-one;

(E)-1-[(3aR,6aR)-5-(1H-benzotriazole-5-carbonyl)-hexahydro-pyrrolo[3,4-c]pyrrol-2-yl]-3-(5-trifluoromethyl-pyridin-2-yl)-prop-2-en-1-one;

(E)-1-[(3aR,6aR)-5-(1H-benzotriazole-5-carbonyl)-hexahydro-pyrrolo[3,4-c]pyrrol-2-yl]-3-(4-pyridin-4-yl-phenyl)-prop-2-en-1-one;

(E)-1-[(3aR,6aR)-5-(1H-benzotriazole-5-carbonyl)-hexahydro-pyrrolo[3,4-c]pyrrol-2-yl]-3-(4-pyridin-3-yl-phenyl)-prop-2-en-1-one;

(E)-1-[(3aR,6aR)-5-(1H-benzotriazole-5-carbonyl)-hexahydro-pyrrolo[3,4-c]pyrrol-2-yl]-3-(4-pyridin-2-yl-phenyl)-prop-2-en-1-one;

1-[(3aS,6aR)-5-(1H-benzotriazole-5-carbonyl)-hexahydro-pyrrolo[3,4-c]pyrrol-2-yl]-2-(4-chloro-3-methyl-phenoxy)-ethanone;

1-[(3aS,6aR)-5-(1H-benzotriazole-5-carbonyl)-hexahydro-pyrrolo[3,4-c]pyrrol-2-yl]-2-(4-chloro-2-methyl-phenoxy)-ethanone;

(E)-1-[(3aR,6aR)-5-(1H-benzotriazole-5-carbonyl)-hexahydro-pyrrolo[3,4-c]pyrrol -2-yl]-3-(5-phenyl-pyridin-2-yl)-prop-2-en-1-one;

(E)-1-((3aR,8aS)-2-(1H-benzo[d][1,2,3]triazole-5-carbonyl)octahydropyrrolo[3,4-d]azepin-6(7H)-yl)-3-(4-(trifluoromethylsulfinyl)phenyl)prop-2-en-1-one;

1-((3aR,8aS)-2-(1H-benzo[d][1,2,3]triazole-5-carbonyl)octahydropyrrolo[3,4-d]azepin-6(7H)-yl)-3-(3-fluoro-4-(trifluoromethoxy)phenyl)propan-1-one;

1-[(3aR,6aR)-5-(1H-benzotriazole-5-carbonyl)-hexahydro-pyrrolo[3,4-c]pyrrol-2-yl]-3-(4-difluoromethoxy-phenyl)-propan-1-one;

1-[(3aR,6aR)-5-(1H-benzotriazole-5-carbonyl)-hexahydro-pyrrolo[3,4-c]pyrrol-2-yl]-3-(2-fluoro-4-trifluoromethoxy-phenyl)-propan-1-one;

1-((3aR,8aS)-2-(1H-benzo[d][1,2,3]triazole-5-carbonyl)octahydropyrrolo[3,4-d]azepin-6(7H)-yl)-3-(4-fluoro-2-(trifluoromethyl)phenyl)propan-1-one;

1-((3aR,8aS)-2-(1H-benzo[d][1,2,3]triazole-5-carbonyl)octahydropyrrolo[3,4-d]azepin-6(7H)-yl)-3-(2-methyl-4-(trifluoromethoxy)phenyl)propan-1-one;

1-((3aR,8aS)-2-(1H-benzo[d][1,2,3]triazole-5-carbonyl)octahydropyrrolo[3,4-d]azepin-6(7H)-yl)-3-(3-fluoro-4-methoxyphenyl)propan-1-one;

1-[(3aS,8aR)-2-(1H-benzotriazole-5-carbonyl)-octahydro-pyrrolo[3,4-d]azepin-6-yl]-3-(2-isopropyl-phenyl)-propan-1-one;

1-[(3aR,6aR)-5-(1H-benzotriazole-5-carbonyl)-hexahydro-pyrrolo[3,4-c]pyrrol-2-yl]-3-(5-trifluoromethyl-pyridin-2-yl)-propan-1-one;

1-[(3aR,6aR)-5-(1H-benzotriazole-5-carbonyl)-hexahydro-pyrrolo[3,4-c]pyrrol-2- yl]-3-(5-phenyl-pyridin-2-yl)-propan-1-one;

1-[(3aR,6aR)-5-(1H-benzotriazole-5-carbonyl)-hexahydro-pyrrolo[3,4-c]pyrrol-2-yl]-3-(4-pyridin-4-yl-phenyl)-propan-1-one;
1-[(3aR,6aR)-5-(1H-benzotriazole-5-carbonyl)-hexahydro-pyrrolo[3,4-c]pyrrol-2-yl]-3-(4-pyridin-3-yl-phenyl)-propan-1-one; and
1-[(3aR,6aR)-5-(1H-benzotriazole-5-carbonyl)-hexahydro-pyrrolo[3,4-c]pyrrol-2-yl]-3-(4-pyridin-2-yl-phenyl)-propan-1-one;
or a pharmaceutically acceptable salt thereof.

39. A compound according to claim 1, selected from
trans-2-(1H-benzotriazole-5-carbonyl)-octahydro-pyrrolo[3,4-c]pyridine-5-carboxylic acid 3-chloro-5-methanesulfonyl-benzyl ester;
trans-2-(1H-benzotriazole-5-carbonyl)-octahydro-pyrrolo[3,4-c]pyridine-5-carboxylic acid 4-trifluoromethoxy-benzyl ester;
1-[trans-2-(1H-benzotriazole-5-carbonyl)-octahydro-pyrrolo[3,4-c]pyridin-5-yl]-2-(4-trifluoromethoxy-phenoxy)-ethanone;
(E)-1-((3aR,8aS)-2-(1H-benzo[d][1,2,3]triazole-5-carbonyl)octahydropyrrolo[3,4-d]azepin-6(7H)-yl)-3-(3-chloro-5-(trifluoromethyl)phenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(4-methoxy-2-(trifluoromethyl)phenyl)prop-2-en-1-one;
(E)-1-((3aR,8aS)-2-(1H-benzo[d][1,2,3]triazole-5-carbonyl)octahydropyrrolo[3,4-d]azepin-6(7H)-yl)-3-(2-cyclopropylphenyl)prop-2-en-1-one;
trans-2-(1H-benzotriazole-5-carbonyl)-octahydro-pyrrolo[3,4-c]pyridine-5-carboxylic acid 4-fluoro-2-trifluoromethyl-benzyl ester;
trans-2-(1H-benzotriazole-5-carbonyl)-octahydro-pyrrolo[3,4-c]pyridine-5-carboxylic acid 2-cyclopropyl-4-trifluoromethyl-benzyl ester;
1-[(3aS,8aR)-2-(1H-benzotriazole-5-carbonyl)-octahydro-pyrrolo[3,4-d]azepin-6-yl]-2-(2-trifluoromethoxy-phenoxy)-ethanone;
trans-2-(1H-benzotriazole-5-carbonyl)-octahydro-pyrrolo[3,4-c]pyridine-5-carboxylic acid 2-methoxy-4-trifluoromethoxy-b enzyl ester;
4-{2-[(3aS,8aR)-2-(1H-benzotriazole-5-carbonyl)-octahydro-pyrrolo[3,4-d]azepin-6-yl]-2-oxo-ethoxy}-3-trifluoromethyl-benzonitrile;
1-[(3aS,8aR)-2-(1H-benzotriazole-5-carbonyl)-octahydro-pyrrolo[3,4-d]azepin-6-yl]-2-(4-chloro-2-isopropyl-5-methyl-phenoxy)-ethanone;
1-[(3aS,8aR)-2-(1H-benzotriazole-5-carbonyl)-octahydro-pyrrolo[3,4-d]azepin-6-yl]-2[4-methyl-2-(1-methyl-pyrrolidin-3-yl)-phenoxy]-ethanone;
1-[(3aS,8aR)-2-(1H-benzotriazole-5-carbonyl)-octahydro-pyrrolo[3,4-d]azepin-6-yl]-2-(2-chloro-4-fluoro-phenoxy)-ethanone;
1-((3aR,8aS)-2-(1H-benzo[d][1,2,3]triazole-5-carbonyl)octahydropyrrolo[3,4-d]azepin-6(7H)-yl)-2-(2-chloro-4-(trifluoromethyl)phenoxy)ethanone;
1-((3aR,8aS)-2-(1H-benzo[d][1,2,3]triazole-5-carbonyl)octahydropyrrolo[3,4-d]azepin-6(7H)-yl)-2-(6-isopropyl-3,3-dimethyl-2,3-dihydro-1H-inden-5-yloxy)ethanone;
(3aS,8aR)-2-(1H-benzotriazole-5-carbonyl)-octahydropyrrolo[3,4-d]azepine-6-carboxylic acid 2-fluoro-4-trifluoromethoxy-benzyl ester;
1-((3aR,8aS)-2-(1H-benzo[d][1,2,3]triazole-5-carbonyl)octahydropyrrolo[3,4-d]azepin-6(7H)-yl)-2-(5-chloro-2-(trifluoromethyl)phenoxy)ethanone;
1-[(3aS,8aR)-2-(1H-benzotriazole-5-carbonyl)-1,3,3a,4,5,7,8,8a-octahydropyrrolo[3,4-d]azepin-6-yl]-2-(2-tert-butyl-4-methoxyphenoxy)ethanone;
4-[2-[(3aS,8aR)-2-(1H-benzotriazole-5-carbonyl)-1,3,3a,4,5,7,8,8a-octahydropyrrolo[3,4-d]azepin-6-yl]-2-oxoethoxy]-3-propan-2-ylbenzonitrile;
1-[(3aS,8aR)-2-(1H-benzotriazole-5-carbonyl)-1,3,3a,4,5,7,8,8a-octahydropyrrolo[3,4-d]azepin-6-yl]-3-[3-fluoro-4-(2,2,2-trifluoroethoxy)phenyl]propan-1-one;
1-[(3aS,8aR)-2-(1H-benzotriazole-5-carbonyl)-1,3,3a,4,5,7,8,8a-octahydropyrrolo[3,4-d]azepin-6-yl]-3-[2-fluoro-4-(2,2,2-trifluoroethoxy)phenyl]propan-1-one;
(3aS,8aR)-2-(1H-benzotriazole-5-carbonyl)-octahydropyrrolo[3,4-d]azepine-6-carboxylic acid 3-fluoro-4-(2,2,2-trifluoro-ethoxy)-benzyl ester;
(3aS,8aR)-2-(1H-benzotriazole-5-carbonyl)-octahydropyrrolo[3,4-d]azepine-6-carboxylic acid 2-fluoro-4-(2,2,2-trifluoro-ethoxy)-benzyl ester;
(3aS,8aR)-2-(1H-benzotriazole-5-carbonyl)-octahydropyrrolo[3,4-d]azepine-6-carboxylic acid 4-(2,2,2-trifluoro-ethoxy)-benzyl ester;
(3aS,6aS)-5-(1H-benzotriazole-5-carbonyl)-hexahydropyrrolo[3,4-c]pyrrole-2-carboxylic acid 4-cyano-benzyl ester;
(3aS,6aS)-5-(1H-benzotriazole-5-carbonyl)-hexahydropyrrolo[3,4-c]pyrrole-2-carboxylic acid 4-(1,1,2,2-tetrafluoro-ethoxy)-benzyl ester;
(3aS,6aS)-5-(1H-benzotriazole-5-carbonyl)-hexahydropyrrolo[3,4-c]pyrrole-2-carboxylic acid 4-difluoromethoxy-3-fluoro-benzyl ester;
(3aS,6aS)-5-(1H-benzotriazole-5-carbonyl)-hexahydropyrrolo[3,4-c]pyrrole-2-carboxylic acid 4-difluoromethoxy-benzyl ester;
(3aS,6aS)-5-(1H-benzotriazole-5-carbonyl)-hexahydropyrrolo[3,4-c]pyrrole-2-carboxylic acid 3-fluoro-4-trifluoromethoxy-benzyl ester;
(3aS,6aS)-5-(1H-benzotriazole-5-carbonyl)-hexahydropyrrolo[3,4-c]pyrrole-2-carboxylic acid 4-(2,2,2-trifluoro-ethoxy)-benzyl ester;
(3aS,6aS)-5-(1H-benzotriazole-5-carbonyl)-hexahydropyrrolo[3,4-c]pyrrole-2-carboxylic acid 5-trifluoromethoxy-pyridin-2-ylmethyl ester;
(3aS,6aS)-5-(1H-benzotriazole-5-carbonyl)-hexahydropyrrolo[3,4-c]pyrrole-2-carboxylic acid 2-fluoro-4-trifluoromethoxy-benzyl ester;
(3aS,6aS)-5-(1H-benzotriazole-5-carbonyl)-hexahydropyrrolo[3,4-c]pyrrole-2-carboxylic acid 4-cyano-2-ethoxy-benzyl ester;
(3aS,6aS)-5-(1H-benzotriazole-5-carbonyl)-hexahydropyrrolo[3,4-c]pyrrole-2-carboxylic acid 4-cyano-2-isopropyl-benzyl ester;
(3aS,6aS)-5-(1H-benzotriazole-5-carbonyl)-hexahydropyrrolo[3,4-c]pyrrole-2-carboxylic acid 4-cyano-2-isopropyl-5-methyl-benzyl ester;
(3aR,6aR)-5-(1H-benzotriazole-5-carbonyl)-hexahydropyrrolo[3,4-c]pyrrole-2-carboxylic acid 4-trifluoromethoxy-benzyl ester;
(3aS,6aS)-5-(1H-benzotriazole-5-carbonyl)-hexahydropyrrolo[3,4-c]pyrrole-2-carboxylic acid 2-fluoro-4-trifluoromethyl-benzyl ester;
(3aS,6aS)-5-(1H-benzotriazole-5-carbonyl)-hexahydropyrrolo[3,4-c]pyrrole-2-carboxylic acid 4-trifluoromethyl-benzyl ester;
(3aS,6aS)-5-(1H-benzotriazole-5-carbonyl)-hexahydropyrrolo[3,4-c]pyrrole-2-carboxylic acid 4-cyano-2-methanesulfonyl-benzyl ester;

(3aS,6aS)-5-(1H-benzotriazole-5-carbonyl)-hexahydro-pyrrolo[3,4-c]pyrrole-2-carboxylic acid 4-cyano-2-ethoxy-5-fluoro-benzyl ester;
(3aS,6aS)-5-(1H-benzotriazole-5-carbonyl)-hexahydro-pyrrolo[3,4-c]pyrrole-2-carboxylic acid 4-cyano-2-cyclobutoxy-benzyl ester;
(3aS,6aS)-5-(1H-benzotriazole-5-carbonyl)-hexahydro-pyrrolo[3,4-c]pyrrole-2-carboxylic acid 4-cyano-2-isopropoxy-benzyl ester;
(3aS,6aS)-5-(1H-benzotriazole-5-carbonyl)-hexahydro-pyrrolo[3,4-c]pyrrole-2-carboxylic acid 4-cyano-2-(2,2,2-trifluoro-ethoxy)-benzyl ester;
(3aS,6aS)-5-(1H-benzotriazole-5-carbonyl)-hexahydro-pyrrolo[3,4-c]pyrrole-2-carboxylic acid 4-chloro-2-ethoxy-5-fluoro-benzyl ester;
(E)-1-[trans-2-(1H-benzotriazol-5-ylmethyl)-octahydro-pyrrolo[3,4-c]pyridin-5-yl]-3-(4-trifluoromethoxy-phenyl)-propenone;
1-[(3aR,6aR)-5-(1H-benzotriazole-5-carbonyl)-hexahydro-pyrrol[3,4-c]pyrrol-2-yl]-3-(6-phenyl-pyridin-3-yl)-propan-1-one;
1-[(3aS,6aS)-5-(1H-benzotriazole-5-carbonyl)-hexahydro-pyrrol[3,4-c]pyrrol-2-yl]-2-(2-isopropyl-phenoxy)-ethanone;
1-[(3aS,6aS)-5-(1H-benzotriazole-5-carbonyl)-hexahydro-pyrrol[3,4-c]pyrrol-2-yl]-2-(2-trifluoromethyl-phenoxy)-ethanone;
1-[(3aS,6aS)-5-(1H-benzotriazole-5-carbonyl)-hexahydro-pyrrol[3,4-c]pyrrol-2-yl]-2-(biphenyl-2-yloxy)-ethanone;
1-[(3aS,6aS)-5-(1H-benzotriazole-5-carbonyl)-hexahydro-pyrrol[3,4-c]pyrrol-2-yl]-2-(2-chloro-4-trifluoromethoxy-phenoxy)-ethanone;
1-[(3aS,6aS)-5-(1H-benzotriazole-5-carbonyl)-hexahydro-pyrrol[3,4-c]pyrrol-2-yl]-2-(2-pyrrol-1-yl-phenoxy)-ethanone;
4-{2-[(3aS,6aS)-5-(1H-benzotriazole-5-carbonyl)-hexahydro-pyrrol[3,4-c]pyrrol-2-yl]-2-oxo-ethoxy}-3-methoxy-benzonitrile;
4-{2-[(3aS,6aS)-5-(1H-benzotriazole-5-carbonyl)-hexahydro-pyrrol[3,4-c]pyrrol-2-yl]-2-oxo-ethoxy}-benzonitrile;
1-[(3aS,6aS)-5-(1H-benzotriazole-5-carbonyl)-hexahydro-pyrrol[3,4-c]pyrrol-2-yl]-2-phenoxy-ethanone;
2-{2-[(3aS,6aS)-5-(1H-benzotriazole-5-carbonyl)-hexahydro-pyrrol[3,4-c]pyrrol-2-yl]-2-oxo-ethoxy}-5-trifluoromethoxy-benzonitrile;
1-((3aR,8aS)-2-(1H-benzo[d][1,2,3]triazole-5-carbonyl)octahydropyrrolo[3,4-d]azepin-6(7H)-yl)-2-(2-isopropyl-5-methylphenoxy)ethanone;
(1H-benzotriazol-5-yl)-[(3aS,6aS)-5-(6-trifluoromethoxy-1H-indole-2-carbonyl)-hexahydro-pyrrolo[3,4-c]pyrrol-2-yl]-methanone;
(1H-benzotriazol-5-yl)-[(3aS,6aS)-5-(5-trifluoromethoxy-1H-indole-2-carbonyl)-hexahydro-pyrrolo[3,4-c]pyrrol-2-yl]-methanone;
1-[trans-2-(1H-benzotriazole-5-carbonyl)-octahydro-pyrrolo[3,4-c]pyridin-5-yl]-3-(4-trifluoromethoxy-phenyl)-propan-1-one;
1-[trans-2-(1H-benzotriazol-5-ylmethyl)-octahydro-pyrrolo[3,4-c]pyridin-5-yl]-3-(4-trifluoromethoxy-phenyl)-propan-1-one;
1-((3aR,8aS)-2-(1H-benzo[d][1,2,3]triazole-5-carbonyl)octahydropyrrolo[3,4-d]azepin-6(7H)-yl)-3-(3-chloro-5-(trifluoromethyl)phenyl)propan-1-one;
1-((3aR,8aS)-2-(1H-benzo[d][1,2,3]triazole-5-carbonyl)octahydropyrrolo[3,4-d]azepin-6(7H)-yl)-3-(4-methoxy-2-(trifluoromethyl)phenyl)propan-1-one;
1-((3aR,8aS)-2-(1H-benzo[d][1,2,3]triazole-5-carbonyl)octahydropyrrolo[3,4-d]azepin-6(7H)-yl)-3-(2-cyclopropylphenyl)propan-1-one;
1-[(3aR,6aR)-5-(1H-benzotriazole-5-carbonyl)-1,3,3a,4,6,6a-hexahydropyrrolo[3,4-c]pyrrol-2-yl]-3-[3-methoxy-5-(trifluoromethoxy)phenyl]propan-1-one;
1-[(3aS,6aS)-5-(1H-benzotriazole-5-carbonyl)-hexahydro-pyrrolo[3,4-c]pyrrol-2-yl]-2-(2-isopropyl-5-methyl-phenoxy)-ethanone;
1-[(3aS,6aS)-5-(1H-benzotriazole-5-carbonyl)-hexahydro-pyrrolo[3,4-c]pyrrol-2-yl]-2-(2-bromo-4-trifluoromethoxy-phenoxy)-ethanone;
(1H-benzotriazol-5-yl)-[(3aR,6aR)-5-(4'-chloro-biphenyl-4-carbonyl)-hexahydro-pyrrolo[3,4-c]pyrrol-2-yl]-methanone;
4-{2-[(3aS,6aS)-5-(1H-benzotriazole-5-carbonyl)-hexahydro-pyrrolo[3,4-c]pyrrol-2-yl]-2-oxo-ethoxy}-3-isopropyl-benzonitrile;
2-(2-Acetyl-phenoxy)-1-[(3aS,6aS)-5-(1H-benzotriazole-5-carbonyl)-hexahydro-pyrrolo[3,4-c]pyrrol-2-yl]-ethanone;
4-{2-[(3aS,6aS)-5-(1H-benzotriazole-5-carbonyl)-hexahydro-pyrrolo[3,4-c]pyrrol-2-yl]-2-oxo-ethoxy}-5-isopropyl-2-methyl-benzonitrile;
(1H-benzotriazol-5-yl)-[(3aR,6aR)-5-(naphthalene-2-carbonyl)-hexahydro-pyrrolo[3,4-c]pyrrol-2-yl]-methanone;
(1H-benzotriazol-5-yl)-[(3aS,6aS)-5-(4-methoxy-naphthalene-2-carbonyl)-hexahydro-pyrrolo[3,4-c]pyrrol-2-yl]-methanone;
4-{2-[(3aS,6aS)-5-(1H-benzotriazole-5-carbonyl)-hexahydro-pyrrolo[3,4-c]pyrrol-2-yl]-2-oxo-ethoxy}-3-ethoxy-benzonitrile;
1-[(3aR,6aR)-5-(1H-benzotriazole-5-carbonyl)-hexahydro-pyrrolo[3,4-c]pyrrol-2-yl]-3-(3-fluoro-4-trifluoromethoxy-phenyl)-propan-1-one;
1-[(3aS,6aS)-5-(1H-benzotriazole-5-carbonyl)-hexahydro-pyrrolo[3,4-c]pyrrol-2-yl]-2-(4-chloro-2-isopropyl-phenoxy)-ethanone;
1-[(3aS,6aS)-5-(1H-benzotriazole-5-carbonyl)-hexahydro-pyrrolo[3,4-c]pyrrol-2-yl]-3-(4-trifluoromethoxy-phenyl)-propan-1-one;
(1H-benzotriazol-5-yl)-[(3aS,6aS)-5-(4'-chloro-biphenyl-4-carbonyl)-hexahydro-pyrrolo[3,4-c]pyrrol-2-yl]-methanone;
1-[(3aS,6aS)-5-(1H-benzotriazole-5-carbonyl)-hexahydro-pyrrolo[3,4-c]pyrrol-2-yl]-2-[2-(tetrahydro-furan-2-yl)-phenoxy]-ethanone;
(1H-benzotriazol-5-yl)-[(3aR,6aR)-5-(4-methoxy-naphthalene-2-carbonyl)-hexahydro-pyrrolo[3,4-c]pyrrol-2-yl]-methanone;
1-[(3aS,6aS)-5-(1H-benzotriazole-5-carbonyl)-hexahydro-pyrrolo[3,4-c]pyrrol-2-yl]-2-(2-tert-butyl-phenoxy)-ethanone;
[(3aR,6aR)-5-(1H-benzotriazole-5-carbonyl)-hexahydro-pyrrolo[3,4-c]pyrrol-2-yl]-[trans-4-(4-chloro-phenyl)-cyclohexyl]-methanone;
1-[(3aR,6aR)-5-(1H-benzotriazole-5-carbonyl)-hexahydro-pyrrolo[3,4-c]pyrrol-2-yl]-3-(3-fluoro-4-trifluoromethyl-phenyl)-propan-1-one;
1-[(3aR,6aR)-5-(1H-benzotriazole-5-carbonyl)-hexahydro-pyrrolo[3,4-c]pyrrol-2-yl]-3-(2-fluoro-4-trifluoromethyl-phenyl)-propan-1-one;

1-[(3aS,6aS)-5-(1H-benzotriazole-5-carbonyl)-1,3,3a,4,
6,6a-hexahydropyrrolo[3,4-c]pyrrol-2-yl]-2-(2-pyridin-3-ylphenoxy)ethanone;
4-[3-[(3aR,6aR)-5-(1H-benzotriazole-5-carbonyl)-1,3,3a,
4,6,6a-hexahydropyrrolo[3,4-c]pyrrol-2-yl]-3-oxopropyl]-2-methyl-5-propan-2-ylbenzonitrile;
4-[3-[(3aR,6aR)-5-(1H-benzotriazole-5-carbonyl)-1,3,3a,
4,6,6a-hexahydropyrrolo[3,4-c]pyrrol-2-yl]-3-oxopropyl]-3-propan-2-ylbenzonitrile;
[(3aR,6aR)-541-(4-chlorophenyl)piperidine-4-carbonyl]-
1,3,3a,4,6,6a-hexahydropyrrolo[3,4-c]pyrrol-2-yl]-
(1H-benzotriazol-5-yl)methanone;
1-[(3aS,6aS)-5-(1H-benzotriazole-5-carbonyl)-1,3,3a,4,
6,6a-hexahydropyrrolo[3,4-c]pyrrol-2-yl]-2-(4-bromo-
2-tert-butylphenoxy)ethanone;
4-[2-[(3aS,6aS)-5-(1H-benzotriazole-5-carbonyl)-1,3,3a,
4,6,6a-hexahydropyrrolo[3,4-c]pyrrol-2-yl]-2-oxoethoxy]-3-tert-butylbenzonitrile;
1-[(3aS,6aS)-5-(1H-benzotriazole-5-carbonyl)-1,3,3a,4,
6,6a-hexahydropyrrolo[3,4-c]pyrrol-2-yl]-2-(2-tert-butyl-4-methoxyphenoxy)ethanone;
((3aS,6aS)-5-(1H-benzo[d][1,2,3]triazole-5-carbonyl)
hexahydropyrrolo[3,4-c]pyrrol-2(1H)-yl)(4-ethoxyquinolin-2-yl)methanone;
((3aS,6aS)-5-(1H-benzo[d][1,2,3]triazole-5-carbonyl)
hexahydropyrrolo[3,4-c]pyrrol-2(1H)-yl)(4-(2,2,2-trifluoroethoxy)quinolin-2-yl)methanone;
((3aS,6aS)-5-(1H-benzo[d][1,2,3]triazole-5-carbonyl)
hexahydropyrrolo[3,4-c]pyrrol-2(1H)-yl)(6-cyclobutoxy-5-(trifluoromethyl)pyridin-3-yl)methanone;
((3aS,6aS)-5-(1H-benzo[d][1,2,3]triazole-5-carbonyl)
hexahydropyrrolo[3,4-c]pyrrol-2(1H)-yl)(5-bromo-6-
(2- methoxyethoxy)pyridin-3-yl)methanone;
((3aS,6aS)-5-(1H-benzo[d][1,2,3]triazole-5-carbonyl)
hexahydropyrrolo[3,4-c]pyrrol-2(1H)-yl)(5-bromo-6-
(cyclopropylmethoxy)pyridin-3-yl)methanone;
((3aS,6aS)-5-(1H-benzo[d][1,2,3]triazole-5-carbonyl)
hexahydropyrrolo[3,4-c]pyrrol-2(1H)-yl)(5-cyclopropyl-6-(2,2,2-trifluoroethoxy)pyridin-3-yl)methanone;
((3aS,6aS)-5-(1H-benzo[d][1,2,3]triazole-5-carbonyl)
hexahydropyrrolo[3,4-c]pyrrol-2(1H)-yl)(6-(2,2,2-trifluoroethoxy)-5-(trifluoromethyl)pyridin-3-yl)methanone;
(1H-benzotriazol-5-yl)-{(3aS,6aS)-5[4-(4-chloro-phenyl)-piperidine-1-carbonyl]-hexahydro-pyrrolo[3,4-c]
pyrrol-2-yl}-methanone; and
(1H-benzotriazol-5-yl)-{(3aS,6aS)-5[4-(4-chloro-phenyl)-piperazine-1-carbonyl -hexahydro-pyrrolo[3,4-c]
pyrrol-2-yl}-methanone;
or a pharmaceutically acceptable salt thereof.

40. A compound according to claim 1, selected from
trans-3,5-dichlorobenzyl 2-(1H-benzo[d][1,2,3]triazole-
5-carbonyl)hexahydro-1H-pyrrolo[3,4-c]pyridine-5
(6H)-carboxylate;
(3aS,6aS)-5-(1H-benzotriazole-5-carbonyl)-hexahydropyrrolo[3,4-c]pyrrole-2-carboxylic acid 3-chloro-5-methanesulfonyl-benzyl ester;
(3aS,6aS)-5-(1H-benzotriazole-5-carbonyl)-hexahydropyrrolo[3,4-c]pyrrole-2-carboxylic acid 4-trifluoromethoxy-benzyl ester;
(E)-1-((3aR,6aR)-5-(1H-benzo[d][1,2,3]triazole-5-carbonyl)hexahydropyrrolo[3,4-c]pyrrol-2(1H)-yl)-3 -(4-
(trifluoromethoxy)phenyl)prop-2-en-1-one;
1-((3aR,6aS)-5-(1H-benzo[d][1,2,3]triazole-5-carbonyl)
hexahydropyrrolo[3,4-c]pyrrol-2(1H)-yl)-3-(4-(trifluoromethoxy)phenyl)propan-1-one;
1-[(3aR,6aR)-5-(1H-benzotriazole-5-carbonyl)-hexahydro-pyrrolo[3,4-c]pyrrol-2-yl]-3-(4-trifluoromethoxy-phenyl)-propan-1-one;
1-[(3aR,6aR)-5-(1H-benzotriazole-5-carbonyl)-hexahydro-pyrrolo[3,4-c]pyrrol-2-yl]-3-(4-trifluoromethyl-phenyl)-propan-1-one; and
1-[(3aS,6aS)-5-(1H-benzotriazole-5-carbonyl)-hexahydro-pyrrolo[3,4-c]pyrrol-2-yl]-2-(4-chloro-2-isopropyl-5-methyl-phenoxy)-ethanone;
or a pharmaceutically acceptable salt thereof.

41. A compound according to claim 1, wherein the compound is:
(3aS,6aS)-5-(1H-benzotriazole-5-carbonyl)-hexahydropyrrolo[3,4-c]pyrrole-2-carboxylic acid 4-difluoromethoxy-3-fluoro-benzyl ester;
or a pharmaceutically acceptable salt thereof.

42. A process to prepare a compound according to claim 1, or a pharmaceutically acceptable salt thereof, comprising the reaction of a compound of formula (II) in the presence of a compound of formula (III)

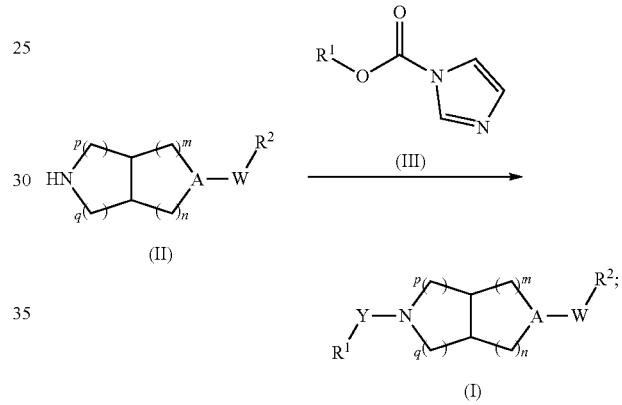

wherein Y is -OC(O)-.

43. A pharmaceutical composition comprising a compound according to claim 1, or a pharmaceutically acceptable salt thereof, and a therapeutically inert carrier.

44. The compound (E)-1-((3aR,8aS)-2-(1H-benzo[d][1,2,
3]triazole-5-carbonyl)octahydropyrrolo[3,4-d]azepin-6
(7H)-yl)-3-(3-chloro-5-(trifluoromethyl)phenyl)prop-2-en-
1-one, or a pharmaceutically acceptable salt thereof.

45. A pharmaceutical composition comprising the compound (E)-1-((3aR,8aS)-2-(1H-benzo[d][1,2,3]triazole-5-
carbonyl)octahydropyrrolo[3,4-d]azepin-6(7H)-yl)-3-(3-
chloro-5-(trifluoromethyl)phenyl)prop-2-en-1-one, or a
pharmaceuticallyacceptable salt thereof, and a therapeutically inert carrier.

46. The compound (E)-1-((3aR,8aS)-2-(1H-benzo[d][1,2,
3]triazole-5-carbonyl)octahydropyrrolo[3,4-d]azepin-6
(7H)-yl)-3-(2-cyclopropylphenyl)prop-2-en-1-one, or a
pharmaceutically acceptable salt thereof.

47. A pharmaceutical composition comprising the compound (E)-1-((3aR,8aS)-2-(1H-benzo[d][1,2,3]triazole-5-
carbonyl)octahydropyrrolo[3,4-d]azepin-6(7H)-yl)-3-(2-cyclopropylphenyl)prop-2-en-1-one, or a pharmaceutically acceptable salt thereof, and a therapeutically inert carrier.

48. The compound trans-3,5-dichlorobenzyl 5-(1H-benzo
[d][1,2,3]triazole-5-carbonyl)hexahydro-1H-pyrrolo[3,4-c]
pyridine-2(3H)-carboxylate, or a pharmaceutically acceptable salt thereof.

49. A pharmaceutical composition comprising the compound trans-3,5-dichlorobenzyl 5-(1H-benzo[d][1,2,3]triazole-5-carbonyl)hexahydro-1H-pyrrolo[3,4-c]pyridine-2(3H)-carboxylate, or a pharmaceutically acceptable salt thereof, and a therapeutically inert carrier.

50. The compound (3aR,8aS)-3,5-dichlorobenzyl 6-(1H-benzo[d][1,2,3]triazole-5-carbonyl)octahydropyrrolo[3,4-d]azepine-2(1H)-carboxylate, or a pharmaceutically acceptable salt thereof.

51. A pharmaceutical composition comprising the compound (3aR,8aS)-3,5-dichlorobenzyl 6-(1H-benzo[d][1,2,3]triazole-5-carbonyl)octahydropyrrolo[3,4-d]azepine-2(1H)-carboxylate, or a pharmaceutically acceptable salt thereof, and a therapeutically inert carrier.

52. The compound (3aS,6aS)-5-(1H-benzotriazole-5-carbonyl)-hexahydro-pyrrolo[3,4-c]pyrrole-2-carboxylic acid 4-trifluoromethoxy-benzyl ester, or a pharmaceutically acceptable salt thereof 53. A pharmaceutical composition comprising the compound, (3aS,6aS)-5-(1H-benzotriazole-5-carbonyl)-hexahydro-pyrrolo[3,4-c]pyrrole-2-carboxylic acid 4-trifluoromethoxy-benzyl ester, or a pharmaceutically acceptable salt thereof, and a therapeutically inert carrier.

54. The compound 1-[(3aR,6aR)-5-(1H-benzotriazole-5-carbonyl)-hexahydro-pyrrolo[3,4-c]pyrrol-2-yl]-3-(4-trifluoromethoxy-phenyl)-propan-1-one, or a pharmaceutically acceptable salt thereof 55. A pharmaceutical composition comprising the compound 1-[(3aR,6aR)-5-(1H-benzotriazole-5-carbonyl)-hexahydro-pyrrolo[3,4-c]pyrrol-2-yl]-3-(4-trifluoromethoxy-phenyl)-propan-1-one, or a pharmaceutically acceptable salt thereof, and a therapeutically inert carrier.

\* \* \* \* \*